(12) United States Patent
Frendewey et al.

(10) Patent No.: US 11,697,828 B2
(45) Date of Patent: Jul. 11, 2023

(54) METHODS AND COMPOSITIONS FOR TARGETED GENETIC MODIFICATION USING PAIRED GUIDE RNAS

(71) Applicant: Regeneron Pharmaceuticals, Inc., Tarrytown, NY (US)

(72) Inventors: David Frendewey, New York, NY (US); Ka-Man Venus Lai, Seattle, WA (US); Wojtek Auerbach, Ridgewood, NJ (US); Gustavo Droguett, New City, NY (US); Anthony Gagliardi, Hopewell Junction, NY (US); David M. Valenzuela, Yorktown Heights, NY (US); Vera Voronina, Sleepy Hollow, NY (US); Lynn Macdonald, Harrison, NY (US); Andrew J. Murphy, Croton-on-Hudson, NY (US); George D. Yancopoulos, Yorktown Heights, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 719 days.

(21) Appl. No.: 16/572,124

(22) Filed: Sep. 16, 2019

(65) Prior Publication Data

US 2020/0002730 A1    Jan. 2, 2020

Related U.S. Application Data

(62) Division of application No. 14/948,221, filed on Nov. 20, 2015, now Pat. No. 10,457,960.

(60) Provisional application No. 62/211,421, filed on Aug. 28, 2015, provisional application No. 62/182,314, filed on Jun. 19, 2015, provisional application No. 62/083,005, filed on Nov. 21, 2014.

(51) Int. Cl.
| | | |
|---|---|---|
| *C12N 15/85* | (2006.01) |
| *C12N 15/90* | (2006.01) |
| *C12N 15/10* | (2006.01) |
| *A01K 67/027* | (2006.01) |
| *C12N 9/22* | (2006.01) |
| *C12Q 1/6888* | (2018.01) |

(52) U.S. Cl.
CPC ........ *C12N 15/907* (2013.01); *A01K 67/0275* (2013.01); *C12N 9/22* (2013.01); *C12N 15/102* (2013.01); *C12N 15/8509* (2013.01); *C12Q 1/6888* (2013.01); *A01K 2227/105* (2013.01)

(58) Field of Classification Search
None
See application file for complete search history.

(56) References Cited

U.S. PATENT DOCUMENTS

| | | |
|---|---|---|
| 6,372,956 B1 | 4/2002 | Goldsmith et al. |
| 6,566,579 B1 | 5/2003 | Jaisser et al. |
| 7,294,754 B2 | 11/2007 | Poueymirou et al. |
| 7,771,967 B2 | 8/2010 | Huang et al. |
| 8,502,018 B2 | 8/2013 | Murphy et al. |
| 8,697,359 B1 | 4/2014 | Zhang |
| 8,921,332 B2 | 12/2014 | Choulika et al. |
| 9,228,208 B2 | 1/2016 | Frendewey et al. |
| 9,546,384 B2* | 1/2017 | Frendewey .............. C12N 9/22 |
| 9,822,370 B2 | 11/2017 | Musunuru et al. |
| 2003/0134318 A1 | 7/2003 | Case et al. |
| 2003/0175968 A1 | 9/2003 | Golic et al. |
| 2004/0018626 A1 | 1/2004 | Murphy et al. |
| 2004/0197317 A1 | 10/2004 | Rao et al. |
| 2005/0144655 A1 | 6/2005 | Economides et al. |
| 2008/0066197 A1 | 3/2008 | Ying et al. |
| 2008/0113437 A1 | 5/2008 | Joly et al. |
| 2008/0299580 A1 | 12/2008 | DeKelver et al. |
| 2009/0055943 A1 | 2/2009 | Economides et al. |
| 2010/0047805 A1 | 2/2010 | Wang |
| 2010/0218264 A1 | 8/2010 | Cui et al. |
| 2011/0207221 A1 | 8/2011 | Cost et al. |
| 2011/0307968 A1 | 12/2011 | Auerbach et al. |
| 2012/0272349 A1 | 10/2012 | Ochiya et al. |
| 2012/0315670 A1 | 12/2012 | Jacobson et al. |
| 2013/0309670 A1 | 11/2013 | Frendewey et al. |
| 2014/0068797 A1 | 3/2014 | Doudna et al. |

(Continued)

FOREIGN PATENT DOCUMENTS

| | | |
|---|---|---|
| EP | 136027 B1 | 9/2012 |
| EP | 3009511 A2 | 4/2016 |

(Continued)

OTHER PUBLICATIONS

Dow, Trends in Molecular Medicine, 2015, vol. 21, No. 10, pp. 609-621 (Year: 2015).*

(Continued)

*Primary Examiner* — Celine X Qian
(74) *Attorney, Agent, or Firm* — Yongjin Choi; Alston & Bird LLP

(57) ABSTRACT

Compositions and methods are provided for creating and promoting biallelic targeted modifications to genomes within cells and for producing non-human animals comprising the modified genomes. Also provided are compositions and methods for modifying a genome within a cell that is heterozygous for an allele to become homozygous for that allele. The methods make use of Cas proteins and two or more guide RNAs that target different locations within the same genomic target locus. Also provided are methods of identifying cells with modified genomes.

33 Claims, 22 Drawing Sheets
(2 of 22 Drawing Sheet(s) Filed in Color)
Specification includes a Sequence Listing.

(56) References Cited

U.S. PATENT DOCUMENTS

| | | |
|---|---|---|
| 2014/0179770 A1 | 6/2014 | Zhang et al. |
| 2014/0242702 A1 | 8/2014 | Chen et al. |
| 2014/0248702 A1 | 9/2014 | Zhang et al. |
| 2014/0273037 A1 | 9/2014 | Wu |
| 2014/0273226 A1 | 9/2014 | Wu |
| 2014/0273231 A1 | 9/2014 | Zhang et al. |
| 2014/0273233 A1 | 9/2014 | Chen et al. |
| 2014/0273234 A1 | 9/2014 | Zhang et al. |
| 2014/0301990 A1 | 10/2014 | Gregory et al. |
| 2014/0309487 A1 | 10/2014 | Lee et al. |
| 2014/0310828 A1 | 10/2014 | Lee et al. |
| 2014/0315985 A1 | 10/2014 | May et al. |
| 2014/0335063 A1 | 11/2014 | Cannon et al. |
| 2014/0342456 A1 | 11/2014 | Mali et al. |
| 2014/0342458 A1 | 11/2014 | Mali et al. |
| 2014/0359795 A1 | 12/2014 | Fahrenkrug et al. |
| 2015/0024500 A1 | 1/2015 | Yu et al. |
| 2015/0071889 A1 | 3/2015 | Musunuru et al. |
| 2015/0079680 A1 | 3/2015 | Bradley et al. |
| 2015/0110762 A1 | 4/2015 | Holmes et al. |
| 2015/0140664 A1 | 5/2015 | Byrne et al. |
| 2015/0152436 A1 | 6/2015 | Musunuru et al. |
| 2015/0159174 A1 | 6/2015 | Frendewey et al. |
| 2015/0159175 A1 | 6/2015 | Frendewey et al. |
| 2015/0176013 A1 | 6/2015 | Musunuru et al. |
| 2015/0184199 A1 | 7/2015 | Horwitz et al. |
| 2015/0232881 A1 | 8/2015 | Glucksmann et al. |
| 2015/0232883 A1 | 8/2015 | Dahlman et al. |
| 2015/0252358 A1 | 9/2015 | Maeder et al. |
| 2015/0291965 A1 | 10/2015 | Zhang et al. |
| 2015/0291966 A1 | 10/2015 | Zhang et al. |
| 2015/0291969 A1 | 10/2015 | Nair et al. |
| 2015/0368670 A1 | 12/2015 | Quake et al. |
| 2015/0376583 A1 | 12/2015 | Quake et al. |
| 2015/0376650 A1 | 12/2015 | Auerbach et al. |
| 2015/0376651 A1 | 12/2015 | Frendewey et al. |
| 2016/0017301 A1 | 1/2016 | Khalili et al. |
| 2016/0032292 A1 | 2/2016 | Storici et al. |
| 2016/0040155 A1 | 2/2016 | Maizels et al. |
| 2016/0046960 A1 | 2/2016 | Frendewey et al. |
| 2016/0060637 A1 | 3/2016 | Hommelsheim et al. |
| 2016/0060655 A1 | 3/2016 | Quake et al. |
| 2016/0060657 A1 | 3/2016 | Frendewey et al. |
| 2016/0074535 A1 | 3/2016 | Ranganathan et al. |
| 2016/0108369 A1 | 4/2016 | Kuno et al. |
| 2016/0122774 A1 | 5/2016 | Duchateau et al. |
| 2016/0138045 A1 | 5/2016 | Koshland et al. |
| 2016/0138046 A1 | 5/2016 | Wu |
| 2016/0145646 A1 | 5/2016 | Frendewey et al. |
| 2016/0153003 A1 | 6/2016 | Joung et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |
| 2016/0160210 A1 | 6/2016 | Mali et al. |
| 2016/0175462 A1 | 6/2016 | Zhang et al. |
| 2016/0177339 A1 | 6/2016 | Voronina et al. |
| 2016/0186213 A1 | 6/2016 | Zhang et al. |
| 2016/0208243 A1 | 7/2016 | Zhang et al. |
| 2016/0208319 A1 | 7/2016 | Berman et al. |
| 2016/0237455 A1 | 8/2016 | Glucksmann et al. |
| 2016/0250300 A1 | 9/2016 | Khalili et al. |
| 2016/0251667 A1 | 9/2016 | Cigan et al. |
| 2016/0257967 A1 | 9/2016 | Russell et al. |
| 2016/0264995 A1 | 9/2016 | Yamamoto et al. |
| 2016/0281111 A1 | 9/2016 | Cotta-Ramusino et al. |
| 2016/0304855 A1 | 10/2016 | Stark et al. |
| 2016/0340661 A1 | 11/2016 | Cong et al. |
| 2016/0355796 A1 | 12/2016 | Davidson et al. |
| 2017/0002380 A1 | 1/2017 | Buerckstuemmer |
| 2017/0266320 A1 | 9/2017 | Wagers et al. |
| 2017/0275611 A1 | 9/2017 | Bradley et al. |
| 2017/0332610 A1 | 11/2017 | Voronina et al. |
| 2018/0020646 A1 | 1/2018 | Ueda et al. |
| 2018/0135073 A1 | 5/2018 | Chen et al. |
| 2018/0327761 A1 | 11/2018 | Duchateau et al. |
| 2018/0334665 A1 | 11/2018 | Yu et al. |
| 2018/0355382 A1 | 12/2018 | Bergstrom et al. |
| 2019/0233846 A1 | 8/2019 | Zhang et al. |
| 2019/0338274 A1 | 11/2019 | Bradley et al. |
| 2020/0002722 A1 | 1/2020 | Chen et al. |
| 2020/0002731 A1 | 1/2020 | Frendewey et al. |
| 2021/0147879 A1 | 5/2021 | Byrne et al. |

FOREIGN PATENT DOCUMENTS

| | | |
|---|---|---|
| EP | 3 239 298 A1 | 11/2017 |
| EP | 3022304 B1 | 12/2018 |
| EP | 3071698 B1 | 9/2019 |
| EP | 3604543 A1 | 2/2020 |
| EP | 3418379 B1 | 12/2020 |
| WO | WO 2002/036789 A2 | 5/2002 |
| WO | WO 2002/066630 A1 | 8/2002 |
| WO | WO 2003/087341 A2 | 10/2003 |
| WO | WO 2006/044962 A1 | 4/2006 |
| WO | WO 2007/117410 A2 | 10/2007 |
| WO | WO 2008/151081 A1 | 12/2008 |
| WO | WO 2011/019385 A1 | 2/2011 |
| WO | WO 2011/051390 A1 | 5/2011 |
| WO | WO 2011/078665 A1 | 6/2011 |
| WO | WO 2011/146121 A1 | 11/2011 |
| WO | WO 2011/154927 A2 | 12/2011 |
| WO | WO 2012/012667 A2 | 1/2012 |
| WO | WO 2012/018726 A1 | 9/2012 |
| WO | WO 2012/129198 A1 | 9/2012 |
| WO | WO 2012/168307 A2 | 12/2012 |
| WO | WO 2013/063361 A1 | 5/2013 |
| WO | WO 2013/163394 A1 | 10/2013 |
| WO | WO 2013/169802 A1 | 11/2013 |
| WO | WO 2013/176772 A1 | 11/2013 |
| WO | WO 2013/188522 A2 | 12/2013 |
| WO | WO 2014/065596 A1 | 5/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093661 A2 | 6/2014 |
| WO | WO 2014/093694 A1 | 6/2014 |
| WO | WO 2014/099744 A1 | 6/2014 |
| WO | WO 2014/099750 A2 | 6/2014 |
| WO | WO 2014093622 A2 | 6/2014 |
| WO | WO 2014/104878 A1 | 7/2014 |
| WO | WO 2014/127287 A1 | 8/2014 |
| WO | WO 2014/130955 A1 | 8/2014 |
| WO | WO 2014/143381 A1 | 9/2014 |
| WO | WO 2014/150624 A1 | 9/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/191518 A1 | 12/2014 |
| WO | WO 2014/201015 A2 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2015/006498 A2 | 1/2015 |
| WO | WO 2015/010114 A1 | 1/2015 |
| WO | WO 2015/013583 A2 | 1/2015 |
| WO | WO 2015/040402 A1 | 3/2015 |
| WO | WO 2015/048577 A2 | 4/2015 |
| WO | WO 2015/048690 A1 | 4/2015 |
| WO | WO 2015/052231 A2 | 4/2015 |
| WO | WO 2015/057980 A1 | 4/2015 |
| WO | WO 2015/070083 A1 | 5/2015 |
| WO | WO 2015/077290 A1 | 5/2015 |
| WO | WO 2015/079057 A2 | 6/2015 |
| WO | WO 2015/088643 A1 | 6/2015 |
| WO | WO 2015/089351 A1 | 6/2015 |
| WO | WO 2015/089427 A1 | 6/2015 |
| WO | WO 2015/089465 A1 | 6/2015 |

(56) References Cited

FOREIGN PATENT DOCUMENTS

| | | |
|---|---|---|
| WO | WO 2015/089473 A1 | 6/2015 |
| WO | WO 2015/095804 A1 | 6/2015 |
| WO | WO 2015/105928 A1 | 7/2015 |
| WO | WO 2015/112790 A2 | 7/2015 |
| WO | WO 2015/116969 A1 | 8/2015 |
| WO | WO 2015/117041 A1 | 8/2015 |
| WO | WO 2015/134812 A1 | 9/2015 |
| WO | WO 2015/138510 A1 | 9/2015 |
| WO | WO 2015/138739 A2 | 9/2015 |
| WO | WO 2015/139008 A1 | 9/2015 |
| WO | WO 2015/148761 A1 | 10/2015 |
| WO | WO 2015/159086 A1 | 10/2015 |
| WO | WO 2015/163733 A1 | 10/2015 |
| WO | WO 2015/166272 A2 | 11/2015 |
| WO | WO 2015/173436 A1 | 11/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188109 A1 | 12/2015 |
| WO | WO 2015/200805 A2 | 12/2015 |
| WO | WO 2016/011210 A2 | 1/2016 |
| WO | WO 2016/011428 A1 | 1/2016 |
| WO | WO 2016/033246 A1 | 3/2016 |
| WO | WO 2016/036754 A1 | 3/2016 |
| WO | WO 2016/049024 A2 | 3/2016 |
| WO | WO 2016/049163 A2 | 3/2016 |
| WO | WO 2016/049258 A2 | 3/2016 |
| WO | WO 2016/054032 A1 | 4/2016 |
| WO | WO 2016/054326 A1 | 4/2016 |
| WO | WO 2016/057821 A2 | 4/2016 |
| WO | WO 2016/057961 A1 | 4/2016 |
| WO | WO 2016/061073 A2 | 4/2016 |
| WO | WO 2016/061374 A1 | 4/2016 |
| WO | WO 2016/061481 A1 | 4/2016 |
| WO | WO 2016/065364 A1 | 4/2016 |
| WO | WO 2016/073955 A2 | 5/2016 |
| WO | WO 2016/073990 A1 | 5/2016 |
| WO | WO 2016/081923 A2 | 5/2016 |
| WO | WO 2016/084084 A1 | 6/2016 |
| WO | WO 2016/089866 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/097751 A1 | 6/2016 |
| WO | WO 2016/100819 A1 | 6/2016 |
| WO | WO 2016/112242 A1 | 7/2016 |
| WO | WO 2016/112351 A1 | 7/2016 |
| WO | WO 2016/115326 A1 | 7/2016 |
| WO | WO 2016/130697 A1 | 8/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/142719 A1 | 9/2016 |
| WO | WO 2016/154579 A2 | 9/2016 |
| WO | WO 2016/160721 A1 | 10/2016 |
| WO | WO 2016/161380 A1 | 10/2016 |
| WO | WO 2016/168890 A1 | 10/2016 |
| WO | WO 2016/174056 A1 | 11/2016 |
| WO | WO 2016/176690 A2 | 11/2016 |
| WO | WO 2016/186772 A1 | 11/2016 |
| WO | WO 2017/062723 A1 | 4/2017 |
| WO | WO 2017/070032 A1 | 4/2017 |
| WO | WO 2016/073990 A2 | 5/2017 |
| WO | WO 2017/079724 A9 | 5/2017 |
| WO | WO 2017/165826 A1 | 9/2017 |
| WO | WO 2017/173004 A1 | 10/2017 |
| WO | WO 2017/180859 A1 | 10/2017 |
| WO | WO 2017/201476 A1 | 11/2017 |
| WO | WO 2019/148166 A1 | 8/2019 |
| WO | WO 2016/138574 A1 | 9/2019 |

OTHER PUBLICATIONS

Mout et al., Bioconjugate Chemistry, 2017, vol. 28, pp. 880-884 (Year: 2017).*
Wang et al (Journal of Cellular Molecular Medicine, 2020, vol. 24, pp. 3256-3270) (Year: 2020).*
Yoshimi et al (Nature Communications, 2014, vol. 5: 4240, pp. 1-9). and supplement figures (Year: 2014).*
Zhang et al., "The CRISPR/Cas9 system produces specific and homozygous targeted gene editing in rice in one generation," Plant Biotechnol. J., vol. 12(6), pp. 797-807, May 23, 2014.
"Stem Cells: Scientific Progress and Future Research Directions," National Institute of Health, Department of Health and Human Services, (2001).
Addgene, Zhang Lab's CRISPR Frequently Asked Questions, www. addgene.org/crispr/zhang/FAQ, accessed Jun. 24, 2015.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Baker, M., "Gene editing at CRISPR speed," Nature Biotechnology (2014), vol. 32(4), p. 309-312.
Bassett, A.R., et al., "CRISPR/Cas9 and Genome Editing in *Drosophila*," Journal of Genetics and Genomics (2014), vol. 41, pp. 7-19.
Benders et al., "Cloning whole bacterial genomes in yeast," Nucleic Acids Res., vol. 38(8), pp. 2558-2569, Mar. 7, 2010.
Berdien, et al., "TALEN-mediated editing of endogenous T-cell receptors facilitates efficient reprogramming of T lymphocytes by lentiviral gene transfer," Gene Therapy, 21, 539-548 (2014).
Bernardini et al., "Site-specific genetic engineering of the Anopheles gambiae Y chromosome," Proc. Natl. Acad. Sci. USA, vol. 111(21), pp. 7600-7605, May 12, 2014.
Beumer et al., "Donor DNA Utilization During Gene Targeting with Zinc-Finger Nucleases," Genes Genomes Genetics, vol. 3, pp. 657-664, Apr. 2013.
Budke et al., "RI-1: a chemical inhibitor of RAD51 that disrupts homologous recombination in human cells," Nucleic Acids Research, vol. 40(15), pp. 1-11, 2012 (epub May 9, 2012).
Byrne et al., "Genome editing in human stem cells," Methods Enzymol. 546:119-138, (2014).
Byrne et al., "Multi-kilobase homozygous targeted gene replacement in human induced pluripotent stem cells," Nucleic Acids Research, Vo. 43(3), p. e21, 2014 (epub Nov. 20, 2014).
Chang et al., "Genome editing with RNA-guided Cas9 nuclease in Zebrafish embryos," Cell Research, vol. 23, pp. 465-472, 2013. (published Mar. 2013).
Chen et al., "High-frequency genome editing using ssDNA oligonucleotides with zinc-finger nucleases," Nature Methods, vol. 8(9), pp. 753-755, 2011. (Jul. 17, 2011).
Cho, et al., "Targeting genome engineering in human cells with the Cas9 RNA-guided endonuclease," Nature Biotechnology, 2013, vol. 31(3):233-239.
Choulika et al., "Induction of Homologous Recombination in Mammalian Chromosomes by Using the I-ScelI System of *Saccharomyces cerevisiae*," Mol. Cell. Biol., vol. 15(4), pp. 1968-1973, 1995.
Chu et al., "Increasing the efficiency of homology-directed repair for CRISPR-Cas9-induced precise gene editing in mammalian cells," Nature Biotech., vol. 33(5), pp. 543-548, 2015. (published Mar. 2015).
Cobb and Zhao, "Direct cloning of large genomic sequences," Nature Biotechnology, 2012, vol. 30(5), pp. 405-406.
Cong et al., "Multiplex Genome Engineering Using CRISPR/Cas Systems," Science, vol. 339(6121), pp. 819-823 plus Supplemental Materials, Jan. 3, 2013.
Cui, et al., "Targeted integration in rat and mouse embryos with zinc-finger nucleases," Nature Biotechnology, vol. 29, No. 1, 64-68 (Dec. 12, 2010).
Dechiara, T.M., et al., "VelociMouse: Fully ES Cell-Derived FO-Generation Mice Obtained from the Injection of ES Cells into Eight-Cell-Stage Embryos," Jan. 1, 2009, Methods in Molecular Biology, 530(16): 311-324.
Ding et al., "Enhanced Efficiency of Human Pluripotent Stem Cell Genome Editing through Replacing TALENs with CRISPRs," Cell Stem Cell, vol. 12, pp. 393-394 plus supplemental materials, 2013 (Apr. 4, 2013).

(56) References Cited

OTHER PUBLICATIONS

Ding, et al., "A TALEN genome-editing system for generating human stem cell-based disease models," Cell Stem Cell, 2013, vol. 12, pp. 238-251.

Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.

Doudna et al., "The new frontier of genome engineering with CRISPR-Cas9," Science, vol. 346(6213), pp. 1258096-1-1258096-9, Nov. 28, 2014.

Elliott et al., "Gene Conversion Tracts from Double-Strand Break Repair in Mammalian Cells," Molecular and Cellular Biology, vol. 18(1), pp. 93-101, 1998.

EP Application No. 19161085.6 Extended European Search Report dated May 7, 2019.

Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.

Flisikowska, et al., "Efficient Immunoglobulin Gene Disruption and Targeted Replacement in Rabbit Using Zinc Finger Nucleases," Plos one, vol. 6 Issue 6 (Jun. 2011).

Frendewey, "VelociGene: Large-scale Modification of Rodent Genomes," Wellcome Trust Advanced Course: Genetic Engineering of Mammalian Stem Cells, Feb. 20, 2015.

Frendewey, "VeiociGene: Large-scale Modification of Rodent Genomes," Wellcome Trust Advanced Course: Genetic Engineering of Mammalian Stem Cells, Mar. 13, 2014.

Frokjaer-Jensen C., "Exciting Prospects for Precise Engineering of Caenorhabditis elegans Genomes with CRISPR/Cas9," Genetics (2013), vol. 195, pp. 635-642.

Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.

Fujii W., et al., "Efficient generation of large-scale genome-modified mice using gRNA and CAS9 endonuclease," Nucleic Acids Research (2013), vol. 41(20), p. e187.

Gaj et al., "ZFN, TALEN, and CRISPR/Cas-based methods for genome engineering," Trends Biotech., vol. 31(7), pp. 397-405, 2013.

Gennequin, et al., "CRISPR/Cas-induced double-strand breaks boost the frequency of gene replacements for humanizing the mouse Cnr2 gene," Biochem. Biophys. Res. Commun., (2013), http://dx.doi.org/10.1016/j.bbrc.2013.10.138.

Gratz et al., "Genome Engineering of *Drosophila* with the CRISPR RNA-Guided Cas9 Nuclease," Genetics, vol. 194, pp. 1029-1035, 2013. (published May 2013).

Gratz et al., "Highly Specific and Efficient CRISPR/Cas9-Catalyzed Homology-Directed Repair in *Drosophila*," Genetics, vol. 196(4), pp. 961-971 plus Supporting Information, Jan. 29, 2014.

Harrison, M.M., et al., "A CRISPR view of development," Genes & Development (2014), vol. 28(17), pp. 1859-1872.

Hsu, P.D., et al., "Development and Applications of CRISPR-Cas9 for Genome Engineering," Cell (2014), vol. 157, pp. 1262-1278.

Hwang et al., "Efficient In Vivo Genome Editing Using RNA-Guided Nucleases," Nat. Biotechnol., vol. 31(3), pp. 227-229 (plus supplemental materials), 2013.

Jallepalli et al., "Securin is required for chromosomal stability in human cells," Cell, vol. 105(4), pp. 445-457, May 18, 2001.

Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.

Jasin, et al., "Repair of Strand Breaks by Homologous Recombination," Cold Spring Harb. Perspect. Biol., vol. 5(11), p. a012740, Nov. 1, 2013.

Johnson, et al., "A rapid assay to quantify the cleavage efficiency of custom-designed nucleases in planta," Plant Mol Biol, 82:207-221 (2013).

Kashimada et al., "Sry: the master switch in mammalian sex determination," Development, vol. 137(23), pp. 3921-3930, Dec. 2, 2010.

Kasparek, T., et al., "DNA double-strand break repair pathways, chromosomal rearrangements and cancer," Seminars in Cell & Developmental Biology (2011), vol. 22, pp. 886-697.

Kato et al., "Production of Sry knockout mouse using TALEN via oocyte injection," Scientific Reports, vol. 3, p. 3136, 2013 (published Nov. 5, 2013).

Kim et al., "Targeted genome editing in human cells with zinc finger nucleases constructed via modular assembly," Genome Res., vol. 19(7), pp. 1279-1288, 2009.

Kondo, et al., "Highly Improved Gene Targeting by Germline-Specific Cas9 Expression in *Drosophila*," Genetics, vol. 195, pp. 715-721, Sep. 3, 2013.

Konermann et al., "Genome-scale transcriptional activation by an engineered CRISPR-Cas9 complex," Nature, vol. 517(7536), pp. 583-588, published online Dec. 10, 2014.

Kosicki et al., "Repair of double-strand breaks induced by CRISPR-Cas9 leads to large deletions and complex rearrangements," Nat. Biotechnol., 36(8): 765-771, (Jul. 16, 2018).

Kuijpers et al., "One-step assembly and targeted integration of multigene constructs assisted by the I-SceI meganuclease in *Saccharomyces cerevisiae*," FEMS Yeast Res., vol. 13(8), pp. 769-781, Oct. 7, 2013.

Kuno et al., "Generation offertile and fecund F0 XY female mice from XY ES cells," Transgenic Research, vol. 24(1), pp. 19-29, 2014 (epub Aug. 3, 2014).

Kuroiwa, et al., "Sequential targeting of the genes encoding immunoglobulin-μ and prion protein in cattle," Nature Genetics, vol. 36, No. 7, (Jul. 2004).

Li et al., "Germline Competent Embryonic Stem Cells Derived from Rat Blastocysts," Cell, vol. 135, pp. 1299-1310, 2008.

Li et al., "Optimization of Genome Engineering Approaches with the CRISPR/Cas9 System," PLoS One, vol. 9(8), p. e105779, Aug. 28, 2014.

Li, M., et al., "A Cut above the Rest: Targeted Genome Editing Technologies in Human Pluripotent Stem Cells," Journal of Biological Chemistry (2014), vol. 289(8), pp. 4594-4599.

Lin et al., "Enhanced homology-directed human genome engineering by controlled timing of CRISPR/Cas9 delivery," eLife, vol. 3, e04766, 2014. (published Dec. 15, 2014).

Lin, S.-C., et al., "Strategies for gene disruption in *Drosophila*," Cell & Bioscience (2014), vol. 4(1), p. 63.

Liu et al., "A one-step cloning method for the construction of somatic cell gene targeting vectors: application to production of human knockout cell lines," BMC Biotechnol., vol. 12, p. 71, Oct. 9, 2012.

Lombardo, et al., "Gene editing in human stem cells using zinc finger nucleases and integrase-defective lentiviral vector delivery," Nature Biotechnology, 2007, vol. 25(11), pp. 1298-1306.

Ma et al., "Heritable multiplex genetic engineering in rats using CRISPR/Cas9," PLoS ONE, vol. 9(3), p. e89413, Mar. 5, 2014.

MacDonald, et al., "Precise and in situ genetic humanization of 6 Mb of mouse immunoglobulin genes," PNAS, vol. 111, No. 14: 5147-5152, (Apr. 8, 2014).

Mali et al., "RNA-Guided Human Genome Engineering via Cas9," Science, vol. 339(6121), pp. 823-826 plus Supplemental Materials, Jan. 3, 2013.

Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.

Mali, et al., "Cas9 as a versatile tool for engineering biology," Nature Methods, vol. 10(10), pp. 957-963, 2013.

Manjunath., et al., "Newer Gene Editing Technologies toward HIV Gene Therapy," Viruses (2013), vol. 5, pp. 2748-2766.

(56) References Cited

OTHER PUBLICATIONS

Maruyama et al., "Increasing the efficiency of precise genome editing with CRISPR-Cas9 by inhibition of nonhomologous end joining," Nature Biotech., vol. 33(5), pp. 538-542, 2015. (published Mar. 2015).
Mashiko et al., "Generation of mutant mice by pronuciear injection of circular plasmid expressing Cas9 and single guided RNA," Sci. Rep., vol. 3, p. 3355, Nov. 27, 2013.
Mashimo et al., "Generation of knockout rats with X-linked severe combined immunodeficiency (X-SCID) using zinc finger nucleases," PLoS One, vol. 5(1), p. e8870, 2010.
Moehle et al., "Targeted gene addition into a specified location in the human genome using designed zinc finger nucleases," Proc. Natl. Acad. Sci. U.S.A., vol. 104(9), pp. 3055-3060, 2007 (epub Feb. 20, 2007).
Musser, "Rodent," Brittanica. Retrieved from the Internet May 31, 2016: http://www.brittanica.com/animal/rodent.
Nakagawa, et al., "Production of knockout mice by DNA microinjection of variousCRISPR/Cas9 vectors into freeze-thawed fertilized oocytes," BMC Biotechnology, 15:33 (2015).
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).
Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.
PCT International Preliminary Report on Patentability for application PCT/US2013/038165 dated Oct. 28, 2014.
PCT International Preliminary Report on Patentability for application PCT/US2014/034412 dated Oct. 30, 2015.
PCT International Search Report and Written Opinion of the International Searching Authority for application PCT/US2014/060788 dated Jan. 26, 2015.
PCT International Search Report and Written Opinion of the International Searching Authority for application PCT/US2015/062023 dated May 13, 2016.
PCT International Search Report for application PCT/US2015/034503 dated Sep. 8, 2015.
PCT Written Opinion of the International Searching Authority for application PCT/US2015/034503 dated Sep. 8, 2015.
PCT/US2013/038165 International Search Report and Written Opinion dated Jul. 12, 2013.
PCT/US2014/034412 International Search Report and Written Opinion of the Searching Authority dated Oct. 9, 2014.
PCT/US2015/038001 Invitation of Pay Additional Fees dated Nov. 13, 2015.
PCT/US2015/062023 Invitation of Pay Additional Fees dated Feb. 8, 2016.
Peng, Y., et al., "Making designer mutants in model organisms," Development (2014), vol. 141, pp. 4042-4054.
Platt et al., "CRISPR-Cas9 Knockin Mice for Genome Editing and Cancer Modeling," Cell, vol. 159, pp. 1-16, Sep. 25, 2014.
Port et al., "Optimized CRISPR/Cas tools for efficient germline and somatic genome engineering in *Drosophila*," Proc. Natl. Acad. Sci. U.S.A., vol. 111(29), pp. E2967-E2976 plus Supporting Information, Jul. 7, 2014.
Porteus, et al., "Gene targeting using zinc finger nucleases," Nature Biotechnology, vol. 23(8), pp. 967-973, 2005.
Poueymirou et al., "F0 generation mice fully derived from gene-targeted embryonic stem cells allowing immediate analysis," Nature Biotechnology, Epub Dec. 24, 2006, vol. 25(1):91-99.
Quinn et al., "A Site-Specific, Single-Copy Transgenesis Strategy to Identity 5' Regulatory Sequences of the Mouse Testis-Determining Gene Sry," PLoS One, vol. 9(4), p. e94813, Apr. 2014.
Ran et al., "Double nicking by RNA-guided CRISPR Cas9 for enhanced genome editing specificity," Cell, vol. 154, pp. 1380-1389, 2013.
Ran et al., "Genome engineering using the CRISPR-Cas9 system," Nature Protocols, vol. 8(11), pp. 2281-2308, Oct. 24, 2013.
Ran et al., "In vivo genome editing using Staphylococcus aureus Cas9," Nature, vol. 520(7546), pp. 186-191, Apr. 1, 2015.
Scharenberg, A.M., et al., "Genome Engineering with TAL-Effector Nucleases and Alternative Modular Nuclease Technologies," Current Gene Therapy (2013), vol. 13, pp. 291-303.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Shan et al., "Targeted genome modification of crop plants using a CRISPR-Cas system," Nature Biotechnology, vol. 31 (8), pp. 686-688, Aug. 1, 2013.
Siao et al., "Single-step homozygous humanization induced by dual CRISPR/Cas9 cleavage," Oct. 28, 2015.
Singh et al., "Cas9-chromatin binding information enables more accurate CRISPR off-target prediction," Nucleic Acids Res., 43(18):e118, (2015).
Singh et al., "A Mouse Geneticist's Practical Guide to CRISPR Applications," Genetics, vol. 199, pp. 1-15, (2015).
Stark et al., "Genetic Steps of Mammalian Homologous Repair with Distinct Mutagenic Consequences," Molecular and Cellular Biology, vol. 24(21), pp. 9305-9316, 2004.
Stemgent Product Specification Sheet, PD0325901, pp. 1-2 (2012).
Storici et al., "Conservative Repair of a Chromosomal Double-Strand Break by SingleStrand DNA through Two Steps of Annealing," Molecular and Cellular Biology, vol. 26(20), pp. 7645-7657, 2006.
Tong et al., "Generating gene knockout rats by homologous recombination in embryonic stem cells," Nature Protocols, vol. 6(6), pp. 827-844, 2011 (epub May 26, 2011).
U.S. Appl. No. 13/870,280 Final Rejection dated Oct. 15, 2015.
U.S. Appl. No. 13/870,280, Requirement for Restriction/Election dated Jul. 22, 2014.
U.S. Appl. No. 14/254,715 Final Office Action dated Nov. 30, 2015.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314.866, Final Office Action dated Jun. 4, 2015.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 14/731,914, Requirement for Restriction/Election dated Dec. 31, 2015.
U.S. Appl. No. 14/948,221 Advisory Action dated Mar. 29, 2018.
U.S. Appl. No. 14/948,221, Non-Final Office Action dated Jul. 20, 2017.
U.S. Appl. No. 14/948,221, Non-Finai Office Action dated Dec. 17, 2018.
U.S. Appl. No. 14/948,221, Notice of Allowance dated Jun. 25, 2019.
U.S. Appl. No. 13/870,280 , Advisory Action dated Jan. 5, 2016.
U.S. Appl. No. 13/870,280, Non-Final Office Action dated Mar. 13, 2015.
U.S. Appl. No. 14/254,715, Requirement for Restriction/Election dated Jun. 4, 2015.
U.S. Appl. No. 14/928,180, Non-Final Office Action dated Jan. 5, 2016.
Van Der Oost, "New tool for genome surgery," Science, 2013, vol. 339(6121), pp. 768-770.
Wang et al., "Cas9-mediated allelic exchange repairs compound heterozygous recessive mutations in mice," Nat. Biotechnol., 36(9):839-842, (2018).
Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).

(56) References Cited

OTHER PUBLICATIONS

Wang et al., "One-Step Generation of Mice Carrying Mutations in Multiple Genes by CRISPR/Cas-Mediated Genome Engineering," Cell, vol. 153, pp. 910-918, 2013. (published May 2013).

Wang et al., "TALEN-mediated editing of the mouse Y chromosome," Nature Biotechnology, vol. 31(6), p. 530-532, 2013 (epub May 12, 2013).

Wang, H., et al., "One-Step Generation of Mice Carrying Mutations in Multiple Genes by CRISPR/Cas-Mediated Genome Engineering," Cell, 2013, vol. 153(4), pp. 910-918.

Wen et al., "Completely ES Cell-Derived Mice Produced by Tetrapioid Complementation Using Inner Cell Mass (ICM) Deficient Blastocysts," PLoS One, vol. 9(4), e94730, Apr. 14, 2014.

Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.

Wu, Y., et al., "Correction of a Genetic Disease in Mouse via Use of CRISPR-Cas9," Cell Stem Cell (2013), vol. 13, pp. 659-662.

Xu, T., et al., "Cas9-Based Tools for Targeted Genome Editing and Transcriptional Control," Applied and Environmental Microbiology (2014), vol. 80(5), pp. 1544-1552.

Yang et al., "One-step generation of mice carrying reporter and conditional alleles by CRISPR/Cas-mediated genome engineering," Cell, vol. 154(6), pp. 1370-1379, Aug. 29, 2013.

Yang et al., "Optimization of scarless human stem cell genome editing," Nucleic Acids Res., vol. 41(19), pp. 9049-9061, 2013 (epub Jul. 31, 2013).

Yang et al., "Site-specific gene targeting in mouse embryonic stem cells with intact bacterial artificial chromosomes," Nat. Biotechnol. 21(4):447-451, (2003).

Yen et al., "Somatic mosaicism and allele complexity induced by CRISPR/Cas9 RNA injections in mouse zygotes," Dev. Biol., vol. 393(1), pp. 3-9, Jun. 28, 2014.

Yoshimi et al., "Allele-specific genome editing and correction of disease-associated phenotypes in rats using the CRISPR-Cas platform," Nature Communications, vol. 5, 4240, 2014 (Jun. 26, 2014).

Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.

Yu et al., "Highly Efficient Genome Modifications Mediated by CRISPR/Cas9 in *Drosophila*," Genetics, vol. 195, pp. 289-291 plus supporting information, Sep. 2013.

Zhang et al., "Biallelic targeting of expressed genes in mouse embryonic stem cells using the Cas9 system," Methods, vol. 69(2), pp. 171-178, Jun. 12, 2014.

Zhou et al., "Dual sgRNAs facilitate CRISPR/Cas9-mediated mouse genome targeting," FEBS J., vol. 281(7), pp. 1717-1725, Feb. 26, 2014.

Zhou, H., et al., "Large chromosomal deletions and heritable small genetic changes induced by CRISPR/Cas9 in rice," Nucleic Acids Research (2014), vol. 42(17), pp. 10903-10914.

Davis, et al., "POLQ suppressed interhomolog recombination and loss of heterozygosity at targeted DNA breaks," Proc. Natl. Acad. Sci. U.S.A. online ahead of print latest articles, (Sep. 1, 2020), retrieved on Sep. 4, 2020 at: https://www.pnas.org/cgi/doi:10.1073/pnas.2008073117.

Sokolowski et al., "Cas6 specificity and CRISPR RNA loading in a complex CRISPR-Cas system," Nucleic Acids Res., 42(10):6532-6541, (2014).

U.S. Appl. No. 16/572,137, Requirement for Restriction/Election dated Aug. 4, 2022.

* cited by examiner

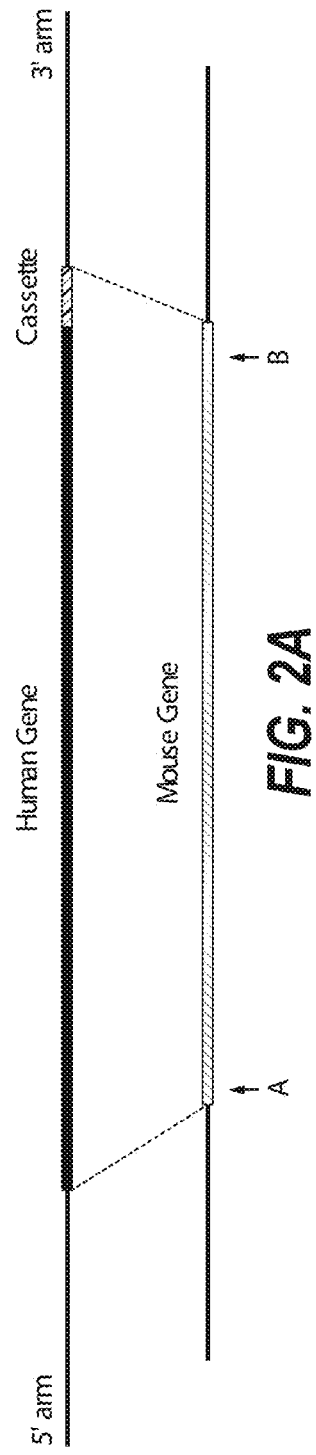

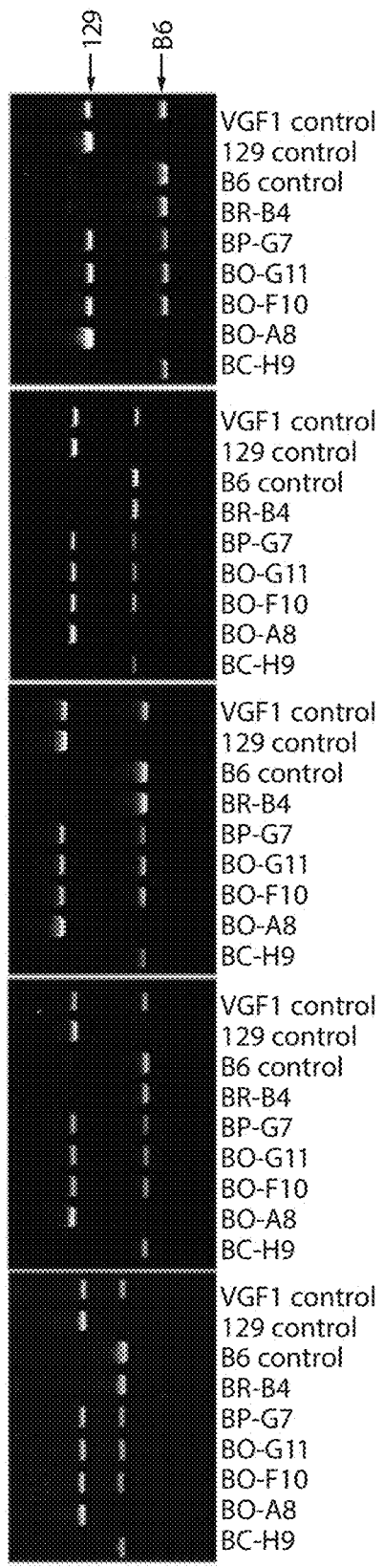

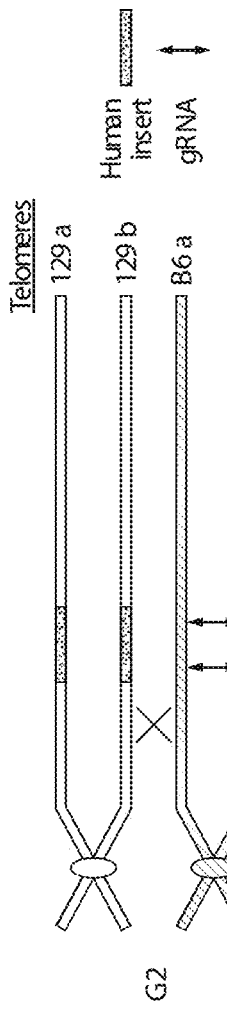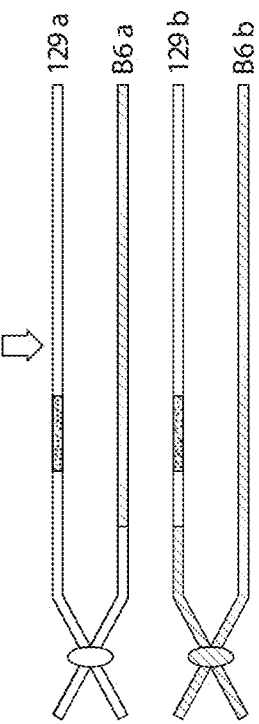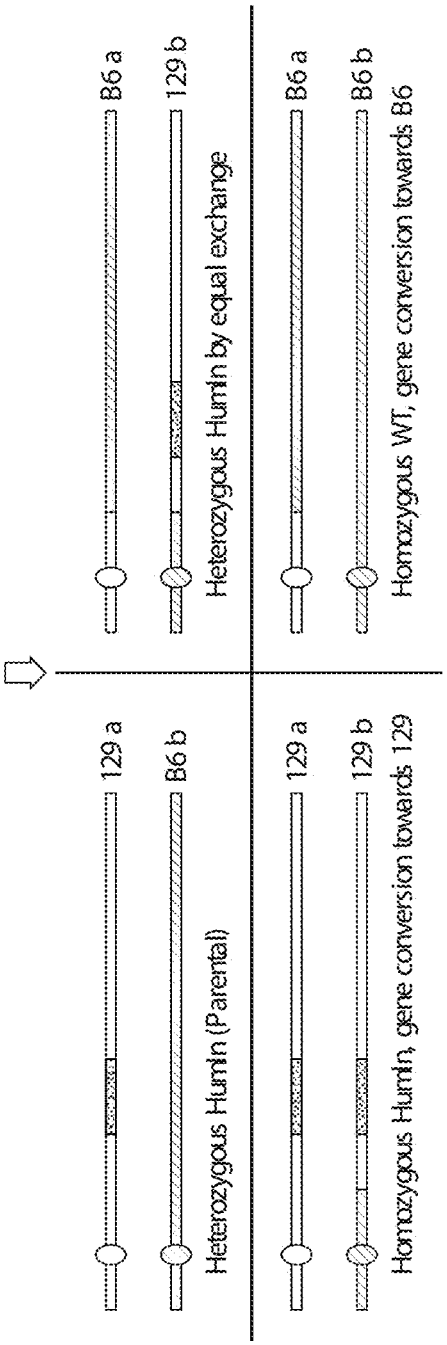

SEQUENCE LISTING

```
<160> NUMBER OF SEQ ID NOS: 176

<210> SEQ ID NO 1
<211> LENGTH: 80
<212> TYPE: RNA
<213> ORGANISM: Artificial Sequence
<220> FEATURE:
<223> OTHER INFORMATION: gRNA

<400> SEQUENCE: 1
guuuuagagc uagaaauagc aaguuaaaau aaggcuaguc cguuaucaac uugaaaagu         60 ggcaccgagu cggugcuuuu                                                   80

<210> SEQ ID NO 2
<211> LENGTH: 42
<212> TYPE: RNA
<213> ORGANISM: Artificial Sequence
<220> FEATURE:
<223> OTHER INFORMATION: gRNA

<400> SEQUENCE: 2
guuuuagagc uagaaauagc aaguuaaaau aaggcuaguc cg                          42

<210> SEQ ID NO 3
<211> LENGTH: 30
<212> TYPE: RNA
<213> ORGANISM: Artificial Sequence
<220> FEATURE:
<223> OTHER INFORMATION: crRNA

<400> SEQUENCE: 3
guuuuagagc uagaaauagc aaguuaaaau                                        30

<210> SEQ ID NO 4
<211> LENGTH: 33
<212> TYPE: RNA
<213> ORGANISM: Artificial Sequence
<220> FEATURE:
<223> OTHER INFORMATION: crRNA

<400> SEQUENCE: 4
guuuuagagc uagaaauagc aaguuaaaau aag                                    33
```

```
<210> SEQ ID NO 5
<211> LENGTH: 26
<212> TYPE: RNA
<213> ORGANISM: Artificial Sequence
<220> FEATURE:
<223> OTHER INFORMATION: crRNA

<400> SEQUENCE: 5
gaguccgagc agaagaagaa guuuua                                              26

<210> SEQ ID NO 6
<211> LENGTH: 12
<212> TYPE: RNA
<213> ORGANISM: Artificial Sequence
<220> FEATURE:
<223> OTHER INFORMATION: tracrRNA

<400> SEQUENCE: 6
aaggcuaguc cg                                                             12

<210> SEQ ID NO 7
<211> LENGTH: 50
<212> TYPE: RNA
<213> ORGANISM: Artificial Sequence
<220> FEATURE:
<223> OTHER INFORMATION: tracrRNA

<400> SEQUENCE: 7
aaggcuaguc cguuaucaac uugaaaaagu ggcaccgagu cggugcuuuu                    50

<210> SEQ ID NO 8
<211> LENGTH: 23
<212> TYPE: DNA
<213> ORGANISM: Artificial Sequence
<220> FEATURE:
<223> OTHER INFORMATION: CRISPR RNA recognition sequence
<220> FEATURE:
<221> NAME/KEY: misc_feature
<222> LOCATION: (2)...(21)
<223> OTHER INFORMATION: n = a, t, c, or g

<400> SEQUENCE: 8
gnnnnnnnnn nnnnnnnnnn ngg                                                 23

<210> SEQ ID NO 9
<211> LENGTH: 23
<212> TYPE: DNA
<213> ORGANISM: Artificial Sequence
<220> FEATURE:
<223> OTHER INFORMATION: CRISPR RNA recognition sequence
<220> FEATURE:
<221> NAME/KEY: misc_feature
<222> LOCATION: (1)...(21)
<223> OTHER INFORMATION: n = a, t, c, or g

<400> SEQUENCE: 9
nnnnnnnnnn nnnnnnnnnn ngg                                                 23

<210> SEQ ID NO 10
<211> LENGTH: 25
<212> TYPE: DNA
<213> ORGANISM: Artificial Sequence
<220> FEATURE:
<223> OTHER INFORMATION: CRISPR RNA recognition sequence
<220> FEATURE:
<221> NAME/KEY: misc_feature
<222> LOCATION: (3)...(23)
```

<223> OTHER INFORMATION: n = a, t, c, or g

<400> SEQUENCE: 10
ggnnnnnnnn nnnnnnnnnn nnngg                                    25

<210> SEQ ID NO 11
<211> LENGTH: 20
<212> TYPE: DNA
<213> ORGANISM: Artificial Sequence
<220> FEATURE:
<223> OTHER INFORMATION: C5 (Hc) gRNA A DNA-targeting segment

<400> SEQUENCE: 11
atcacaaacc agttaaccgg                                          20

<210> SEQ ID NO 12
<211> LENGTH: 20
<212> TYPE: DNA
<213> ORGANISM: Artificial Sequence
<220> FEATURE:
<223> OTHER INFORMATION: C5 (Hc) gRNA B DNA-targeting segment

<400> SEQUENCE: 12
tttcagacga gccgacccgg                                          20

<210> SEQ ID NO 13
<211> LENGTH: 20
<212> TYPE: DNA
<213> ORGANISM: Artificial Sequence
<220> FEATURE:
<223> OTHER INFORMATION: C5 (Hc) gRNA C DNA-targeting segment

<400> SEQUENCE: 13
tgtgtgtcat agcgatgtcg                                          20

<210> SEQ ID NO 14
<211> LENGTH: 20
<212> TYPE: DNA
<213> ORGANISM: Artificial Sequence
<220> FEATURE:
<223> OTHER INFORMATION: C5 (Hc) gRNA D DNA-targeting segment

<400> SEQUENCE: 14
aacaggtacc ctatcctcac                                          20

<210> SEQ ID NO 15
<211> LENGTH: 20
<212> TYPE: DNA
<213> ORGANISM: Artificial Sequence
<220> FEATURE:
<223> OTHER INFORMATION: C5 (Hc) gRNA E DNA-targeting segment

<400> SEQUENCE: 15
ggcccggacc tagtctctct                                          20

<210> SEQ ID NO 16
<211> LENGTH: 20
<212> TYPE: DNA
<213> ORGANISM: Artificial Sequence
<220> FEATURE:
<223> OTHER INFORMATION: C5 (Hc) gRNA E2 DNA-targeting segment

<400> SEQUENCE: 16
tcgtggttgc atgcgcactg                                          20

```
<210> SEQ ID NO 17
<211> LENGTH: 20
<212> TYPE: DNA
<213> ORGANISM: Artificial Sequence
<220> FEATURE:
<223> OTHER INFORMATION: Lrp5 gRNA A DNA-targeting segment

<400> SEQUENCE: 17
gggaacccac agcatactcc                                               20

<210> SEQ ID NO 18
<211> LENGTH: 20
<212> TYPE: DNA
<213> ORGANISM: Artificial Sequence
<220> FEATURE:
<223> OTHER INFORMATION: Lrp5 gRNA B DNA-targeting segment

<400> SEQUENCE: 18
gaatcatgca cggctacccc                                               20

<210> SEQ ID NO 19
<211> LENGTH: 20
<212> TYPE: DNA
<213> ORGANISM: Artificial Sequence
<220> FEATURE:
<223> OTHER INFORMATION: Lrp5 gRNA B2 DNA-targeting segment

<400> SEQUENCE: 19
tgctcctatg gggaggcgcg                                               20

<210> SEQ ID NO 20
<211> LENGTH: 20
<212> TYPE: DNA
<213> ORGANISM: Artificial Sequence
<220> FEATURE:
<223> OTHER INFORMATION: Lrp5 gRNA C DNA-targeting segment

<400> SEQUENCE: 20
actgagatca atgaccccga                                               20

<210> SEQ ID NO 21
<211> LENGTH: 20
<212> TYPE: DNA
<213> ORGANISM: Artificial Sequence
<220> FEATURE:
<223> OTHER INFORMATION: Lrp5 gRNA D DNA-targeting segment

<400> SEQUENCE: 21
gggtcgcccg gaacctctac                                               20

<210> SEQ ID NO 22
<211> LENGTH: 20
<212> TYPE: DNA
<213> ORGANISM: Artificial Sequence
<220> FEATURE:
<223> OTHER INFORMATION: Lrp5 gRNA E2 DNA-targeting segment

<400> SEQUENCE: 22
cttggataac attgataccc                                               20

<210> SEQ ID NO 23
<211> LENGTH: 20
<212> TYPE: DNA
<213> ORGANISM: Artificial Sequence
<220> FEATURE:
<223> OTHER INFORMATION: Lrp5 gRNA E DNA-targeting segment
```

```
<400> SEQUENCE: 23
ggggcagagc ccttatatca                                                    20

<210> SEQ ID NO 24
<211> LENGTH: 20
<212> TYPE: DNA
<213> ORGANISM: Artificial Sequence
<220> FEATURE:
<223> OTHER INFORMATION: Lrp5 gRNA F DNA-targeting segment

<400> SEQUENCE: 24
tcgctcacat taatccctag                                                    20

<210> SEQ ID NO 25
<211> LENGTH: 20
<212> TYPE: DNA
<213> ORGANISM: Artificial Sequence
<220> FEATURE:
<223> OTHER INFORMATION: Ror1 gRNA A DNA-targeting segment

<400> SEQUENCE: 25
tgtgggcctt tgctgatcac                                                    20

<210> SEQ ID NO 26
<211> LENGTH: 20
<212> TYPE: DNA
<213> ORGANISM: Artificial Sequence
<220> FEATURE:
<223> OTHER INFORMATION: Ror1 gRNA B DNA-targeting segment

<400> SEQUENCE: 26
aatctatgat cctatggcct                                                    20

<210> SEQ ID NO 27
<211> LENGTH: 20
<212> TYPE: DNA
<213> ORGANISM: Artificial Sequence
<220> FEATURE:
<223> OTHER INFORMATION: Ror1 gRNA D DNA-targeting segment

<400> SEQUENCE: 27
tgccaatagc agtgacttga                                                    20

<210> SEQ ID NO 28
<211> LENGTH: 20
<212> TYPE: DNA
<213> ORGANISM: Artificial Sequence
<220> FEATURE:
<223> OTHER INFORMATION: Ror1 gRNA C DNA-targeting segment

<400> SEQUENCE: 28
gggaagaatg ggctattgtc                                                    20

<210> SEQ ID NO 29
<211> LENGTH: 20
<212> TYPE: DNA
<213> ORGANISM: Artificial Sequence
<220> FEATURE:
<223> OTHER INFORMATION: Ror1 gRNA E DNA-targeting segment

<400> SEQUENCE: 29
ggttgtttgt gctgatgacg                                                    20

<210> SEQ ID NO 30
<211> LENGTH: 20
```

```
<212> TYPE: DNA
<213> ORGANISM: Artificial Sequence
<220> FEATURE:
<223> OTHER INFORMATION: Ror1 gRNA F DNA-targeting segment

<400> SEQUENCE: 30
ccgtcctagg ccttctacgt                                          20

<210> SEQ ID NO 31
<211> LENGTH: 20
<212> TYPE: DNA
<213> ORGANISM: Artificial Sequence
<220> FEATURE:
<223> OTHER INFORMATION: Trpa1 gRNA A DNA-targeting segment

<400> SEQUENCE: 31
gtactgggga atcggtggtc                                          20

<210> SEQ ID NO 32
<211> LENGTH: 20
<212> TYPE: DNA
<213> ORGANISM: Artificial Sequence
<220> FEATURE:
<223> OTHER INFORMATION: Trpa1 gRNA A2 DNA-targeting segment

<400> SEQUENCE: 32
cacgcactcc aaatttatcc                                          20

<210> SEQ ID NO 33
<211> LENGTH: 20
<212> TYPE: DNA
<213> ORGANISM: Artificial Sequence
<220> FEATURE:
<223> OTHER INFORMATION: Trpa1 gRNA B DNA-targeting segment

<400> SEQUENCE: 33
ctaagtgtgt atcagtacat                                          20

<210> SEQ ID NO 34
<211> LENGTH: 20
<212> TYPE: DNA
<213> ORGANISM: Artificial Sequence
<220> FEATURE:
<223> OTHER INFORMATION: Trpa1 gRNA C DNA-targeting segment

<400> SEQUENCE: 34
tgccctgcac aataagcgca                                          20

<210> SEQ ID NO 35
<211> LENGTH: 20
<212> TYPE: DNA
<213> ORGANISM: Artificial Sequence
<220> FEATURE:
<223> OTHER INFORMATION: Trpa1 gRNA D DNA-targeting segment

<400> SEQUENCE: 35
actcattgaa acgttatggc                                          20

<210> SEQ ID NO 36
<211> LENGTH: 20
<212> TYPE: DNA
<213> ORGANISM: Artificial Sequence
<220> FEATURE:
<223> OTHER INFORMATION: Trpa1 gRNA E2 DNA-targeting segment

<400> SEQUENCE: 36
```
agtaagggtg gattaaattc    20

<210> SEQ ID NO 37
<211> LENGTH: 20
<212> TYPE: DNA
<213> ORGANISM: Artificial Sequence
<220> FEATURE:
<223> OTHER INFORMATION: Trpa1 gRNA E DNA-targeting segment

<400> SEQUENCE: 37
gccatctaga ttcatgtaac    20

<210> SEQ ID NO 38
<211> LENGTH: 20
<212> TYPE: DNA
<213> ORGANISM: Artificial Sequence
<220> FEATURE:
<223> OTHER INFORMATION: Trpa1 gRNA F DNA-targeting segment

<400> SEQUENCE: 38
gactagaaat gttctgcacc    20

<210> SEQ ID NO 39
<211> LENGTH: 21
<212> TYPE: DNA
<213> ORGANISM: Artificial Sequence
<220> FEATURE:
<223> OTHER INFORMATION: 190045 forward primer

<400> SEQUENCE: 39
gagctcatag ccaacagctt g    21

<210> SEQ ID NO 40
<211> LENGTH: 20
<212> TYPE: DNA
<213> ORGANISM: Artificial Sequence
<220> FEATURE:
<223> OTHER INFORMATION: 190061 forward primer

<400> SEQUENCE: 40
atgcatcaga tcacgctcag    20

<210> SEQ ID NO 41
<211> LENGTH: 20
<212> TYPE: DNA
<213> ORGANISM: Artificial Sequence
<220> FEATURE:
<223> OTHER INFORMATION: 190068 forward primer

<400> SEQUENCE: 41
gtccttgtgg catttccaac    20

<210> SEQ ID NO 42
<211> LENGTH: 24
<212> TYPE: DNA
<213> ORGANISM: Artificial Sequence
<220> FEATURE:
<223> OTHER INFORMATION: 190030 forward primer

<400> SEQUENCE: 42
ccagtatggt gtcagttaat agcg    24

<210> SEQ ID NO 43
<211> LENGTH: 19
<212> TYPE: DNA
<213> ORGANISM: Artificial Sequence -continued

```
<220> FEATURE:
<223> OTHER INFORMATION: 190033 forward primer

<400> SEQUENCE: 43
ctgtgcagaa agcagcctc                                              19

<210> SEQ ID NO 44
<211> LENGTH: 20
<212> TYPE: DNA
<213> ORGANISM: Artificial Sequence
<220> FEATURE:
<223> OTHER INFORMATION: 190013 forward primer

<400> SEQUENCE: 44
cctctccctc taggcacctg                                             20

<210> SEQ ID NO 45
<211> LENGTH: 20
<212> TYPE: DNA
<213> ORGANISM: Artificial Sequence
<220> FEATURE:
<223> OTHER INFORMATION: 190045 reverse primer

<400> SEQUENCE: 45
tctttaaggg ctccgttgtc                                             20

<210> SEQ ID NO 46
<211> LENGTH: 20
<212> TYPE: DNA
<213> ORGANISM: Artificial Sequence
<220> FEATURE:
<223> OTHER INFORMATION: 190061 reverse primer

<400> SEQUENCE: 46
aagaccaacc attcacccag                                             20

<210> SEQ ID NO 47
<211> LENGTH: 20
<212> TYPE: DNA
<213> ORGANISM: Artificial Sequence
<220> FEATURE:
<223> OTHER INFORMATION: 190068 reverse primer

<400> SEQUENCE: 47
ttcccagtcc aagtcaaagg                                             20

<210> SEQ ID NO 48
<211> LENGTH: 20
<212> TYPE: DNA
<213> ORGANISM: Artificial Sequence
<220> FEATURE:
<223> OTHER INFORMATION: 190030 reverse primer

<400> SEQUENCE: 48
ctgttatctg caaggcaccc                                             20

<210> SEQ ID NO 49
<211> LENGTH: 20
<212> TYPE: DNA
<213> ORGANISM: Artificial Sequence
<220> FEATURE:
<223> OTHER INFORMATION: 190033 reverse primer

<400> SEQUENCE: 49
acaactggat cctgattcgc                                             20
```

```
<210> SEQ ID NO 50
<211> LENGTH: 20
<212> TYPE: DNA
<213> ORGANISM: Artificial Sequence
<220> FEATURE:
<223> OTHER INFORMATION: 190013 reverse primer

<400> SEQUENCE: 50
taagagggca tgggtgagac                                                    20

<210> SEQ ID NO 51
<211> LENGTH: 20
<212> TYPE: DNA
<213> ORGANISM: Artificial Sequence
<220> FEATURE:
<223> OTHER INFORMATION: C2 probe (B6)

<400> SEQUENCE: 51
aattcagaag acctatcgta                                                    20

<210> SEQ ID NO 52
<211> LENGTH: 21
<212> TYPE: DNA
<213> ORGANISM: Artificial Sequence
<220> FEATURE:
<223> OTHER INFORMATION: T3 probe (B6)

<400> SEQUENCE: 52
tatgtgtata ggtgtttgga t                                                  21

<210> SEQ ID NO 53
<211> LENGTH: 19
<212> TYPE: DNA
<213> ORGANISM: Artificial Sequence
<220> FEATURE:
<223> OTHER INFORMATION: T6 probe (B6)

<400> SEQUENCE: 53
tacattgcta aatgaaacc                                                     19

<210> SEQ ID NO 54
<211> LENGTH: 16
<212> TYPE: DNA
<213> ORGANISM: Artificial Sequence
<220> FEATURE:
<223> OTHER INFORMATION: T7 probe (B6)

<400> SEQUENCE: 54
cgcagtcatg cacata                                                        16

<210> SEQ ID NO 55
<211> LENGTH: 20
<212> TYPE: DNA
<213> ORGANISM: Artificial Sequence
<220> FEATURE:
<223> OTHER INFORMATION: T8 probe (B6)

<400> SEQUENCE: 55
ttataaagcc cagtatgtac                                                    20

<210> SEQ ID NO 56
<211> LENGTH: 14
<212> TYPE: DNA
<213> ORGANISM: Artificial Sequence
<220> FEATURE:
<223> OTHER INFORMATION: T9 probe (B6)
```

```
<400> SEQUENCE: 56
tgctgcataa tcag                                                        14

<210> SEQ ID NO 57
<211> LENGTH: 18
<212> TYPE: DNA
<213> ORGANISM: Artificial Sequence
<220> FEATURE:
<223> OTHER INFORMATION: T10 probe (B6)

<400> SEQUENCE: 57
tcaggagtga attggata                                                    18

<210> SEQ ID NO 58
<211> LENGTH: 16
<212> TYPE: DNA
<213> ORGANISM: Artificial Sequence
<220> FEATURE:
<223> OTHER INFORMATION: T11 probe (B6)

<400> SEQUENCE: 58
ctgctactta cctttg                                                      16

<210> SEQ ID NO 59
<211> LENGTH: 13
<212> TYPE: DNA
<213> ORGANISM: Artificial Sequence
<220> FEATURE:
<223> OTHER INFORMATION: T13 probe (B6)

<400> SEQUENCE: 59
aggaggaaaa cgc                                                         13

<210> SEQ ID NO 60
<211> LENGTH: 17
<212> TYPE: DNA
<213> ORGANISM: Artificial Sequence
<220> FEATURE:
<223> OTHER INFORMATION: T14 probe (B6)

<400> SEQUENCE: 60
cctttgttcc tcataag                                                     17

<210> SEQ ID NO 61
<211> LENGTH: 20
<212> TYPE: DNA
<213> ORGANISM: Artificial Sequence
<220> FEATURE:
<223> OTHER INFORMATION: C2 probe (129)

<400> SEQUENCE: 61
aattcagaag acctattgta                                                  20

<210> SEQ ID NO 62
<211> LENGTH: 21
<212> TYPE: DNA
<213> ORGANISM: Artificial Sequence
<220> FEATURE:
<223> OTHER INFORMATION: T3 probe (129)

<400> SEQUENCE: 62
tatgtgtata ggtgtttgca t                                                21

<210> SEQ ID NO 63
```

```
<211> LENGTH: 16
<212> TYPE: DNA
<213> ORGANISM: Artificial Sequence
<220> FEATURE:
<223> OTHER INFORMATION: T6 probe (129)

<400> SEQUENCE: 63
cattgctaca tgaaac                                                        16

<210> SEQ ID NO 64
<211> LENGTH: 16
<212> TYPE: DNA
<213> ORGANISM: Artificial Sequence
<220> FEATURE:
<223> OTHER INFORMATION: T7 probe (129)

<400> SEQUENCE: 64
cgcagtcatg cacgta                                                        16

<210> SEQ ID NO 65
<211> LENGTH: 23
<212> TYPE: DNA
<213> ORGANISM: Artificial Sequence
<220> FEATURE:
<223> OTHER INFORMATION: T8 probe (129)

<400> SEQUENCE: 65
tgagaattta taaagcccaa tat                                                23

<210> SEQ ID NO 66
<211> LENGTH: 14
<212> TYPE: DNA
<213> ORGANISM: Artificial Sequence
<220> FEATURE:
<223> OTHER INFORMATION: T9 probe (129)

<400> SEQUENCE: 66
tgctgcatga tcag                                                          14

<210> SEQ ID NO 67
<211> LENGTH: 15
<212> TYPE: DNA
<213> ORGANISM: Artificial Sequence
<220> FEATURE:
<223> OTHER INFORMATION: T10 probe (129)

<400> SEQUENCE: 67
tcaggagtga atcgg                                                         15

<210> SEQ ID NO 68
<211> LENGTH: 16
<212> TYPE: DNA
<213> ORGANISM: Artificial Sequence
<220> FEATURE:
<223> OTHER INFORMATION: T11 probe (129)

<400> SEQUENCE: 68
ctgctagtta cctttg                                                        16

<210> SEQ ID NO 69
<211> LENGTH: 15
<212> TYPE: DNA
<213> ORGANISM: Artificial Sequence
<220> FEATURE:
<223> OTHER INFORMATION: T13 probe (129)

<400> SEQUENCE: 69
```

```
aggaggaaga cgcag                                               15

<210> SEQ ID NO 70
<211> LENGTH: 17
<212> TYPE: DNA
<213> ORGANISM: Artificial Sequence
<220> FEATURE:
<223> OTHER INFORMATION: T14 probe (129)

<400> SEQUENCE: 70
ctttgttctt cataagc                                             17

<210> SEQ ID NO 71
<211> LENGTH: 25
<212> TYPE: DNA
<213> ORGANISM: Artificial Sequence
<220> FEATURE:
<223> OTHER INFORMATION: C2 forward primer

<400> SEQUENCE: 71
atgagggatt tccttaatca gacaa                                    25

<210> SEQ ID NO 72
<211> LENGTH: 29
<212> TYPE: DNA
<213> ORGANISM: Artificial Sequence
<220> FEATURE:
<223> OTHER INFORMATION: T3 forward primer

<400> SEQUENCE: 72
tggtatgttt attcttactc aaggttttg                                29

<210> SEQ ID NO 73
<211> LENGTH: 22
<212> TYPE: DNA
<213> ORGANISM: Artificial Sequence
<220> FEATURE:
<223> OTHER INFORMATION: T6 forward primer

<400> SEQUENCE: 73
gggcaactga tggaaagaac tc                                       22

<210> SEQ ID NO 74
<211> LENGTH: 23
<212> TYPE: DNA
<213> ORGANISM: Artificial Sequence
<220> FEATURE:
<223> OTHER INFORMATION: T7 forward primer

<400> SEQUENCE: 74
gactgacgca caaacttgtc ctt                                      23

<210> SEQ ID NO 75
<211> LENGTH: 26
<212> TYPE: DNA
<213> ORGANISM: Artificial Sequence
<220> FEATURE:
<223> OTHER INFORMATION: T8 forward primer

<400> SEQUENCE: 75
cccaaagcat ataacaagaa caaatg                                   26

<210> SEQ ID NO 76
<211> LENGTH: 18
<212> TYPE: DNA
```

```
<213> ORGANISM: Artificial Sequence
<220> FEATURE:
<223> OTHER INFORMATION: T9 forward primer

<400> SEQUENCE: 76
gcaggacgca ggcgttta                                                   18

<210> SEQ ID NO 77
<211> LENGTH: 23
<212> TYPE: DNA
<213> ORGANISM: Artificial Sequence
<220> FEATURE:
<223> OTHER INFORMATION: T10 forward primer

<400> SEQUENCE: 77
gcatcctcat ggcagtctac atc                                             23

<210> SEQ ID NO 78
<211> LENGTH: 20
<212> TYPE: DNA
<213> ORGANISM: Artificial Sequence
<220> FEATURE:
<223> OTHER INFORMATION: T11 forward primer

<400> SEQUENCE: 78
cctgcccctt gatgagtgtt                                                 20

<210> SEQ ID NO 79
<211> LENGTH: 23
<212> TYPE: DNA
<213> ORGANISM: Artificial Sequence
<220> FEATURE:
<223> OTHER INFORMATION: T13 forward primer

<400> SEQUENCE: 79
ccctctttga tatgctcgtg tgt                                             23

<210> SEQ ID NO 80
<211> LENGTH: 22
<212> TYPE: DNA
<213> ORGANISM: Artificial Sequence
<220> FEATURE:
<223> OTHER INFORMATION: T14 forward primer

<400> SEQUENCE: 80
tcccacaggt ccatgtcttt aa                                              22

<210> SEQ ID NO 81
<211> LENGTH: 28
<212> TYPE: DNA
<213> ORGANISM: Artificial Sequence
<220> FEATURE:
<223> OTHER INFORMATION: C2 reverse primer

<400> SEQUENCE: 81
agactacaat gagctaccat cataaggt                                        28

<210> SEQ ID NO 82
<211> LENGTH: 24
<212> TYPE: DNA
<213> ORGANISM: Artificial Sequence
<220> FEATURE:
<223> OTHER INFORMATION: T3 reverse primer

<400> SEQUENCE: 82
caaccatcta aaactccagt tcca                                            24
```

<210> SEQ ID NO 83
<211> LENGTH: 28
<212> TYPE: DNA
<213> ORGANISM: Artificial Sequence
<220> FEATURE:
<223> OTHER INFORMATION: T6 reverse primer

<400> SEQUENCE: 83
tgtgtaacag gacagttgaa tgtagaga                                    28

<210> SEQ ID NO 84
<211> LENGTH: 19
<212> TYPE: DNA
<213> ORGANISM: Artificial Sequence
<220> FEATURE:
<223> OTHER INFORMATION: T7 reverse primer

<400> SEQUENCE: 84
cttaaaaccc gccctgcat                                              19

<210> SEQ ID NO 85
<211> LENGTH: 26
<212> TYPE: DNA
<213> ORGANISM: Artificial Sequence
<220> FEATURE:
<223> OTHER INFORMATION: T8 reverse primer

<400> SEQUENCE: 85
ctacaggaga tgtggctgtt ctatgt                                      26

<210> SEQ ID NO 86
<211> LENGTH: 22
<212> TYPE: DNA
<213> ORGANISM: Artificial Sequence
<220> FEATURE:
<223> OTHER INFORMATION: T9 reverse primer

<400> SEQUENCE: 86
tcagcgtgat tcgcttgtag tc                                          22

<210> SEQ ID NO 87
<211> LENGTH: 26
<212> TYPE: DNA
<213> ORGANISM: Artificial Sequence
<220> FEATURE:
<223> OTHER INFORMATION: T10 reverse primer

<400> SEQUENCE: 87
tgcatagctg tttgaataat gacaag                                      26

<210> SEQ ID NO 88
<211> LENGTH: 21
<212> TYPE: DNA
<213> ORGANISM: Artificial Sequence
<220> FEATURE:
<223> OTHER INFORMATION: T11 reverse primer

<400> SEQUENCE: 88
tgcagcatct ctgtcaagca a                                           21

<210> SEQ ID NO 89
<211> LENGTH: 24
<212> TYPE: DNA
<213> ORGANISM: Artificial Sequence
<220> FEATURE:

```
<223> OTHER INFORMATION: T13 reverse primer

<400> SEQUENCE: 89
gcaacaacat aacccacagc ataa                                          24

<210> SEQ ID NO 90
<211> LENGTH: 23
<212> TYPE: DNA
<213> ORGANISM: Artificial Sequence
<220> FEATURE:
<223> OTHER INFORMATION: T14 reverse primer

<400> SEQUENCE: 90
gctaagcgtt tggaagaaat tcc                                           23

<210> SEQ ID NO 91
<211> LENGTH: 20
<212> TYPE: DNA
<213> ORGANISM: Artificial Sequence
<220> FEATURE:
<223> OTHER INFORMATION: SV 13.7 forward primer

<400> SEQUENCE: 91
taggctctaa ggatgctggc                                               20

<210> SEQ ID NO 92
<211> LENGTH: 20
<212> TYPE: DNA
<213> ORGANISM: Artificial Sequence
<220> FEATURE:
<223> OTHER INFORMATION: SV 13.7 reverse primer

<400> SEQUENCE: 92
aagcagcttc aaaccctctg                                               20

<210> SEQ ID NO 93
<211> LENGTH: 20
<212> TYPE: DNA
<213> ORGANISM: Artificial Sequence
<220> FEATURE:
<223> OTHER INFORMATION: SV 20.0 forward primer

<400> SEQUENCE: 93
ttacttggcc ttggaactgc                                               20

<210> SEQ ID NO 94
<211> LENGTH: 21
<212> TYPE: DNA
<213> ORGANISM: Artificial Sequence
<220> FEATURE:
<223> OTHER INFORMATION: SV 20.0 reverse primer

<400> SEQUENCE: 94
tgattcgtaa tcgtcactgc c                                             21

<210> SEQ ID NO 95
<211> LENGTH: 20
<212> TYPE: DNA
<213> ORGANISM: Artificial Sequence
<220> FEATURE:
<223> OTHER INFORMATION: SV 36.9 forward primer

<400> SEQUENCE: 95
tcctgtcccg agaaactgtc                                               20
```

```
<210> SEQ ID NO 96
<211> LENGTH: 20
<212> TYPE: DNA
<213> ORGANISM: Artificial Sequence
<220> FEATURE:
<223> OTHER INFORMATION: SV 36.9 reverse primer

<400> SEQUENCE: 96
agctggcttt cagagagctg                                                    20

<210> SEQ ID NO 97
<211> LENGTH: 20
<212> TYPE: DNA
<213> ORGANISM: Artificial Sequence
<220> FEATURE:
<223> OTHER INFORMATION: SV 56.7 forward primer

<400> SEQUENCE: 97
ttagaaagtg ccaaccaggc                                                    20

<210> SEQ ID NO 98
<211> LENGTH: 20
<212> TYPE: DNA
<213> ORGANISM: Artificial Sequence
<220> FEATURE:
<223> OTHER INFORMATION: SV 56.7 reverse primer

<400> SEQUENCE: 98
ctctggctag gaacaatggc                                                    20

<210> SEQ ID NO 99
<211> LENGTH: 25
<212> TYPE: DNA
<213> ORGANISM: Artificial Sequence
<220> FEATURE:
<223> OTHER INFORMATION: m-lr-f primer

<400> SEQUENCE: 99
gttaggtgca gggtctactc agctg                                              25

<210> SEQ ID NO 100
<211> LENGTH: 20
<212> TYPE: DNA
<213> ORGANISM: Artificial Sequence
<220> FEATURE:
<223> OTHER INFORMATION: m-5'-f primer

<400> SEQUENCE: 100
ggaggagagg agaagcagcc                                                    20

<210> SEQ ID NO 101
<211> LENGTH: 20
<212> TYPE: DNA
<213> ORGANISM: Artificial Sequence
<220> FEATURE:
<223> OTHER INFORMATION: m-A primer

<400> SEQUENCE: 101
ggaggagagg agaagcagcc                                                    20

<210> SEQ ID NO 102
<211> LENGTH: 26
<212> TYPE: DNA
<213> ORGANISM: Artificial Sequence
<220> FEATURE:
<223> OTHER INFORMATION: h-lr-r primer
```

<400> SEQUENCE: 102
gcaaacagcc ttcttcccac attcgg                                         26

<210> SEQ ID NO 103
<211> LENGTH: 24
<212> TYPE: DNA
<213> ORGANISM: Artificial Sequence
<220> FEATURE:
<223> OTHER INFORMATION: m-5'-r primer

<400> SEQUENCE: 103
ttgctttcag tagttcaggt gtgc                                           24

<210> SEQ ID NO 104
<211> LENGTH: 20
<212> TYPE: DNA
<213> ORGANISM: Artificial Sequence
<220> FEATURE:
<223> OTHER INFORMATION: h-5'-r primer

<400> SEQUENCE: 104
ggcgttgtca ggaagttgcc                                                20

<210> SEQ ID NO 105
<211> LENGTH: 22
<212> TYPE: DNA
<213> ORGANISM: Artificial Sequence
<220> FEATURE:
<223> OTHER INFORMATION: m-F primer

<400> SEQUENCE: 105
tgaagttgag aggcacatga gg                                             22

<210> SEQ ID NO 106
<211> LENGTH: 24
<212> TYPE: DNA
<213> ORGANISM: Artificial Sequence
<220> FEATURE:
<223> OTHER INFORMATION: m-E2 primer

<400> SEQUENCE: 106
tagagtagcc acaggcagca aagc                                           24

<210> SEQ ID NO 107
<211> LENGTH: 21
<212> TYPE: RNA
<213> ORGANISM: Artificial Sequence
<220> FEATURE:
<223> OTHER INFORMATION: Cmah gRNA A DNA-targeting segment

<400> SEQUENCE: 107
gugacaggaa ggcuucucac c                                              21

<210> SEQ ID NO 108
<211> LENGTH: 21
<212> TYPE: RNA
<213> ORGANISM: Artificial Sequence
<220> FEATURE:
<223> OTHER INFORMATION: Cmah gRNA B DNA-targeting segment

<400> SEQUENCE: 108
gcuuacaagc aauuugcuga c                                              21

<210> SEQ ID NO 109
<211> LENGTH: 108

```
<212> TYPE: DNA
<213> ORGANISM: Artificial Sequence
<220> FEATURE:
<223> OTHER INFORMATION: Cmah locus

<400> SEQUENCE: 109
ttgccagtga ccctgtttgc agttagagtt gacaggaagg cttctcaccc gggacatttt    60
aaatgaccca gtcagcaaat tgcttgtaag ttttggtgtt ctttcatt                108

<210> SEQ ID NO 110
<211> LENGTH: 46
<212> TYPE: DNA
<213> ORGANISM: Artificial Sequence
<220> FEATURE:
<223> OTHER INFORMATION: Cmah locus upstream of gRNA A cut

<400> SEQUENCE: 110
ttgccagtga ccctgtttgc agttagagtt gacaggaagg cttctc                   46

<210> SEQ ID NO 111
<211> LENGTH: 35
<212> TYPE: DNA
<213> ORGANISM: Artificial Sequence
<220> FEATURE:
<223> OTHER INFORMATION: Cmah locus downstream of gRNA B cut

<400> SEQUENCE: 111
agcaaattgc ttgtaagttt tggtgttctt tcatt                               35

<210> SEQ ID NO 112
<211> LENGTH: 27
<212> TYPE: DNA
<213> ORGANISM: Artificial Sequence
<220> FEATURE:
<223> OTHER INFORMATION: Cmah locus sequence excised by gRNAs A and B

<400> SEQUENCE: 112
acccgggaca ttttaaatga cccagtc                                        27

<210> SEQ ID NO 113
<211> LENGTH: 21
<212> TYPE: DNA
<213> ORGANISM: Artificial Sequence
<220> FEATURE:
<223> OTHER INFORMATION: C5 primer m-5'-F

<400> SEQUENCE: 113
accccagcat ctgacgacac c                                              21

<210> SEQ ID NO 114
<211> LENGTH: 20
<212> TYPE: DNA
<213> ORGANISM: Artificial Sequence
<220> FEATURE:
<223> OTHER INFORMATION: C5 primer m-5'-R

<400> SEQUENCE: 114
agaaagaccg cagtggaacc                                                20

<210> SEQ ID NO 115
<211> LENGTH: 21
<212> TYPE: DNA
<213> ORGANISM: Artificial Sequence
<220> FEATURE:
<223> OTHER INFORMATION: C5 primer h-5'-R
```

```
<400> SEQUENCE: 115
tccccacatg cctagtagga g                                            21

<210> SEQ ID NO 116
<211> LENGTH: 22
<212> TYPE: DNA
<213> ORGANISM: Artificial Sequence
<220> FEATURE:
<223> OTHER INFORMATION: Cmah TaqMan forward primer

<400> SEQUENCE: 116
gtgaccctgt ttgcagttag ag                                           22

<210> SEQ ID NO 117
<211> LENGTH: 23
<212> TYPE: DNA
<213> ORGANISM: Artificial Sequence
<220> FEATURE:
<223> OTHER INFORMATION: Cmah TaqMan probe

<400> SEQUENCE: 117
acaggaaggc ttctcacccg gga                                          23

<210> SEQ ID NO 118
<211> LENGTH: 24
<212> TYPE: DNA
<213> ORGANISM: Artificial Sequence
<220> FEATURE:
<223> OTHER INFORMATION: Cmah TaqMan reverse primer

<400> SEQUENCE: 118
tgaagtcagg aaactgttcc aatg                                         24

<210> SEQ ID NO 119
<211> LENGTH: 22
<212> TYPE: DNA
<213> ORGANISM: Artificial Sequence
<220> FEATURE:
<223> OTHER INFORMATION: 7064retU forward primer

<400> SEQUENCE: 119
cctcctgagc tttcctttgc ag                                           22

<210> SEQ ID NO 120
<211> LENGTH: 25
<212> TYPE: DNA
<213> ORGANISM: Artificial Sequence
<220> FEATURE:
<223> OTHER INFORMATION: 7064retU reverse primer

<400> SEQUENCE: 120
cctagacaac acagacactg tatca                                        25

<210> SEQ ID NO 121
<211> LENGTH: 23
<212> TYPE: DNA
<213> ORGANISM: Artificial Sequence
<220> FEATURE:
<223> OTHER INFORMATION: 7064retU TaqMan probe

<400> SEQUENCE: 121
ttctgccctt gaaaggaga ggc                                           23

<210> SEQ ID NO 122
<211> LENGTH: 18
```

```
<212> TYPE: DNA
<213> ORGANISM: Artificial Sequence
<220> FEATURE:
<223> OTHER INFORMATION: 7064retD forward primer

<400> SEQUENCE: 122
cctctgaggc cacctgaa                                                 18

<210> SEQ ID NO 123
<211> LENGTH: 23
<212> TYPE: DNA
<213> ORGANISM: Artificial Sequence
<220> FEATURE:
<223> OTHER INFORMATION: 7064retD reverse primer

<400> SEQUENCE: 123
ccctgacaag ttctgccttc tac                                           23

<210> SEQ ID NO 124
<211> LENGTH: 21
<212> TYPE: DNA
<213> ORGANISM: Artificial Sequence
<220> FEATURE:
<223> OTHER INFORMATION: 7064retD TaqMan probe

<400> SEQUENCE: 124
tgcccaagcc tctgcagctt t                                             21

<210> SEQ ID NO 125
<211> LENGTH: 19
<212> TYPE: DNA
<213> ORGANISM: Artificial Sequence
<220> FEATURE:
<223> OTHER INFORMATION: 7140retU forward primer

<400> SEQUENCE: 125
cccagcatct gacgacacc                                                19

<210> SEQ ID NO 126
<211> LENGTH: 21
<212> TYPE: DNA
<213> ORGANISM: Artificial Sequence
<220> FEATURE:
<223> OTHER INFORMATION: 7140retU reverse primer

<400> SEQUENCE: 126
gaccactgtg ggcatctgta g                                             21

<210> SEQ ID NO 127
<211> LENGTH: 27
<212> TYPE: DNA
<213> ORGANISM: Artificial Sequence
<220> FEATURE:
<223> OTHER INFORMATION: 7140retU TaqMan probe

<400> SEQUENCE: 127
ccgagtctgc tgttactgtt agcatca                                       27

<210> SEQ ID NO 128
<211> LENGTH: 20
<212> TYPE: DNA
<213> ORGANISM: Artificial Sequence
<220> FEATURE:
<223> OTHER INFORMATION: 7140retD forward primer

<400> SEQUENCE: 128
```
cccgacacct tctgagcatg                                                      20

<210> SEQ ID NO 129
<211> LENGTH: 21
<212> TYPE: DNA
<213> ORGANISM: Artificial Sequence
<220> FEATURE:
<223> OTHER INFORMATION: 7140retD reverse primer

<400> SEQUENCE: 129
tgcaggctga gtcaggattt g                                                    21

<210> SEQ ID NO 130
<211> LENGTH: 25
<212> TYPE: DNA
<213> ORGANISM: Artificial Sequence
<220> FEATURE:
<223> OTHER INFORMATION: 7140retD TaqMan probe

<400> SEQUENCE: 130
tagtcacgtt ttgtgacacc ccaga                                                25

<210> SEQ ID NO 131
<211> LENGTH: 22
<212> TYPE: DNA
<213> ORGANISM: Artificial Sequence
<220> FEATURE:
<223> OTHER INFORMATION: mADAM6-2 LOA forward primer

<400> SEQUENCE: 131
agggctgagg gagaacatat ac                                                   22

<210> SEQ ID NO 132
<211> LENGTH: 20
<212> TYPE: DNA
<213> ORGANISM: Artificial Sequence
<220> FEATURE:
<223> OTHER INFORMATION: mADAM6-2 LOA reverse primer

<400> SEQUENCE: 132
aggcctgatg caggagctat                                                      20

<210> SEQ ID NO 133
<211> LENGTH: 26
<212> TYPE: DNA
<213> ORGANISM: Artificial Sequence
<220> FEATURE:
<223> OTHER INFORMATION: mADAM6-2 LOA probe

<400> SEQUENCE: 133
tcctctcagc tggattaaca gcatca                                               26

<210> SEQ ID NO 134
<211> LENGTH: 20
<212> TYPE: DNA
<213> ORGANISM: Artificial Sequence
<220> FEATURE:
<223> OTHER INFORMATION: hIgH31 LOA forward primer

<400> SEQUENCE: 134
atcacactca tcccatcccc                                                      20

<210> SEQ ID NO 135
<211> LENGTH: 20
<212> TYPE: DNA
<213> ORGANISM: Artificial Sequence

```
<220> FEATURE:
<223> OTHER INFORMATION: hIgH31 LOA reverse primer

<400> SEQUENCE: 135
cacagggaag caggaactgc                                              20

<210> SEQ ID NO 136
<211> LENGTH: 29
<212> TYPE: DNA
<213> ORGANISM: Artificial Sequence
<220> FEATURE:
<223> OTHER INFORMATION: hIgH31 LOA probe

<400> SEQUENCE: 136
cccttcccta agtaccacag agtgggctc                                    29

<210> SEQ ID NO 137
<211> LENGTH: 19
<212> TYPE: DNA
<213> ORGANISM: Artificial Sequence
<220> FEATURE:
<223> OTHER INFORMATION: hIgH9 LOA forward primer

<400> SEQUENCE: 137
tcctccaacg acaggtccc                                               19

<210> SEQ ID NO 138
<211> LENGTH: 20
<212> TYPE: DNA
<213> ORGANISM: Artificial Sequence
<220> FEATURE:
<223> OTHER INFORMATION: hIgH9 LOA reverse primer

<400> SEQUENCE: 138
gatgaactga cgggcacagg                                              20

<210> SEQ ID NO 139
<211> LENGTH: 24
<212> TYPE: DNA
<213> ORGANISM: Artificial Sequence
<220> FEATURE:
<223> OTHER INFORMATION: hIgH9 LOA probe

<400> SEQUENCE: 139
tccctggaac tctgccccga caca                                         24

<210> SEQ ID NO 140
<211> LENGTH: 19
<212> TYPE: DNA
<213> ORGANISM: Artificial Sequence
<220> FEATURE:
<223> OTHER INFORMATION: hIgH1 LOA forward primer

<400> SEQUENCE: 140
cagtcccgtt gatccagcc                                               19

<210> SEQ ID NO 141
<211> LENGTH: 21
<212> TYPE: DNA
<213> ORGANISM: Artificial Sequence
<220> FEATURE:
<223> OTHER INFORMATION: hIgH1 LOA reverse primer

<400> SEQUENCE: 141
ggatatgcag cactgtgcca c                                            21
```

```
<210> SEQ ID NO 142
<211> LENGTH: 30
<212> TYPE: DNA
<213> ORGANISM: Artificial Sequence
<220> FEATURE:
<223> OTHER INFORMATION: hIgH1 LOA probe

<400> SEQUENCE: 142
cccatcaggg attttgtatc tctgtggacg                                30

<210> SEQ ID NO 143
<211> LENGTH: 19
<212> TYPE: DNA
<213> ORGANISM: Artificial Sequence
<220> FEATURE:
<223> OTHER INFORMATION: Neo GOA forward primer

<400> SEQUENCE: 143
ggtggagagg ctattcggc                                            19

<210> SEQ ID NO 144
<211> LENGTH: 17
<212> TYPE: DNA
<213> ORGANISM: Artificial Sequence
<220> FEATURE:
<223> OTHER INFORMATION: Neo GOA reverse primer

<400> SEQUENCE: 144
gaacacggcg gcatcag                                              17

<210> SEQ ID NO 145
<211> LENGTH: 23
<212> TYPE: DNA
<213> ORGANISM: Artificial Sequence
<220> FEATURE:
<223> OTHER INFORMATION: Neo GOA probe

<400> SEQUENCE: 145
tgggcacaac agacaatcgg ctg                                       23

<210> SEQ ID NO 146
<211> LENGTH: 19
<212> TYPE: DNA
<213> ORGANISM: Artificial Sequence
<220> FEATURE:
<223> OTHER INFORMATION: 5' IgH Arm1 retention assay forward primer

<400> SEQUENCE: 146
aggatgctgg gaaacagac                                            19

<210> SEQ ID NO 147
<211> LENGTH: 20
<212> TYPE: DNA
<213> ORGANISM: Artificial Sequence
<220> FEATURE:
<223> OTHER INFORMATION: 5' IgH Arm1 retention assay reverse primer

<400> SEQUENCE: 147
gaccactctc aggactctca                                           20

<210> SEQ ID NO 148
<211> LENGTH: 24
<212> TYPE: DNA
<213> ORGANISM: Artificial Sequence
<220> FEATURE:
<223> OTHER INFORMATION: 5' IgH Arm1 retention assay probe
```

```
<400> SEQUENCE: 148
tggaaggtcc caaaggaaac caca                                          24

<210> SEQ ID NO 149
<211> LENGTH: 22
<212> TYPE: DNA
<213> ORGANISM: Artificial Sequence
<220> FEATURE:
<223> OTHER INFORMATION: mIgM398 retention assay forward primer

<400> SEQUENCE: 149
gagctcacac cttgaccttt ca                                            22

<210> SEQ ID NO 150
<211> LENGTH: 22
<212> TYPE: DNA
<213> ORGANISM: Artificial Sequence
<220> FEATURE:
<223> OTHER INFORMATION: mIgM398 retention assay reverse primer

<400> SEQUENCE: 150
tggtgggacg aacacattta ca                                            22

<210> SEQ ID NO 151
<211> LENGTH: 24
<212> TYPE: DNA
<213> ORGANISM: Artificial Sequence
<220> FEATURE:
<223> OTHER INFORMATION: mIgM398 retention assay probe

<400> SEQUENCE: 151
ccagctgtcg cagagatgaa cccc                                          24

<210> SEQ ID NO 152
<211> LENGTH: 22
<212> TYPE: DNA
<213> ORGANISM: Artificial Sequence
<220> FEATURE:
<223> OTHER INFORMATION: mIgM1045 retention assay forward primer

<400> SEQUENCE: 152
tccctccaca gacatcctaa cc                                            22

<210> SEQ ID NO 153
<211> LENGTH: 21
<212> TYPE: DNA
<213> ORGANISM: Artificial Sequence
<220> FEATURE:
<223> OTHER INFORMATION: mIgM1045 retention assay reverse primer

<400> SEQUENCE: 153
gttagcggac ttgctgagga a                                             21

<210> SEQ ID NO 154
<211> LENGTH: 22
<212> TYPE: DNA
<213> ORGANISM: Artificial Sequence
<220> FEATURE:
<223> OTHER INFORMATION: mIgM1045 retention assay probe

<400> SEQUENCE: 154
tcaccatccc cccctccttt gc                                            22

<210> SEQ ID NO 155
```

```
<211> LENGTH: 22
<212> TYPE: DNA
<213> ORGANISM: Artificial Sequence
<220> FEATURE:
<223> OTHER INFORMATION: 3' IgH Arm2 retention assay forward primer

<400> SEQUENCE: 155
ggtcatgtgg caaggctatt tg                                          22

<210> SEQ ID NO 156
<211> LENGTH: 21
<212> TYPE: DNA
<213> ORGANISM: Artificial Sequence
<220> FEATURE:
<223> OTHER INFORMATION: 3' IgH Arm2 retention assay reverse primer

<400> SEQUENCE: 156
agcctggact ttcggtttgg t                                           21

<210> SEQ ID NO 157
<211> LENGTH: 30
<212> TYPE: DNA
<213> ORGANISM: Artificial Sequence
<220> FEATURE:
<223> OTHER INFORMATION: 3' IgH Arm2 retention assay probe

<400> SEQUENCE: 157
ccactaggta aacttgtagc tgtggtttga                                  30

<210> SEQ ID NO 158
<211> LENGTH: 17
<212> TYPE: DNA
<213> ORGANISM: Artificial Sequence
<220> FEATURE:
<223> OTHER INFORMATION: mIgHp2 parental forward primer

<400> SEQUENCE: 158
gccatgcaag gccaagc                                                17

<210> SEQ ID NO 159
<211> LENGTH: 24
<212> TYPE: DNA
<213> ORGANISM: Artificial Sequence
<220> FEATURE:
<223> OTHER INFORMATION: mIgHp2 parental reverse primer

<400> SEQUENCE: 159
agttcttgag ccttagggtg ctag                                        24

<210> SEQ ID NO 160
<211> LENGTH: 24
<212> TYPE: DNA
<213> ORGANISM: Artificial Sequence
<220> FEATURE:
<223> OTHER INFORMATION: mIgHp2 parental probe

<400> SEQUENCE: 160
ccaggaaaat gctgccagag cctg                                        24

<210> SEQ ID NO 161
<211> LENGTH: 20
<212> TYPE: DNA
<213> ORGANISM: Artificial Sequence
<220> FEATURE:
<223> OTHER INFORMATION: mIgKd2 parental forward primer

<400> SEQUENCE: 161
```

```
gcaaacaaaa accactggcc                                             20

<210> SEQ ID NO 162
<211> LENGTH: 19
<212> TYPE: DNA
<213> ORGANISM: Artificial Sequence
<220> FEATURE:
<223> OTHER INFORMATION: mIgKd2 parental reverse primer

<400> SEQUENCE: 162
ggccacattc catgggttc                                              19

<210> SEQ ID NO 163
<211> LENGTH: 37
<212> TYPE: DNA
<213> ORGANISM: Artificial Sequence
<220> FEATURE:
<223> OTHER INFORMATION: mIgKd2 parental probe

<400> SEQUENCE: 163
ctgttcctct aaaactggac tccacagtaa atggaaa                          37

<210> SEQ ID NO 164
<211> LENGTH: 20
<212> TYPE: DNA
<213> ORGANISM: Artificial Sequence
<220> FEATURE:
<223> OTHER INFORMATION: hIgK5 parental forward primer

<400> SEQUENCE: 164
ccccgtcctc ctcctttttc                                             20

<210> SEQ ID NO 165
<211> LENGTH: 19
<212> TYPE: DNA
<213> ORGANISM: Artificial Sequence
<220> FEATURE:
<223> OTHER INFORMATION: hIgK5 parental reverse primer

<400> SEQUENCE: 165
tgcaagtgct gccagcaag                                              19

<210> SEQ ID NO 166
<211> LENGTH: 32
<212> TYPE: DNA
<213> ORGANISM: Artificial Sequence
<220> FEATURE:
<223> OTHER INFORMATION: hIgK5 parental probe

<400> SEQUENCE: 166
tcatgtccat taacccattt accttttgcc ca                               32

<210> SEQ ID NO 167
<211> LENGTH: 21
<212> TYPE: DNA
<213> ORGANISM: Artificial Sequence
<220> FEATURE:
<223> OTHER INFORMATION: 3' gRNA_I DNA-targeting sequence

<400> SEQUENCE: 167
gactactacg gtatggacgt c                                           21

<210> SEQ ID NO 168
<211> LENGTH: 21
<212> TYPE: DNA
```

```
<213> ORGANISM: Artificial Sequence
<220> FEATURE:
<223> OTHER INFORMATION: 3' gRNA_II DNA-targeting sequence

<400> SEQUENCE: 168
gctactacgg tatggacgtc t                                            21

<210> SEQ ID NO 169
<211> LENGTH: 20
<212> TYPE: DNA
<213> ORGANISM: Artificial Sequence
<220> FEATURE:
<223> OTHER INFORMATION: 5' gRNA_I DNA-targeting sequence

<400> SEQUENCE: 169
gaagctgact agtttacgca                                              20

<210> SEQ ID NO 170
<211> LENGTH: 21
<212> TYPE: DNA
<213> ORGANISM: Artificial Sequence
<220> FEATURE:
<223> OTHER INFORMATION: 5' gRNA_II DNA-targeting sequence

<400> SEQUENCE: 170
gtagcattct tacacctagc a                                            21

<210> SEQ ID NO 171
<211> LENGTH: 23
<212> TYPE: DNA
<213> ORGANISM: Artificial Sequence
<220> FEATURE:
<223> OTHER INFORMATION: 5' IgH Arm2 retention assay forward primer

<400> SEQUENCE: 171
ctgagcatac tgctgcctaa cac                                          23

<210> SEQ ID NO 172
<211> LENGTH: 25
<212> TYPE: DNA
<213> ORGANISM: Artificial Sequence
<220> FEATURE:
<223> OTHER INFORMATION: 5' IgH Arm2 retention assay reverse primer

<400> SEQUENCE: 172
gagcagtgca tttcttagtt aagga                                        25

<210> SEQ ID NO 173
<211> LENGTH: 26
<212> TYPE: DNA
<213> ORGANISM: Artificial Sequence
<220> FEATURE:
<223> OTHER INFORMATION: 5' IgH Arm2 retention assay probe

<400> SEQUENCE: 173
tgaaatggca gttcttctcc agctgg                                       26

<210> SEQ ID NO 174
<211> LENGTH: 20
<212> TYPE: DNA
<213> ORGANISM: Artificial Sequence
<220> FEATURE:
<223> OTHER INFORMATION: 3' IgH Arm1 retention assay forward primer

<400> SEQUENCE: 174
ggtggagtcc ctggatgatg                                              20
```

```
<210> SEQ ID NO 175
<211> LENGTH: 21
<212> TYPE: DNA
<213> ORGANISM: Artificial Sequence
<220> FEATURE:
<223> OTHER INFORMATION: 3' IgH Arm1 retention assay reverse primer

<400> SEQUENCE: 175
atccctccag ccataggatt g                                              21

<210> SEQ ID NO 176
<211> LENGTH: 28
<212> TYPE: DNA
<213> ORGANISM: Artificial Sequence
<220> FEATURE:
<223> OTHER INFORMATION: 3' IgH Arm1 retention assay probe

<400> SEQUENCE: 176
ctttggaggc tcatttgagg gagatgct                                       28
```

METHODS AND COMPOSITIONS FOR TARGETED GENETIC MODIFICATION USING PAIRED GUIDE RNAS

CROSS REFERENCE TO RELATED APPLICATIONS

This application is a division of application Ser. No. 14/948,221 filed Nov. 20, 2015, which claims the benefit of U.S. Application No. 62/083,005, filed Nov. 21, 2014, U.S. Application No. 62/182,314, filed Jun. 19, 2015, and U.S. Application No. 62/211,421, filed Aug. 28, 2015, each of which is incorporated herein by reference in its entirety for all purposes.

REFERENCE TO A SEQUENCE LISTING SUBMITTED AS A TEXT FILE VIA EFS WEB

The Sequence Listing written in file 535063 SEQLIST.txt is 32.7 kb, was created on Sep. 16, 2019, and is hereby incorporated by reference.

BACKGROUND

Although progress has been made in targeting various genomic loci, there still remain many types of genomic loci that cannot be targeted efficiently or genomic modifications that cannot be achieved properly or efficiently with conventional targeting strategies. For example, difficulties arise when attempting to create large targeted genomic deletions or other large targeted genetic modifications, particularly in eukaryotic cells and organisms.

In particular, it is difficult to efficiently produce cells or animals that are homozygous or compound heterozygous (e.g., hemizygous) for a large targeted genomic deletion or other genomic modification when using conventional targeting strategies. For example, although F0 generation mice heterozygous for a large targeted genomic deletion are obtainable via conventional targeting strategies, subsequent breeding of these heterozygous mice is required to produce F2 generation mice that are homozygous for the deletion. These additional breeding steps are costly and time-consuming.

SUMMARY

Methods and compositions are provided for modifying a genome within a cell. In one aspect, the invention provides methods for making a modification to a genome within a cell, comprising contacting the genome with: (a) a first Cas protein; (b) a first CRISPR RNA that hybridizes to a first CRISPR RNA recognition sequence within a genomic target locus; (c) a second CRISPR RNA that hybridizes to a second CRISPR RNA recognition sequence within the genomic target locus; (d) a tracrRNA; and (e) a targeting vector comprising a nucleic acid insert flanked by a 5' homology arm that hybridizes to a 5' target sequence and a 3' homology arm that hybridizes to a 3' target sequence, provided that if the cell is a one-cell stage embryo the targeting vector is no more than 5 kb in length; wherein the genome comprises a pair of first and second homologous chromosomes comprising the genomic target locus; and wherein the first Cas protein cleaves at least one of the first and second CRISPR RNA recognition sequences to generate at least one double-strand break in at least one of the first and second homologous chromosomes. In one aspect, the invention provides methods for making a biallelic modification to a genome within a cell, comprising contacting the genome with: (a) a first Cas protein; (b) a first CRISPR RNA that hybridizes to a first CRISPR RNA recognition sequence within a genomic target locus; (c) a second CRISPR RNA that hybridizes to a second CRISPR RNA recognition sequence within the genomic target locus; (d) a tracrRNA; and (e) a targeting vector comprising a nucleic acid insert flanked by a 5' homology arm that hybridizes to a 5' target sequence and a 3' homology arm that hybridizes to a 3' target sequence, provided that if the cell is a one-cell stage embryo the targeting vector is no more than 5 kb in length; wherein the genome comprises a pair of first and second homologous chromosomes comprising the genomic target locus; and wherein the first Cas protein cleaves at least one of the first and second CRISPR RNA recognition sequences to generate at least one double-strand break in at least one of the first and second homologous chromosomes.

The methods can further comprise identifying a cell comprising the modified genome. In some methods, the nucleic acid insert comprises a selection cassette adjacent to a first homology arm that hybridizes to a first target sequence, wherein the first homology arm is the 5' homology arm and the first target sequence is the 5' target sequence, or wherein the first homology arm is the 3' homology arm and the first target sequence is the 3' target sequence, wherein the identifying comprises: (a) obtaining DNA from the cell; (b) exposing the DNA of the cell to a probe that binds within the first target sequence, a probe that binds within the nucleic acid insert, and a probe that binds within a reference gene having a known copy number, wherein each probe generates a detectable signal upon binding; (c) detecting the signals from the binding of each of the probes; and (d) comparing the signal from the reference gene probe to the signal from the first target sequence probe to determine a copy number for the first target sequence, and comparing the signal from the reference gene probe to the signal from the nucleic acid insert probe to determine a copy number for the nucleic acid insert, wherein a nucleic acid insert copy number of one or two and a first target sequence copy number of two indicates targeted insertion of the nucleic acid insert at the genomic target locus, and wherein a nucleic acid insert copy number of one or more and a first target sequence copy number of three or more indicates a random insertion of the nucleic acid insert at a genomic locus other than the genomic target locus.

In some methods, the first Cas protein cleaves at least one of the first and second CRISPR RNA recognition sequences in each of the first and second homologous chromosomes to generate at least one double-strand break in each of the first and second homologous chromosomes. In some methods, the first Cas protein cleaves the first and second CRISPR RNA recognition sequences in at least one of the first and second homologous chromosomes to generate at least two double-strand breaks in at least one of the first and second homologous chromosomes.

Some methods further comprise contacting the genome with: a third CRISPR RNA that hybridizes to a third CRISPR RNA recognition sequence within the genomic target locus; and a fourth CRISPR RNA that hybridizes to a fourth CRISPR RNA recognition sequence within the genomic target locus. Optionally, the first CRISPR RNA recognition sequence and the third CRISPR RNA recognition sequence are separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 6 kb, about 6 kb to about 7 kb, about 7 kb to about 8 kb, about 8 kb to about 9 kb, about 9 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, or about 90 kb to about 100 kb. Optionally, the second CRISPR RNA recognition sequence and the fourth CRISPR RNA recognition sequence are separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 6 kb, about 6 kb to about 7 kb, about 7 kb to about 8 kb, about 8 kb to about 9 kb, about 9 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, or about 90 kb to about 100 kb. Optionally, the first and third CRISPR RNA recognition sequences are a first pair of CRISPR RNA recognition sequences, and the second and fourth CRISPR RNA recognition sequences are a second pair of CRISPR RNA recognition sequences, wherein the first pair and second pair are separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

In some methods, the first Cas protein cleaves at least two of the first, second, third and fourth CRISPR RNA recognition sequences to generate at least two double-strand breaks in at least one of the first and second homologous chromosomes. In some methods, the first Cas protein cleaves at least two of the first, second, third and fourth CRISPR RNA recognition sequences to generate at least two double-strand breaks in both the first and second homologous chromosomes.

In some methods, the nucleic acid insert is inserted between the 5' and 3' target sequences. Optionally, the 5' and 3' target sequences are within the genomic target locus. Optionally, the cell is not a one-cell stage embryo, and the targeting vector is a large targeting vector (LTVEC) that is at least 10 kb.

In some methods, contacting the genome with both the first and second CRISPR RNAs results in increased biallelic modification efficiency compared to contacting the genome with either the first CRISPR RNA or second CRISPR RNA alone. In some methods, the cell is diploid, and the biallelic modification results in homozygosity or compound heterozygosity at the genomic target locus. Optionally, the compound heterozygosity is hemizygosity. In some methods, the biallelic modification comprises a deletion between the first and second CRISPR RNA recognition sequences in the first homologous chromosome. In some methods, the biallelic modification comprises the deletion between the first and second CRISPR RNA recognition sequences in both the first and second homologous chromosomes. In some methods, the biallelic modification further comprises insertion of the nucleic acid insert between the 5' and 3' target sequences in both the first and second homologous chromosomes. In some methods, the biallelic modification comprises: (1) the deletion between the first and second CRISPR RNA recognition sequences in both the first and second homologous chromosomes; and (2) insertion of the nucleic acid insert between the 5' and 3' target sequences in the first homologous chromosome but not in the second homologous chromosome. In some methods, the biallelic modification comprises: (1) the deletion between the first and second CRISPR RNA recognition sequences in the first homologous chromosome; and (2) disruption of a locus between the first and second CRISPR RNA recognition sequences in the second homologous chromosome. In some of methods, the biallelic modification comprises: (1) the deletion between the first and second CRISPR RNA recognition sequences in the first homologous chromosome; (2) an insertion of the nucleic acid insert between the 5' and 3' target sequences in the first homologous chromosome; and (3) disruption of a locus between the 5' and 3' target sequences in the second homologous chromosome. In some methods, the biallelic modification comprises: (1) the deletion between the first and second CRISPR RNA recognition sequences in the first homologous chromosome; and (2) an insertion of the nucleic acid insert between the 5' and 3' target sequences in the first homologous chromosome, wherein the nucleic acid insert sequence is homologous or orthologous to the deleted sequence.

In some methods, the first and second CRISPR RNA recognition sequences are separated by about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb. In some methods, the first and second CRISPR RNA recognition sequences are separated by at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb. In some methods, the first and second CRISP RNA recognition sequences are separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, or about 900 bp to about 1 kb. In some methods, the first and second CRISPR RNA recognition sequences are separated by less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb.

In some methods, the first and second CRISPR RNA recognition sequences are each located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, or at least 100 kb from both the 5' and 3' target sequences. In some methods, the first and second CRISPR RNA recognition sequences are each located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, or about 50 kb to about 100 kb from both the 5' and 3' target sequences. In some methods, the first and second CRISPR RNA recognition sequences are each located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from both the 5' and 3' target sequences.

In some methods, the deleted nucleic acid is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. In some methods, the deleted nucleic acid is at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb. Optionally, the deleted nucleic acid is at least 550 kb, at least 600 kb, at least 650 kb, at least 700 kb, at least 750 kb, at least 800 kb, at least 850 kb, at least 900 kb, at least 950 kb, at least 1 Mb, at least 1.5 Mb, or at least 2 Mb.

In some methods, the targeting vector is in linear form. Optionally, the targeting vector is single-stranded or double-stranded. In some methods, the cell is not a one-cell stage embryo, and the targeting vector is a large targeting vector (LTVEC) that is at least 10 kb. In some methods, the cell is not a one-cell stage embryo, and the targeting vector is a large targeting vector (LTVEC), wherein the sum total of the 5' and 3' homology arms of the LTVEC is at least 10 kb. Optionally, the LTVEC is from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb. Optionally, the sum total of the 5' and 3' homology arms of the LTVEC is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

In some methods, the cell is a eukaryotic cell. Optionally, the eukaryotic cell is a mammalian cell, a human cell, a non-human cell, a rodent cell, a mouse cell, and a rat cell. Optionally, the eukaryotic cell is a pluripotent cell, a non-pluripotent cell, a non-human pluripotent cell, a human pluripotent cell, a rodent pluripotent cell, a mouse pluripotent cell, a rat pluripotent cell, a mouse embryonic stem (ES) cell, a rat ES cell, a human ES cell, a human adult stem cell, a developmentally restricted human progenitor cell, or a human induced pluripotent stem (iPS) cell. Optionally, the eukaryotic cell is a one-cell stage embryo. Optionally, the eukaryotic cell is a one-cell stage embryo, and the targeting vector is between about 50 nucleotides to about 5 kb in length. Optionally, the eukaryotic cell is a one-cell stage embryo, and the targeting vector is single-stranded DNA and is between about 60 to about 200 nucleotides in length.

In some methods, the first Cas protein is Cas9. In some methods, the first Cas protein has nuclease activity on both strands of double-stranded DNA.

In some methods, the first Cas protein is a nickase. Some methods further comprise contacting the genome with: (f) a second Cas protein that is a nickase; (g) a third CRISPR RNA that hybridizes to a third CRISPR RNA recognition sequence; and (h) a fourth CRISPR RNA that hybridizes to a fourth CRISPR RNA recognition sequence; wherein the first Cas protein cleaves a first strand of genomic DNA within the first CRISPR RNA recognition sequence and within the second CRISPR RNA recognition sequence, and the second Cas protein cleaves a second strand of genomic DNA within the third CRISPR RNA recognition sequence and within the fourth CRISPR RNA recognition sequence.

In some methods, the first CRISPR RNA and the tracrRNA are fused together as a first guide RNA (gRNA), and/or the second CRISPR RNA and the tracrRNA are fused together as a second gRNA. In some methods, the first CRISPR RNA and the tracrRNA are separate RNA molecules, and/or the second CRISPR RNA and the tracrRNA are separate RNA molecules.

In some methods, the contacting comprises introducing the first Cas protein, the first and second CRISPR RNAs, and the tracrRNA into the cell. In some methods, (a) the first Cas protein is introduced into the cell in the form of a protein, a messenger RNA (mRNA) encoding the first Cas protein, or a DNA encoding the first Cas protein; (b) the first CRISPR RNA is introduced into the cell in the form of an RNA or in the form of a DNA encoding the first CRISPR RNA; (c) the second CRISPR RNA is introduced into the cell in the form of an RNA or in the form of a DNA encoding the second CRISPR RNA; and/or (d) the tracrRNA is introduced into the cell in the form of an RNA or in the form of a DNA encoding the tracrRNA. In some methods, the first Cas protein, the first CRISPR RNA, and the tracrRNA are introduced into the cell as a first protein-RNA complex, and/or the first Cas protein, the second CRISPR RNA, and the tracrRNA are introduced into the cell as a second protein-RNA complex. In some methods, (a) the DNA encoding the first Cas protein is operably linked to a first promoter in a first expression construct; (b) the DNA encoding the first CRISPR RNA is operably linked to a second promoter in a second expression construct; (c) the DNA encoding the second CRISPR RNA is operably linked to a third promoter in a third expression construct; and/or (d) the DNA encoding the tracrRNA is operably linked to a fourth promoter in a fourth expression construct; wherein the first, second, third, and fourth promoters are active in the cell. Optionally, the first, second, third, and/or fourth expression constructs are components of a single nucleic acid molecule. In some methods, (a) the DNA encoding the first Cas protein is operably linked to a first promoter in a first expression construct; (b) the DNAs encoding the first CRISPR RNA and the tracrRNA are fused together in a DNA encoding a first guide RNA (gRNA) and are operably linked to a second promoter in a second expression construct; and/or (c) the DNAs encoding the second CRISPR RNA and the tracrRNA are fused together in a DNA encoding a second gRNA and are operably linked to a third promoter in a third expression construct; wherein the first, second, and third promoters are active in the cell. Optionally, the first, second, and/or third expression constructs are components of a single nucleic acid molecule.

In some methods, the cell has been modified to decrease non-homologous end joining (NHEJ) and/or to increase gene conversion or homology-directed repair (HDR). Optionally, the cell has been modified to decrease DNA-PK expression or activity and/or to decrease PARP1 expression or activity. Optionally, the cell has been modified to decrease ligase IV expression or activity. Optionally, the decrease in expression or activity is inducible, reversible, temporally specific, and/or spatially specific.

In some methods, (1) the cell is not a one-cell stage embryo, and the targeting vector is a large targeting vector, wherein the 5' and 3' homology arms have a sum total of at least 10 kb; (2) the first and second CRISPR RNA recognition sequences are each located more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from both the 5' and 3' target sequences; (3) the first Cas protein cleaves the first and second CRISPR RNA recognition sequences in at least one of the first and second homologous chromosomes to generate at least two double-strand breaks in at least one of the first and second homologous chromosomes; and (4) the biallelic modification comprises the deletion between the first and second CRISPR RNA recognition sequences in the first homologous chromosome and an insertion of the nucleic acid insert between the 5' and 3' target sequences in the first homologous chromosome, wherein the nucleic acid insert sequence is homologous or orthologous to the deleted sequence.

The invention also provides methods for producing an F0 generation non-human animal, comprising: (a) introducing a non-human ES cell into a non-human host embryo, wherein the non-human ES cell was produced by any of the above methods; and (b) gestating the non-human host embryo in a surrogate mother; wherein the surrogate mother produces the F0 generation non-human animal comprising the biallelic modification. Some methods comprise: (a) contacting the genome in a non-human ES cell with: (i) a first Cas protein; (ii) a first CRISPR RNA that hybridizes to a first CRISPR RNA recognition sequence within a genome target locus; (iii) a second CRISPR RNA that hybridizes to a second CRISPR RNA recognition sequence within the genomic target locus; (iv) a tracrRNA; and (v) a targeting vector comprising a nucleic acid insert flanked by a 5' homology arm and a 3' homology arm, wherein the genome comprises a pair of first and second homologous chromosomes comprising the genomic target locus; and wherein the first Cas protein cleaves at least one of the first and second CRISPR RNA recognition sequences to generate at least one double-strand break in at least one of the first and second homologous chromosomes; (b) identifying a non-human ES cell comprising the biallelic modification; (c) introducing the non-human ES cell comprising the biallelic modification into a non-human host embryo; and (d) gestating the non-human host embryo in a surrogate mother; wherein the surrogate mother produces the F0 generation non-human animal comprising the biallelic modification.

In some methods, the first Cas protein cleaves at least one of the first and second CRISPR RNA recognition sequences in each of the first and second homologous chromosomes to generate at least one double-strand break in each of the first and second homologous chromosomes. In some methods, the first Cas protein cleaves the first and second CRISPR RNA recognition sequences in at least one of the first and second homologous chromosomes to generate at least two double-strand breaks in at least one of the first and second homologous chromosomes.

In some methods, the non-human animal is a mouse, the non-human ES cell is a mouse ES cell, and the non-human host embryo is a mouse host embryo. In some methods, the non-human animal is a rat, the non-human ES cell is a rat ES cell, and the non-human host embryo is a rat host embryo.

In some methods, the biallelic modification results in homozygosity or compound heterozygosity at the genomic target locus. Optionally, the compound heterozygosity is hemizygosity.

In some methods, the first CRISPR RNA and the tracrRNA are fused together as a first guide RNA (gRNA), and/or the second CRISPR RNA and the tracrRNA are fused together as a second gRNA. In some methods, the first CRISPR RNA and the tracrRNA are separate RNA molecules, and/or the second CRISPR RNA and the tracrRNA separate RNA molecules.

In some methods, the contacting comprises introducing the first Cas protein, the first and second CRISPR RNAs, and the tracrRNA into the cell. In some methods, (a) the first Cas protein is introduced into the cell in the form of a protein, a messenger RNA (mRNA) encoding the first Cas protein, or a DNA encoding the first Cas protein; (b) the first CRISPR RNA is introduced into the cell in the form of an RNA or in the form of a DNA encoding the first CRISPR RNA; (c) the second CRISPR RNA is introduced into the cell in the form of an RNA or in the form of a DNA encoding the second CRISPR RNA; and/or (d) the tracrRNA is introduced into the cell in the form of an RNA or in the form of a DNA encoding the tracrRNA. In some methods, the first Cas protein, the first CRISPR RNA, and the tracrRNA are introduced into the cell as a first protein-RNA complex, and/or the first Cas protein, the second CRISPR RNA, and the tracrRNA are introduced into the cell as a second protein-RNA complex. In some methods, (a) the DNA encoding the first Cas protein is operably linked to a first promoter in a first expression construct; (b) the DNA encoding the first CRISPR RNA is operably linked to a second promoter in a second expression construct; (c) the DNA encoding the second CRISPR RNA is operably linked to a third promoter in a third expression construct; and/or (d) the DNA encoding the tracrRNA is operably linked to a fourth promoter in a fourth expression construct; wherein the first, second, third, and fourth promoters are active in the cell. Optionally, the first, second, third, and/or fourth expression constructs are components of a single nucleic acid molecule. In some methods, (a) the DNA encoding the first Cas protein is operably linked to a first promoter in a first expression construct; (b) the DNAs encoding the first CRISPR RNA and the tracrRNA are fused together in a DNA encoding a first guide RNA (gRNA) and are operably linked to a second promoter in a second expression construct; and/or (c) the DNAs encoding the second CRISPR RNA and the tracrRNA are fused together in a DNA encoding a second gRNA and are operably linked to a third promoter in a third expression construct; wherein the first, second, and third promoters are active in the cell. Optionally, the first, second, and/or third expression constructs are components of a single nucleic acid molecule.

In some methods, the first Cas protein is Cas9. In some methods, the first Cas protein has nuclease activity on both strands of double-stranded DNA.

In some methods, the first Cas protein is a nickase. Some methods further comprise contacting the genome with: (f) a second Cas protein that is a nickase; (g) a third CRISPR RNA that hybridizes to a third CRISPR RNA recognition sequence; and (h) a fourth CRISPR RNA that hybridizes to a fourth CRISPR RNA recognition sequence; wherein the first Cas protein cleaves a first strand of genomic DNA within the first CRISPR RNA recognition sequence and within the second CRISPR RNA recognition sequence, and the second Cas protein cleaves a second strand of genomic DNA within the third CRISPR RNA recognition sequence and within the fourth CRISPR RNA recognition sequence.

In some methods, the cell has been modified to decrease non-homologous end joining (NHEJ) and/or to increase gene conversion or homology-directed repair (HDR). Optionally, the cell has been modified to decrease DNA-PK expression or activity and/or to decrease PARP1 expression or activity. Optionally, the cell has been modified to decrease ligase IV expression or activity. Optionally, the decrease in expression or activity is inducible, reversible, temporally specific, and/or spatially specific.

The invention also provides methods for producing an F0 generation non-human animal, comprising implanting a genetically modified one-cell stage embryo that was produced by any of the above methods into a surrogate mother; wherein the surrogate mother produces the F0 generation non-human animal comprising the biallelic modification.

The invention also provides methods for modifying a genome within a cell that is heterozygous for a first allele, comprising contacting the genome with: (a) a first Cas protein; (b) a tracrRNA; (c) a first CRISPR RNA that hybridizes to a first CRISPR RNA recognition sequence within a second allele, wherein the first allele is on a first homologous chromosome and the second allele is at a corresponding locus on a second homologous chromosome; and (d) a second CRISPR RNA that hybridizes to a second CRISPR RNA recognition sequence within the second allele; wherein the first Cas protein cleaves at least one of the first and second CRISPR RNA recognition sequences to generate at least one double-strand break and end sequences that undergo recombination, wherein the recombination is between the first and second alleles to form a modified genome that is homozygous for the first allele. Some methods further comprise identifying a cell that is homozygous for the first allele.

In some methods, the first Cas protein cleaves the first CRISPR RNA recognition sequence and the second CRISPR RNA recognition sequence. In some methods, the first Cas protein cleaves the first CRISPR RNA recognition sequence and the second CRISPR RNA recognition sequence to generate at least two double-strand breaks and end sequences that undergo recombination. In some methods, the first and second CRISPR RNA recognition sequences are located within the second allele but not the first allele. In some methods, the Cas protein and the first CRISPR RNA do not naturally occur together.

In some methods, the first and second CRISPR RNA recognition sequences are separated by about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb. In some methods, the first and second CRISPR RNA recognition sequences are separated by at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb. In some methods, the first and second CRISP RNA recognition sequences are separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, or about 900 bp to about 1 kb. In some methods, the first and second CRISPR RNA recognition sequences are separated by less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb.

In some methods, the sequence differences between the first allele and second allele span about 100 bp to about 200 bp, about 200 bp to about 400 bp, about 400 bp to about 600 bp, about 600 bp to about 800 bp, about 800 bp to about 1 kb, about 1 kb to about 2 kb, about 2 kb to about 3 kb, about 4 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb. In some methods, the sequence differences between the first allele and the second allele span at least 100 bp, at least 200 bp, at least 300 bp, at least 400 bp, at least 500 bp, at least 600 bp, at least 700 bp, at least 800 bp, at least 800 bp, at least 1 kb, at least 2 kb, at least 3 kb, at least 4 kb, at least 5 kb, at least 6 kb, at least 7 kb, at least 8 kb, at least 9 kb, at least 10 kb, 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb.

In some methods, the first allele comprises a targeted modification and the second allele is a wild type allele. In some methods, the first allele is a wild type allele, and the second allele comprises a disease-causing mutation.

In some methods, the recombination comprises gene conversion. In some methods, the recombination comprises loss of heterozygosity (LOH).

In some methods, the cell is a eukaryotic cell. Optionally, the eukaryotic cell is a mammalian cell, a human cell, a non-human cell, a rodent cell, a mouse cell, or a rat cell. Optionally, the eukaryotic cell is a pluripotent cell, a non-pluripotent cell, a non-human pluripotent cell, a human pluripotent cell, a rodent pluripotent cell, a mouse pluripotent cell, a rat pluripotent cell, a mouse embryonic stem (ES) cell, a rat ES cell, a human ES cell, a human adult stem cell, a developmentally restricted human progenitor cell, or a human induced pluripotent stem (iPS) cell.

In some methods, the first Cas protein is Cas9. In some methods, the first Cas protein has nuclease activity on both strands of double-stranded DNA.

In some methods, the first Cas protein is a nickase. Some methods further comprise contacting the genome with: (f) a second Cas protein that is a nickase; (g) a third CRISPR RNA that hybridizes to a third CRISPR RNA recognition sequence; and (h) a fourth CRISPR RNA that hybridizes to a fourth CRISPR RNA recognition sequence; wherein the first Cas protein cleaves a first strand of genomic DNA within the first CRISPR RNA recognition sequence and within the second CRISPR RNA recognition sequence, and the second Cas protein cleaves a second strand of genomic DNA within the third CRISPR RNA recognition sequence and within the fourth CRISPR RNA recognition sequence.

In some methods, the first CRISPR RNA and the tracrRNA are fused together as a first guide RNA (gRNA), and/or the second CRISPR RNA and the tracrRNA are fused together as a second gRNA. In some methods, the first CRISPR RNA and the tracrRNA are separate RNA molecules, and/or the second CRISPR RNA and the tracrRNA are separate RNA molecules.

In some methods, the contacting comprises introducing the first Cas protein, the first and second CRISPR RNAs, and the tracrRNA into the cell. In some methods, (a) the first Cas protein is introduced into the cell in the form of a protein, a messenger RNA (mRNA) encoding the first Cas protein, or a DNA encoding the first Cas protein; (b) the first CRISPR RNA is introduced into the cell in the form of an RNA or in the form of a DNA encoding the first CRISPR RNA; (c) the second CRISPR RNA is introduced into the cell in the form of an RNA or in the form of a DNA encoding the second CRISPR RNA; and/or (d) the tracrRNA is introduced into the cell in the form of an RNA or in the form of a DNA encoding the tracrRNA. In some methods, the first Cas protein, the first CRISPR RNA, and the tracrRNA are introduced into the cell as a first protein-RNA complex, and/or the first Cas protein, the second CRISPR RNA, and the tracrRNA are introduced into the cell as a second protein-RNA complex. In some methods, (a) the DNA encoding the first Cas protein is operably linked to a first promoter in a first expression construct; (b) the DNA encoding the first CRISPR RNA is operably linked to a second promoter in a second expression construct; (c) the DNA encoding the second CRISPR RNA is operably linked to a third promoter in a third expression construct; and/or (d) the DNA encoding the tracrRNA is operably linked to a fourth promoter in a fourth expression construct; wherein the first, second, third, and fourth promoters are active in the cell. Optionally, the first, second, third, and/or fourth expression constructs are components of a single nucleic acid molecule. In some methods, (a) the DNA encoding the first Cas protein is operably linked to a first promoter in a first expression construct; (b) the DNAs encoding the first CRISPR RNA and the tracrRNA are fused together in a DNA encoding a first guide RNA (gRNA) and are operably linked to a second promoter in a second expression construct; and/or (c) the DNAs encoding the second CRISPR RNA and the tracrRNA are fused together in a DNA encoding a second gRNA and are operably linked to a third promoter in a third expression construct; wherein the first, second, and third promoters are active in the cell. Optionally, the first, second, and/or third expression constructs are components of a single nucleic acid molecule.

In some methods, the cell has been modified to decrease non-homologous end joining (NHEJ) and/or to increase gene conversion or homology-directed repair (HDR). Optionally, the cell has been modified to decrease DNA-PK expression or activity and/or to decrease PARP1 expression or activity. Optionally, the cell has been modified to decrease ligase IV expression or activity. Optionally, the decrease in expression or activity is inducible, reversible, temporally specific, and/or spatially specific.

The invention also provides methods for modifying a genome within a cell that is heterozygous for a first allele, comprising contacting the genome with: (a) a first Cas protein; (b) a tracrRNA; and (c) a first CRISPR RNA that hybridizes to a first non-allele-specific CRISPR RNA recognition sequence, wherein the first allele is on a first homologous chromosome and the CRISPR RNA recognition sequence is centromeric to the locus corresponding to the first allele on a second homologous chromosome; and wherein the first Cas protein cleaves the first CRISPR RNA recognition sequence to generate a double-strand break and the cell is modified to become homozygous for the first allele. Some methods further comprise identifying a cell that is homozygous for the first allele. In some methods, the Cas protein and the first CRISPR RNA do not naturally occur together.

Such methods can further comprise contacting the genome with a second CRISPR RNA that hybridizes to a second non-allele-specific CRISPR RNA recognition sequence centromeric to the locus corresponding to the first allele on a second homologous chromosome, wherein the first Cas protein cleaves at least one of the first and second CRISPR RNA recognition sequences to generate at least one double-strand break. In some methods, the first Cas protein cleaves the first CRISPR RNA recognition sequence and the second CRISPR RNA recognition sequence.

In some methods, loss of heterozygosity occurs telomeric of the double-strand break.

In some methods, the first and second CRISPR RNA recognition sequences are located on the second homologous chromosome but not the first homologous chromosome. In some methods, the first CRISPR RNA recognition site is from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb from the centromere. In some methods, the first allele is from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb from the first CRISPR RNA recognition site. In some methods, the region of the second homologous chromosome being replaced by loss of heterozygosity is from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

In some methods, the cell is a eukaryotic cell. Optionally, the eukaryotic cell is a mammalian cell, a human cell, a non-human cell, a rodent cell, a mouse cell, a rat cell, a pluripotent cell, a non-pluripotent cell, a non-human pluripotent cell, a human pluripotent cell, a rodent pluripotent cell, a mouse pluripotent cell, a rat pluripotent cell, a mouse embryonic stem (ES) cell, a rat ES cell, a human ES cell, a human adult stem cell, a developmentally restricted human progenitor cell, a human induced pluripotent stem (iPS) cell, or a one-cell stage embryo.

In some methods, the first Cas protein is Cas9. In some methods, the first Cas protein has nuclease activity on both strands of double-stranded DNA. In some methods, the first Cas protein is a nickase. Optionally, the first Cas protein is a nickase, and wherein the method further comprises contacting the genome with a second Cas protein that is a nickase, a third CRISPR RNA that hybridizes to a third CRISPR RNA recognition sequence, and a fourth CRISPR RNA that hybridizes to a fourth CRISPR RNA recognition sequence, wherein the first Cas protein cleaves a first strand of genomic DNA within the first CRISPR RNA recognition sequence and within the second CRISPR RNA recognition sequence, and the second Cas protein cleaves a second strand of genomic DNA within the third CRISPR RNA recognition sequence and within the fourth CRISPR RNA recognition sequence.

In some methods, the first CRISPR RNA and the tracrRNA are fused together as a first guide RNA (gRNA), and/or the second CRISPR RNA and the tracrRNA are fused together as a second gRNA. In some methods, the first CRISPR RNA and the tracrRNA are separate RNA molecules, and/or the second CRISPR RNA and the tracrRNA are separate RNA molecules.

In some methods, the contacting comprises introducing the first Cas protein, the first and second CRISPR RNAs, and the tracrRNA into the cell. In some methods, the first Cas protein is introduced into the cell in the form of a protein, a messenger RNA (mRNA) encoding the first Cas protein, or a DNA encoding the first Cas protein. Optionally, the DNA encoding the first Cas protein is operably linked to a first promoter in a first expression construct, wherein the first promoter is active in the cell. In some methods, the first CRISPR RNA is introduced into the cell in the form of an RNA or in the form of a DNA encoding the first CRISPR RNA. Optionally, the DNA encoding the first CRISPR RNA is operably linked to a second promoter in a second expression construct, wherein the second promoter is active in the cell. In some methods, the second CRISPR RNA is introduced into the cell in the form of an RNA or in the form of a DNA encoding the second CRISPR RNA. Optionally, the DNA encoding the second CRISPR RNA is operably linked to a third promoter in a third expression construct, wherein the third promoter is active in the cell. In some methods, the tracrRNA is introduced into the cell in the form of an RNA or in the form of a DNA encoding the tracrRNA. Optionally, the DNA encoding the tracrRNA is operably linked to a fourth promoter in a fourth expression construct, wherein the fourth promoter is active in the cell. Optionally, the first, second, third, and/or fourth expression constructs are components of a single nucleic acid molecule.

Optionally, the DNA encoding the first Cas protein is operably linked to a first promoter in a first expression construct; the DNAs encoding the first CRISPR RNA and the tracrRNA are fused together in a DNA encoding a first guide RNA (gRNA) and are operably linked to a second promoter in a second expression construct; and/or the DNAs encoding the second CRISPR RNA and the tracrRNA are fused together in a DNA encoding a second gRNA and are operably linked to a third promoter in a third expression construct; wherein the first, second, and third promoters are active in the cell. Optionally, the first, second, and/or third expression constructs are components of a single nucleic acid molecule.

Optionally, the first Cas protein, the first CRISPR RNA, and the tracrRNA are introduced into the cell as a first protein-RNA complex, and/or the first Cas protein, the second CRISPR RNA, and the tracrRNA are introduced into the cell as a second protein-RNA complex.

In some methods, the cell has been modified to decrease non-homologous end joining (NHEJ) and/or to increase gene conversion or homology-directed repair (HDR). Optionally, the cell has been modified to decrease the expression or activity of one or more of the following: DNA-PK, PARP1, and ligase IV. Optionally, the decrease in expression or activity is inducible, reversible, temporally specific, and/or spatially specific.

In some methods, the first allele comprises a mutation. Optionally, the mutation is a targeted modification. In some methods, the first allele is a wild type allele, and the corresponding locus on the second homologous chromosome comprises a mutation.

The invention also provides methods identifying targeted insertion of a nucleic acid insert at a target genomic locus in a diploid cell that is not a one-cell stage embryo, comprising: (a) obtaining DNA from the cell, wherein the cell has been contacted with a large targeting vector (LTVEC) comprising the nucleic acid insert flanked by a first homology arm that hybridizes to a first target sequence and a second homology arm that hybridizes to a second target sequence, wherein the nucleic acid insert comprises a selection cassette adjacent to the first homology arm; (b) exposing the DNA of the cell to a probe that binds within the first target sequence, a probe that binds within the nucleic acid insert, and a probe that binds within a reference gene having a known copy number, wherein each probe generates a detectable signal upon binding; (c) detecting the signals from the binding of each of the probes; and (d) comparing the signal from the reference gene probe to the signal from the first target sequence probe to determine a copy number for the first target sequence, and comparing the signal from the reference gene probe to the signal from the nucleic acid insert probe to determine a copy number for the nucleic acid insert, wherein a nucleic acid insert copy number of one or two and a first target sequence copy number of two indicates targeted insertion of the nucleic acid insert at the target genomic locus, and wherein a nucleic acid insert copy number of one or more and a first target sequence copy number of three or more indicates a random insertion of the nucleic acid insert at a genomic locus other than the target genomic locus.

In some methods, the signal from the binding of the first target sequence probe is used to determine a threshold cycle (Ct) value for the first target sequence, the signal from the binding of the reference gene probe is used to determine a threshold cycle (Ct) value for the reference gene, and the copy number of the first target sequence is determined by comparing the first target sequence Ct value and the reference gene Ct value. In some methods, the signal from the binding of the nucleic acid insert probe is used to determine a threshold cycle (Ct) value for the nucleic acid insert, and the copy number of the nucleic acid insert is determined by comparing the first target sequence Ct value and the reference gene Ct value.

In some methods, the selection cassette comprises a drug resistance gene.

In some methods, the nucleic acid insert is at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb. In some methods, the distance between the sequences to which the probes bind in the first target sequence and the selection cassette is no more than 100 nucleotides, 200 nucleotides, 300 nucleotides, 400 nucleotides, 500 nucleotides, 600 nucleotides, 700 nucleotides, 800 nucleotides, 900 nucleotides, 1 kb, 1.5 kb, 2 kb, 2.5 kb, 3 kb, 3.5 kb, 4 kb, 4.5 kb, or 5 kb.

Some methods further comprise determining the copy number of the second target sequence. Optionally, step (b) further comprises exposing the DNA of the cell to a probe that binds the second target sequence, step (c) further comprises detecting the signal from the binding of second target sequence probe, and step (d) further comprises comparing the signal from the reference gene probe to the signal from the second target sequence probe to determine a copy number for the second target sequence.

Some methods further comprise determining the copy number of one or more additional sequences within the nucleic acid insert. Optionally, step (b) further comprises exposing the DNA of the cell to one or more additional probes that bind the nucleic acid insert, step (c) further comprises detecting the signal from the binding of the one or more additional probes, and step (d) further comprises comparing the signal from the reference gene probe to the signal from the one or more additional nucleic acid insert probes to determine copy numbers for the one or more additional sequences within the nucleic acid insert. Optionally, the one or more additional sequences within the nucleic acid insert comprise a sequence adjacent to the second target sequence.

In some methods, the LTVEC is designed to delete an endogenous sequence from the target genomic locus, or the cell has further been contacted with a Cas protein, a first CRISPR RNA that hybridizes to a first CRISPR RNA recognition sequence within a target genomic locus, a second CRISPR RNA that hybridizes to a second CRISPR RNA recognition sequence within the target genomic locus, and a tracrRNA. Optionally, such methods further comprise determining the copy number of the endogenous sequences at target genomic locus. Optionally, step (b) further comprises exposing the DNA of the cell to a probe that binds the endogenous sequence at the target genomic locus, step (c) further comprises detecting the signal from the binding of the endogenous sequence probe, and step (d) further comprises comparing the signal from the reference gene probe to the signal from the endogenous sequence probe to determine a copy number for the endogenous sequence.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A shows a general schematic for simultaneous deletion of a mouse gene and replacement with a corresponding human version using an LTVEC and two guide RNAs (guide RNAs A and B). The LTVEC is shown in the top portion of FIG. 2A, and the mouse gene locus is shown in the bottom portion of FIG. 2A. The positions of the Cas9 cleavage sites guided by the two guide RNAs are indicated by the arrows below the mouse gene sequence.

FIGS. 2B-E show the unique biallelic modifications (allele types) that occur at a greater frequency when two guide RNAs are used. The thick lines with diagonal hatching indicate the mouse gene, the dotted lines indicate deletions in the mouse gene, and the thick black lines indicate insertion of the human gene. FIG. 2B shows homozygous collapsed alleles (large CRISPR-induced deletion). FIG. 2C shows homozygous targeted alleles. FIG. 2D shows hemizygous targeted alleles. FIG. 2E shows compound heterozygous alleles.

FIG. 3A shows results from long-range PCR assays for selected ES cell clones using primers m-lr-f and m-5'-r, which establish linkage between the human insert and sequences outside of those homologous to the 5' homology arm, thereby proving correct targeting. FIG. 3B shows results from 5' Del J, 5' Ins J, Del A+F, and Del A+E2 PCR assays. 5' Del J depicts the PCR products using m-5'-f and m-5-r primers, which amplifies the wild-type sequence surrounding the gRNA A cleavage site to establish retention or loss of this sequence. 5' Ins J depicts the PCR products using m-5'-f and h-5'-r primers, which establish a linkage between the human insert and the mouse genome. The assay will give a positive result in both targeted and random integrated clones. Del A+F depicts the expected amplicon size (359 bp) and actual bands for large deletion mediated by dual gRNA A and F cleavage in clones BO-F10 and AW-A8. Del A+E2 depicts the same idea for clone BA-A7. NT indicates no template, +/+ indicates parental VGF1 hybrid ES cell wild-type control, H/+ indicates heterozygous humanized genotype, H/Δ indicates hemizygous humanized genotype, H/H indicates homozygous humanized genotype, and Δ/Δ indicates homozygous deleted genotype.

FIG. 10A-E show the results of structural variation (SV) assays of clones BR-B4, BP-G7, BO-G11, BO-F10, BO-A8, and BC-H9, with VGF1 (F1H4), 129, and B6 DNA used as controls. The assays were done at the following distances telomeric to the Lrp5 locus: 13.7 Mb (FIG. 10A), 20.0 Mb (FIG. 10B), 36.9 Mb (FIG. 10C), 48.3 Mb (FIG. 10D), and 56.7 Mb (FIG. 10E). The positions of the PCR products for B6 and 129 alleles are shown by the arrows.

FIG. 12A-C is a schematic showing a possible mechanism for mitotic recombination during G2 phase of the cell cycle that can produce homozygous events and wide-spread gene conversion detected by loss of heterozygosity. FIG. 12A shows replicated homologous chromosomes showing the two chromatids in a hybrid 129/B6 ES cell heterozygous for a targeted humanization on the 129 homolog. Double-headed arrows indicate potential double strand breaks generated by dual gRNA-directed Cas9 cleavage that promotes reciprocal exchange by homologous recombination between chromatids on homologous chromosomes, shown as a cross-over on the centromeric side of the targeted allele, resulting in the hybrid chromatids shown in FIG. 12B. FIG. 12C shows that after mitosis and cell division, four types of chromosomes segregation into daughter cells are possible. Two with retention of heterozygosity, a parental type heterozygote (Hum/+, upper left) and a heterozygote by equal exchange (Hum/+, upper right), cannot be distinguished by LOH assays. Two others show loss of heterozygosity, a humanized homozygote (Hum/Hum, e.g. clone BO-A8, lower left) with loss of telomeric B6 alleles and a wild type homozygote (+/+, lower right) with loss of telomeric 129 alleles. This latter type will be lost because it does not retain the drug resistance cassette of the humanized allele.

FIG. 16A shows reciprocal chromatid exchange by mitotic crossover where a heterozygous modification occurs on the 129 chromosome before genome replication or after genome replication followed by gene conversion between sister chromatids. FIG. 16B shows reciprocal chromatid exchange by mitotic crossover where a single 129 chromatid is modified after genome replication. FIG. 16C shows reciprocal chromatid exchange by mitotic crossover where no LTVEC targeting has occurred, but Cas9 cleavage has occurred on either the 129 or B6 chromosome (B6 cleavage shown). FIG. 16D shows chromatid copying by break-induced replication where a heterozygous modification occurs on the 129 chromosome before genome replication or after genome replication followed by gene conversion between sister chromatids. FIG. 16E shows chromatid copying by break-induced replication where a single 129 chromatid is modified after genome replication.

FIG. 17A shows a standard modification of allele (MOA) screening strategy to detect heterozygous targeting by a large targeting vector (LTVEC) in which an endogenous sequence in a mouse chromosome is deleted and replaced with a Neo-SDC insert. The strategy uses TaqMan® probes mTU and mTD against upstream and downstream regions of the endogenous sequence targeted for deletion. FIG. 17B shows use of TaqMan® retention assays (retU and retD probes) in combination with modification of allele (MOA) assays (mTGU, mTM, and mTGD probes for loss of allele (LOA) assay, and hTU and hTD probes for gain of allele (GOA) assay) to screen for CRISPR/Cas9-assisted humanization. FIG. 17C shows use of TaqMan® retention assays (retU and retD probes) in combination with loss of allele (LOA) assays (mTGU, mTM, and mTGD probes) to screen for CRISPR/Cas9-assisted deletions using paired guide RNAs (gU and gD).

DEFINITIONS

Figure 1:
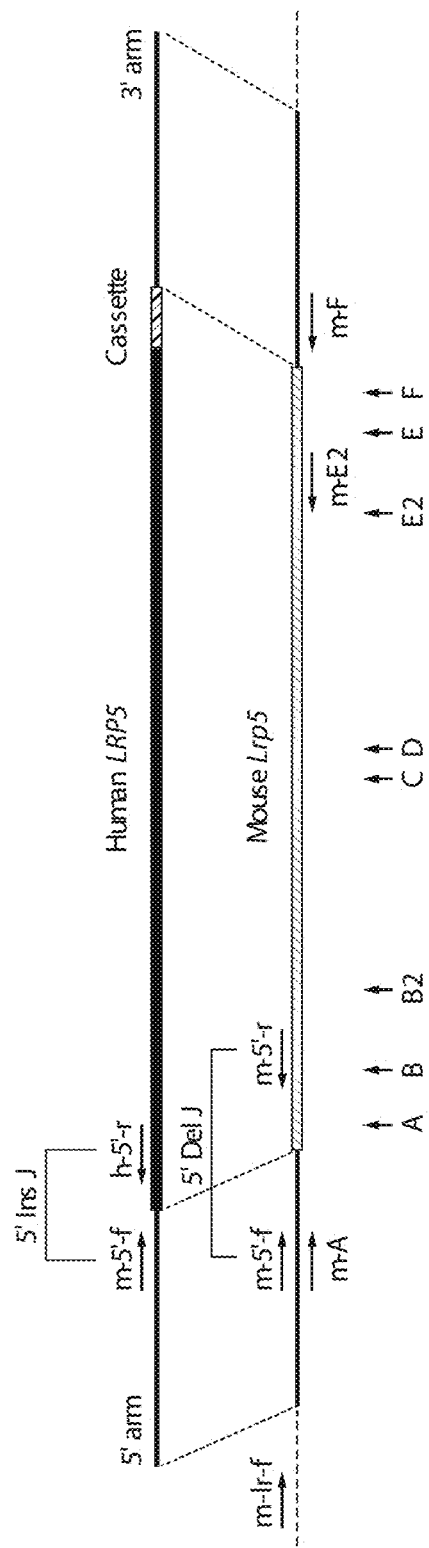
FIG. 1 shows a schematic for simultaneous deletion of the mouse Lrp5 ectodomain and replacement with a corresponding human LRP5 version using an LTVEC and either one or two 5' region (A, B, B2), middle region (C, D), and 3' region (E2, E, F) gRNAs. The LTVEC is shown in the top portion of the figure, and the mouse Lrp5 gene locus is shown in the bottom portion of the figure. The positions of the Cas9 cleavage sites guided by the eight guide RNAs are indicated by the vertical arrows below the mouse gene sequence. Horizontal arrows represent PCR primers for mouse and human sequences.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

DETAILED DESCRIPTION

I. Overview

Methods and compositions are provided for modifying a genome within a cell. The methods and compositions employ CRISPR/Cas systems using two guide RNAs (gRNAs) targeting different sites within a single genomic target locus. For example, the methods and compositions can employ CRISPR/Cas systems using the two guide RNAs (gRNAs) to create paired double-strand breaks at different sites within a single genomic target locus. Alternatively, the methods and compositions can employ CRISPR/Cas systems using the two guide RNAs (gRNAs) to create paired single-strand breaks at different sites within a single genomic target locus. In some methods, two or more guide RNAs (e.g., three or four) can be used, e.g., to create two or more single-strand breaks or double-strand breaks at different sites within a single genomic target locus.

Some methods promote biallelic genetic modifications and comprise genome collapsing, whereby a large nucleic acid sequence is deleted from a chromosome between two cleavage sites. Other methods promote biallelic genetic modifications and comprise simultaneous deletion of a nucleic acid sequence within the cell and replacement with an exogenous nucleic acid sequence. As outlined in further detail below, these methods using two gRNAs increase the efficiency of generating cells or animals with biallelic targeted genetic modifications by promoting the generation of such cells and animals in a single targeting step. Consequently, the number of animals and breedings necessary to generate an animal with a biallelic targeted genetic modification is reduced.

Other methods comprise gene conversion or loss of heterozygosity, whereby a genome that is heterozygous for an allele is modified to become homozygous for the allele via cleavage at sites determined by two gRNAs in the corresponding allele on a corresponding homologous chromosome. As outlined in further detail below, the use of two gRNAs in these methods increases the frequency of gene conversion and enables gene conversion over large tracts of chromosomal DNA.

II. CRISPR/Cas Systems

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

A. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

In some instances, a Cas protein is from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp *Microcoleus chthonoplastes, Oscillatoria* sp., *Petrotoga mobilis, Thermosipho africanus*, or *Acaryochloris marina*. Additional examples of the Cas9 family members include those described in WO 2014/131833, herein incorporated by reference in its entirety. In a specific example, the Cas9 protein is a Cas9 protein from *S. pyogenes* or is derived therefrom. The amino acid sequence of a Cas9 protein from *S. pyogenes* can be found, for example, in the SwissProt database under accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using well-known methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference in its entirety for all purposes.

Cas proteins can also be fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

One example of a Cas fusion protein is a Cas protein fused to a heterologous polypeptide that provides for subcellular localization. Such sequences can include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J Biol. Chem.* 282:5101-5105, herein incorporated by reference in its entirety for all purposes. For example, Cas proteins can be fused to one or more nuclear localization signals (e.g., two or three nuclear localization signals). Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also comprise a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety for all purposes. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g. eBFP, eBFP2, Azurite, mKalamal, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include, for example, promoters active in a pluripotent rat, eukaryotic, mammalian, non-human mammalian, human, rodent, mouse, or hamster cell. Promoters active in a one-cell stage embryo can also be used. Such promoters can be, for example, conditional promoters, inducible promoters, constitutive promoters, or tissue-specific promoters. Examples of other promoters are described elsewhere herein.

B. Guide RNAs (gRNAs)

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference in its entirety for all purposes. The terms "guide RNA" and "gRNA" are inclusive, including both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. TracrRNAs can be in any form (e.g., full-length tracrRNAs or active partial tracrRNAs) and of varying lengths. Forms of tracrRNA can include primary transcripts or processed forms. For example, in *S. pyogenes*, different forms of tracrRNAs include 171-nucleotide, 89-nucleotide, 75-nucleotide, and 65-nucleotide versions. See, for example, Deltcheva et al. (2011) Nature 471:602-607 and WO 2014/093661, each of which is herein incorporated by reference in its entirety for all purposes.

The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for example, Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from S. pyogenes include 171-nucleotide, 89-nucleotide, 75-nucleotide, and 65-nucleotide versions. See, for example, Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, herein incorporated by reference in its entirety for all purposes.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). In some cases, the percent complementarity between the DNA-targeting sequence and the CRISPR RNA recognition sequence within the target DNA is at least 60% over about 20 contiguous nucleotides. In one example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. In another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, etc.); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

A gRNA can comprise a nucleic acid sequence encoding a crRNA and a tracrRNA. For example, a gRNA can comprise: (a) a chimeric RNA having the nucleic acid sequence 5'-GUUUUAGAGCUA-GAAAUAGCAAGUUAAAAUAAGGCUAGU-CCGUUAUCAACUUGA AAAAGUGGCACCGAGUCG-GUGCUUUU-3' (SEQ ID NO: 1); or (b) a chimeric RNA having the nucleic acid sequence 5'-GUUUUAGAGCUA-GAAAUAGCAAGUUAAAAUAAGGCUAGUCCG-3' (SEQ ID NO: 2).

In some cases, the crRNA comprises 5'-GUUUUA-GAGCUAGAAAUAGCAAGUUAAAAU-3' (SEQ ID NO: 3); 5'-GUUUUAGAGCUA-GAAAUAGCAAGUUAAAAUAAG (SEQ ID NO: 4); or 5'-GAGUCCGAGCAGAAGAAGAAGUUUUA-3' (SEQ ID NO: 5).

In some cases, the tracrRNA comprises, 5'-AAGGCUA-GUCCG-3' (SEQ ID NO: 6) or 5'-AAGGCUAGU-CCGUUAUCAACUUGAAAAAGUGGCACCGAGUCG-GUGCUUUU-3' (SEQ ID NO: 7).

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

When a DNA encoding a gRNA is introduced into the cell, the gRNA can be transiently, conditionally, or constitutively expressed in the cell. DNAs encoding gRNAs can be stably integrated in the genome of the cell and operably linked to a promoter active in the cell. Alternatively, DNAs encoding gRNAs can be operably linked to a promoter in an expression construct. For example, the DNA encoding the gRNA can be in a targeting vector comprising a nucleic acid insert and/or a vector comprising a nucleic acid encoding a Cas protein. Alternatively, it can be in a vector or a plasmid that is separate from the targeting vector comprising the nucleic acid insert and/or separate from the vector comprising the nucleic acid encoding the Cas protein. Promoters that can be used in such expression constructs include promoters active, for example, in a pluripotent rat, eukaryotic, mammalian, non-human mammalian, human, rodent, mouse, or hamster cell. Promoters active in a one-cell stage embryo can also be used. Such promoters can be, for example, conditional promoters, inducible promoters, constitutive promoters, or tissue-specific promoters. In some instances, the promoter is an RNA polymerase III promoter, such as a human U6 promoter, a rat U6 polymerase III promoter, or a mouse U6 polymerase III promoter. Examples of other promoters are described elsewhere herein.

Alternatively, gRNAs can be prepared by various other methods. For example, gRNAs can be prepared by in vitro transcription using, for example, T7 RNA polymerase (see, for example, WO 2014/089290 and WO 2014/065596, each of which is herein incorporated by reference in its entirety for all purposes). Guide RNAs can also be a synthetically produced molecule prepared by chemical synthesis.

C. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked on the 3' end by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-$CCN_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein, such as $GN_{19}$NGG (SEQ ID NO: 8) or $N_{20}$NGG (SEQ ID NO: 9) (see, for example, WO 2014/165825, herein incorporated by reference in its entirety for all purposes). The guanine at the 5' end can facilitate transcription by RNA polymerase in cells. Other examples of CRISPR RNA recognition sequences can include two guanine nucleotides at the 5' end (e.g., $GGN_{20}$NGG; SEQ ID NO: 10) to facilitate efficient transcription by T7 polymerase in vitro. See, for example, WO 2014/065596, herein incorporated by reference in its entirety for all purposes. Other CRISPR RNA recognition sequences can have between 4-22 nucleotides in length of SEQ ID NOS: 8-10, including the 5' G or GG and the 3' GG or NGG. Yet other CRISPR RNA recognition sequences can have between 14 and 20 nucleotides in length of SEQ ID NOS: 8-10. Specific examples of CRISPR RNA recognition sequences include DNA sequences complementary to nucleic acids comprising any one of SEQ ID NOS: 11-38.

The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both. In some cases, the CRISPR RNA recognition sequence can be within a disease-associated gene or nucleic acid and/or within a signaling pathway-associated gene or nucleic acid. A disease-associated gene or nucleic acid includes any gene or nucleic acid which yields transcription or translation products at an abnormal level or in an abnormal form in cells derived from disease-affected tissues compared with tissues or cells of a non-disease control. For example, a disease-associated gene may possess one or mutations or genetic variations that are directly responsible for the etiology of a disease or are in linkage disequilibrium with one or more genes that are responsible for the etiology of a disease. The transcribed or translated products may be known or unknown, and may be at a normal or abnormal level. Examples of disease-associated genes and nucleic acids are available from McKusick-Nathans Institute of Genetic Medicine, Johns Hopkins University (Baltimore, Md.) and National Center for Biotechnology Information, National Library of Medicine (Bethesda, Md.), available on the World Wide Web. For additional examples of disease-associated genes and nucleic acids, see U.S. Pat. No. 8,697,359, herein incorporated by reference in its entirety for all purposes.

Mutations in disease-causing genes can be recessive mutations or dominant mutations. Diploid organisms (i.e., organisms having two copies of each chromosome) typically carry two copies of each gene. If the two copies in an individual are identical, the individual is homozygous for the gene. If the copies are different alleles, the individual is heterozygous for the gene. The term genotype includes whether an individual carries mutations in a single gene (or genes), and the term phenotype includes the physical and functional consequences of that genotype. Recessive mutations include mutations in which both alleles must be mutant in order for a mutant phenotype to be observed (i.e., the organism must be homozygous for the mutant allele to show the mutant phenotype). Recessive mutations can, for example, inactivate an affected gene and lead to a loss of function. For example, a recessive mutation may remove all or part of a gene from a chromosome, disrupt expression of a gene, or alter the structure of the encoded protein, thereby altering its function. In contrast, dominant mutations include mutations in which the mutant phenotype is observed in an organism that is heterozygous for the mutation (i.e., the organism carries one mutant allele and one wild type allele). A dominant mutation can, for example, lead to a gain of function. For example, a dominant mutation may increase the activity of a given gene product, confer a new activity on the gene product, or lead to its inappropriate spatial and temporal expression. A dominant mutation can also be associated with a loss of function. In some cases, if two copies of a gene are required for normal function, removing a single copy can cause a mutant phenotype. Such genes are haplo-insufficient. In other cases, mutations in one allele may lead to a structural change in the protein that interferes with the function of the wild type protein encoded by the other allele. Such mutations are dominant negative mutations. Some alleles can be associated with both a recessive and a dominant phenotype.

Some CRISPR RNA recognition sequences are within a gene or nucleic acid comprising a mutation. The mutation can be, for example, a dominant mutation or a recessive mutation. In some instances, the dominant mutation is within a cell that is heterozygous for the dominant mutation (i.e., the cell comprises a wild type allele and a mutant allele comprising the dominant mutation). In some such cases, the CRISPR RNA recognition sequence can be within the mutant allele but not the wild type allele. Alternatively, the CRISPR RNA recognition sequence can be within the wild type allele but not the mutant allele.

III. Targeting Vectors and Nucleic Acid Inserts

The methods and compositions disclosed herein can also utilize targeting vectors comprising nucleic acid inserts and homology arms to modify a genome within a cell. In such methods, the nucleic acid insert is integrated into a genomic target locus determined by the homology arms through a homologous recombination event. The methods provided herein can take advantage of nuclease agents (e.g., Cas proteins) in combination with the homologous recombination event. Such methods employ the nick or double-strand break created by the nuclease agent at a nuclease cleavage site in combination with homologous recombination to facilitate the targeted integration of the nucleic acid insert into the genomic target locus.

A. Targeting Vectors and Nucleic Acid Inserts for Cells Other than One-Cell Stage Embryos (1) Nucleic Acid Insert One or more separate nucleic acid inserts can be employed in the methods disclosed herein, and they can be introduced into a cell via separate targeting vectors or on the same targeting vector. Nucleic acid inserts include segments of DNA to be integrated at genomic target loci. Integration of a nucleic acid insert at a target locus can result in addition of a nucleic acid sequence of interest to the target locus, deletion of a nucleic acid sequence of interest at the target locus, and/or replacement of a nucleic acid sequence of interest at the target locus (i.e., deletion and insertion).

The nucleic acid insert or the corresponding nucleic acid at the target locus being replaced can be a coding region, an intron, an exon, an untranslated region, a regulatory region, a promoter, an enhancer, or any combination thereof. Moreover, the nucleic acid insert or the corresponding nucleic acid at the target locus being replaced can be of any desired length, including, for example, between 10-100 nucleotides in length, 100-500 nucleotides in length, 500 nucleotides-1 kb in length, 1 kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other cases, the length can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In yet other cases, the length can be at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, or greater. Some nucleic acid inserts can be even smaller. As an example, an insert of about 4 nucleotides to about 12 nucleotides in length can be inserted to create a restriction enzyme site.

In some targeting vectors, the nucleic acid insert can be from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb. Alternatively, the nucleic acid insert can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In some cases, the replacement of the nucleic acid at the target locus results in the deletion of a nucleic acid sequence ranging from about 1 kb to about 200 kb, from about 2 kb to about 20 kb, or from about 0.5 kb to about 3 Mb. In some cases, the extent of the deletion is greater than a total length of the 5' homology arm and the 3' homology arm.

In some cases, the extent of the deletion of the nucleic acid sequence ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In other cases, the nucleic acid insert or the corresponding nucleic acid at the target locus being replaced can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest.

The nucleic acid insert and/or the nucleic acid at the target locus can comprise a coding sequence or a non-coding sequence, such as a regulatory element (e.g., a promoter, an enhancer, or a transcriptional repressor-binding element). For example, the nucleic acid insert can comprise a knock-in allele of at least one exon of an endogenous gene, or a knock-in allele of the entire endogenous gene (i.e., "gene-swap knock-in").

For example, the nucleic acid insert can be homologous or orthologous to a sequence being targeted for deletion at the genomic target locus. The homologous or orthologous nucleic acid insert can replace the sequence being targeted for deletion at the genomic locus of interest. A homologous sequence includes a nucleic acid sequence that is either identical or substantially similar to a known reference sequence, such that it is at least 70%, at least 75%, at least 80%, at least 85%, at least 90%, at least 95%, at least 96%, at least 97%, at least 98%, at least 99%, or 100% identical to the known reference sequence. An orthologous sequence includes a nucleic acid sequence from one species that is functionally equivalent to a known reference sequence in another species. This can result in humanization of a locus if insertion of the nucleic acid insert results in replacement of a non-human nucleic acid sequence with a homologous or orthologous human nucleic acid sequence (i.e., the nucleic acid insert is inserted in place of the corresponding non-human DNA sequence at its endogenous genomic locus).

The nucleic acid insert can also comprise a conditional allele. The conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, for example, US 2011/0104799, herein incorporated by reference in its entirety for all purposes. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See US 2011/0104799, herein incorporated by reference in its entirety for all purposes.

Some nucleic acid inserts comprise a polynucleotide encoding a selection marker. The selection marker can be contained in a selection cassette. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

In some targeting vectors, the nucleic acid insert comprises a reporter gene. Examples of reporter genes are genes encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, alkaline phosphatase, and a combination thereof. Such reporter genes can be operably linked to a promoter active in a cell being targeted. Examples of promoters are described elsewhere herein.

In some targeting vectors, the nucleic acid insert comprises one or more expression cassettes or deletion cassettes. A given cassette can comprise a nucleotide sequence of interest, a nucleic acid encoding a selection marker, and/or a reporter gene, along with various regulatory components that influence expression. Examples of selectable markers and reporter genes that can be included are discussed in detail elsewhere herein.

In some targeting vectors, the nucleic acid insert comprises a nucleic acid flanked with site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, and a combination thereof. In one example, the site-specific recombination sites flank a polynucleotide encoding a selection marker and/or a reporter gene contained within the nucleic acid insert. Following integration of the nucleic acid insert at a targeted locus, the sequences between the site-specific recombination sites can be removed.

(2) Targeting Vectors

Targeting vectors can be employed to introduce the nucleic acid insert into a genomic target locus and comprise the nucleic acid insert and homology arms that flank the nucleic acid insert. Targeting vectors can be in linear form or in circular form, and can be single-stranded or double-stranded. Targeting vectors can be deoxyribonucleic acid (DNA) or ribonucleic acid (RNA). For ease of reference, the homology arms are referred to herein as 5' and 3' (i.e., upstream and downstream) homology arms. This terminology relates to the relative position of the homology arms to the nucleic acid insert within the targeting vector. The 5' and 3' homology arms correspond to regions within the targeted locus, which are referred to herein as "5' target sequence" and "3' target sequence," respectively. Some targeting vectors comprise 5' and 3' homology arms with no nucleic acid insert. Such targeting vectors can function to delete the sequence between the 5' and 3' target sequences without inserting a nucleic acid insert.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found on the targeting vector can be any degree of sequence identity that allows for homologous recombination to occur. For example, the amount of sequence identity shared by the homology arm of the targeting vector (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination at the cleaved recognition site. For example, a given homology arm and/or corresponding target sequence can comprise corresponding regions of homology that are at least about 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or more (such as described in the LTVEC vectors described elsewhere herein) such that the homology arm has sufficient homology to undergo homologous recombination with the corresponding target sequences within the genome of the cell.

The homology arms can correspond to a locus that is native to a cell (e.g., the targeted locus), or alternatively they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library. In certain instances, the homology arms of the targeting vector correspond to a locus that is native, heterologous, or exogenous to a prokaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest. In some cases, the homology arms correspond to a locus of the cell that is not targetable using a conventional method or that can be targeted only incorrectly or only with significantly low efficiency in the absence of a nick or double-strand break induced by a nuclease agent (e.g., a Cas protein). In some cases, the homology arms are derived from synthetic DNA.

In some targeting vectors, the 5' and 3' homology arms correspond to a targeted genome. Alternatively, the homology arms can be from a related genome. For example, the targeted genome is a mouse genome of a first strain, and the targeting arms are from a mouse genome of a second strain, wherein the first strain and the second strain are different. In certain instances, the homology arms are from the genome of the same animal or are from the genome of the same strain, e.g., the targeted genome is a mouse genome of a first strain, and the targeting arms are from a mouse genome from the same mouse or from the same strain.

A homology arm of a targeting vector can be of any length that is sufficient to promote a homologous recombination event with a corresponding target sequence, including, for example, at least 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length or greater. As described in further detail below, large targeting vectors can employ targeting arms of greater length.

Nuclease agents (e.g., CRISPR/Cas systems) can be employed in combination with targeting vectors to aid in the modification of a target locus. Such nuclease agents may promote homologous recombination between the targeting vector and the target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between the target sequences and the homology arms upon a nick or double-strand break at the nuclease cleavage site. The term "nuclease cleavage site" includes a DNA sequence at which a nick or double-strand break is created by a nuclease agent (e.g., a Cas9 cleavage site). The target sequences within the targeted locus that correspond to the 5' and 3' homology arms of the targeting vector are "located in sufficient proximity" to a nuclease cleavage site if the distance is such as to promote the occurrence of a homologous recombination event between the 5' and 3' target sequences and the homology arms upon a nick or double-strand break at the recognition site. Thus, in specific instances, the target sequences corresponding to the 5' and/or 3' homology arms of the targeting vector are within at least 1 nucleotide of a given recognition site or are within at least 10 nucleotides to about 14 kb of a given recognition site. In some cases, the nuclease cleavage site is immediately adjacent to at least one or both of the target sequences.

The spatial relationship of the target sequences that correspond to the homology arms of the targeting vector and the nuclease cleavage site can vary. For example, target sequences can be located 5' to the nuclease cleavage site, target sequences can be located 3' to the nuclease cleavage site, or the target sequences can flank the nuclease cleavage site.

Combined use of the targeting vector (including, for example, a large targeting vector) with a nuclease agent can result in an increased targeting efficiency compared to use of the targeting vector alone. For example, when a targeting vector is used in conjunction with a nuclease agent, targeting efficiency of the targeting vector can be increased by at least two-fold, at least three-fold, at least 4-fold, or at least 10-fold when compared to use of the targeting vector alone.

(3) Large Targeting Vectors

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; 7,105,348; and WO 2002/036789 (PCT/US01/45375), each of which is herein incorporated by reference. LTVECs can be in linear form or in circular form.

LTVECs can be of any length, including, for example, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR.

In some cases, an LTVEC comprises a nucleic acid insert ranging from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In other cases, the nucleic acid insert can range from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb.

In some LTVECS, the sum total of the 5' homology arm and the 3' homology arm is at least 10 kb. In other LTVECs, the 5' homology arm ranges from about 5 kb to about 100 kb and/or the 3' homology arm ranges from about 5 kb to about 100 kb. Each homology arm can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.

In some cases, the LTVEC and nucleic acid insert are designed to allow for a deletion at the target locus from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. Alternatively, the deletion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In other cases, the LTVEC and nucleic acid insert are designed to allow for an insertion into the target locus of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb. Alternatively, the insertion can be at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater.

In yet other cases, the nucleic acid insert and/or the region of the endogenous locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

B. Targeting Vectors and Nucleic Acid Inserts for One-Cell Stage Embryos

Targeting vectors for use in one-cell stage embryos are no more than 5 kb in length and can be deoxyribonucleic acid (DNA) or ribonucleic acid (RNA), they can be single-stranded or double-stranded, and they can be in circular form or linear form. An exemplary targeting vector for use in one-cell stage embryos is between about 50 nucleotides to about 5 kb in length. For example, a targeting vector for use in one-cell stage embryos can be between about 50 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Alternatively, a targeting vector for use in one-cell stage embryos can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. Alternatively, a targeting vector for use in one-cell stage embryos can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. In the case of single-stranded DNA donors, exemplary targeting vectors can be between about 60 nucleotides and about 200 nucleotides (e.g., about 60 nucleotides to about 80 nucleotides, about 80 nucleotides to about 100 nucleotides, about 100 nucleotides to about 120 nucleotides, about 120 nucleotides to about 140 nucleotides, about 140 nucleotides to about 160 nucleotides, about 160 nucleotides to about 180 nucleotides, or about 180 nucleotides to about 200 nucleotides).

Such targeting vectors comprise 5' and 3' homology arms corresponding to regions within the targeted locus (5' target sequence and 3' target sequence, respectively). Optionally, the targeting vector comprises a nucleic acid insert (e.g., a segment of DNA to be integrated at a genomic target locus) flanked by the 5' and 3' homology arms. Integration of a nucleic acid insert at a target locus can result in addition of a nucleic acid sequence of interest to the target locus, deletion of a nucleic acid sequence of interest at the target locus, or replacement of a nucleic acid sequence of interest at the target locus (i.e., deletion and insertion).

A corresponding region of homology between the homology arm and the corresponding target sequence can be of any length that is sufficient to promote homologous recombination. Exemplary homology arms for use in one-cell stage embryos are between about 20 nucleotides to about 2.5 kb in length (e.g., about 30 nucleotides to about 100 nucleotides in length). For example, a given homology arm and/or corresponding target sequence can comprise corresponding regions of homology that are between about 20 to about 30, about 30 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the genome of the cell. Alternatively, a given homology arm and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. In the case of single-stranded DNA donors, exemplary homology arms can be between about 30 nucleotides and about 60 nucleotides (e.g., about 30 to about 40 nucleotides, about 40 nucleotides to about 50 nucleotides, or about 50 nucleotides to about 60 nucleotides).

As described above, the homology arms can correspond to a locus that is native to a cell (e.g., the targeted locus), or alternatively they can correspond to a region of a heterologous or exogenous segment of DNA that was integrated into the genome of the cell. As described above, the 5' and 3' target sequences are preferably located in sufficient proximity to the Cas cleavage site so as to promote the occurrence of a homologous recombination event between the target sequences and the homology arms upon a single-strand break (nick) or double-strand break at the Cas cleavage site.

The nucleic acid insert or the corresponding nucleic acid at the target locus being deleted and/or replaced can be various lengths. An exemplary nucleic acid insert or corresponding nucleic acid at the target locus being deleted and/or replaced is between about 10 nucleotides to about 5 kb in length. For example, a nucleic acid insert or a corresponding nucleic acid at the target locus being deleted and/or replaced can be between about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, about 190 to about 200, about 200 to about 300, about 300 to about 400, about 400 to about 500, about 500 to about 600, about 600 to about 700, about 700 to about 800, about 800 to about 900, or about 900 to about 1,000 nucleotides in length. As an example, an insert of about 4 nucleotides to about 12 nucleotides in length can be inserted to create a restriction enzyme site. Likewise, a nucleic acid insert or a corresponding nucleic acid at the target locus being deleted and/or replaced can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. A nucleic acid being deleted from a genomic target locus can also be between about 5 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, about 90 kb to about 100 kb, about 100 kb to about 200 kb, about kb to about 300 kb, about 300 kb to about 400 kb, about 400 kb to about 500 kb, about 500 kb to about 600 kb, about 600 kb to about 700 kb, about 700 kb to about 800 kb, about 800 kb to about 900 kb, about 900 kb to about 1 Mb or longer. Alternatively, a nucleic acid being deleted from a genomic target locus can be between about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

As described above, the nucleic acid insert can comprise genomic DNA or any other type of DNA, the nucleic acid insert or the corresponding nucleic acid at the target locus being deleted and/or replaced can be a coding region or a non-coding region, and the nucleic acid insert can be homologous or orthologous to a sequence being targeted for deletion at the target genomic locus. The nucleic acid insert can also comprise a conditional allele, a polynucleotide encoding a selection marker, a reporter gene, one or more expression cassettes, one or more deletion cassettes, or a nucleic acid insert comprising a nucleic acid flanked with site-specific recombination target sequences as described above.

C. Promoters

Various nucleic acid sequences described herein can be operably linked to promoters. Such promoters can be active, for example, in a pluripotent rat, eukaryotic, mammalian, non-human mammalian, human, rodent, mouse, or hamster cell. A promoter active in a one-cell stage embryo can also be used. A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

A promoter can also be selected based on cell type. For example, various known promoters find use in a eukaryotic cell, a mammalian cell, a non-human mammalian cell, a pluripotent cell, a non-human pluripotent cell, a human pluripotent cell, a human ES cell, a human adult stem cell, a developmentally-restricted human progenitor cell, a human iPS cell, a human cell, a rodent cell, a rat cell, a mouse cell, a hamster cell, a fibroblast, or a CHO cell.

IV Methods of Modifying Genomes and Making Genetically Modified Non-Human Animals A. Methods of Modifying a Genome Various methods are provided for modifying a genome within a cell through use of two guide RNAs to target different regions within a single genomic target locus. Methods using two or more guide RNAs (e.g., three guide RNAs or four guide RNAs) to target different regions within a single genomic target locus are also provided. The methods can occur in vitro, ex vivo, or in vivo. Such methods promote the creation of biallelic genetic modifications and can comprise genome collapsing or other targeted modifications such as simultaneous deletion of a nucleic acid sequence within the genome and replacement with an exogenous nucleic acid sequence.

Targeted gene modification by homologous recombination between a targeting vector and a target locus can be very inefficient, especially in cell types other than rodent embryonic stem cells. Use of a targeting vector in combination with a nuclease-directed double-strand DNA break at the target locus can greatly enhance heterozygous targeting efficiency for simple modifications, such as small deletions or insertions.

Combining a targeting vector with a CRISPR/Cas9 nuclease guided by one guide RNA (gRNA) can also increase heterozygous targeting efficiency for very large and low efficiency gene modifications, such as the deletion of a mouse gene and simultaneous replacement with its human counterpart (humanization). Such modifications can involve very large (e.g., >50 kb) deletions and insertions (see Lrp5, C5 (Hc), Ror1, and Trpa1 targeting in Example 1).

During homology-directed repair of one or more double-strand breaks generated by a nuclease such as Cas9 at a target genomic locus, the one or more breaks are first processed to create a 3'-single-strand overhang by resection of the 5' end. Rad51 then polymerizes on the single-stranded DNA to search for a homologous sequence, strand invasion occurs into the undamaged homologous template duplex DNA (e.g., the targeting vector), and an intermediate D-loop structure is formed to facilitate repair of the one or more double-strand breaks using the undamaged homologous DNA (e.g., the targeting vector) as a template. The chromosomal sequences are then replaced by the nucleic acid insert from the targeting vector by a double crossover event involving the flanking homology regions. Whether this process proceeds properly is affected by several factors, such as the size of the nucleic acid insert, the length of the regions homologous to the homology arms of the targeting vector, and the positions of the regions homologous to the homology arms of the targeting vector (e.g., in relation to the one or more double strand breaks).

As the size of the nucleic acid insert or the deleted sequence at the target genomic locus increase, the resection process becomes more unpredictable, the stability of the intermediate D loop structure decreases and becomes more unpredictable, and the success of the recombination process in general decreases and becomes more unpredictable. For example, as the size of the targeted modification increases, the risk of internal recombination increases, particularly when there is similarity between the sequence being replaced and the sequence being inserted. When such internal recombination occurs, homologous recombination exchange takes place internal to the intended target region, and the full nucleic acid insert is not incorporated into the genomic target locus. In addition, conventional thinking is that the efficiency of HR-mediated insertions decreases as the distance between the double-strand break and the mutation or insertion site increases (e.g., beyond 100 bp or 200 bp). See Beumer et al. (2013) *Genes\Genomes\Genetics* 3:657-664; Elliott et al. (1998) *Mol. Cell. Biol.* 18:93-101; and Byrne et al. (2015) *Nucleic Acids Research* 43(3):e21, each of which is herein incorporated by reference in its entirety for all purposes.

To achieve a targeted gene modification that creates a large deletion at a target genomic locus and simultaneously inserts a large piece of foreign DNA requires the formation of a double omega structure as a recombination intermediate. The larger the modification, the lower the stability of the structure. In cell types other than one-cell stage embryos, LTVECs having a sum total of 10 kb or greater total homology can be used. LTVECs with homology arms having a sum total of 10 kb or greater total homology increase the stability of the double omega recombination intermediate to facilitate a nuclease-mediated simultaneous large deletion and replacement with a large nucleic acid insert and further enable not only double-strand breaks adjacent to the homology regions to enhance targeting efficiency but also enable those far away from the homology regions to enhance targeting efficiency.

For gene modifications that involve very large humanizations, combining a targeting vector with a CRISPR/Cas9 nuclease system guided by two gRNAs can further enhance targeting efficiency beyond that achieved with one gRNA (see Lrp5, C5 (Hc), Ror1, and Trpa1 humanizations in Example 1). Use of two gRNAs produces unexpected results in this regard. In comparison to targeting with one gRNA, which produces biallelic modifications at a low frequency or not at all, targeting with two gRNAs results in the creation of homozygously targeted cells, homozygously deleted cells, and compound heterozygously targeted cells (including hemizygously targeted cells) at a significantly increased rate.

The method for creating three allele types—homozygously targeted, homozygously deleted, and compound heterozygously targeted (particularly hemizygously targeted)—in a single targeting experiment provides new possibilities and enhanced efficiencies for targeted gene modifications. For a simple gene modification, such as the targeted deletion of a gene in mouse ES cells and its replacement with a sequence encoding a protein that reports gene expression (e.g., β-galactosidase or a fluorescent protein), combining a targeting vector with a CRISPR/Cas9 system guided by two gRNAs enhances the production of heterozygously targeted ES cells, which can then be used to produce fully ES cell-derived F0 generation mice by the VelociMouse® method. See Poueymirou et al. (2007) *Nat. Biotech.* 25:91-99, herein incorporated by reference in its entirety for all purposes. These mice are useful for studying tissue specific gene expression with the reporter knock-in allele. Homozygously targeted ES cell clones produced in the same experiment can be converted to VelociMice with a homozygously targeted gene deletion, which can be studied for phenotypic consequences of the gene knockout as well as gene expression from the reporter. Production of VelociMice from ES cells having a homozygous CRISPR-induced deletion of the target gene enables verification of the knockout phenotype seen in the homozygously targeted mice and can reveal phenotypic differences between a clean gene deletion and a deletion accompanied by insertion of the reporter and a drug selection cassette. Compound heterozygous (and particularly hemizygous) ES cell clones carrying both the targeted deletion-insertion allele and the CRISPR-induced deletion enable the production of VelociMice with the same opportunities for study as those derived from the homozygously targeted and homozygously deleted clones. In addition, these mice can be bred to establish both targeted and simple deletion mutant mouse lines from a single ES cell clone.

These advantages have added value when extended to the case of a humanization. An important use of humanization of a mouse gene is to create an animal model in which to test a human-specific therapeutic. For a humanization to be an effective model, the mouse gene must be ablated or inactivated to avoid interactions between the mouse and human gene products that might impair biological function or proper interaction with the drug. At the same time, the human gene must be able to substitute for the biological functions of its mouse counterpart. These requirements can be tested by combining a Cas9 nuclease guided by two gRNAs with a targeting vector designed to make a simultaneous deletion of a mouse gene and replacement with the human gene. VelociMice derived from ES cells having a homozygously targeted humanization can be compared with VelociMice derived from ES cells having a homozygous CRISPR-induced deletion of the mouse gene. If the knockout deletion causes an observable mutant phenotype and the humanized mice do not express this phenotype but are instead normal, then the human gene is able to substitute for the mouse gene's biological functions. Either the homozygous humanized mice or those carrying a compound heterozygous (e.g., hemizygous) combination of a humanized allele and a CRISPR-induced deletion allele can be used as animal models to study the mechanism of action and efficacy of the human-specific therapeutic. The compound heterozygous (e.g., hemizygous) VelociMice can also be used to generate both humanized and deletion knockout lines of mice by conventional breeding. Thus, from a single gene targeting experiment that combines a two-gRNA CRISPR system with a targeting vector, genetically modified mice are produced that create both valuable mouse models for pre-clinical testing of a therapeutic and knockout lines for studying the biological function of the mouse homolog of the human drug target.

(1) Methods Generating, Promoting, or Increasing Frequency of Biallelic Genetic Modifications Methods are provided herein to make biallelic modifications to a genome within a cell or to promote or increase the frequency of biallelic modifications to a genome within a cell. Such methods can result, for example, in collapsing a genome to remove a large section of genomic DNA between two sequences of genomic DNA that subsequently recombine. Such methods can also result in insertion of a nucleic acid insert or deletion of a large section of genomic DNA and replacement with a nucleic acid insert.

The methods provided herein for modifying a genome within a cell comprise contacting the genome with a first Cas protein, a first CRISPR RNA that hybridizes to a first CRISPR RNA recognition sequence within a genomic target locus, a second CRISPR RNA that hybridizes to a second CRISPR RNA recognition sequence within the genomic target locus, and a tracrRNA. Optionally, the genome can be further contacted with additional CRISPR RNAs that hybridize to CRISPR RNA recognition sequences within the genomic target locus, such as a third CRISPR RNA that hybridizes to a third CRISPR RNA recognition sequence within the genomic target locus and/or a fourth CRISPR RNA that hybridizes to a fourth CRISPR RNA recognition sequence within the genomic target locus. Biallelic modifications can be generated by contacting the genome with a first Cas protein, a first CRISPR RNA that hybridizes to a first CRISPR RNA recognition sequence within a genomic target locus, a second CRISPR RNA that hybridizes to a second CRISPR RNA recognition sequence within the genomic target locus, and a tracrRNA. As described in further detail below, the Cas protein, CRISPR RNAs, and tracrRNA can be introduced into the cell in any form and by any means. Likewise, all or some of the Cas protein, CRISPR RNAs, and tracrRNA can be introduced simultaneously or sequentially in any combination. The contacting of the genome can occur directly (i.e., a component directly contacts the genome itself) or indirectly (i.e., a component interacts with another component which directly contacts the genome).

The genome can comprise a pair of first and second homologous chromosomes comprising the genomic target locus. The first Cas protein can cleave one or both of these chromosomes within one or both of the first and second CRISPR RNA recognition sequences (i.e., at a first cleavage site within the first CRISPR RNA recognition sequence and/or at a second cleavage site within the second CRISPR RNA recognition sequence). If third and/or fourth CRISPR RNAs are also used, the first Cas protein can cleave one or both of these chromosomes within one or both of the third and/or fourth CRISPR RNA recognition sequences (i.e., at a third cleavage site within the third CRISPR RNA recognition sequence and/or at a fourth cleavage site within the fourth CRISPR RNA recognition sequence). The cleavage events can then generate at least one double-strand break in one or both of the chromosomes. The cleavage events can also generate at least two double-strand breaks in one or both of the chromosomes. If Cas nickases are used, the cleavage events can generate at least one single-strand break in one or both of the chromosomes, or at least two single-strand breaks in one or both of the chromosomes. If third and/or fourth CRISPR RNAs are used, the cleavage events can generate at least three of four single-strand or double-strand breaks in one or both of the chromosomes. The end sequences generated by the double-strand breaks can then undergo recombination, or the end sequences generated by the single-strand breaks can then undergo recombination. A cell having the modified genome comprising the biallelic modification can then be identified.

For example, the first Cas protein can cleave the genome at a first cleavage site within the first CRISPR RNA recognition sequence in the first and second homologous chromosomes and at a second cleavage site within the second CRISPR RNA recognition sequence in at least the first homologous chromosome, thereby generating end sequences in the first and second homologous chromosomes. The end sequences can then undergo recombination to form a genome with a biallelic modification comprising a targeted modification. The targeted modification can comprise a deletion between the first and second CRISPR RNA recognition sequences in at least the first chromosome.

The first and second CRISPR RNA recognition sequences can be anywhere within a genomic target locus. The first and second CRISPR RNA recognition sequences can flank any genomic region of interest. For example, the first and second CRISPR RNA recognition sequences can flank all or part of a coding sequence for a gene, such as the Lrp5 locus, the C5 (Hc) locus, the Ron 1 locus, or the Trpa1 locus. The first and second CRISPR RNA recognition sequences can also flank all or part of a coding sequence for the Cmah gene. Alternatively, the first and second CRISPR RNA recognition sequences can flank a non-coding sequence, such as a regulatory element (e.g., a promoter), or both coding and non-coding sequences. The third and fourth CRISPR RNA recognition sequences can be, for example, anywhere within the genomic region of interest that is flanked by the first and second CRISPR RNA recognition sequences.

As an example, the third CRISPR RNA recognition sequence can be adjacent to the first CRISPR RNA recognition sequence, and the fourth CRISPR RNA recognition sequence can be adjacent to the second CRISPR RNA recognition sequence. Thus, the first and third CRISPR RNA recognition sequences can be a first pair of CRISPR RNA recognition sequences, and the second and fourth CRISPR RNA recognition sequences can be a second pair of CRISPR RNA recognition sequences. For example, the first and third CRISPR RNA recognition sequences (and/or the second and fourth CRISPR RNA recognition sequences) can be separated by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, about 4.5 kb to about 5 kb, about 5 kb to about 6 kb, about 6 kb to about 7 kb, about 7 kb to about 8 kb, about 8 kb to about 9 kb, or about 9 kb to about 10 kb. As an example, the first and third CRISPR RNA recognition sequences (and/or the second and fourth CRISPR RNA recognition sequences) can be separated by about 100 bp to about 1 kb. Alternatively, the first and third CRISPR RNA recognition sequences (and/or second and fourth CRISPR RNA recognition sequences) can overlap.

The first pair of CRISPR RNA recognition sequences can be located near the 5' end of the genomic target locus and the second pair can be located near the 3' end of the genomic target locus. Alternatively, the first and second pairs can both be located near the 5' end of the genomic target locus or can both be located near the 3' end of the target locus. Alternatively, one or both of the pairs can be located internally within the genomic target locus. For example, the first CRISPR RNA recognition sequence or the first pair of CRISPR RNA recognition sequences can be less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb from the 5' end of the genomic target locus. Likewise, the second CRISPR RNA recognition sequence or the first pair of CRISPR RNA recognition sequences can be less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb from the 3' end of the genomic target locus.

Alternatively, the first CRISPR RNA recognition sequence or the first pair of CRISPR RNA recognition sequences can be, for example, at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb from the 5' end of the genomic target locus. Likewise, the second CRISPR RNA recognition sequence or the first pair of CRISPR RNA recognition sequences can be, for example, at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb from the 3' end of the genomic target locus.

Alternatively, the first CRISPR RNA recognition sequence or the first pair of CRISPR RNA recognition sequences can be, for example, about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 6 kb, about 6 kb to about 7 kb, about 7 kb to about 8 kb, about 8 kb to about 9 kb, about 9 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, or about 90 kb to about 100 kb from the 5' end of the genomic target locus. Likewise, the second CRISPR RNA recognition sequence or the first pair of CRISPR RNA recognition sequences can be, for example, about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 6 kb, about 6 kb to about 7 kb, about 7 kb to about 8 kb, about 8 kb to about 9 kb, about 9 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, or about 90 kb to about 100 kb from the 3' end of the genomic target locus.

The first and second cleavage sites or first and second CRISPR RNA recognition sequences can be separated, for example, by about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb. The first and second cleavage sites or first and second CRISPR RNA recognition sequences can also be separated, for example, by about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb. The first and second cleavage sites or first and second CRISPR RNA recognition sequences can also be separated, for example, by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, or about 900 bp to about 1 kb. Likewise, the first pair of CRISPR RNA recognition sequences can be separated from the second pair CRISPR RNA recognition sequences, for example, by about 25 bp to about 50 bp, about 50 bp to about 100 bp, about 100 bp to about 150 bp, about 150 bp to about 200 bp, about 200 bp to about 250 bp, about 250 bp to about 300 bp, about 300 bp to about 350 bp, about 350 bp to about 400 bp, about 400 bp to about 450 bp, about 450 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

Alternatively, the first and second cleavage sites or first and second CRISPR RNA recognition sequences can be separated, for example, by at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb or greater. Likewise, the first pair of CRISPR RNA recognition sequences can be separated from the second pair CRISPR RNA recognition sequences, for example, by at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb or greater.

Alternatively, the first and second cleavage sites or first and second CRISPR RNA recognition sequences can be separated by less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb. Likewise, the first pair of CRISPR RNA recognition sequences can be separated from the second pair CRISPR RNA recognition sequences, for example, by less than 25 bp, less than 50 bp, less than 100 bp, less than 150 bp, less than 200 bp, less than 250 bp, less than 300 bp, less than 350 bp, less than 400 bp, less than 450 bp, less than 500 bp, less than 600 bp, less than 700 bp, less than 800 bp, less than 900 bp, less than 1 kb, less than 2 kb, less than 3 kb, less than 4 kb, less than 5 kb, or less than 10 kb.

The end sequences created by cleavage of the genome at the first and/or second cleavage sites can be blunt ends or staggered ends, and the deletion between the first and second CRISPR RNA recognition sequences can include all or part of the nucleic acid sequence between and including the first and second CRISPR RNA recognition sequences. Likewise, the end sequences created by cleavage of the genome at the third and/or fourth cleavage sites can be blunt ends or staggered ends. For example, the deletion can include only a portion of the nucleic acid sequence between the first and second CRISPR RNA recognition sequences and/or only a portion of the first CRISPR RNA recognition sequence and/or the second CRISPR RNA recognition sequence. Alternatively, the deletion between the first and second CRISPR RNA recognition sequences can include all of the nucleic acid sequence between the first and second CRISPR RNA recognition sequences. Likewise, the deletion can include the first CRISPR RNA recognition sequence and/or the second CRISPR RNA recognition sequence, or portions thereof. In some cases, the deletion further comprises sequences located outside of the first and second CRISPR RNA recognition sequences (i.e., sequences not including and not between the first and second CRISPR RNA recognition sequences).

The deletion between the first and second CRISPR RNA recognition sequences can be any length. For example, the deleted nucleic acid can be from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

Alternatively, the deleted nucleic acid can be, for example, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb or greater. In some cases, the deleted nucleic acid can be at least 550 kb, at least 600 kb, at least 650 kb, at least 700 kb, at least 750 kb, at least 800 kb, at least 850 kb, at least 900 kb, at least 950 kb, at least 1 Mb, at least 1.5 Mb, at least 2 Mb, at least 2.5 Mb, at least 3 Mb, at least 4 Mb, at least 5 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb (e.g., most of a chromosome).

The deletion between the first and second CRISPR RNA recognition sequences can be a precise deletion wherein the deleted nucleic acid consists of only the nucleic acid sequence between the first and second Cas protein cleavage sites such that there are no additional deletions or insertions at the modified genomic target locus. The deletion between the first and second CRISPR RNA recognition sequences can also be an imprecise deletion extending beyond the first and second Cas protein cleavage sites, consistent with imprecise repair by non-homologous end joining (NHEJ), resulting in additional deletions and/or insertions at the modified genomic locus. For example, the deletion can extend about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more beyond the first and second Cas protein cleavage sites. Likewise, the modified genomic locus can comprise additional insertions consistent with imprecise repair by NHEJ, such as insertions of about 1 bp, about 2 bp, about 3 bp, about 4 bp, about 5 bp, about 10 bp, about 20 bp, about 30 bp, about 40 bp, about 50 bp, about 100 bp, about 200 bp, about 300 bp, about 400 bp, about 500 bp, or more.

The contacting can occur in the absence of an exogenous donor sequence or the presence of an exogenous donor sequence, provided that if the cell is a one-cell stage embryo, the exogenous donor sequence is no more than 5 kb in length. Exogenous molecules or sequences include molecules or sequences that are not normally present in a cell. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence. In contrast, endogenous molecules or sequences include molecules or sequences that are normally present in a particular cell at a particular developmental stage under particular environmental conditions.

The exogenous donor sequence can be within a targeting vector and can comprise a nucleic acid insert flanked by 5' and 3' homology arms that correspond to 5' and 3' target sequences within the genome, provided that if the cell is a one-cell stage embryo, the targeting vector is no more than 5 kb in length. In cell types other than one-cell stage embryos, the targeting vector can be longer. In cell types other than one-cell stage embryos, the targeting vector can be, for example, a large targeting vector (LTVEC) as described herein, and can be at least 10 kb. Thus, in some methods, the genome is further contacted with a targeting vector, and the nucleic acid insert is inserted between the 5' and 3' target sequences.

Alternatively, the exogenous donor sequence can comprise 5' and 3' homology arms with no nucleic acid insert. Such targeting vectors with no nucleic acid insert can facilitate precise deletions between the 5' and 3' target sequences within the genome. Such precise deletions can be, for example, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, at least 500 kb, at least 550 kb, at least 600 kb, at least 650 kb, at least 700 kb, at least 750 kb, at least 800 kb, at least 850 kb, at least 900 kb, at least 950 kb, at least 1 Mb, at least 1.5 Mb, or at least 2 Mb or greater.

In some such methods, the 5' and 3' homology arms correspond to 5' and 3' target sequences at the genomic target locus comprising the first CRISPR RNA recognition sequence of the first CRISPR RNA and/or the second CRISPR RNA recognition sequence of the second CRISPR RNA. The first and second CRISPR RNA recognition sequences or first and second cleavage sites can be adjacent to the 5' target sequence, adjacent to the 3' target sequence, or adjacent to neither the 5' target sequences nor the 3' target sequence. Alternatively, the first CRISPR RNA recognition sequence or first cleavage site can be adjacent to the 5' target sequence, and the second CRISPR RNA recognition sequence or second cleavage site can be adjacent to the 3' target sequence. Alternatively, the first CRISPR RNA recognition sequence or first cleavage site can be adjacent to either the 5' target sequence or the 3' target sequence, and the second CRISPR RNA recognition sequence or second cleavage site can be adjacent to neither the 5' target sequence nor the 3' target sequence.

For example, the first and/or second CRISPR RNA recognition sequences can be located between the 5' and 3' target sequences or can be adjacent to or in proximity to the 5' target sequence and/or the 3' target sequence, such as within 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 250 kb, 300 kb, 350 kb, 400 kb, 450 kb, or 500 kb of the 5' and/or 3' target sequences. Likewise, the first and/or second cleavage sites can be located between the 5' and 3' target sequences or can be adjacent to or in proximity to the 5' target sequence and/or the 3' target sequence, such as within 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 250 kb, 300 kb, 350 kb, 400 kb, 450 kb, or 500 kb of the 5' and/or 3' target sequences. For example, the first CRISPR RNA recognition sequence or the first cleavage site can be within 50 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 250 kb, 300 kb, 350 kb, 400 kb, 450 kb, or 500 kb of the 5' target sequence or both the 5' and 3' target sequences. Likewise, the second CRISPR RNA recognition sequence or the second cleavage site can be within 50 bp, 100 bp, 200 bp, 300 bp, 400 bp, 500 bp, 600 bp, 700 bp, 800 bp, 900 bp, 1 kb, 2 kb, 3 kb, 4 kb, 5 kb, 6 kb, 7 kb, 8 kb, 9 kb, 10 kb, 20 kb, 30 kb, 40 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 250 kb, 300 kb, 350 kb, 400 kb, 450 kb, or 500 kb of the 3' target sequence or both the 5' and 3' target sequences.

Alternatively, the first and/or second CRISPR RNA recognition sequences can be located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb from the 5' and/or 3' target sequences. Likewise, the first and/or second cleavage sites can be located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb from the 5' and/or 3' target sequences. For example, the first CRISPR RNA recognition sequence or the first cleavage site can be located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb from the 5' target sequence or from both the 5' and 3' target sequences. Likewise, the second CRISPR RNA recognition sequence of the second cleavage site can be located at least 50 bp, at least 100 bp, at least 200 bp, at least 300 bp, at least 400 bp, at least 500 bp, at least 600 bp, at least 700 bp, at least 800 bp, at least 900 bp, at least 1 kb, at least 2 kb, at least 3 kb, at least 4 kb, at least 5 kb, at least 6 kb, at least 7 kb, at least 8 kb, at least 9 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb from the 3' target sequence or from both the 5' and 3' target sequences.

For example, the first and/or second CRISPR RNA recognition sequence can be located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 100 kb, about 100 kb to about 150 kb, about 150 kb to about 200 kb, about 200 kb to about 300 kb, about 300 kb to about 400 kb, or about 400 kb to about 500 kb from the 5' and/or 3' target sequences. Likewise, the first and/or second cleavage sites can be located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 100 kb, about 100 kb to about 150 kb, about 150 kb to about 200 kb, about 200 kb to about 300 kb, about 300 kb to about 400 kb, or about 400 kb to about 500 kb from the 5' and/or 3' target sequences. For example, the first CRISPR RNA recognition sequence or the first cleavage site can be located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 100 kb, about 100 kb to about 150 kb, about 150 kb to about 200 kb, about 200 kb to about 300 kb, about 300 kb to about 400 kb, or about 400 kb to about 500 kb from the 5' target sequence or from both the 5' and 3' target sequences. Likewise, the second CRISPR RNA recognition sequence or the second cleavage site can be located between about 50 bp to about 100 bp, about 200 bp to about 300 bp, about 300 bp to about 400 bp, about 400 bp to about 500 bp, about 500 bp to about 600 bp, about 600 bp to about 700 bp, about 700 bp to about 800 bp, about 800 bp to about 900 bp, about 900 bp to about 1 kb, about 1 kb to about 2 kb, about 2 kb to about 3 kb, about 3 kb to about 4 kb, about 4 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 100 kb, about 100 kb to about 150 kb, about 150 kb to about 200 kb, about 200 kb to about 300 kb, about 300 kb to about 400 kb, or about 400 kb to about 500 kb from the 3' target sequence or from both the 5' and 3' target sequences.

Alternatively, the first and/or second CRISPR RNA recognition sequences or the first and/or second cleavage sites can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 5' and/or 3' target sequences. For example, the first CRISPR RNA recognition sequence or the first cleavage site can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 5' target sequence or from both the 5' and 3' target sequences. Likewise, the second CRISPR RNA recognition sequence or the second cleavage site can be located more than 50 bp, more than 100 bp, more than 200 bp, more than 300 bp, more than 400 bp, more than 500 bp, more than 600 bp, more than 700 bp, more than 800 bp, more than 900 bp, more than 1 kb, more than 2 kb, more than 3 kb, more than 4 kb, more than 5 kb, more than 6 kb, more than 7 kb, more than 8 kb, more than 9 kb, more than 10 kb, more than 20 kb, more than 30 kb, more than 40 kb, more than 50 kb, more than 60 kb, more than 70 kb, more than 80 kb, more than 90 kb, or more than 100 kb from the 3' target sequence or from both the 5' and 3' target sequences.

The methods described herein promote and increase the frequency of biallelic modifications. In particular, by contacting the genome with both the first and second CRISPR RNAs, the efficiency of producing biallelic modifications can be increased compared to contacting the genome with either the first CRISPR RNA or the second CRISPR RNA alone. The efficiency of producing biallelic modifications can also be increased by contacting the genome with the first, second, and third CRISPR RNAs, or the first, second, third, and fourth CRISPR RNAs. Biallelic modifications include events in which the same modification is made to the same locus on corresponding homologous chromosomes (e.g., in a diploid cell), or in which different modifications are made to the same locus on corresponding homologous chromosomes. Homologous chromosomes include chromosomes that have the same genes at the same loci but possibly different alleles (e.g., chromosomes that are paired during meiosis). The term allele includes any of one or more alternative forms of a genetic sequence. In a diploid cell or organism, the two alleles of a given sequence typically occupy corresponding loci on a pair of homologous chromosomes.

A biallelic modification can result in homozygosity for a targeted modification or compound heterozygosity (e.g., hemizygosity) for the targeted modification. A single targeting experiment with a population of cells can produce cells that are homozygous for a targeted modification (e.g., humanization of a locus), cells that are compound heterozygous for that targeted modification (including cells that are hemizygous for the targeted modification), and cells that are homozygously collapsed between the first and second CRISPR RNA recognition sequences (i.e., a large nucleic acid sequence is deleted between two CRISPR RNA recognition sequences). Homozygosity includes situations in which both alleles of a target locus (i.e., corresponding alleles on both homologous chromosomes) have the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele). Disruption of the endogenous nucleic acid sequence can result, for example, when a double-strand break created by the Cas protein is repaired by non-homologous end joining (NHEJ)-mediated DNA repair, which generates a mutant allele comprising an insertion or a deletion of a nucleic acid sequence and thereby causes disruption of that genomic locus. Examples of disruption include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation). Disruption can result in inactivation (i.e., loss of function) or loss of the allele.

For example, a biallelic modification can result in compound heterozygosity if the cell has one allele with the targeted modification and another allele that is not capable of being expressed or is not otherwise functional. Compound heterozygosity includes hemizygosity. Hemizygosity includes situations in which only one allele (i.e., an allele on one of two homologous chromosomes) of the target locus is present. For example, a biallelic modification can result in hemizygosity for a targeted modification if the targeted modification occurs in one allele with a corresponding loss or deletion of the other allele.

In a specific example, the biallelic modification can comprise a deletion between the first and second CRISPR RNA recognition sequences in the pair of first and second homologous chromosomes. The deletions can occur simultaneously, or the deletion can occur initially in the first homologous chromosome, with homozygosity then being achieved by the cell using the first homologous chromosome as a donor sequence to repair one or more double-strand breaks in the second homologous chromosome via homologous recombination, such as by gene conversion. The deleted nucleic acid sequence in the first and second homologous chromosomes can be the same, partially overlapping, or different. Alternatively, the biallelic modification can comprise a deletion between the first and second CRISPR RNA recognition sequences in the first homologous chromosome and loss of the corresponding allele or locus in the second homologous chromosome. Alternatively, the biallelic modification can comprise a deletion between the first and second CRISPR RNA recognition sequences in the first homologous chromosome and inactivation or disruption of the corresponding allele or locus between the first and second CRISPR RNA recognition sequences in the second homologous chromosome.

If a donor sequence is used, the biallelic modification can comprise a deletion between the first and second CRISPR RNA recognition sequences as well as an insertion of the nucleic acid insert between the 5' and 3' target sequences in the pair of first and second homologous chromosomes, thereby resulting in a homozygous modified genome. The deletion and insertion can occur simultaneously in both chromosomes, or the deletion and insertion can initially occur in the first homologous chromosome, with homozygosity then being achieved by the cell using the first homologous chromosome as a donor sequence to repair the double-strand break(s) in the second homologous chromosome via homologous recombination, such as by gene conversion. For example, without wishing to be bound by any particular theory, insertion of the nucleic acid insert could occur in the first homologous chromosome (with or without cleavage by the Cas protein), and the second homologous chromosome can then be modified by a gene conversion event that is stimulated by cleavage by the Cas protein on the second homologous chromosome.

Alternatively, the biallelic modification can result in a compound heterozygous modified genome. For example, the targeted modification can comprise a deletion between the first and second CRISPR RNA recognition sequences in both the first and second homologous chromosomes and an insertion of the nucleic acid insert in the first homologous chromosome but not in the second homologous chromosome. Alternatively, the targeted modification can comprise a deletion between the first and second CRISPR RNA recognition sequences as well as insertion of the nucleic acid insert in the first homologous chromosome and inactivation or disruption of the corresponding allele or locus in the second homologous chromosome. Alternatively, the biallelic modification can result in a hemizygous modified genome in which the targeted modification can comprise a deletion between the first and second CRISPR RNA recognition sequences as well as the insertion of the nucleic acid insert in the first homologous chromosome and loss or deletion of the corresponding allele or locus in the second homologous chromosome.

Homozygous and compound heterozygous (particularly hemizygous) targeted genetic modifications are advantageous because the process for making genetically modified animals with these modifications (described in more detail below) can be more efficient and less time-consuming. In many situations, such as removing a gene to study the effect of its absence, mere heterozygosity for a targeted genetic modification (i.e., modification in one allele and no change to the other allele) is not sufficient. With conventional targeting strategies, F0 generation animals that are heterozygous for a large targeted genomic deletion might be obtainable, but subsequent interbreeding of these heterozygous animals is required to produce F1 generation animals that are homozygous for the deletion. These additional breeding steps are costly and time-consuming. The capability of creating F0 generation genetically modified animals that are homozygous or compound heterozygous (particularly hemizygous) for a targeted genetic modification results in significant efficiency gains and time savings because fewer breeding steps are required.

(2) Gene Conversion or Loss of Heterozygosity

In some methods, the genome to be modified is within a cell that is heterozygous for a first allele, and the gene is modified to become homozygous for the first allele. The term heterozygous includes situations in which a genome comprises different alleles at one or more corresponding chromosomal loci (e.g., different alleles at corresponding loci on homologous chromosomes). The term homozygous includes situations in which a genome comprises the same allele at corresponding chromosomal loci (e.g., on corresponding homologous chromosomes). In some such methods, homozygosity can be achieved by the cell using the first allele as a donor sequence to repair a double-strand break in a corresponding second allele via homologous recombination, such as gene conversion. Typically, the extent of gene conversion is limited to a few hundred base pairs. See, e.g., Kasparek & Humphrey (2011) *Seminars in Cell &Dev. Biol.* 22:886-897, herein incorporated by reference in its entirety for all purposes. However, use of paired guide RNAs that direct cleavage at different cleavage sites within a single locus can promote and enhance gene conversion capabilities over longer tracts.

Such methods can be useful in several contexts. The first allele can comprise a mutation. In some methods, for example, the first allele contains a desired targeted genetic modification. Achieving homozygosity for that targeted genetic modification can result in significant time and cost savings if, for example, the goal is to create a non-human animal that is homozygous for that modification. In other methods, the first allele is a wild type allele of a gene that corresponds to a second disease-causing allele of the gene. Alternatively, the second allele can comprise any mutation. The methods can then be used to achieve the ultimate gene therapy goal of replacing the disease-causing allele with the wild type allele at its natural chromosomal locus.

In some such methods for modifying a genome that is heterozygous for a first allele to become homozygous for the first allele, the genome is contacted with a Cas protein, a tracrRNA, and a first CRISPR RNA that hybridizes to a first CRISPR RNA recognition sequence within a second allele, and a second CRISPR RNA that hybridizes to a second CRISPR RNA recognition sequence within the second allele, wherein the first allele is on a first homologous chromosome and the second allele is at a corresponding locus on a second homologous chromosome (i.e., the first allele and second allele can be corresponding alleles in a pair of first and second homologous chromosomes). Optionally, the genome can be contacted with additional CRISPR RNAs (e.g., a third CRISPR RNA, or third and fourth CRISPR RNAs) that hybridize to CRISPR RNA recognition sequences within the second allele. The Cas protein can cleave one or both of the first and second CRISPR RNA recognition sequences (i.e., at a first cleavage site within the first CRISPR RNA recognition sequence and/or at a second cleavage site within the second CRISPR RNA recognition sequence). The cleavage of the genome at the first and/or second cleavage sites can create blunt ends in the genomic DNA or can create staggered ends. The cleavage sites can then be repaired through recombination between the first and second alleles, resulting in a modified genome that is homozygous for the first allele. A cell having the modified genome can then be identified.

In some methods, the first and/or second CRISPR RNA recognition sequences are located within the second allele but not within the first allele. The first and/or second alleles can be wild type alleles or can comprise targeted modifications or other deviations from a wild type allele. For example, the first allele can comprise a desired targeted modification and the second allele can be a wild type allele. Alternatively, the first allele can be a wild type allele, and the second allele can comprise an undesired modification, such as a disease-causing mutation. In some such methods, targeted gene repair or targeted gene correction occurs such that the disease-causing mutation in the second allele is corrected via recombination using the first allele as the donor sequence.

The first and second cleavage sites or first and second CRISPR RNA recognition sequences can be separated, for example, by about 1 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb.

Alternatively, the first and second cleavage sites or first and second CRISPR RNA recognition sequences can be separated, for example, by at least 1 kb, at least 2 kb, at least 3 kb, at least 4 kb, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb.

In some methods, the sequence differences between the first allele and second allele span about 100 bp to about 200 bp, about 200 bp to about 400 bp, about 400 bp to about 600 bp, about 600 bp to about 800 bp, about 800 bp to about 1 kb, about 1 kb to about 2 kb, about 2 kb to about 3 kb, about 4 kb to about 5 kb, about 5 kb to about 10 kb, about 10 kb to about 20 kb, about 20 kb to about 40 kb, about 40 kb to about 60 kb, about 60 kb to about 80 kb, about 80 kb to about 100 kb, about 100 kb to about 150 kb, about 150 kb to about 200 kb, about 200 kb to about 300 kb, about 300 kb to about 400 kb, about 400 kb to about 500 kb, about 500 kb to about 1 Mb, about 1 Mb to about 1.5 Mb, about 1.5 Mb to about 2 Mb, about 2 Mb to about 2.5 Mb, or about 2.5 Mb to about 3 Mb.

In other methods, the differences between the first allele and the second allele span at least 100 bp, at least 200 bp, at least 300 bp, at least 400 bp, at least 500 bp, at least 600 bp, at least 700 bp, at least 800 bp, at least 800 bp, at least 1 kb, at least 2 kb, at least 3 kb, at least 4 kb, at least 5 kb, at least 6 kb, at least 7 kb, at least 8 kb, at least 9 kb, at least 10 kb, 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, at least 200 kb, at least 250 kb, at least 300 kb, at least 350 kb, at least 400 kb, at least 450 kb, or at least 500 kb.

In other such methods for modifying a genome in a cell that is heterozygous for a first allele to become homozygous for the first allele, the genome is contacted with a Cas protein, a tracrRNA, and a first non-allele-specific CRISPR RNA that hybridizes to a first CRISPR RNA recognition sequence. The first allele is on a first homologous chromosome, and the CRISPR RNA recognition sequence is centromeric (i.e., closer to the centromere) to the locus corresponding to the first allele on a second homologous chromosome. The Cas protein can cleave the first CRISPR RNA recognition sequence to generate a double-strand break. Recombination can then occur to modify the cell to become homozygous for the first allele.

Optionally, the cell is heterozygous for one or more additional alleles, the first CRISPR RNA recognition sequence is centromeric to the loci corresponding to the one or more additional alleles on the second homologous chromosome, and the recombination modifies the cell to become homozygous for the one or more additional alleles.

Optionally, the method can further comprise contacting the genome with a second non-allele-specific CRISPR RNA that hybridizes to a second CRISPR RNA recognition sequence centromeric to the locus corresponding to the first allele in the second homologous chromosome, wherein the Cas protein cleaves at least one of the first and second CRISPR RNA recognition sequences to generate at least one double-strand break. Optionally, the method can further comprise contacting the genome with additional non-allele-specific CRISPR RNAs (e.g., a third CRISPR RNA, or third and fourth CRISPR RNAs) that hybridize to CRISPR RNA recognition sequences centromeric to the locus corresponding to the first allele on a second homologous chromosome. A cell having the modified genome can then be identified.

In some methods, the first (or second, third, or fourth) CRISPR RNA recognition sequences are located on the second homologous chromosome but not the first homologous chromosome. The first (or second, third, or fourth) CRISPR RNA recognition site can be from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb from the centromere.

The first allele and/or the one or more additional alleles can comprise a mutation such as a targeted modification. Alternatively, the first allele and/or the one or more additional alleles can be a wild type allele, and the corresponding loci on the second homologous chromosome can comprise mutations such as a disease-causing mutation. The first allele can be from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb from the first CRISPR RNA recognition site. Alternatively, the first allele can be at least 100 bp, at least 1 kb, at least 10 kb, at least 100 kb, at least 1 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb or more from the first CRISPR RNA recognition site.

The Cas protein can be Cas9. It can have nuclease activity on both strands of double-stranded DNA, or it can be a nickase. In some methods, the Cas protein and the first CRISPR RNA do not naturally occur together.

The recombination can comprise loss of heterozygosity telomeric (i.e., toward the telomere) of the double-strand break (e.g., a polar or directional gene conversion or loss of heterozygosity). The region of the second homologous chromosome being replaced by loss of heterozygosity can be from about 100 bp to about 1 kb, about 1 kb to about 10 kb, about 10 kb to about 100 kb, about 100 kb to about 1 Mb, about 1 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb. Alternatively, the region of the second homologous chromosome being replaced can be at least 100 bp, at least 1 kb, at least 10 kb, at least 100 kb, at least 1 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb or more. For example, most of the chromosome can be replaced.

B. Methods of Making a Genetically Modified Non-Human Animal

Genetically modified non-human animals can be generated employing the various methods disclosed herein. In some cases, the method of producing a genetically modified non-human animal comprise: (1) modifying the genome of a pluripotent cell using the methods described above; (2) selecting the genetically modified pluripotent cell; (3) introducing the genetically modified pluripotent cell into a host embryo; and (4) implanting the host embryo comprising the genetically modified pluripotent cell into a surrogate mother. A progeny from the genetically modified pluripotent cell is generated. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be an ES cell (e.g., a mouse ES cell or a rat ES cell) as discussed elsewhere herein. See, for example, U.S. Pat. No. 7,294,754, herein incorporated by reference in its entirety for all purposes.

Alternatively, the method of producing a genetically modified non-human animal can comprise: (1) modifying the genome of a one-cell stage embryo using the methods described above; (2) selecting the genetically modified embryo; and (3) implanting the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference in its entirety for all purposes.

Some methods of making a genetically modified non-human animal comprise methods of producing an F0 generation non-human animal. Such methods can comprise contacting the genome in a non-human ES cell with a Cas protein, a first CRISPR RNA that hybridizes to a first CRISPR RNA recognition sequence, a second CRISPR RNA that hybridizes to a second CRISPR RNA recognition sequence, and a tracrRNA. The Cas protein can cleave the genome within the first and second CRISPR RNA recognition sequences to generate end sequences. The end sequences can undergo recombination to form a genome with a targeted modification, and the targeted modification can comprise a deletion between the first and second CRISPR RNA recognition sequences.

The methods can further comprise: (1) identifying a non-human ES cell comprising the targeted modification; (2) introducing the non-human ES cell comprising the targeted modification into a non-human host embryo; and (3) gestating the non-human host embryo in a surrogate mother. The surrogate mother can then produce the F0 generation non-human animal comprising the targeted modification. The host embryo comprising the genetically modified pluripotent or totipotent cell (e.g., a non-human ES cell) can be incubated until the blastocyst stage and then implanted into a surrogate mother to produce an F0 animal. Animals bearing the genetically modified genomic locus can be identified via a modification of allele (MOA) assay as described herein.

The various methods provided herein allow for the generation of a genetically modified non-human F0 animal wherein the cells of the genetically modified F0 animal that comprise the targeted modification. It is recognized that depending on the method used to generate the F0 animal, the number of cells within the F0 animal that have the nucleotide sequence of interest and lack the recombinase cassette and/or the selection cassette will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. In specific instances, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal comprises a cell population having the targeted modification. In other instances, at least one or more of the germ cells of the F0 animal have the targeted modification.

In some instances, the cells of the genetically modified F0 animal are heterozygous or compound heterozygous for the targeted modification. For example, the cells of the genetically modified F0 animal can be hemizygous for the targeted modification. In other instances, the cells of the genetically modified F0 animal are homozygous for the targeted modification.

In some cases, the F0 animal generated by the methods and compositions disclosed herein can be bred to a wild-type animal to generate an F1 generation that is heterozygous for the targeted modification. Animals from the F1 generation can then be bred to each other to generate an F2 animal homozygous for the targeted modification. The F1 progeny can be genotyped using specific primers and/or probes to determine if the targeted genetic modification is present.

C. Genomes and Target Genomic Loci

A genome or genomic target locus modified by the methods disclosed herein can include any segment or region of DNA within a cell. The genome or genomic target locus can be native to the cell, can be a heterologous or exogenous segment of DNA that was integrated into the genome of the cell, or can be a combination thereof. Such heterologous or exogenous segments of DNA can include transgenes, expression cassettes, polynucleotide encoding selection makers, or heterologous or exogenous regions of genomic DNA.

The genome or genomic target locus can also include extrachromosomal DNA within the cell, such as a yeast artificial chromosome (YAC), a bacterial artificial chromosome (BAC), a human artificial chromosome, or any other engineered genomic region contained in an appropriate host cell.

D. Forms of Cas9 and Guide RNA

In some methods, the contacting of the genome comprises introducing one or more Cas proteins, one or more CRISPR RNAs, and one or more tracrRNAs into the cell. The introducing can be accomplished by any means, and one or more of the components (e.g., two of the components, or all of the components) can be introduced into the cell simultaneously or sequentially in any combination.

A CRISPR RNA and a tracrRNA can be fused together as a guide RNA (gRNA) to be introduced into a cell. Alternatively, a CRISPR RNA and the tracrRNA can be distinct RNA molecules. A CRISPR RNA can be introduced into the cell in the form of an RNA or in the form of a DNA encoding the CRISPR RNA. Likewise, a tracrRNA can be introduced into the cell in the form of an RNA or in the form of a DNA encoding the tracrRNA, and a gRNA can be introduced into the cell in the form of an RNA or in the form of a DNA encoding the gRNA.

A Cas protein can be introduced into the cell in the form of a protein, a messenger RNA (mRNA) encoding the Cas protein, or a DNA encoding the Cas protein. In some methods, a Cas protein, a CRISPR RNA, and a tracrRNA can be introduced into the cell as a protein-RNA complex. Likewise, a Cas protein and a gRNA can be introduced into the call as a protein-RNA complex. The Cas protein can be a cell-permeable Cas protein (e.g., Cas protein with a cell-penetrating domain).

A DNA encoding a Cas protein, a CRISPR RNA, or a tracrRNA can be operably linked to a promoter active in the cell. Such DNAs can be in one or more expression constructs. In some methods, one or more of such expression constructs can be components of a single nucleic acid molecule. For example, DNAs encoding one or more Cas proteins, DNAs encoding one or more CRISPR RNAs, and DNAs encoding one or more tracrRNAs can all be components of a single nucleic acid molecule. Alternatively, they can be separated in any combination among two, three, four, or more nucleic acid molecules.

Similarly, a DNA encoding a Cas protein or a DNA encoding a gRNA can be operably linked to a promoter active in the cell. Such DNAs can also be in one or more expression constructs. In some methods, one or more of such expression constructs can be components of a single nucleic acid molecule. For example, DNAs encoding one or more Cas proteins and DNAs encoding one or more gRNAs can all be components of a single nucleic acid molecule. Alternatively, they can be separated in any combination among two, three, four, or more nucleic acid molecules.

In some methods, the Cas protein and the CRISPR RNA and/or tracrRNA do not naturally occur together. In some methods, for example, the Cas protein and the first CRISPR RNA do not naturally occur together, the Cas protein and the second CRISPR RNA do not naturally occur together, and/or the Cas protein and the tracrRNA do not naturally occur together.

In some methods, the Cas protein is a Cas9 protein. The Cas protein can be fused to a heterologous polypeptide, such as a nuclear localization signal (NLS). The Cas protein can have full cleavage activity and create double-strand breaks within the genomic DNA (e.g., a double-strand break with blunt ends), or it can be a nickase that can cleave only strand of genomic DNA.

In some methods, paired nickases are employed. For example, the genome can be contacted with first and second nickases that cleave opposite strands of DNA, whereby the genome is modified through double nicking. The first nickase can cleave a first strand of genomic DNA (i.e., the complementary strand), and the second nickase can cleave a second strand of genomic DNA (i.e., the non-complementary strand). Alternatively, both nickases can cleave the same strand. The first and second nickases can be created, for example, by mutating a catalytic residue in the RuvC domain (e.g., the D10A mutation described elsewhere herein) of the first nickase and mutating a catalytic residue in the HNH domain (e.g., the H840A mutation described elsewhere herein) of the second nickase. Alternatively, the first nickase can be used to create both nicks.

In some such methods, the double nicking can be employed to create one or more double-strand breaks having staggered ends. For example, the double nicking is employed to create staggered ends at first and second cleavage sites. The first nickase can cleave the first strand of DNA within first and second CRISPR RNA recognition sequences to which first and second CRISPR RNAs hybridize, and the second nickase can cleave the second strand of DNA within third and fourth target CRISPR RNA recognition sequences to which third and fourth CRISPR RNAs hybridize. Alternatively, the first nickase can be used to nick the first, second, third, and fourth CRISPR RNA recognition sequences. The first and third target CRISPR RNA recognition sequences can be positioned to create a first cleavage site such that the nicks created by the first and second nickases on the first and second strands of DNA create a double-strand break (i.e., the first cleavage site comprises the nicks within the first and third CRISPR RNA recognition sequences). Likewise, the second and fourth CRISPR RNA recognition sequences can be positioned to create a second cleavage site such that the nicks created by the first and second nickases on the first and second strands of DNA create a double-strand break (i.e., the second cleavage site comprises the nicks within the second and fourth CRISPR RNA recognition sequences). In some cases, the nicks within the first and third CRISPR RNA recognition sequences and/or the second and fourth CRISPR RNA recognition sequences can be off-set nicks. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes.

E. Methods of Introducing Nucleic Acids and Proteins into Cells

Various methods and compositions are provided herein to allow for introduction of a nucleic acid into a cell. In some cases, the system employed for introducing the nucleic acid allows for the targeted integration at a specific genomic locus. Such systems employ a variety of components and for ease of reference, the term "targeted genomic integration system" generically includes all the components required for an integration event (e.g., one or more of nuclease agents, nuclease cleavage sites, insert DNA polynucleotides, targeting vectors, target genomic loci, and polynucleotides of interest).

The methods provided herein can comprise introducing into a cell one or more polynucleotides or polypeptide constructs comprising one or more components of a targeted genomic integration system. "Introducing" includes presenting to the cell the sequence (polypeptide or polynucleotide) in such a manner that the sequence gains access to the interior of the cell. The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

In some cases, the cells employed in the methods and compositions have a DNA construct stably incorporated into their genome. For example, a cell employed in the methods disclosed herein may have a preexisting Cas-encoding gene stably incorporated into its genome (i.e., a Cas-ready cell). "Stably incorporated" or "stably introduced" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc Natl Acad Sci USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

In some cases, the introduction of nucleic acids or proteins into a cell is mediated by electroporation, by intracytoplasmic injection, by viral infection, by adenovirus, by lentivirus, by retrovirus, by transfection, by lipid-mediated transfection, or by Nucleofection™.

Introduction of nucleic acids or proteins into a cell (e.g., a one-cell stage embryo) can also be accomplished by microinjection. In one-cell stage embryos, microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a nucleic acid molecule encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, N.Y.: Cold Spring Harbor Laboratory Press); Meyer et al. (2010) *Pros Natl Acad Sci USA* 107:15022-15026 and Meyer et al. (2012) *Proc Natl Acad Sci USA* 109:9354-9359, each of which is herein incorporated by reference in its entirety for all purposes.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

When both nuclease agents and targeting vectors (e.g., LTVECs for cells other than one-cell stage embryos) are introduced into the cell, they can be introduced simultaneously. Alternatively, the nuclease agent can be introduced separately from the targeting vector. For example, the nuclease agent can be introduced prior to the introduction of the targeting vector, or it can be introduced following introduction of the targeting vector.

F. Mechanisms of Recombination and Methods for Altering Prevalence of Non-Homologous End Joining, Gene Conversion, or Homologous Recombination Recombination includes any process of exchange of genetic information between two polynucleotides and can occur by any mechanism. Recombination in response to double-strand breaks (DSBs) occurs principally through two conserved DNA repair pathways: non-homologous end joining (NHEJ) and homologous recombination (HR). See Kasparek & Humphrey (2011) *Seminars in Cell &Dev. Biol.* 22:886-897, herein incorporated by reference in its entirety for all purposes. NHEJ includes the repair of double-strand breaks in a nucleic acid by direct ligation of the break ends to one another without the need for a homologous template. Ligation of non-contiguous sequences by NHEJ can often result in deletions, insertions, or translocations near the site of the double-strand break. Recombination can also occur via homology directed repair (HDR) or homologous recombination (HR). HDR or HR includes a form of nucleic acid repair that can require nucleotide sequence homology, uses a "donor" molecule to template repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA.

In the context of modifying the genome of a cell that is heterozygous for an allele to become homozygous for that allele, recombination can include any means by which homozygous cells are derived from heterozygous cells. Such means can include, for example, loss of heterozygosity (LOH), gene conversion, or crossover events occurring by any known recombination mechanism. Without wishing to be bound by theory, LOH can occur, for example, via mitotic recombination, with or without gene conversion, or via chromosome loss and duplication. See, e.g., Lefebvre et al. (2001) *Nat. Genet.* 27:257-258, herein incorporated by reference in its entirety for all purposes. Gene conversion in this context can include unidirectional transfer of genetic material from a donor sequence to a highly homologous acceptor (i.e., the non-reciprocal exchange of genetic information from one molecule to its homologue). Gene conversion includes any means for copying of an allele by any known recombination mechanism. For example, gene conversion can involve the non-reciprocal transfer of genetic information from an intact sequence to a homologous region containing a double-strand break, and it can occur between sister chromatids, homologous chromosomes, or homologous sequences on either the same chromatid or on different chromosomes. See, e.g., Chen et al. (2007) *Nat. Rev. Genet.* 8:762-775, herein incorporated by reference in its entirety for all purposes. In specific cases, gene conversion results directly from homologous recombination as a result of copying genetic information from a homologous chromosome. This can lead to localized loss of heterozygosity (LOH) when the homologous sequences are non-identical.

As an example, LOH could occur through reciprocal chromatid exchange by mitotic cross over, or by chromatid copying by break-induced replication. In either case, a heterozygous modification could occur in which one chromosome is targeted before genome replication. Alternatively, a single chromatid could be targeted after genome replication, followed by inter-chromatid gene conversion.

In any of the methods disclosed herein, the cell can be a cell that has been modified to increase or decrease NHEJ activity. Likewise, the cell can be a cell that has been modified to increase gene conversion or HDR activity. Such modifications can comprise modifications in the expression or activity of genes involved in regulating NHEJ, gene conversion, and/or HDR. For example, decreasing the activity of NHEJ and/or increasing the activity of HDR can promote biallelic collapsing of genomic regions between CRISPR RNA recognition sequences corresponding to two gRNAs. Without wishing to be bound by any particular theory, one mechanism by which a biallelic genomic collapse can occur is by NHEJ-mediated repair or HDR-mediated repair within a first allele and creation of an identical second allele via HDR mechanisms, such as gene conversion (see Example 1). Thus, promoting HDR-mediated pathways (e.g., by decreasing NHEJ activity or by increasing HDR activity can also promote biallelic collapsing of genomic regions. Similarly, without wishing to be bound by any particular theory, conversion of a heterozygous cell to a homozygous cell by using paired guide RNAs that target a single locus can be promoted if NHEJ activity is decreased and HDR activity (e.g., gene conversion activity) is correspondingly increased.

Inhibitors can be used to increase or decrease NHEJ activity or to increase or decrease HDR activity. Such inhibitors can be, for example, small molecules or inhibitory nucleic acids such as short interfering nucleic acids (e.g., short interfering RNA (siRNA), double-stranded RNA (dsRNA), micro-RNA (miRNA), and short hairpin RNA (shRNA)) or antisense oligonucleotides specific for a gene transcript. Inhibitors can be directed at enzymes involved in NHEJ or HDR or their upstream regulation by post-translational modification via, for example, phosphorylation, ubiquitylation, and sumoylation.

In mammalian cells, NHEJ is the predominant DSB repair mechanism and is active throughout the cell cycle. In vertebrates, the "canonical" or "classical" NHEJ pathway (C-NHEJ) requires several core factors, including DNA-PK, Ku70-80, Artemis, ligase IV (Lig4), XRCC4, CLF, and Pol μ to repair a DSB. See Kasparek & Humphrey (2011) *Seminars in Cell &Dev. Biol.* 22:886-897, herein incorporated by reference in its entirety for all purposes. During NHEJ, DNA ends are bound by the highly abundant end-protecting Ku protein, which functions as a docking station for loading of the other NHEJ components.

Thus, in some of the methods disclosed herein, the cell has been modified to reduce or eliminate or to increase the expression or activity of factors involved in C-NHEJ. For example, in some methods, the cell has been modified to reduce or eliminate DNA-PK, Ku70-80, Artemis, ligase IV (Lig4), XRCC4, CLF, and/or Pol μ expression or activity. In specific methods, the cell has been modified to reduce or eliminate DNA-PK expression or activity or to increase DNA-PK expression or activity (e.g., expression or activity of DNA-PKcs; exemplary UniProt sequence designated P97313). Examples of DNA-PKcs inhibitors include, for example, NU7026, and NU7441. See, e.g., U.S. Pat. No. 6,974,867, herein incorporated by reference in its entirety for all purposes. In specific methods, the cell has been modified to reduce or eliminate ligase IV expression or activity or to increase ligase IV expression or activity. An example of a ligase IV inhibitor is SCR7.

Inhibitors targeting cell cycle checkpoint proteins like ATM (e.g., KU55933), CHK1/CHK2 (e.g., KLD1162 or CHIR-124) and ATR (e.g., VE 821) can also be used to either synergistically enhance the effects of specific DNA repair inhibitors or to prevent unintended side-effects like cell cycle arrest and/or apoptosis (see Ciccia et al. (2010) *Mol Cell* 40:179, herein incorporated by reference in its entirety for all purposes).

Disruption of C-NHEJ can increase levels of abnormal joining mediated by "alternative" NHEJ (A-NHEJ) pathways and can also increase HR repair. A-NHEJ pathways display a bias towards microhomology-mediated joins and follow slower kinetics than C-NHEJ. Several factors, including the MRN complex (MRE11, RAD50, NBS1), CtIP, XRCC1, PARP, Lig1, and Lig3 have been proposed to participate. See Kasparek & Humphrey (2011) *Seminars in Cell &Dev. Biol.* 22:886-897 and Claybon et al. (2010) *Nucleic Acids Res.* 38(21):7538-7545, each of which is herein incorporated by reference in its entirety for all purposes.

Thus, in some of the methods disclosed herein, the cell has been modified to reduce or eliminate or to increase the expression or activity of factors involved in A-NHEJ. For example, in some methods, the cell has been modified to reduce or eliminate MRE11, RAD50, NBS1, CtIP, XRCC1, PARP (e.g., PARP1), Lig1, and/or Lig3 expression or activity. In other methods, the cell has been modified to increase MRE11, RAD50, NBS1, CtIP, XRCC1, PARP (e.g., PARP1), Lig1, and/or Lig3 expression or activity. In specific methods, the cell has been modified to reduce or eliminate PARP1 expression or activity or to increase PARP1 expression or activity (exemplary UniProt sequence designated P11103). Examples of PARP inhibitors (e.g., NU1025, Iniparib, Olaparib) include nicotinamides; isoquinolinones and dihydroisoquinolinones; benzimidazoles and indoles; phthalazin-1(2H)-ones and quinazolinones; isoindolinones and analogues and derivatives thereof; phenanthridines and phenanthridinones; benzopyrones and analogues and derivatives thereof; unsaturated hydroximic acid derivatives and analogues and derivatives thereof; pyridazines, including fused pyridazines and analogues and derivatives thereof and/or other compounds such as caffeine, theophylline, and thymidine, and analogues and derivatives thereof. See, e.g., U.S. Pat. No. 8,071,579, herein incorporated by reference in its entirety for all purposes.

C-NHEJ also exhibits a competitive relationship with HR such that disrupting C-NHEJ can also lead to increased HR repair. Such competition between NHEJ and HR can be exploited as disrupting NHEJ can lead to enhanced gene targeting through reduced random integration and possibly increased target integration by homologous recombination.

There are several forms of homologous recombination repair, including single-strand annealing, gene conversion, crossovers, and break-induced replication. Single-strand annealing is a minor form of HR repair in which homologous single-stranded sequences on either side of a resected DSB anneal, resulting in chromosome reconstitution. Single-strand annealing generates deletions of varying size, depending on the distance separating the two regions of sequence homology. Gene conversion includes the non-reciprocal exchange of genetic information from one molecule to its homologue, resulting directly from HR as a result of copying genetic information from a homologous chromosome. This can lead to localized LOH when the homologous sequences are non-identical. Normally, the extent of gene conversion is limited to a few hundred base pairs. However, long tract gene conversion has been reported in some genetic backgrounds, including RAD51C deficiency. See Nagaraju et al. (2006) *Mol. Cell. Biol.* 26:8075-8086, herein incorporated by reference in its entirety for all purposes. Crossovers can occur, for example, between homologous chromosomes, and have the potential to lead to reciprocal translocations if occurring in G1 or non-reciprocal translocations and LOH extending from the break site to the distal telomere if occurring in G2. Break-induced replication is a variant of HR in which following strand invasion, DNA replication continues through to the end of the chromosome. Thus, there are many mechanisms by which HR can promote LOH.

Thus, in some of the methods disclosed herein, the cell has been modified to reduce or eliminate or to increase the expression or activity of factors involved in HR. For example, in some methods, the cell has been modified to increase RAD51, RAD52, RAD54, RAD55, RAD51C, BRCA1, and/or BRCA2 expression or activity. In other methods, the cell has been modified to reduce or eliminate RAD51, RAD52, RAD54, RAD55, RAD51C, BRCA1, and/or BRCA2 expression or activity.

In some methods, the expression or activity of yet other proteins involved in regulating NHEJ and/or HR can be altered. For example, in some methods, the cell has been modified to reduce or eliminate Chk2 expression or activity, to reduce or eliminate Clspn expression or activity, to reduce or eliminate Setd2 expression or activity, to increase Kat2a expression or activity, and/or to increase Rad51 expression or activity. In other methods, the cell has been modified to increase Chk2 expression or activity, to increase Clspn expression or activity, to increase Setd2 expression or activity, to reduce or eliminate Kat2a expression or activity, and/or to reduce or eliminate Rad51 expression or activity.

Chk2 (also known as Chek2 and Rad53; *S. pombe* homolog is Cds1) is a serine/threonine protein kinase required for checkpoint-mediated cell cycle arrest, activation of DNA repair, and apoptosis in response to the presence of DNA double-strand breaks. See Blaikley et al. (2014) *Nucleic Acids Research* 42:5644-5656, herein incorporated by reference in its entirety for all purposes. Clspn (also known as Claspin; *S. pombe* homolog is Mrc1) is a protein required for checkpoint mediated cell cycle arrest in response to DNA damage. Deletion of homologs of Chk2 or Clspn in *S. pombe* has been reported to result in a hyper-recombinant phenotype exhibiting significantly elevated levels of break-induced gene conversion compared to wild type. Specifically, levels of gene conversion were reported to be significantly increased, whereas levels of non-homologous end joining (NHEJ), sister chromatid conversion (SCC), and loss of heterozygosity (LOH) were reported to be decreased. See Blaikley et al. (2014) *Nucleic Acids Research* 42:5644-5656.

Kat2a (also known as Gcn5 and Gcn512) is a ubiquitous histone acetyltransferase that promotes transcriptional activation and has been reported to be associated with double-strand break repair. Kat2a-dependent histone H3 lysine 36 (H3K36) acetylation increases chromatin accessibility, increases resection, and promotes homologous recombination while suppressing non-homologous end joining. See Pai et al. (2014) *Nat. Commun.* 5:4091, herein incorporated by reference in its entirety for all purposes. Setd2 (also known as Kiaa1732, Kmt3a, and Set2) is a histone methyltransferase that specifically trimethylates lysine 36 of histone H3 (H3K36me3) using demethylated lysine 36 (H3K36me2) as a substrate. Setd2-dependent H3K36 methylation reduces chromatin accessibility, reduces resection, and promotes NHEJ. See Pai et al. (2014) *Nat. Commun.* 5:4091.

Rad 51 (also known as Reca, Rad51A, and DNA repair protein Rad51 homolog 1) is a protein that functions with Rad52 and other proteins to effect strand exchange during homologous recombination, forming heteroduplex DNA that is resolved by mismatch repair to yield a gene conversion tract. In mammalian cells, Rad51 and Rad52 overexpression have been reported to increase the frequency of homologous recombination and gene conversion. See Yanez & Porter (1999) *Gene Ther.* 6:1282-1290 and Lambert & Lopez (2000) *EMBO J.* 19:3090-3099, herein incorporated by reference in its entirety for all purposes.

Modifications in the expression or activity of genes involved in regulating NHEJ, gene conversion, and/or homology-directed repair can be spatially or temporally specific and can also be inducible or temporary and reversible. For example, various forms of cassettes can be constructed to allow for deletion in specific cell or tissue types, at specific developmental stages, or upon induction. Such cassettes can employ a recombinase system in which the cassette is flanked on both sides by recombinase recognition sites and can be removed using a recombinase expressed in the desired cell type, expressed at the desired developmental stage, or expressed or activated upon induction. Such cassettes can further be constructed to include an array of pairs of different recombinase recognition sites that are placed such that null, conditional, or combination conditional/null alleles can be generated, as described in US 2011/0104799, herein incorporated by reference in its entirety for all purposes. Regulation of recombinase genes can be controlled in various ways, such as by operably linking a recombinase gene to a cell-specific, tissue-specific, or developmentally regulated promoter (or other regulatory element), or by operably linking a recombinase gene to a 3'-UTR that comprises a recognition site for an miRNA that is active only in particular cell types, tissue types, or developmental stages. A recombinase can also be regulated, for example, by employing a fusion protein placing the recombinase under the control of an effector or metabolite (e.g., CreER$^{T2}$, whose activity is positively controlled by tamoxifen), or by placing the recombinase gene under the control of an inducible promoter (e.g., one whose activity is controlled by doxycycline and TetR or TetR variants). Examples of various forms of cassettes and means of regulating recombinase genes are provided, for example, in U.S. Pat. Nos. 8,518,392; 8,354,389; and 8,697,851, each of which is incorporated by reference in its entirety.

G. Cells and Animals

Various compositions and methods provided herein employ cells, such as cells from an animal. Such cells can be from a non-human animal. Such cells can be eukaryotic cells, including, for example, fungal cells (e.g., yeast), plant cells, animal cells, mammalian cells, and human cells. A mammalian cell can be, for example, a non-human mammalian cell, a human cell, a rodent cell, a rat cell, a mouse cell, a hamster cell, a fibroblast, or a CHO cell. The eukaryotic cell can be a totipotent cell, a pluripotent cell, such as a non-human pluripotent cell (e.g., a mouse embryonic stem (ES) cell or a rat ES cell) or a human pluripotent cell, or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, embryonic stem (ES) cells or ES-like cells, such as an induced pluripotent stem (iPS) cells. Embryonic stem cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

A eukaryotic cell can also be a cell that is not a primary somatic cell. Somatic cells can include any cell that is not a gamete, germ cell, gametocyte, or undifferentiated stem cell.

Eukaryotic cells also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

Eukaryotic cells also include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK 293 cells), and mouse embryonic fibroblast cells (e.g., 3T3 cells). Numerous types of immortalized cells are well known in the art.

Immortalized or primary cells include cells that are typically used for culturing or for expressing recombinant genes or proteins.

Eukaryotic cells can also include one-cell stage embryos (i.e., fertilized oocytes or zygotes). Such one-cell stage embryos can be from any genetic background (e.g., BALB/c, C57BL/6, 129, or a combination thereof), can be fresh or frozen, and can be derived from natural breeding or in vitro fertilization.

The term "animal," in reference to cells, pluripotent and/or totipotent cells, ES cells, donor cells, and/or host embryos, includes mammals, fishes, and birds. Mammals include, for example, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, for example, chickens, turkeys, ostrich, geese, ducks, etc. Domesticated animals and agricultural animals are also included. The term "non-human animal" excludes humans.

Mouse pluripotent and/or totipotent cells can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2. See, for example, Festing et al. (1999) *Mammalian Genome* 10:836), herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Mouse pluripotent and/or totipotent cells can also be from a mix of an aforementioned 129 strain and an aforementioned C57BL/6 strain (e.g., 50% 129 and 50% C57BL/6). Likewise, mouse pluripotent and/or totipotent calls can be from a mix of aforementioned 129 strains or a mix of aforementioned BL/6 strains (e.g., the 129S6 (129/SvEvTac) strain) A specific example of a mouse ES cell is a VGF1 mouse ES cell. See, for example, Auerbach et al. (2000) *Biotechniques* 29, 1024-1028, 1030, 1032, herein incorporated by reference in its entirety for all purposes.

A rat pluripotent and/or totipotent cell can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of a rat ES cell line from a DA rat are the DA.2B rat ES cell line and the DA.2C rat ES cell line. In some cases, the rat pluripotent and/or totipotent cells are from an inbred rat strain. See, e.g., U.S. 2014/0235933 A1, filed on Feb. 20, 2014, and herein incorporated by reference in its entirety for all purposes.

Examples of human pluripotent cells include human ES cells, human adult stem cells, developmentally restricted human progenitor cells, and human induced pluripotent stem (iPS) cells, such as primed human iPS cells and naïve human iPS cells. Induced pluripotent stem cells include pluripotent stem cells that can be derived directly from a differentiated adult cell. Human iPS cells can be generated by introducing specific sets of reprogramming factors into a cell which can include, for example, Oct3/4, Sox family transcription factors (e.g., Sox1, Sox2, Sox3, Sox15), Myc family transcription factors (e.g., c-Myc, 1-Myc, n-Myc), Krüppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, e.g., Takahashi and Yamanaka (2006) *Cell* 126:663-676, herein incorporated by reference in its entirety for all purposes. Primed human ES cells and primed human iPS cells include cells that express characteristics similar to those of post-implantation epiblast cells and are committed for lineage specification and differentiation. Naïve human ES cells and naïve human iPS cells include cells that express characteristics similar to those of ES cells of the inner cell mass of a pre-implantation embryo and are not committed for lineage specification. See, e.g., Nichols and Smith (2009) *Cell Stem Cell* 4:487-492, herein incorporated by reference in its entirety for all purposes.

Cells that have been implanted into a host embryo can be referred to as "donor cells." The genetically modified pluripotent and/or totipotent cell can be from the same strain as the host embryo or from a different strain. Likewise, the surrogate mother can be from the same strain as the genetically modified pluripotent and/or totipotent cell and/or the host embryo, or the surrogate mother can be from a different strain as the genetically modified pluripotent and/or totipotent cell and/or the host embryo.

A variety of host embryos can be employed in the methods and compositions disclosed herein. For example, the pluripotent and/or totipotent cells having the targeted genetic modification can be introduced into a pre-morula stage embryo (e.g., an 8-cell stage embryo) from a corresponding organism. See, e.g., U.S. Pat. Nos. 7,576,259, 7,659,442, 7,294,754, and US 2008/0078000 A1, each of which is herein incorporated by reference in its entirety for all purposes. In other cases, the donor ES cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo, an uncompacted morula stage embryo, or a compacted morula stage embryo. When employing a mouse embryo, the host embryo stage can be a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York, herein incorporated by reference in its entirety for all purposes. For example, the Theiler Stage can be selected from TS1, TS2, TS3, and TS4. In some cases, the host embryo comprises a zona pellucida, and the donor cell is an ES cell that is introduced into the host embryo through a hole in the zona pellucida. In other cases, the host embryo is a zona-less embryo. In yet other cases, the morula-stage host embryo is aggregated.

H. Methods of Identifying Cells with Modified Genomes

Some of the above methods further comprise identifying a cell having a modified genome. Various methods can be used to identify cells having a targeted modification, such as a deletion or an insertion. Such methods can comprise identifying one cell having the targeted modification at a target locus (e.g., between first and second CRISPR RNA recognition sequences). Screening can be done to identify such cells with modified genomic loci.

The screening step can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

The screening step can also comprise a retention assay, which is an assay used to distinguish between correct targeted insertions of a nucleic acid insert into a target genomic locus from random transgenic insertions of the nucleic acid insert into genomic locations outside of the target genomic locus. Conventional assays for screening for targeted modifications, such as long-range PCR or Southern blotting, link the inserted targeting vector to the targeted locus. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/0178879 and Frendewey et al. (2010) *Methods Enzymol.* 476:295-307, herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TaqMan® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TaqMan® amplifications (each with its respective probe) are performed. One TaqMan® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TaqMan® probes, i.e. a less abundant sequence requires more cycles of PCR to reach the threshold cycle. Decreasing by half the number of copies of the template sequence for a TaqMan® reaction will result in an increase of about one Ct unit. TaqMan® reactions in cells where one allele of the target gene(s) or locus(loci) has been replaced by homologous recombination will result in an increase of one Ct for the target TaqMan® reaction without an increase in the Ct for the reference gene when compared to DNA from non-targeted cells. For a GOA assay, another TaqMan® probe can be used to determine the Ct of the nucleic acid insert that is replacing the targeted gene(s) or locus(loci) by successful targeting.

Because paired gRNAs can create large Cas-mediated deletions at a target genomic locus, it can be useful augment standard LOA and GOA assays to verify correct targeting by LTVECs (i.e., in cells other than one-cell stage embryos). For example, LOA and GOA assays alone may not distinguish correctly targeted cell clones from clones in which a large Cas-induced deletion of the target genomic locus coincides with random integration of a LTVEC elsewhere in the genome, particularly if the GOA assay employs a probe against a selection cassette within the LTVEC insert. Because the selection pressure in the targeted cell is based on the selection cassette, random transgenic integration of the LTVEC elsewhere in the genome will generally include the selection cassette and adjacent regions of the LTVEC but will exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, generally the 3' homology arm but not the 5' homology arm will be transgenically integrated with the selection cassette. Alternatively, if the selection cassette adjacent to the 5' homology arm, generally the 5' homology arm but not the 3' homology arm will be transgenically integrated with the selection cassette. As an example, if LOA and GOA assays are used to assess targeted integration of the LTVEC, and the GOA assay utilizes probes against the selection cassette, a heterozygous deletion at the target genomic locus combined with a random transgenic integration of the LTVEC will give the same readout as a heterozygous targeted integration of the LTVEC at the target genomic locus. To verify correct targeting by the LTVEC, retention assays can be used, alone or in conjunction with LOA and/or GOA assays.

Retention assays determine copy numbers of a DNA template in the 5' target sequence (corresponding to the 5' homology arm of the LTVEC) and/or the 3' target sequence (corresponding to the 3' homology arm of the LTVEC). In particular, determining the copy number of a DNA template in the target sequence corresponding to the homology arm that is adjacent to the selection cassette is useful. In diploid cells, copy numbers greater than two generally indicate transgenic integration of the LTVEC randomly outside of the target genomic locus rather than at the target genomic locus, which is undesirable. Correctly targeted clones will retain a copy number of two. In addition, copy numbers of less than two in such retention assays generally indicate large Cas-mediated deletions extending beyond the region targeted for deletion, which are also undesirable.

In an exemplary retention assay for identifying a targeted insertion of a nucleic acid insert at a target genomic locus in a diploid cell, DNA is first obtained from a cell that has been contacted with a large targeting vector (LTVEC) comprising the nucleic acid insert flanked by a first homology arm that hybridizes to a first target sequence and a second homology arm that hybridizes to a second target sequence, wherein the nucleic acid insert comprises a selection cassette adjacent to the first homology arm. Optionally, the selection cassette can comprise a drug resistance gene. The DNA is then exposed a probe that binds within the first target sequence, a probe that binds within the nucleic acid insert, and a probe that binds within a reference gene having a known copy number, wherein each probe generates a detectable signal upon binding. Signals from the binding of each of the probes are then detected. The signal from the reference gene probe is compared to the signal from the first target sequence probe to determine a copy number for the first target sequence, and the signal from the reference gene probe is compared to the signal from the nucleic acid insert probe to determine a copy number for the nucleic acid insert. A nucleic acid insert copy number of one or two and a first target sequence copy number of two generally indicates targeted insertion of the nucleic acid insert at the target genomic locus, and a nucleic acid insert copy number of one or more and a first target sequence copy number of three or more generally indicates a random insertion of the nucleic acid insert at a genomic locus other than the target genomic locus.

The signal from the binding of the first target sequence probe can be used to determine a threshold cycle (Ct) value for the first target sequence, the signal from the binding of the reference gene probe can be used to determine a threshold cycle (Ct) value for the reference gene, and the copy number of the first target sequence can be determined by comparing the first target sequence Ct value and the reference gene Ct value. Likewise, the signal from the binding of the nucleic acid insert probe can be used to determine a threshold cycle (Ct) value for the nucleic acid insert, and the copy number of the nucleic acid insert can be determined by comparing the first target sequence Ct value and the reference gene Ct value.

The nucleic acid insert in the LTVEC can be, for example, at least 5 kb, at least 10 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb. The distance between the sequences to which the probes bind in the first target sequence and the selection cassette can be, for example, no more than 100 nucleotides, 200 nucleotides, 300 nucleotides, 400 nucleotides, 500 nucleotides, 600 nucleotides, 700 nucleotides, 800 nucleotides, 900 nucleotides, 1 kb, 1.5 kb, 2 kb, 2.5 kb, 3 kb, 3.5 kb, 4 kb, 4.5 kb, or 5 kb.

Such methods can further comprise additional retention assays to determine the copy number of the second target sequence. For example, such methods can further comprise exposing the DNA of the cell to a probe that binds the second target sequence, detecting the signal from the binding of second target sequence probe, and comparing the signal from the reference gene probe to the signal from the second target sequence probe to determine a copy number for the second target sequence.

Likewise, such methods can further comprise additional GOA assays to determine the copy number of one or more additional sequences within the nucleic acid insert. For example, such methods can further comprise exposing the DNA of the cell to one or more additional probes that bind the nucleic acid insert, detecting the signal from the binding of the one or more additional probes, and comparing the signal from the reference gene probe to the signal from the one or more additional nucleic acid insert probes to determine copy numbers for the one or more additional sequences within the nucleic acid insert.

Likewise, when the LTVEC is designed to delete an endogenous sequence from the target genomic locus or when paired gRNAs are used (e.g., to create paired double-strand breaks at different sites within a single genomic target locus and delete the intervening endogenous sequence), such methods can further comprise a LOA assay to determine the copy number of the endogenous sequences at target genomic locus. For example, such methods can further comprise exposing the DNA of the cell to a probe that binds the endogenous sequence at the target genomic locus, detecting the signal from the binding of the endogenous sequence probe, and comparing the signal from the reference gene probe to the signal from the endogenous sequence probe to determine a copy number for the endogenous sequence.

Other examples of suitable quantitative assays include fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, or Eclipse™ probe technology (see, for example, US2005/0144655, herein incorporated by reference in its entirety for all purposes).

For targeted genetic modifications generated without the use of LTVECs, conventional assays for screening for targeted modifications, such as long-range PCR, Southern blotting, or Sanger sequencing, can be used. Such assays typically are used to obtain evidence for a linkage between the inserted targeting vector and the targeted genomic locus. For example, for a long-range PCR assay, one primer can recognize a sequence within the inserted DNA while the other recognizes a target locus sequence beyond the ends of the targeting vector's homology arms.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

TABLE 1

Description of Sequences.

| SEQ ID NO | Type | Description |
|---|---|---|
| 1 | RNA | gRNA |
| 2 | RNA | gRNA |
| 3 | RNA | crRNA |
| 4 | RNA | crRNA |
| 5 | RNA | crRNA |
| 6 | RNA | tracrRNA |
| 7 | RNA | tracrRNA |
| 8 | DNA | CRISPR RNA recognition sequence |
| 9 | DNA | CRISPR RNA recognition sequence |
| 10 | DNA | CRISPR RNA recognition sequence |
| 11 | DNA | C5 (Hc) gRNA A DNA-targeting segment (100 bp from target locus endpoint) |
| 12 | DNA | C5 (Hc) gRNA B DNA-targeting segment (500 bp from target locus endpoint) |
| 13 | DNA | C5 (Hc) gRNA C DNA-targeting segment (38200 and 37500 bp from target locus endpoints) |
| 14 | DNA | C5 (Hc) gRNA D DNA-targeting segment (43500 and 32200 bp from target locus endpoints) |
| 15 | DNA | C5 (Hc) gRNA E DNA-targeting segment (500 bp from target locus endpoint) |
| 16 | DNA | C5 (Hc) gRNA E2 DNA-targeting segment (100 bp from target locus endpoint) |

TABLE 1-continued

Description of Sequences.

Figure 5:
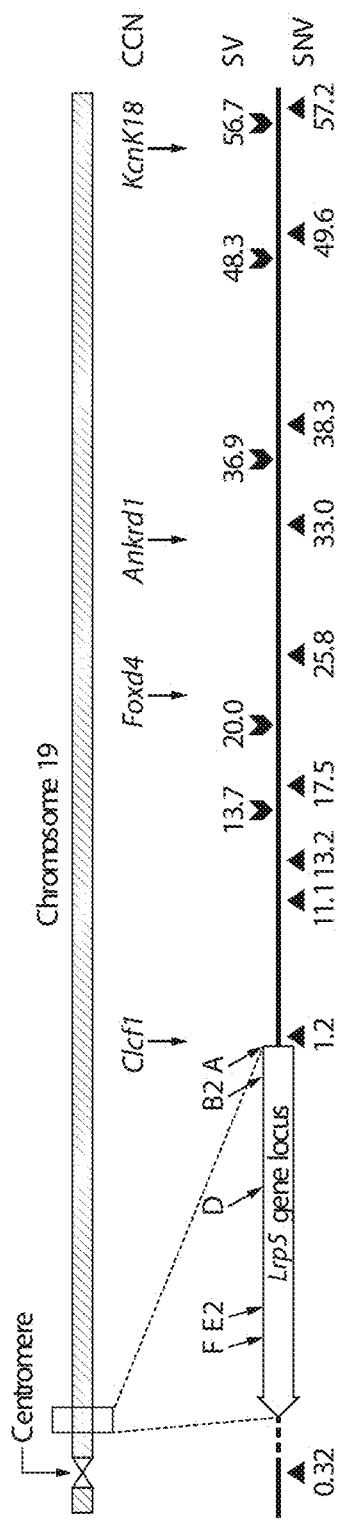
FIG. 5 shows a schematic of chromosome 19 with assays designed to examine gene conversion or mitotic recombination events mediated by two guide RNAs by analyzing loss of heterozygosity (LOH) in VGF1 hybrid ES cells. The approximate positions of TaqMan® qPCR chromosomal copy number (CCN) assays are shown by arrows. The approximate positions of the structural variant (SV) polymorphism PCR assays are shown by chevrons with their distances (in Mb) from the Lrp5 locus given above. The approximate positions of the single nucleotide variant (SNV) TaqMan® allelic discrimination assays are shown by arrowheads with their distances (in Mb) from the Lrp5 locus given below. The positions of the gRNA recognition sites for F, E2, D, B2, and A are shown by diagonal arrows above the representation of the Lrp5 gene.

| SEQ ID NO | Type | Description |
|---|---|---|
| 17 | DNA | Lrp5 gRNA A DNA-targeting segment (50 bp from target locus end point) |
| 18 | DNA | Lrp5 gRNA B DNA-targeting segment (500 bp from target locus end point) |
| 19 | DNA | Lrp5 gRNA B2 DNA-targeting segment (1000 bp from target locus end point) |
| 20 | DNA | Lrp5 gRNA C DNA-targeting segment (29900 and 38430 bp from target locus end points) |
| 21 | DNA | Lrp5 gRNA D DNA-targeting segment (29950 and 38380 bp from target locus end points) |
| 22 | DNA | Lrp5 gRNA E2 DNA-targeting segment (1000 bp from target locus end point) |
| 23 | DNA | Lrp5 gRNA E DNA-targeting segment (500 bp from target locus end point) |
| 24 | DNA | Lrp5 gRNA F DNA-targeting segment (50 bp from target locus end point) |
| 25 | DNA | Ror1 gRNA A DNA-targeting segment (200 bp from target locus end point) |
| 26 | DNA | Ror1 gRNA B DNA-targeting segment (1000 bp from target locus end point) |
| 27 | DNA | Ror1 gRNA D DNA-targeting segment (54300 and 55500 bp from target locus end points) |
| 28 | DNA | Ror1 gRNA C DNA-targeting segment (54500 and 55300 bp from target locus end points) |
| 29 | DNA | Ror1 gRNA E DNA-targeting segment (1000 bp from target locus end point) |
| 30 | DNA | Ror1 gRNA F DNA-targeting segment (200 bp from target locus end point) |
| 31 | DNA | Trpa1 gRNA A DNA-targeting segment (100 bp from target locus end point) |
| 32 | DNA | Trpa1 gRNA A2 DNA-targeting segment (500 bp from target locus end point) |
| 33 | DNA | Trpa1 gRNA B DNA-targeting segment (1000 bp from target locus end point) |
| 34 | DNA | Trpa1 gRNA C DNA-targeting segment (25600 and 19740 bp from target locus end points) |
| 35 | DNA | Trpa1 gRNA D DNA-targeting segment (26970 and 18370 bp from target locus end points) |
| 36 | DNA | Trpa1 gRNA E2 DNA-targeting segment (1000 bp from target locus end point) |
| 37 | DNA | Trpa1 gRNA E DNA-targeting segment (500 bp from target locus end point) |
| 38 | DNA | Trpa1 gRNA F DNA-targeting segment (100 bp from target locus end point) |
| 39 | DNA | 190045 forward primer |
| 40 | DNA | 190061 forward primer |
| 41 | DNA | 190068 forward primer |
| 42 | DNA | 190030 forward primer |
| 43 | DNA | 190033 forward primer (same as forward primer for SV 48.3 in FIG. 5) |
| 44 | DNA | 190013 forward primer |
| 45 | DNA | 190045 reverse primer |
| 46 | DNA | 190061 reverse primer |
| 47 | DNA | 190068 reverse primer |
| 48 | DNA | 190030 reverse primer |
| 49 | DNA | 190033 reverse primer (same as reverse primer for SV 48.3 in FIG. 5) |
| 50 | DNA | 190013 reverse primer |
| 51 | DNA | C2 probe (B6) - SNV 0.32 in FIG. 5 |
| 52 | DNA | T3 probe (B6) - SNV 1.2 in FIG. 5 |
| 53 | DNA | T6 probe (B6) - SNV 11.1 in FIG. 5 |
| 54 | DNA | T7 probe (B6) - SNV 13.2 in FIG. 5 |
| 55 | DNA | T8 probe (B6) - SNV 17.5 in FIG. 5 |
| 56 | DNA | T9 probe (B6) - SNV 25.8 in FIG. 5 |
| 57 | DNA | T10 probe (B6) - SNV 33.0 in FIG. 5 |
| 58 | DNA | T11 probe (B6) - SNV 38.3 in FIG. 5 |
| 59 | DNA | T13 probe (B6) - SNV 49.6 in FIG. 5 |
| 60 | DNA | T14 probe (B6) - SNV 57.2 in FIG. 5 |
| 61 | DNA | C2 probe (129) - SNV 0.32 in FIG. 5 |
| 62 | DNA | T3 probe (129) - SNV 1.2 in FIG. 5 |
| 63 | DNA | T6 probe (129) - SNV 11.1 in FIG. 5 |
| 64 | DNA | T7 probe (129) - SNV 13.2 in FIG. 5 |
| 65 | DNA | T8 probe (129) - SNV 17.5 in FIG. 5 |
| 66 | DNA | T9 probe (129) - SNV 25.8 in FIG. 5 |
| 67 | DNA | T10 probe (129) - SNV 33.0 in FIG. 5 |
| 68 | DNA | T11 probe (129) - SNV 38.3 in FIG. 5 |

TABLE 1-continued

Description of Sequences.

Figure 13:
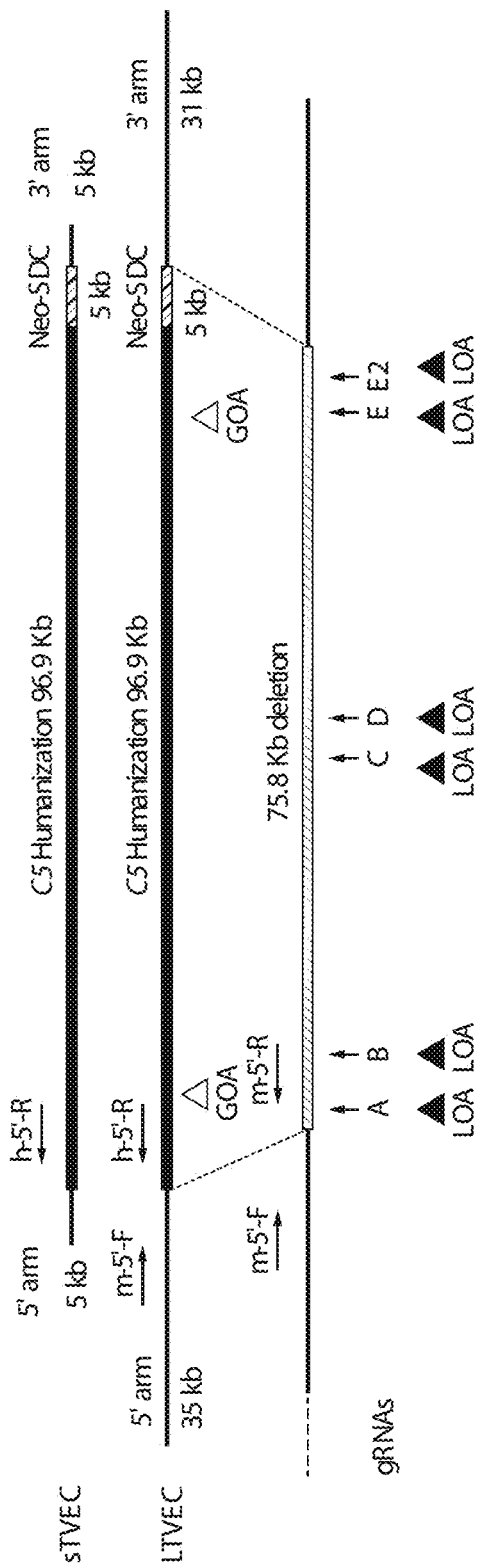
FIG. 13 shows a schematic for simultaneous deletion of the region from exon 2 to the stop codon of the mouse C5 (Hc) gene and replacement with a corresponding human C5 version using a targeting vector with homology arm sizes of 35 kb and 31 kb (LTVEC) or a targeting vector with homology arm sizes of 5 kb each (sTVEC) and either one or two 5' region (A, B), middle region (C, D), and 3' region (E, E2) gRNAs. The two targeting vectors are shown in the top portion of the figure, and the mouse C5 (Hc) gene locus is shown in the bottom portion of the figure. The positions of the Cas9 cleavage sites guided by the six guide RNAs are indicated by the vertical arrows below the mouse gene sequence, and the primers used for screening are indicated by horizontal arrows. The positions of the gain of allele (GOA) assays that quantify the insert copy number and the loss of allele (LOA) assays that quantify the mouse sequence targeted for deletion are indicated by the triangles.
Figure 15:
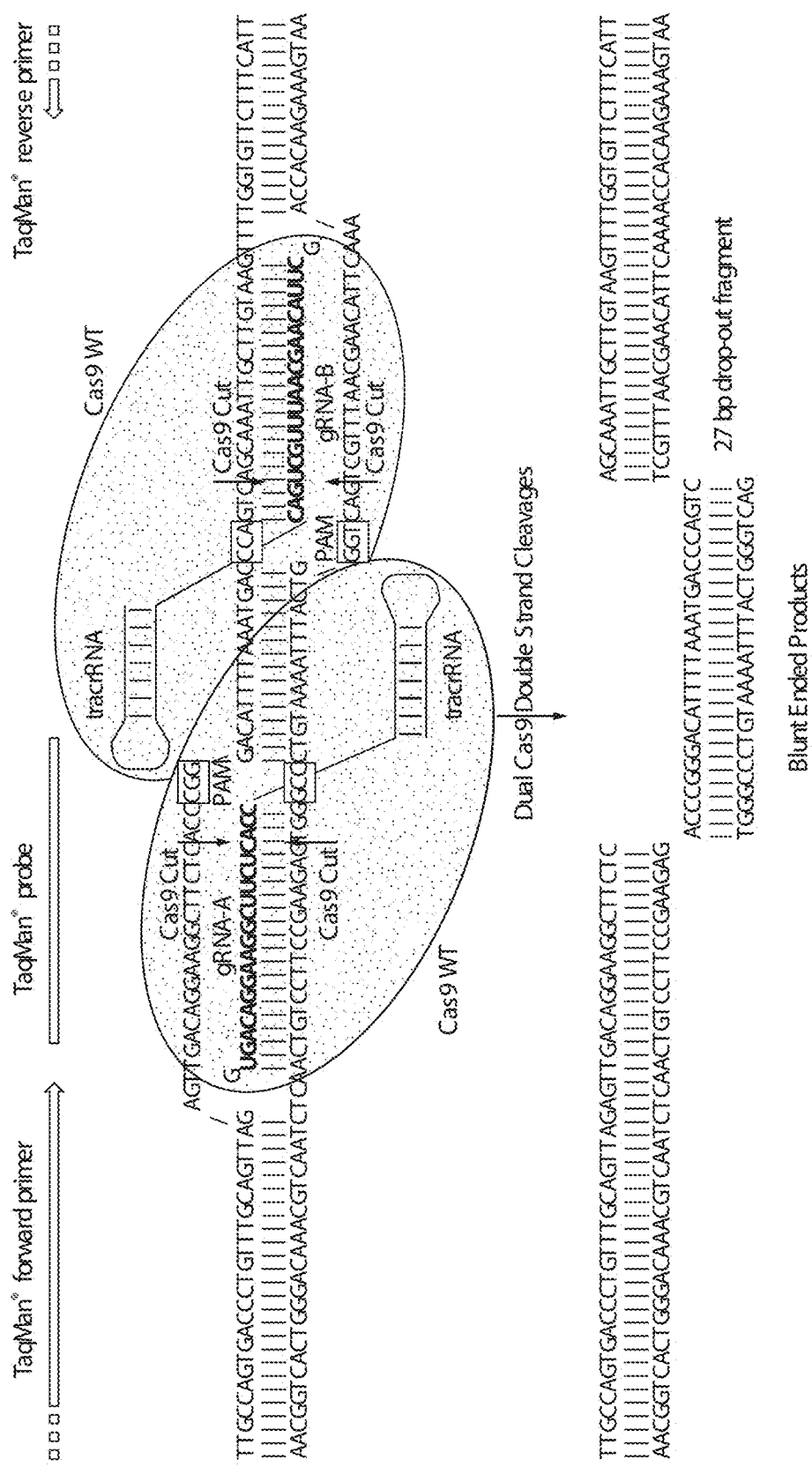
FIG. 15 shows a schematic of the cleavage events and the excision product produced (SEQ ID NO: 112) when the mouse Cmah gene locus (SEQ ID NO: 109) is targeted with two 5' region gRNAs (A and B; SEQ ID NOS: 107 and 108, respectively). The gRNA sequences hybridized to the Cmah gene locus are in bold, the Cas9 proteins are represented by the speckled ovals, the Cas9 cleavage sites are indicated by the vertical arrows, and the protospacer adjacent motifs (PAM) are boxed. The approximate positions of the TaqMan® LOA assay forward primer, probe, and reverse primer are indicated by the horizontal bars and arrows at the top of the figure. The 5' and 3' fragments produced after cleavage and excision are SEQ ID NOS: 110 and 111, respectively.
Figure 16A:
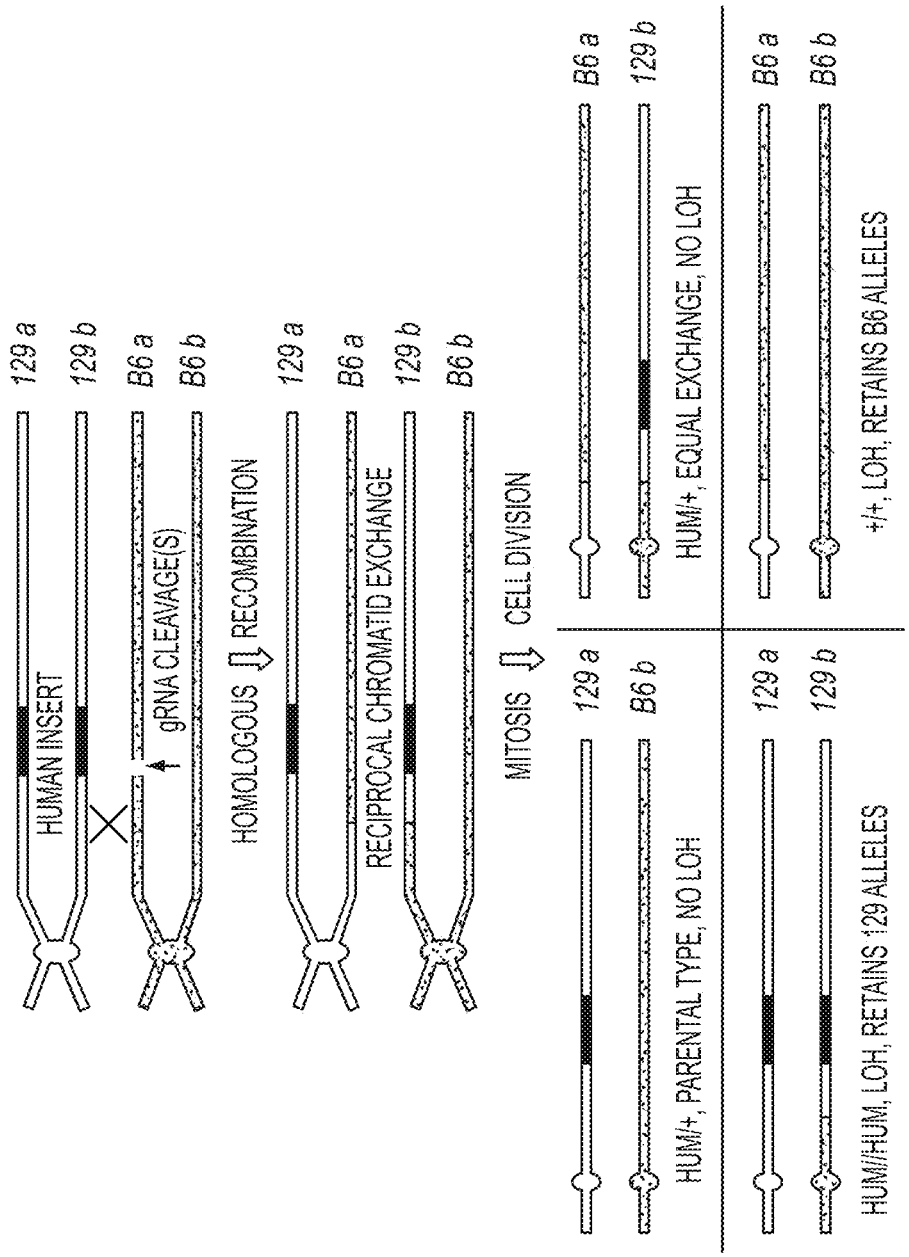
FIGS. 16A-E show possible mechanisms explaining the results observed, including loss of heterozygosity (LOH), in CRISPR/Cas9-assisted humanization experiments in F1 hybrid mouse ES cells having one haploid chromosome complement derived from the 12956/SvEvTac mouse strain and one haploid chromosome complement derived from the C57BL/6NTac (B6) mouse strain.
Figure 16B:
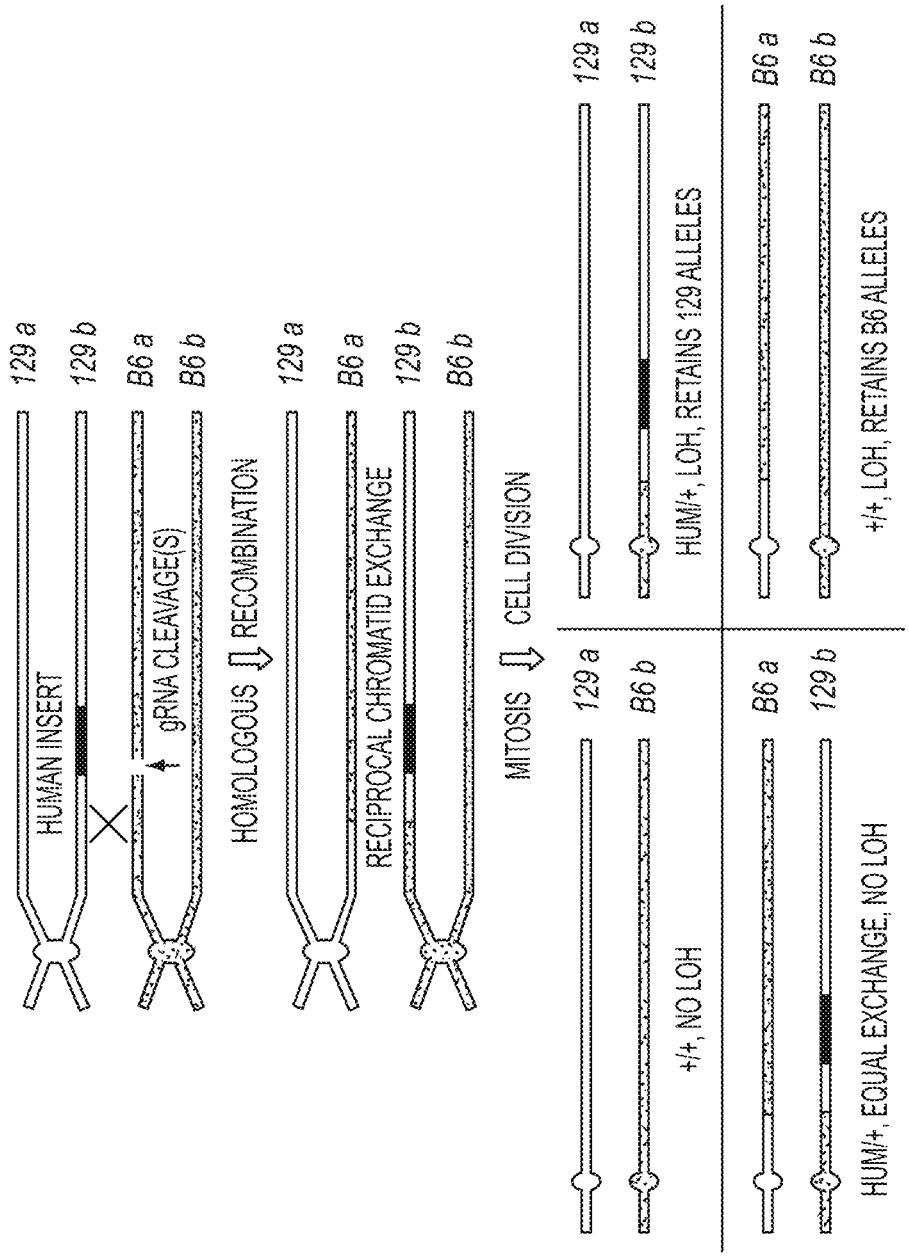
Figure 16C:
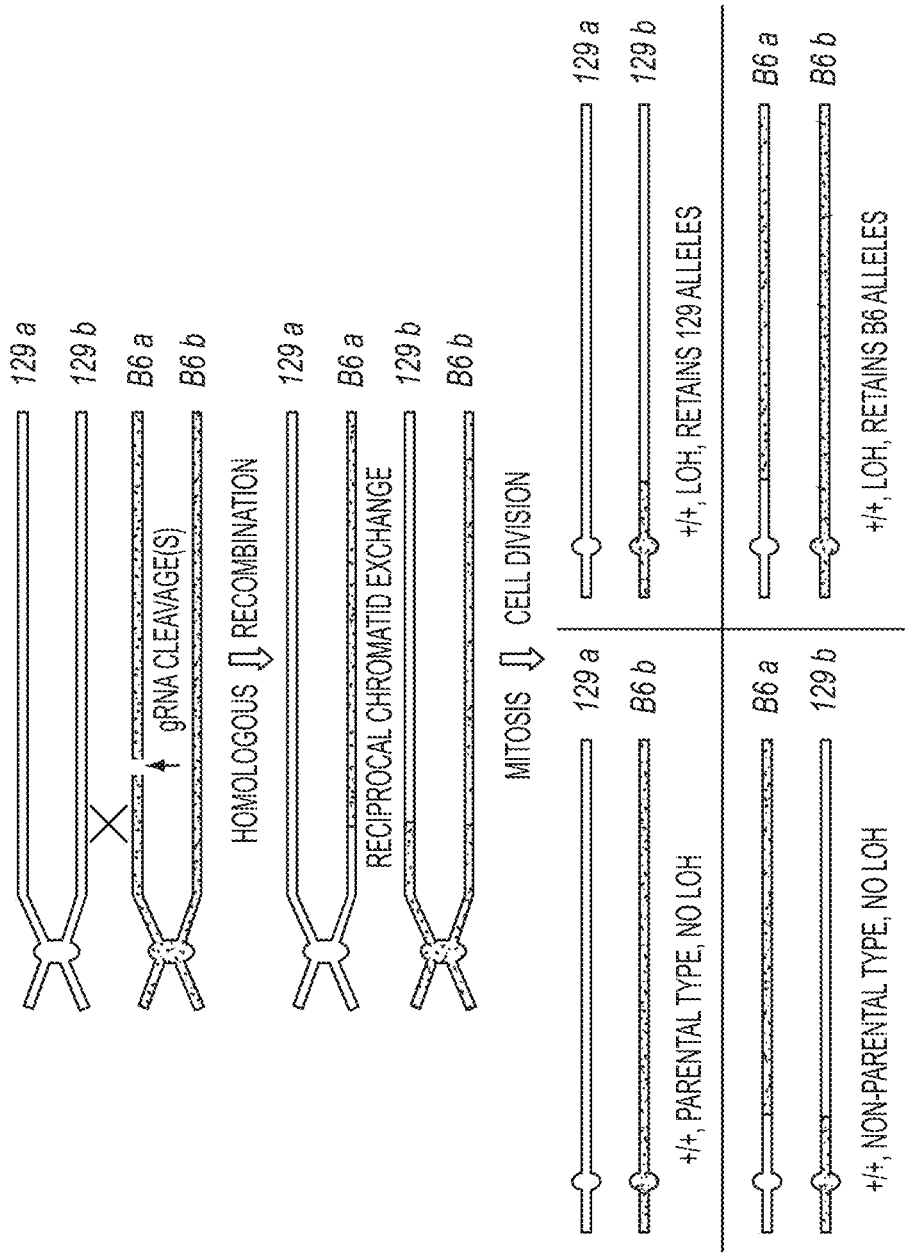
Figure 16D:
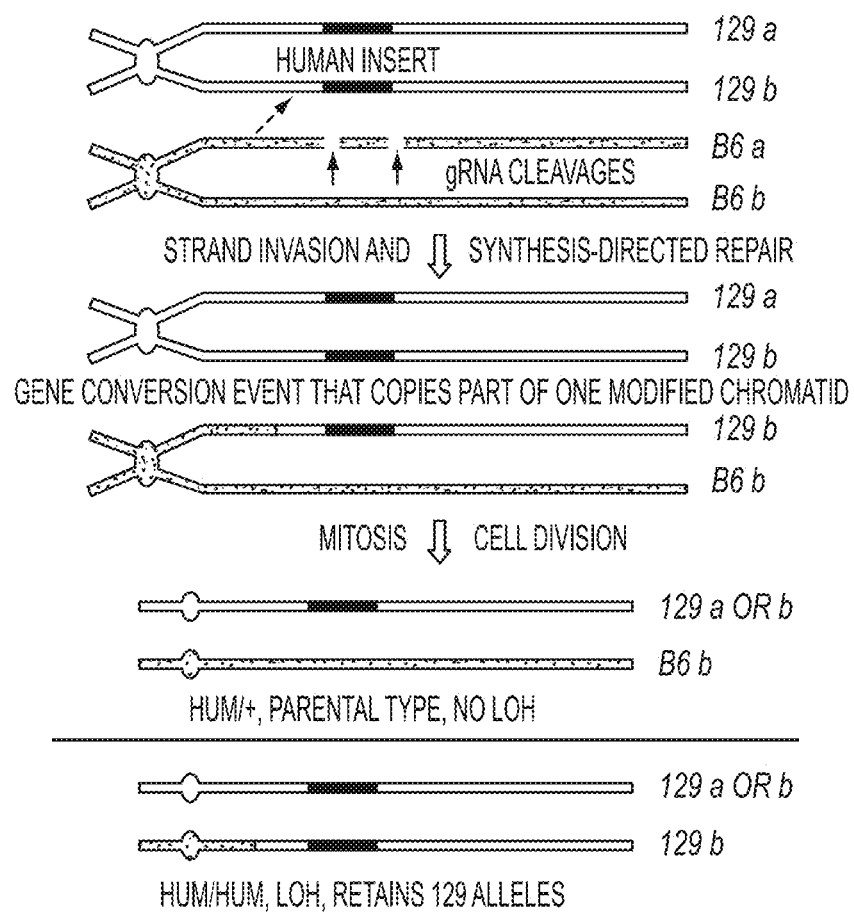
Figure 16E:
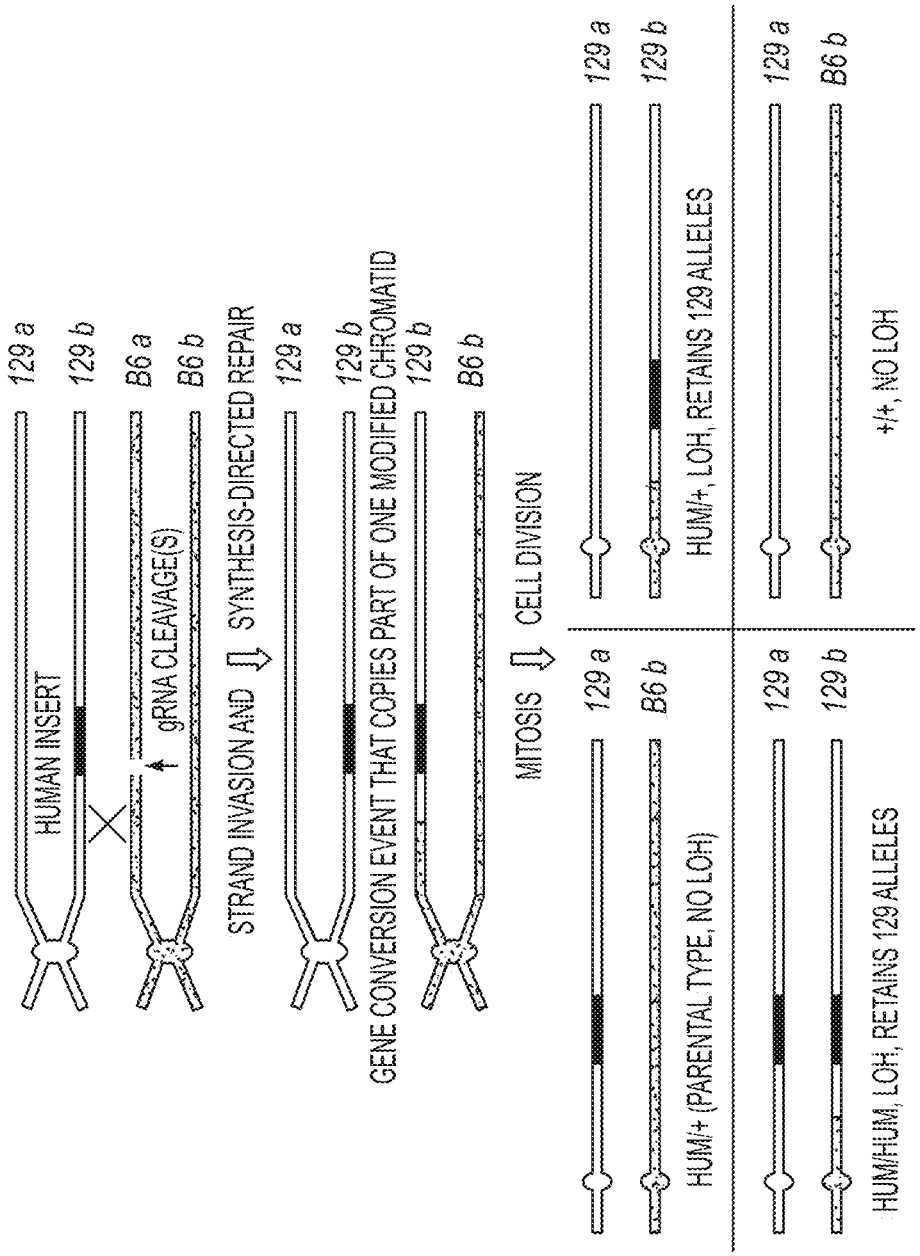
Figure 16F:
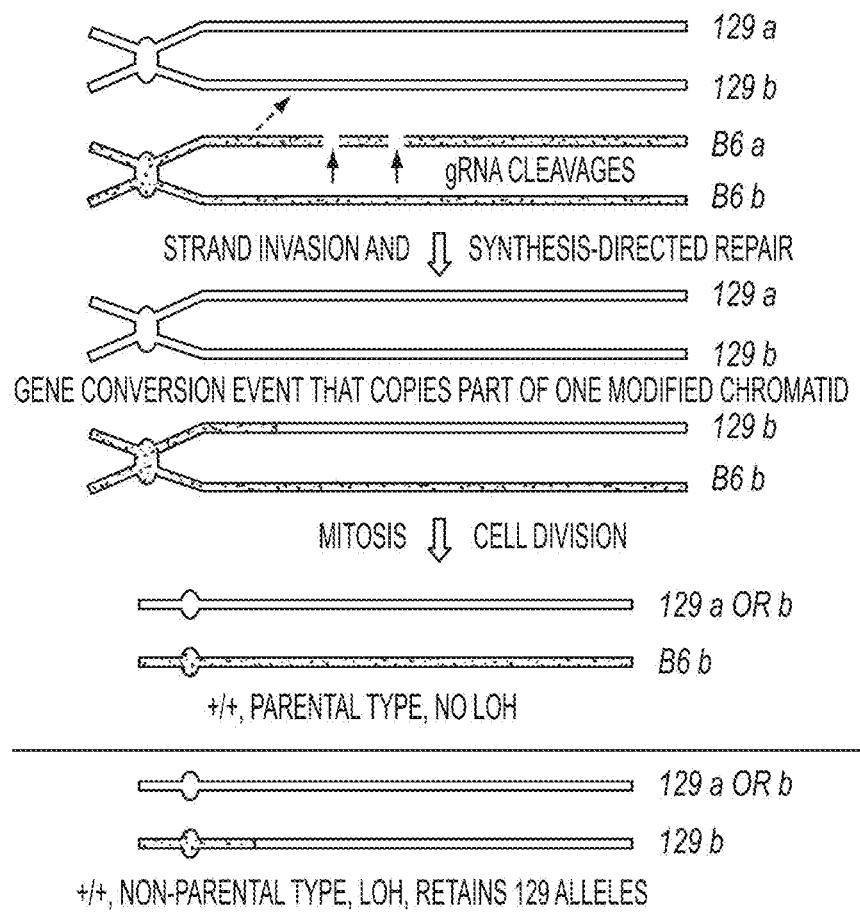
FIG. 16F shows chromatid copying by break-induced replication where no LTVEC targeting has occurred, but Cas9 cleavage has occurred on either the 129 or B6 chromosome (B6 cleavage shown).

| SEQ ID NO | Type | Description |
|---|---|---|
| 69 | DNA | T13 probe (129) - SNV 49.6 in FIG. 5 |
| 70 | DNA | T14 probe (129) - SNV 57.2 in FIG. 5 |
| 71 | DNA | C2 forward primer - SNV 0.32 in FIG. 5 |
| 72 | DNA | T3 forward primer - SNV 1.2 in FIG. 5 |
| 73 | DNA | T6 forward primer - SNV 11.1 in FIG. 5 |
| 74 | DNA | T7 forward primer - SNV 13.2 in FIG. 5 |
| 75 | DNA | T8 forward primer - SNV 17.5 in FIG. 5 |
| 76 | DNA | T9 forward primer - SNV 25.8 in FIG. 5 |
| 77 | DNA | T10 forward primer - SNV 33.0 in FIG. 5 |
| 78 | DNA | T11 forward primer - SNV 38.3 in FIG. 5 |
| 79 | DNA | T13 forward primer - SNV 49.6 in FIG. 5 |
| 80 | DNA | T14 forward primer - SNV 57.2 in FIG. 5 |
| 81 | DNA | C2 reverse primer - SNV 0.32 in FIG. 5 |
| 82 | DNA | T3 reverse primer - SNV 1.2 in FIG. 5 |
| 83 | DNA | T6 reverse primer - SNV 11.1 in FIG. 5 |
| 84 | DNA | T7 reverse primer - SNV 13.2 in FIG. 5 |
| 85 | DNA | T8 reverse primer - SNV 17.5 in FIG. 5 |
| 86 | DNA | T9 reverse primer - SNV 25.8 in FIG. 5 |
| 87 | DNA | T10 reverse primer - SNV 33.0 in Fig. 5 |
| 88 | DNA | T11 reverse primer - SNV 38.3 in Fig. 5 |
| 89 | DNA | T13 reverse primer - SNV 49.6 in FIG. 5 |
| 90 | DNA | T14 reverse primer - SNV 57.2 in FIG. 5 |
| 91 | DNA | Forward primer for SV 13.7 in FIG. 5 |
| 92 | DNA | Reverse primer for SV 13.7 in FIG. 5 |
| 93 | DNA | Forward primer for SV 20.0 in FIG. 5 |
| 94 | DNA | Reverse primer for SV 20.0 in FIG. 5 |
| 95 | DNA | Forward primer for SV 36.9 in FIG. 5 |
| 96 | DNA | Reverse primer for SV 36.9 in FIG. 5 |
| 97 | DNA | Forward primer for SV 56.7 in FIG. 5 |
| 98 | DNA | Reverse primer for SV 56.7 in FIG. 5 |
| 99 | DNA | m-lr-f primer in FIG. 1 |
| 100 | DNA | m-5'-f primer in FIG. 1 |
| 101 | DNA | m-A primer in FIG. 1 |
| 102 | DNA | h-lr-r primer in FIG. 1 |
| 103 | DNA | m-5'-r primer in FIG. 1 |
| 104 | DNA | h-5'-r primer in FIG. 1 |
| 105 | DNA | m-F primer in FIG. 1 |
| 106 | DNA | m-E2 primer in FIG. 1 |
| 107 | RNA | Cmah gRNA A DNA-targeting segment |
| 108 | RNA | Cmah gRNA B DNA-targeting segment |
| 109 | DNA | Cmah locus |
| 110 | DNA | Cmah locus upstream of gRNA A cut |
| 111 | DNA | Cmah locus downstream of gRNA B cut |
| 112 | RNA | Cmah locus sequence excised by gRNAs A and B |
| 113 | DNA | C5 primer m-5'-F in FIG. 13 |
| 114 | DNA | C5 primer m-5'-R in FIG. 13 |
| 115 | DNA | C5 primer h-5'-R in FIG. 13 |
| 116 | DNA | Cmah TaqMan ® forward primer in FIG. 15 |
| 117 | DNA | Cmah TaqMan ® probe in FIG. 15 |
| 118 | DNA | Cmah TaqMan ® reverse primer in FIG. 15 |
| 119 | DNA | 7064retU forward primer |
| 120 | DNA | 7064retU reverse primer |
| 121 | DNA | 7064retU TaqMan ® probe |
| 122 | DNA | 7064retD forward primer |
| 123 | DNA | 7064retD reverse primer |
| 124 | DNA | 7064retD TaqMan ® probe |
| 125 | DNA | 7140retU forward primer |
| 126 | DNA | 7140retU reverse primer |
| 127 | DNA | 7140retU TaqMan ® probe |
| 128 | DNA | 7140retD forward primer |
| 129 | DNA | 7140retD reverse primer |
| 130 | DNA | 7140retD TaqMan ® probe |
| 131 | DNA | mADAM6-2 LOA forward primer |
| 132 | DNA | mADAM6-2 LOA reverse primer |
| 133 | DNA | mADAM6-2 LOA probe |
| 134 | DNA | hIgH31 LOA forward primer |
| 135 | DNA | hIgH31 LOA reverse primer |
| 136 | DNA | hIgH31 LOA probe |
| 137 | DNA | hIgH9 LOA forward primer |
| 138 | DNA | hIgH9 LOA reverse primer |
| 139 | DNA | hIgH9 LOA probe |
| 140 | DNA | hIgH1 LOA forward primer |
| 141 | DNA | hIgH1 LOA reverse primer |
| 142 | DNA | hIgH1 LOA probe |
| 143 | DNA | Neo GOA forward primer |
| 144 | DNA | Neo GOA reverse primer |
| 145 | DNA | Neo GOA probe |
| 146 | DNA | 5' IgH Arm1 retention assay forward primer |
| 147 | DNA | 5' IgH Arm1 retention assay reverse primer |
| 148 | DNA | 5' IgH Arm1 retention assay probe |
| 149 | DNA | mIgM398 retention assay forward primer |
| 150 | DNA | mIgM398 retention assay reverse primer |
| 151 | DNA | mIgM398 retention assay probe |
| 152 | DNA | mIgM1045 retention assay forward primer |
| 153 | DNA | mIgM1045 retention assay reverse primer |
| 154 | DNA | mIgM1045 retention assay probe |
| 155 | DNA | 3' IgH Arm2 retention assay forward primer |
| 156 | DNA | 3' IgH Arm2 retention assay reverse primer |
| 157 | DNA | 3' IgH Arm2 retention assay probe |
| 158 | DNA | mIgHp2 parental forward primer |
| 159 | DNA | mIgHp2 parental reverse primer |
| 160 | DNA | mIgHp2 parental probe |
| 161 | DNA | mIgKd2 parental forward primer |
| 162 | DNA | mIgKd2 parental reverse primer |
| 163 | DNA | mIgKd2 parental probe |
| 164 | DNA | hIgK5 parental forward primer |
| 165 | DNA | hIgK5 parental reverse primer |
| 166 | DNA | hIgK5 parental probe |
| 167 | DNA | 3' gRNA_I DNA-targeting sequence |
| 168 | DNA | 3' gRNA_II DNA-targeting sequence |
| 169 | DNA | 5' gRNA_I DNA-targeting sequence |
| 170 | DNA | 5' gRNA_II DNA-targeting sequence |
| 171 | DNA | 5' IgH Arm2 retention assay forward primer |
| 172 | DNA | 5' IgH Arm2 retention assay reverse primer |
| 173 | DNA | 5' IgH Arm2 retention assay probe |
| 174 | DNA | 3' IgH Arm1 retention assay forward primer |
| 175 | DNA | 3' IgH Arm1 retention assay reverse primer |
| 176 | DNA | 3' IgH Arm1 retention assay probe |

EXAMPLES

Example 1. CRISPR/Cas9-Mediated Targeting Using One Guide RNA or Two Guide RNAs

Materials and Methods

ES Cell Culture, Screening, and Electroporation

The experiments described herein were performed with VGF1, our C57BL6NTac/129S6SvEvF1 hybrid XY ES cell line (Poueymirou et al. (2007) Nat. Biotechnol. 25:91-99; Valenzuela et al. (2003) Nat. Biotechnol. 21:652-659). ES cells were cultured as previously described (Matise et al. (2000) in Joyner, A. L. ed. Gene Targeting: a practical approach, pp. 100-132, Oxford University Press, New York).

Electroporations (EPs) were performed with 7.5 million cells in a 2 mm gap cuvette in a final volume of 0.12 ml. Electrical conditions for EP were 700V, 400 ohms resistance, and 25 microF capacitance using a BTX ECM 630 electroporation system (Harvard Apparatus, Holliston, Mass.). The amount of LTVEC per EP was 0.0015 mg, Cas9 expressing plasmid was 0.005 mg and sgRNA expressing plasmid was 0.010 mg. Some EPs were performed with the addition of 100 ng of a plasmid conferring puromycin resistance to allow for the selection of clones without selecting for neomycin resistance expressed by the LTVECs.

Following EP, cells were plated onto two 15 cm gelatinized dishes and media was changed daily. Selection media containing either 100 ug/ml G-418 sulfate or 0.0015 mg/ml puromycin began 48 hours after EP and continued until 10 days post-EP. Colonies were picked in PBS and added to a 96-well dish containing 0.05% trypsin and allowed to dissociate for 15 minutes, neutralized with media and used for the isolation of DNA for screening.

The modification-of-allele method (Frendewey et al. (2010) *Methods Enzymol.* 476:295-307) was used to identify correctly targeted ES cell clones and to determine mouse allele genotypes.

Design of Guide Sequences

Approximately 200 bp of DNA surrounding the 50 bp, 100 bp, 500 bp, or 1 kb position inside the deleted portion of Lrp5 or other targeted genes, both upstream and downstream, was entered into the CRISPR design tool (crispr.mit.edu) to retrieve possible gRNA sequences. Potential gRNA sequences were then filtered to ensure that they would only allow for cutting of the endogenous DNA and not the humanization insert in the LTVEC.

Single Guide RNA Cloning sgRNAs were either cloned as duplex oligos (IDT) into pMB_sgRNA (U6 promoter) at BsmbI sites fused to the 77 bp scaffold for seamless RNA expression, or purchased as validated expression plasmids from GeneCopoeia (LRP5 guides A, B, B2, E2, E, and F). In-house-produced plasmids were confirmed by PCR and Sanger sequencing.

DNA Template for Genotype Confirmation

DNA was purified from ES cell, clones derived from ES cells that had been electroporated with a targeting vector and a plasmid expressing Cas9 and a plasmid expressing one of several guide RNAs (gRNAs) or two plasmids expressing different gRNA combinations. Clones identified by modification-of-allele (i.e., loss-of-allele or gain-of-allele) quantitative PCR assays as having a targeted deletion of the mouse target locus and insertion of the targeting vector or having Cas9/gRNA-induced deletions were selected for follow-up conventional PCR assays.

Oligonucleotide Design

Two PCR assays were designed for each combination of gRNAs. The first PCR was a deletion assay to detect collapse between the CRISPR RNA recognition sequences of different gRNA combinations. The second PCR assay, which is a 5' assay, included two PCR assays. The first was a 5' human assay for humanized alleles and was designed across the mouse-human junction. The second was a 5' mouse assay for endogenous mouse alleles and was designed across the 5' targeted deletion junction.

PCR Reaction and TOPO Cloning

TaKaRa LA Taq DNA Polymerase (Cat. # RR002M) was used to amplify the ES cell DNA template. Each PCR assay reaction mix was run with a water negative control. Assay mixtures contained the following: 0.005 mL ES cell DNA Template; 1×LA PCR Buffer II ($Mg^{2+}$ plus); 0.01 mM dNTP mixture; 0.0075 mM Forward Oligo (each); 0.0075 mM Reverse Oligo (each); 5000 units/mL LA Taq Polymerase; and dd$H_2O$ to 0.025 mL.

The PCR Thermocycle program consisted of 94° C. for one minute; followed by 35 cycles of 94° C. for 30 seconds, 60° C. annealing gradient for 30 seconds, and 68° C. for one minute per kb amplified; followed by polymerization at 72° C. for 10 minutes.

PCR products were fractionated by electrophoresis on a 2% agarose gel with an Invitrogen 1 kb plus DNA ladder (Cat. #10787-018) and/or Invitrogen 50 bp DNA Ladder (Cat. #10416-014). Remaining PCR products were cloned into pCR4-TOPO Vector following instructions from Invitrogen's TOPO TA cloning kit (Cat. # K4575-02) for sequencing. Cloning reactions were chemically transformed into One Shot Top10 cells and plated on 0.06 mg/mL X-gal and 0.025 mg/mL kanamycin agar plates.

Sequencing

White colonies were inoculated into LB containing 0.025 mg/mL kanamycin and incubated overnight with shaking at 37° C. Each colony represented one amplicon from a population of assayed products. DNA was extracted from each bacterial culture using the QIAGEN plasmid miniprep kit (Cat. #12123). The DNA sequence of the inserts was determined in a sequencing reaction mix that included 0.002 mL TOPO cloned PCR, 1×PCRx Enhancer Solution (10× stock) (Cat. X11495-017), 0.0075 mM oligo (M13F or M13R), and dd$H_2O$ to 0.015 mL.

Sequencing Analysis

Sequencing results were trimmed of indeterminant sequence and pCR4-TOPO Vector sequence, isolating the PCR insert sequence. Sequenced fragments were then aligned to a reference and variations were analyzed.

Sequencing Collapsed Clones

PCR products from the collapsed positive clones were cloned into the pCR4-TOPO Vector following the manufacturer's instructions (Invitrogen cat. # K4575-02), then chemically transformed into One Shot Top10 cells and plated on 0.060 mg/mL X-gal and 0.025 mg/mL Kanamycin agar plates. DNA was extracted from bacterial cultures using QIAGEN plasmid miniprep kit (Cat. #12123). Insert sequencing results were then aligned to a predicted collapse reference and indel variations were analyzed. Cas9 was predicted to cleave 3 base pairs from the PAM into the sequence recognized by the gRNA. The sequence within the predicted cleavage was deleted from the reference and the remaining was used to align to the results.

TaqMan® Allelic Discrimination Assays for Single Nucleotide Variants (SNVs)

The TaqMan® Allelic Discrimination reaction was 0.008 ml containing genomic DNA, specific probes/primers for each polymorphism, and TaqMan® Gene Expression PCR Master mix. The probes were ordered from Life Technologies (Thermo) and the primers from IDT. The probe for allele 129 was labeled with VIC dye; the probe for allele B6 was labeled with FAM dye. Each TaqMan® allelic assay was performed in quadruplicate on a 384-well plate and run on Applied BioSystems ViiA 7 platform. The SNV PCR cycling program was as follows: 95° C. for 10 minutes follow by 40 cycles of the following: 95° C. for 15 seconds, 60° C. for 60 seconds, and 60° C. for 30 seconds. The analysis of the run and evaluation of the results was done using ViiA 7 Software v 1.1.

FISH Analysis

Selected ES cell clones were analyzed by either Cell Line Genetics (Madison, Wis.) or the Van Andel Institute (Grand Rapids, Mich.) using fluorescence in situ hybridization (FISH) by their standard procedures. We provided mouse and human BACs as probes for 2-color analysis.

Enhanced Genome Collapsing and/or Humanization of Target Loci

To effect a precise, single-step deletion of all or part of a rodent gene and optionally simultaneous replacement with all or part of its human homolog, we introduced by electroporation into rodent ES cells the following nucleic acid molecules: (1) an LTVEC; (2) a plasmid or mRNA encoding a Cas9 endonuclease; and (3) one or more plasmids encoding one or more CRISPR single guide RNAs (gRNAs) or the gRNAs themselves. In each experiment, the LTVEC was linearized. In some experiments, the LTVEC comprised all or part of a human gene that encodes the gene product (protein or RNA) flanked by homology arms of rodent DNA designed to direct a homologous recombination event that deletes the rodent gene and inserts the human gene. In other experiments, the LTVEC was designed to target a separate locus such as the Ch25h locus. In either case, the LTVEC also carried a drug selection cassette that directs the expression of an enzyme (e.g., neomycin phosphotransferase) that imparts resistance to an antibiotic drug (for example, G418).

ES cells that took up the LTVEC and incorporated it into their genomes were able to grow and form colonies on a tissue culture dish in a growth medium containing the antibiotic drug. Because we introduced 500 to 1,000 times more CRISPR/Cas9-encoding and gRNA-encoding nucleic molecules than LTVEC molecules, most of the LTVEC-containing drug resistant colonies also contained, at least transiently, the CRISPR/Cas9 components. We picked drug resistant colonies and screened them by the modification-of-allele method (Valenzuela et al. (2003) *Nat. Biotech.* 21:652-660; Frendewey et al. (2010) *Methods Enzymol.* 476:295-307; incorporated herein by reference in their entireties) to identify clones that had the correctly targeted humanized allele. In addition, real-time PCR assays recognizing sequences in the homology arms of the LTVEC, referred to as retention assays, were used to verify correct targeting of the LTVEC into the mouse genome. Determining the copy number of these retention assays provided further clarification to help distinguish correctly targeted ES clones, which retained a copy number of two, from clones in which a large Cas9-induced deletion of the target mouse locus coincides with random integration of the LTVEC elsewhere in the genome, in which case retention assays had a copy number of three (or more). The ability of paired gRNAs to create large Cas9-mediated deletions at the target mouse locus meant that standard LOA and GOA assays as previously described could be augmented by retention assays to provide further clarification and to verify correct targeting. Therefore, retention assays were designed and used in conjunction with LOA and GOA assays.

In each experiment, either one or two gRNAs were used. The gRNAs used singly directed Cas9 cleavage near the 5' end of the target locus (i.e., the targeted mouse gene deletion), the middle of the target locus, or the 3' end of the target locus. When two gRNAs were used, one gRNA directed Cas9 cleavage near the 5' end of the target locus and the other gRNA directed Cas9 cleavage in the middle of the target locus or near the 3' end of the target locus.

Lrp5 Locus

In one set of experiments, the LTVEC was designed to create a 68 kb deletion of the portion of the mouse Lrp5 (low-density lipoprotein receptor-related protein 5) gene encoding the ectodomain and a simultaneous replacement with a 91 kb fragment of the homologous sequence from the human LRP5 gene (FIG. 1). The LTVEC comprised the 91 kb fragment of the human LRP5 gene flanked by homology arms containing 7 kb and 33 kb of genomic DNA derived from parts of the mouse Lrp5 locus that flank the 68 kb sequence of the mouse Lrp5 gene intended for deletion. In separate experiments, the Lrp5 humanizing LTVEC was combined with a plasmid encoding Cas9 and a second plasmid encoding one of eight gRNAs (A, B, B2, C, D, E2, E, F) designed to create double-strand breaks within the region of the mouse Lrp5 gene that was targeted for deletion. The gRNAs were designed to avoid recognition of any sequence in the inserted portion of the human LRP5 gene. In other experiments, we combined the LTVEC and the Cas9-encoding plasmid with plasmids encoding two different gRNAs that target different sites within the region of the mouse Lrp5 gene that was targeted for deletion.

Drug-resistant ES cell clones were screened for targeted humanizations by modification-of-allele assays (Valenzuela et al. (2003) *Nat. Biotechnol.* 21:652-659; Frendewey et al. (2010) *Methods Enzymol.* 476:295-307) for sequences within the deletion and for sequences within the drug selection cassette and the human gene insert. Clones were scored as correctly targeted if they had lost one of the two endogenous mouse gene sequences and gained one copy of the human insert, and also retained two copies of retention sequences (located in the homology arm of the LTVEC). The two retention assays for this screening were TaqMan® assays using the following primers and probes: 7064retU forward primer CCTCCTGAGCTTTCCTTTGCAG (SEQ ID NO: 119); 7064retU reverse primer CCTAGACAACACAGACACTGTATCA (SEQ ID NO: 120); 7064retU TaqMan® probe TTCTGCCCTTGAAAAGGAGAGGC (SEQ ID NO: 121); 7064retD forward primer CCTCTGAGGCCACCTGAA (SEQ ID NO: 122); 7064retD reverse primer CCCTGACAAGTTCTGCCTTCTAC (SEQ ID NO: 123); 7064retD TaqMan® probe TGCCCAAGCCTCTGCAGCTTT (SEQ ID NO: 124).

The results of the CRISPR/Cas9-assisted humanization of the Lrp5 gene are summarized in Table 2. When the LTVEC alone was introduced into ES cells, 1.9% of the screened drug resistant clones carried a correctly targeted heterozygous humanized allele (see Het. Targ. column in Table 2, which includes clones in which the non-targeted allele was not mutated at all or had a small CRISPR-induced mutation such as a small deletion caused by NHEJ). In contrast, combining the LTVEC with Cas9 endonucleases guided by seven of the eight tested gRNAs (A, B, B2, C, D, E2, E and F; see Table 1) produced correctly targeted monoallelic heterozygous mutations at efficiencies that ranged from 2.1 to 7.8%. For Cas9-guided cleavage by B2 and D, in addition to monoallelic targeting, biallelic homozygous humanization was detected at a frequency of 1.0-2.1%. We have never observed biallelic targeting with an LTVEC on its own, even for small, simple deletion alleles. The homozygous Lrp5 humanized ES cells can be converted by the VELOCIMOUSE® method (Poueymirou et al. (2007) *Nat. Biotech.* 25:91-99, incorporated herein by reference in its entirety) directly into completely ES cell-derived mice ready for phenotypic and drug efficacy studies.

MOA assays devised to detect gRNA/Cas9-induced NHEJ mutations at or near the predicted cleavage sites demonstrated mutation activity for all the gRNAs tested (data not shown). The proportion of either monoallelic or biallelic gRNA-induced mutations detected among all clones assayed varied by locus and position. There was not a strong correlation between gRNA mutation activity and LTVEC targeting, but the lowest targeting efficiencies were often associated with gRNAs that had the lowest mutation frequencies.

Combining two gRNAs that recognize different ends of the region of the Lrp5 gene that was targeted for deletion increased the total humanization targeting efficiency, predominantly by increasing the frequency of homozygous targeting events for three of the five combinations tested (Table 2). Because the combination of gRNAs has the potential to create large deletions between the Cas9 cleavage sites programmed by the gRNAs, we also observed hemizygous ES cell clones that carried a targeted humanization on one Lrp5 allele and a large CRISPR-induced deletion on the other allele (gRNA combination A+F, Table 2). In addition, for two of the gRNA combinations (A+F and A+E2), we identified ES cell clones with a unique genotype: large CRISPR-mediated deletions on both Lrp5 alleles.

TABLE 2

Screening Results for CRISPR/Cas9-Assisted Humanization of the Lrp5 Ectodomain Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 50 (5') | 7.8 | | | 7.8 | |
| B | 500 (5') | 4.2 | | | 4.2 | |
| B2 | 1000 (5') | 6.2 | | 1.0 | 7.2 | |
| C | 29900 (5')/38430 (3') | 4.1 | | | 4.1 | |
| D | 29950 (5')/38380 (3') | 5.2 | | 2.1 | 7.3 | |
| E2 | 1000 (3') | 2.1 | | | 2.1 | |
| E | 500 (3') | 0.0 | | | 0.0 | |
| F | 50 (3') | 4.2 | | | 4.2 | |
| A + F | A: 50 (5') F: 50 (3') | 6.6 | 2.9 | 2.2 | 11.7 | 2.9 |
| B + E | B: 500 (5') E: 500 (3') | 2.5 | | | 2.5 | |
| B2 + E2 | B2: 1000 (5') E2: 1000 (3') | 4.2 | | 2.1 | 6.3 | |
| A + E | A: 50 (5') E: 500 (3') | 4.6 | | 6.2 | 10.8 | |
| A + E2 | A: 50 (5') E2: 1000 (3') | 2.0 | | 4.0 | 6.0 | 4.0 |
| None | N/A | 1.9 | | | 1.9 | |

As demonstrated in Table 2, a significant increase in the percentage of clones that had biallelic targeting was observed when using two gRNAs that target a single locus rather than one gRNA (see FIG. 2A), indicating that use of gRNA combinations promotes biallelic modifications. FIG. 2A shows a general schematic for simultaneous deletion of a mouse gene and replacement with a corresponding human version using an LTVEC and two guide RNAs (A and B). Unique mutant allele types that are observed at a much higher frequency when using two gRNAs include homozygously collapsed alleles (FIG. 2B; A/A), homozygously targeted alleles (FIG. 2C; Hum/Hum), hemizygously targeted alleles (FIG. 2D; (Hum/A)), and other compound heterozygously targeted alleles (e.g., one allele has an LTVEC-targeted humanization and the other allele has a CRISPR-induced mutation such as a small deletion) (FIG. 2E).

Figure 3A:
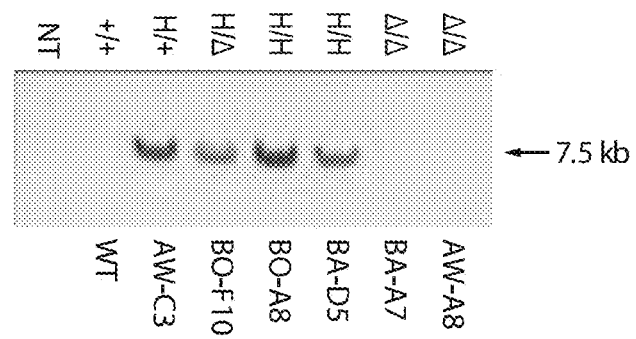
FIGS. 3A and 3B show PCR assays confirming genotypes of selected clones.
Figure 3B:
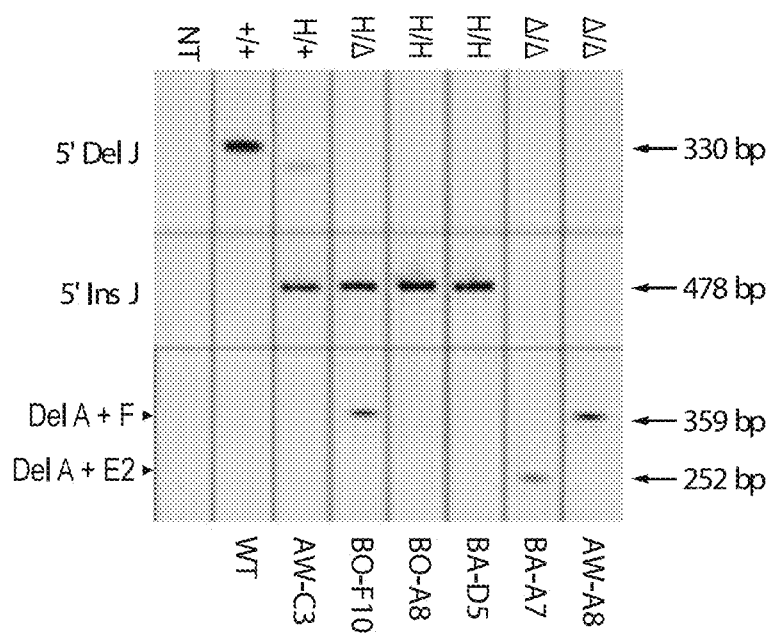
Figure 4A:
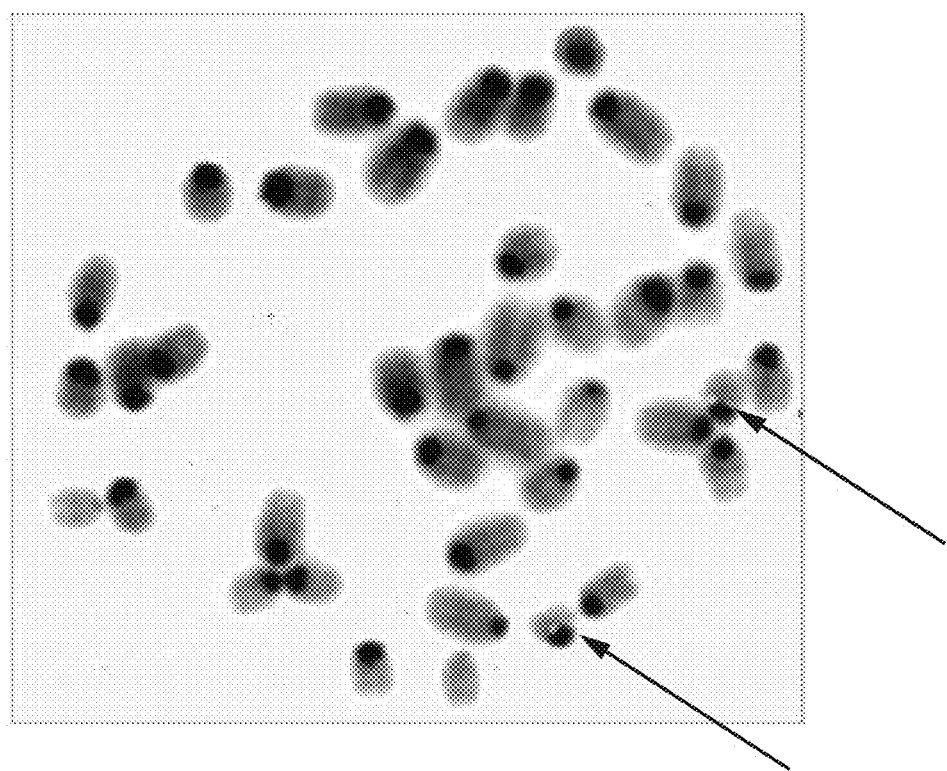
FIG. 4A-C show fluorescence in situ hybridization (FISH) analysis of mouse ES cell clones AW-D9 (FIG. 4A) and BA-D5 (FIG. 4C), which were targeted with the Lrp5 humanization LTVEC combined with Cas9 and two gRNAs, and clone BS-C4 (FIG. 4B), which was targeted with the LTVEC alone. Arrows indicate the positions of hybridization signals on band B of chromosome 19. A red signal indicates hybridization with only the mouse probe (dashed arrow, FIG. 4B). A yellow mixed color signal indicates hybridization with both the red mouse probe and the green human probe. One chromosome 19 band B having a red signal (dashed arrow) and the other chromosome 19 band B having a yellow signal (solid arrow) confirmed targeting to the correct locus and the heterozygous genotype for the BS-C4 clone (FIG. 4B). The B bands of both chromosomes 19 having a yellow signal (solid arrows, FIGS. 4A and 4C) confirmed targeting to the correct locus and the homozygous genotypes for the AW-D9 and BS-C4 clones.
Figures 4B, 4C:
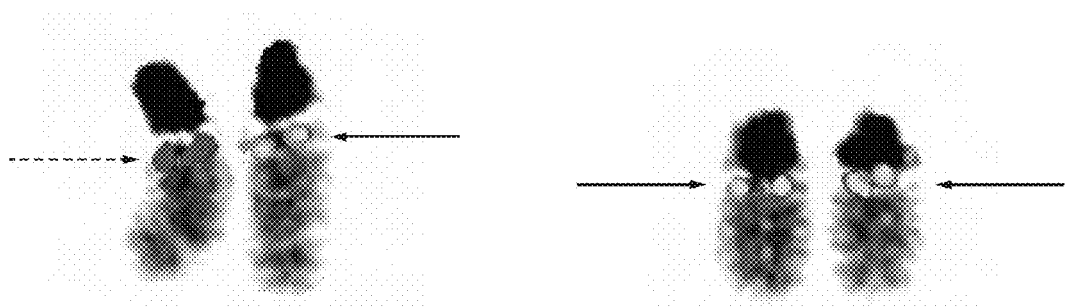

Several PCR assays were performed to support and confirm the genotypes based on MOA assays. The primers are shown in FIG. 1 and can be found in Table 1. The Lrp5 LTVEC had a 5' homology arm that was short enough (6.9 kb) to prove targeting by a PCR that assayed for a physical connection between the human insert and the adjacent mouse genomic sequence (FIG. 1). We observed the expected 7.5 kb PCR product with DNA from clones scored as heterozygous, hemizygous, or homozygous but not with DNA from the parental ES cell line or from clones scored as having biallelic large deletions (FIG. 3A), thus confirming the targeting calls made by MOA (i.e., LOA and GOA) screening and supporting the inferred biallelic large deletions. The 5'-Del-J PCR assay, which examined sequences at the deletion and insertion junctions (FIG. 3B), produced a 330 bp product with DNA from the parental ES cell line and from most heterozygous humanized clones (data not shown). For heterozygous clone AW-C3, the 5'-Del-J assay produced a smaller than expected product (FIG. 3B), suggesting that gRNA A/Cas9 cleavage induced a small deletion mutation on the non-targeted allele, which was also detected by a MOA assay for gRNA A cleavage (data not shown). As expected, the 5'-Del-J assay was negative for clones with hemizygous, homozygous, and biallelic deletion alleles. The 5'-Ins-J PCR (FIG. 3B), which examined sequences at the junction between the 5' end of the human DNA insert and the adjacent mouse flanking sequence, produced a 478 bp product in heterozygous, hemizygous, and homozygous clones, as these have at least one targeted humanized allele. The 5'-Ins-J PCR assay produced no product for clones with biallelic large deletions (FIG. 3B). To confirm the large deletions in hemizygous and biallelic deletion clones, we performed PCRs with primers that recognized sequences outside of the dual gRNA target sites. The Del(A+F) PCR, which assayed for a deletion between the A and F gRNA sites (FIG. 1), produced a single product of approximately 360 bp with DNA from clones AW-A8 and BO-F10 (FIG. 3B), confirming that at least one of the Lrp5 alleles had a large deletion. Likewise, the Del(A+E2) PCR, which assayed for a large deletion between the A and E2 gRNA sites, produced a single product of approximately 250 bp with DNA from clone BA-A7. The deletion PCRs, together with the junction, LOA, and GOA assays, support a biallelic large deletion genotype. The assay results shown in FIGS. 3A and 3B are representative examples of similar assays that we performed in addition to fluorescent in situ hybridization (FISH; FIG. 4A-C) to confirm the biallelic genotypes summarized in Table 2.

Fluorescence in situ hybridization (FISH) was used to confirm homozygous targeted humanization of the Lrp5 gene. ES cell clones scored by quantitative and conventional PCR assays as homozygous targeted from targeting experiments in which the Lrp5 humanization LTVEC (FIG. 1) was combined with Cas9 and two gRNAs (A plus F or A plus E2) were sent to a commercial cytology service for FISH and karyotype analysis. A bacterial artificial chromosome (BAC) carrying the mouse Lrp5 gene was labeled with a red fluorescent marker and used as a probe to identify endogenous Lrp5 loci, and a BAC carrying the human LRP5 gene was labeled with a green fluorescent marker and used as a probe to identify the chromatids targeted with the human insert. The labeled BAC probes were hybridized to metaphase spreads from the targeted clones and visualized by fluorescence microscopy. Chromosomes on the spreads were visualized by staining with DAPI (4',6-diamidino-2-phenylindole), and separate karyotypes for each clone were determined by Giemsa staining. A typical result is shown in FIG. 4A for clone AW-D9, which was found to have a normal 40XY karyotype (not shown). The composite photograph in FIG. 4A shows that both the red mouse BAC probe signal and the green human BAC probe signal co-localized to cytological band B on both copies of mouse chromosome 19, the known location of the Lrp5 gene. The composite photograph in FIG. 4C shows the same homozygous targeting for another clone (BA-D5). These results confirm that the 91 kb fragment of the human LRP5 gene in the humanization LTVEC (FIG. 1) was correctly inserted at the intended mouse Lrp5 locus on both chromosome 19 homologs in clones AW-D9 and BA-D5. In contrast, the composite photograph in FIG. 4B shows that both the red mouse BAC probe signal and the green human BAC probe signal co-localized to cytological band B on a single copy of mouse chromosome 19 (solid arrow), whereas only the red mouse BAC probe signal localizes to cytological band B on the other copy of mouse chromosome 19. These results confirm that the 91 kb fragment of the human LRP5 gene in the humanization LTVEC (FIG. 1) was correctly inserted at the intended mouse Lrp5 locus on only one copy of chromosome 19 (heterozygous targeting). They also indicate (along with other controls not shown) that the human BAC probe does not cross-hybridize to the mouse Lrp5 locus but only recognizes the human LRP5 insert.

The presence in certain clones of identical CRISPR-induced indel mutations formed at both alleles by apparent non-homologous end-joining repair suggested the occurrence of gene conversion events in F1H4 hybrid cells (which are comprised of 50% 129SvS6 strain and 50% C57BL/6N strain). To gain insight into the mechanism underlying the enhanced biallelic targeting when two gRNAs are used, seven clones were screened that had either targeted homozygous humanizations or homozygous CRISPR-induced large deletions following targeting with the LTVEC and either the A plus F or the A plus E2 gRNA combinations.

FIG. 5 shows examples of assays designed to examine gene conversion events mediated by two guide RNAs. Specifically, the possibility of gene conversion was examined by analyzing loss of heterozygosity (LOH) in F1H4 hybrid ES cells (which are comprised of 50% 129 SvS6 strain and 50% C57BL/6N strain). Gene conversion can be demonstrated by loss of heterozygosity in known polymorphisms between 129SvS6 (129) and C57BL/6N (B6), and thus PCR assays were designed to differentiate between these two allele types. Structural variants (SV) polymorphisms were assayed by conventional PCRs designed to detect the differences between the 129 and B6 alleles. Although only one of the SV assays used below is shown in FIG. 5, the concept is the same for each. Primers were designed based on structural variations (SVs) between B6 and 129 mouse strains and are shown in Table 1. The primer design conditions were constrained to identify ~25 bp SVs and produce ~300 bp PCR products; these conditions were selected such that any changes would be visible by gel electrophoresis.

Prior to running PCRs on the clones, the assays were validated and optimized against wild-type ES-cell DNA from the B6, 129 strains and from the F1H4 ES cell line. Primer sets that produced distinguishable PCR bands specific to either B6 or 129 alleles and were consistent in producing these same two distinguishable bands using F1H4 DNA were selected for testing on clones. For chromosome 19 (the location of the Lrp5 gene), six primer sets—IDs 190045, 190061, 190068, 190030, 190033, 190013—were selected for use on Lrp5 humanized clones genotyped as either "homozygous targeted" or "homozygous collapsed" by modification-of-allele (MOA) assays and conventional PCR. The SV PCR assays were spaced out along chromosome 19 from the Lrp5 locus to the telomeric end of the chromosome, ranging from ~13.7 to ~56.2 Mb from the Lrp5 locus. The approximate distances (in Mb) of the SV assays on chromosome 19 from the Lrp5 locus are as follows: 13.7 for assay 190045, 19.0 for assay 190061, 35.0 for assay 190068, 37.4 for assay 190030, 48.3 for assay 190033, and 56.2 for assay 190013. Only assay 190033 is shown in FIG. 5 (shown as SV 48.3), but the primers for assays 190045, 190061, 190068, 190030, 190033, and 190013 are shown in Table 1.

PCRs were run on DNA from these clones as well as on F1H4 control DNA, 129 control DNA, and B6 control DNA. PCR products were fractionated by electrophoresis on 6% polyacrylamide gels, which were subsequently stained with GelRed. Clones producing two bands matched up to the F1H4 control, which from the previous optimization showed that the top band was specific to the 129 allele and the bottom band was specific to the B6 allele. Clones that produced only one band displayed either just the B6 or just the 129 band. Clones AW-A7, AW-F10, BA-D5, BA-F2, BC-H9, and BR-B4 showed only the B6 band for all six assays, whereas clone BO-A8 showed only the 129 band for all six assays. As previously mentioned, these clones were genotyped as either homozygous targeted or homozygous collapsed by MOA and/or PCR, and involved various gRNA combinations (A plus F, A plus E2, B2, and D). The presence of just a single allelic band suggested that a gene conversion event is taking place—if there were no conversion, both bands would still be present as in the F1H4 control.

In addition, single nucleotide variants (SNVs) between the 129 and B6 alleles were assayed by TaqMan® allelic discrimination assays. The approximate positions of the SNV assays on the chromosome 19 map in FIG. 5 are shown by arrowheads with their distances (in Mb) from the Lrp5 locus given below. The distances (in Mb) from the Lrp5 locus are as follows: 0.32 centromeric of Lrp5 (C2), 1.2 telomeric of Lrp5 (T3), 11.1 telomeric of Lrp5 (T6), 13.2 telomeric of Lrp5 (T7), 17.5 telomeric of Lrp5 (T8), 25.8 telomeric of Lrp5 (T9), 33.0 telomeric of Lrp5 (T10), 38.3 telomeric of Lrp5 (T11), 49.6 telomeric of Lrp5 (T13), and 57.2 telomeric of Lrp5 (T14). The 129-specific and B6-specific probes and the primer pairs are shown in Table 1.

Table 3 shows seven examples of ES cell clones that exhibited apparent gene conversion events over the long arm of chromosome 19 in a direction telomeric from the Lrp5 target locus by LOH for both SV and SNV alleles. The ES cell clones were derived from independent targeting experiments that combined the Lrp5 humanization LTVEC (FIG. 1) with one or two gRNAs, as indicated. The positions of the gRNA recognition sites are shown above the representation of the Lrp5 gene in FIG. 5 (thick leftward pointing arrow). Genotyping assays indicated that six of the seven clones had homozygously targeted humanizations of the Lrp5 gene, while the one had a homozygous collapse (large deletion between the gRNA sites). In six of the seven clones, the 129 alleles were lost, leaving only the B6 alleles. In the other clone, the B6 alleles were lost, leaving only the 129 alleles. All clones remained heterozygous for alleles assayed on the centromeric side of the Lrp5 locus (i.e., all clones were heterozygous B6/129 with the C2 SNV assay). The LOH observed in the seven clones indicates that one mechanism by which homozygous genetically modified alleles are obtained when an LTVEC is combined with one, or more frequently, two gRNAs is a first targeted genetic modification on one allele followed by a homology directed recombination gene conversion event that copies the targeted genetic modification from one chromosome to its homolog.

TABLE 3

Loss of Heterozygosity Assay Results.

| Clone | gRNAs | Lrp5 Allele Type | Loss of Heterozygosity Assays (SV and SNV) |
|---|---|---|---|
| AW-A7 | A + F | Homozygous Targeted | Only B6 alleles detected |
| AW-F10 | A + F | Homozygous Collapse | Only B6 alleles detected |
| BO-A8 | A + F | Homozygous Targeted | Only 129 alleles detected |
| BA-D5 | A + E2 | Homozygous Targeted | Only B6 alleles detected |
| BA-F2 | A + E2 | Homozygous Targeted | Only B6 alleles detected |
| BC-H9 | B2 | Homozygous Targeted | Only B6 alleles detected |
| BR-B4 | D | Homozygous Targeted | Only B6 alleles detected |

C5 (Hc) Locus

Figure 6:
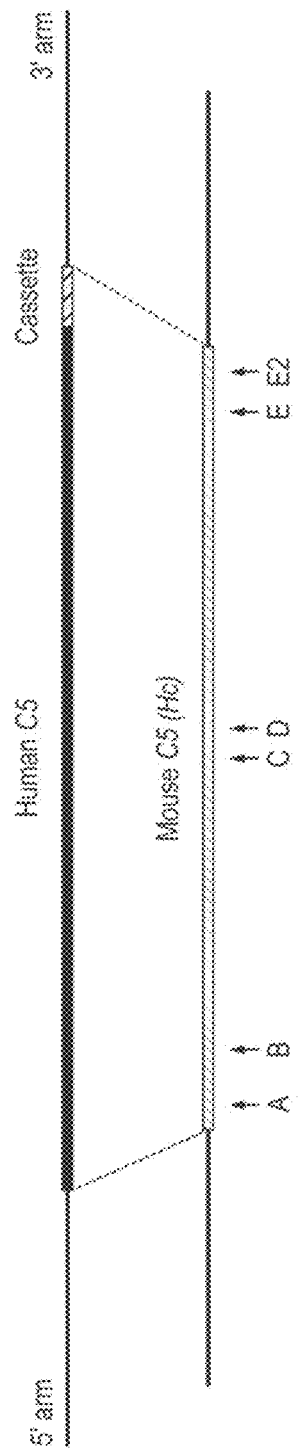
FIG. 6 shows a schematic for simultaneous deletion of the region from exon 2 to the stop codon of the mouse C5 (Hc) gene and replacement with a corresponding human C5 version using an LTVEC and either one or two 5' region (A, B), middle region (C, D), and 3' region (E, E2) gRNAs. The LTVEC is shown in the top portion of the figure, and the mouse C5 (Hc) gene locus is shown in the bottom portion of the figure. The positions of the Cas9 cleavage sites guided by the six guide RNAs are indicated by the arrows below the mouse gene sequence.

In another set of experiments, the LTVEC was designed to create a 76 kb deletion of the mouse gene for complement component 5 (C5 or Hc (hemolytic complement)) and a simultaneous replacement with a 97 kb fragment of the homologous human C5 gene (FIG. 6). The target locus comprised exon 2 to the stop codon of the C5 (Hc) gene. The LTVEC comprised the 97 kb fragment of the human C5 gene flanked by homology arms containing 35 kb and 31 kb of genomic DNA derived from parts of the mouse C5 (Hc) locus that flank the 76 kb sequence of the mouse C5 (Hc) gene intended for deletion. In separate experiments, the C5 (Hc) humanizing LTVEC was combined with a plasmid encoding Cas9 and a second plasmid encoding one of six gRNAs (A, B, C, D, E, and E2; see Table 1) designed to create double-strand breaks within the region of the mouse C5 (Hc) gene that was targeted for deletion. The gRNAs were designed to avoid recognition of any sequence in the inserted portion of the human C5 gene. In other experiments, we combined the LTVEC and the Cas9-encoding plasmid with plasmids encoding two different gRNAs that target different sites within the region of the mouse C5 (Hc) gene that was targeted for deletion. In some experiments, a control LTVEC that targets the Ch25h locus was used instead of the C5 (Hc) humanizing LTVEC. The control LTVEC, which is designed to delete the entire coding sequence of Ch25h (~1 kb) and insert puromycin and neomycin selection cassettes into the Ch25h locus, was used as a means to select drug-resistant clones that were not targeted for homologous recombination at the C5 (Hc) locus.

The results of the CRISPR/Cas9-assisted humanization of the C5 (Hc) gene are shown in Table 4 and are similar to the results obtained for CRISPR/Cas9-assisted humanization of the Lrp5 gene. The targeting efficiency with the LTVEC alone was higher (6.1%) for the C5 (Hc) humanization than for Lrp5, but addition of Cas9 and gRNAs enhanced the targeting efficiency for four of the six gRNAs tested. As with Lrp5, combining gRNAs (i.e., use of two gRNAs) for the C5 (Hc) humanization further increased total targeting efficiency, predominantly by increasing the frequency of hemizygous and homozygous targeting events. We also found ES cell clones with large CRISPR-induced deletions on both alleles (observed at frequencies of 1.8% to 3.6%). In addition, when the LTVEC targeting the Ch25h locus was used in combination with two C5 (Hc) gRNAs, clones with homozygous alleles that were collapsed between the two gRNA CRISPR RNA recognition sequences were observed at frequencies of 1.2% to 6%, indicating that the collapse events occur independently of homologous recombination events at the target locus. As with Lrp5, retention assays were used to confirm correctly targeted clones. The two retention assays for this screening were TaqMan® assays using the following primers and probes: 7140retU forward primer CCCAGCATCTGACGACACC (SEQ ID NO: 125); 7140retU reverse primer GACCACTGTGGG-CATCTGTAG (SEQ ID NO: 126); 7140retU TaqMan® probe CCGAGTCTGCTGTTACTGTTAGCATCA (SEQ ID NO: 127); 7140retD forward primer CCCGACACCTTCT-GAGCATG (SEQ ID NO: 128); 7140retD reverse primer TGCAGGCTGAGTCAGGATTTG (SEQ ID NO: 129); 7140retD TaqMan® probe TAGT-CACGTTTTGTGACACCCCAGA (SEQ ID NO: 130).

TABLE 4

Screening Results for CRISPR/Cas9-Assisted Humanization of the C5 (Hc) Gene Using Individual gRNAs and Combined gRNAs.

| | Distance of gRNA Site | | Targeting Efficiency by Allele Type | | | | |
|---|---|---|---|---|---|---|---|
| gRNA | from 5'/3' Ends of Targeted Deletion (bp) | LTVEC | Het. Targ. (% Eff.) | Hemi. Targ. (% Eff.) | Homo. Targ. (% Eff.) | Total Targ. (% Eff.) | Homo. Del. (% Eff.) |
| A | 100 (5') | C5 | 16.6 | | | 16.6 | |
| B | 500 (5') | C5 | 14.5 | | | 14.5 | |
| C | 38200 (5')/37500 (3') | C5 | 11.4 | | | 11.4 | |
| D | 43500 (5')/32200 (3') | C5 | 7.3 | | | 7.3 | |
| E | 500 (3') | C5 | 4.2 | | | 4.2 | |
| E2 | 100 (3') | C5 | 6.2 | | | 6.2 | |
| A + C | A: 100 (5') C: 37500 (3') | C5 | 19.6 | 7.1 | 0.6 | 27.3 | 0.6 |
| A + C | A: 100 (5') C: 37500 (3') | Ch25h | N/A | N/A | N/A | N/A | 6.0 |
| A + E2 | A: 100 (5') E2: 100 (3') | C5 | 19.0 | 3.6 | 1.2 | 23.8 | 3.0 |
| A + E2 | A: 100 (5') E2: 100 (3') | Ch25h | N/A | N/A | N/A | N/A | 1.2 |
| None | N/A | C5 | 6.1 | | | 6.1 | |

Figures 7A, 7B:
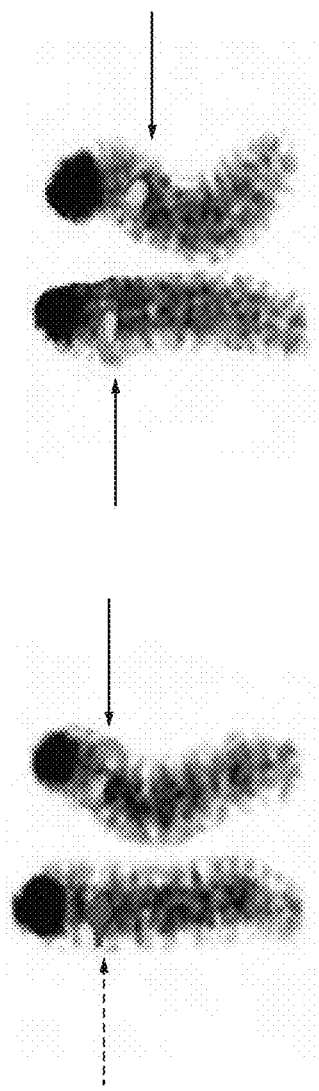
FIGS. 7A and 7B show fluorescence in situ hybridization (FISH) analysis of mouse ES cell clones Q-E9 (FIG. 7A) and O-E3 (FIG. 7B), which were targeted with the Hc humanization LTVEC combined with Cas9 and two gRNAs. Arrows indicate the positions of hybridization signals on band B of chromosome 2. A red signal indicates hybridization with only the mouse probe (dashed arrow, FIG. 7A). A yellow mixed color signal indicates hybridization with both the red mouse probe and the green human probe (solid arrow). One chromosome 2 band B having a red signal (dashed arrow) and the other chromosome 2 band B having a yellow signal (solid arrow) confirmed targeting to the correct locus and the heterozygous genotype for the Q-E9 clone (FIG. 7A). The B bands of both chromosomes 2 having a yellow signal (solid arrows, FIG. 7B) confirmed targeting to the correct locus and the homozygous genotype for the O-E3 clone.

Fluorescence in situ hybridization (FISH) was used to confirm homozygous targeted humanization of the C5 (Hc) gene. ES cell clones scored by quantitative and conventional PCR assays as homozygous targeted from targeting experiments in which the C5 (Hc) humanization LTVEC (FIG. 6) was combined with Cas9 and two gRNAs were sent to a commercial cytology service for FISH and karyotype analysis. A bacterial artificial chromosome (BAC) carrying the mouse C5 (Hc) gene was labeled with a red fluorescent marker and used as a probe to identify endogenous loci, and a BAC carrying the human C5 gene was labeled with a green fluorescent marker and used as a probe to identify chromatids targeted with the human insert. The labeled BAC probes were hybridized to metaphase spreads from the targeted clones and visualized by fluorescence microscopy. Chromosomes on the spreads were visualized by staining with DAPI (4',6-diamidino-2-phenylindole), and separate karyotypes for each clone were determined by Giemsa staining. A typical result is shown in FIG. 7B for clone O-E. The composite photograph in FIG. 7B shows that both the red mouse BAC probe signal and the green human BAC probe signal co-localized to the C5 (Hc) locus on both copies of mouse chromosome 2, the known location of the C5 (Hc) gene. These results confirm that the 97 kb fragment of the human C5 gene in the humanization LTVEC (FIG. 6) was correctly inserted at the intended mouse C5 (Hc) locus on both chromosome 2 homologs in clone O-E3. In contrast, the composite photograph in FIG. 7A shows that both the red mouse BAC probe signal and the green human BAC probe signal co-localized on a single copy of mouse chromosome 2 (solid arrow), whereas only the red mouse BAC probe signal localizes to the C5 (Hc) locus on the other copy of mouse chromosome 2. These results confirm that the 97 kb fragment of the human C5 gene in the humanization LTVEC (FIG. 6) was correctly inserted at the intended mouse C5 (Hc) locus on only one copy of chromosome 2 (heterozygous targeting) in clone Q-E9.

Ror1 Locus

Figure 8:
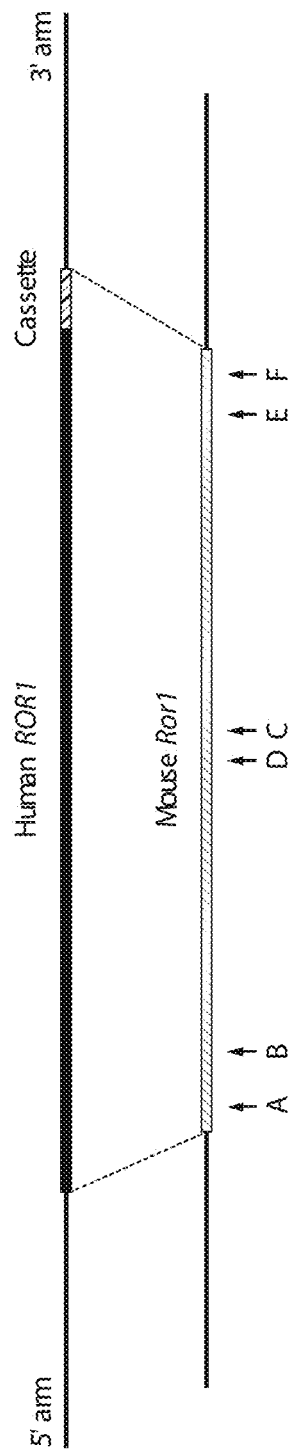
FIG. 8 shows a schematic for simultaneous deletion of the mouse Ron 1 gene and replacement with a corresponding human ROR1 version using an LTVEC and either one or two 5' region (A, B), middle region (D, C), and 3' region (E, F) gRNAs. The LTVEC is shown in the top portion of the figure, and the mouse Ron 1 gene locus is shown in the bottom portion of the figure. The positions of the Cas9 cleavage sites guided by the six guide RNAs are indicated by the arrows below the mouse gene sequence.

In another set of experiments, the LTVEC was designed to create a 110 kb deletion of the mouse Ron 1 (tyrosine-protein kinase transmembrane receptor ROR1) gene and a simultaneous replacement with a 134 kb fragment of the homologous human ROR1 gene (FIG. 8). The LTVEC comprised the 134 kb fragment of the human ROR1 gene flanked by homology arms containing 41.8 kb and 96.4 kb of genomic DNA derived from parts of the mouse Ror1 locus that flank the 110 kb sequence of the mouse Ror1 gene intended for deletion. In separate experiments, the Ror1 humanizing LTVEC was combined with a plasmid encoding Cas9 and a second plasmid encoding one of six gRNAs (A, B, C, D, E, and F; see Table 1) designed to create double-strand breaks within the region of the mouse Ror1 gene that was targeted for deletion. The gRNAs were designed to avoid recognition of any sequence in the inserted portion of the human ROR1 gene. In other experiments, we combined the LTVEC and the Cas9-encoding plasmid with plasmids encoding two different gRNAs that target different sites within the Ror1 gene that was targeted for deletion.

The results of the CRISPR/Cas9-assisted humanization of the Ror1 gene are shown in Table 5 and are similar to the results obtained for CRISPR/Cas9-assisted humanization of the Lrp5 and C5 (Hc) genes. The targeting efficiency with LTVEC alone was 0.3%, and addition of Cas9 and gRNAs slightly increased the targeting efficiency for two of the six gRNAs tested. Combining the A and F gRNAs increased the total Ron 1 targeting efficiency to 6.3% by increasing the frequency of both the heterozygous and hemizygous targeting events. We also found ES cell clones with large CRISPR-induced deletions on both alleles (observed at a frequency of 1.6%).

TABLE 5

Screening Results for CRISPR/Cas9-Assisted Humanization of the Ror1 Gene Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 200 (5') | 0.7 | | | 0.7 | |
| B | 1000 (5') | 0.0 | | | 0.0 | |
| D | 54300 (5')/55500 (3') | 0.7 | | | 0.7 | |
| C | 54500 (5')/55300 (3') | 0.0 | | | 0.0 | |
| E | 1000 (3') | 0.0 | | | 0.0 | |
| F | 200 (3') | 0.3 | | | 0.3 | |
| A + F | A: 200 (5') F: 200 (3') | 4.2 | 2.1 | | 6.3 | 1.6 |
| None | N/A | 0.3 | | | 0.3 | |

Trpa1 Locus

Figure 9:
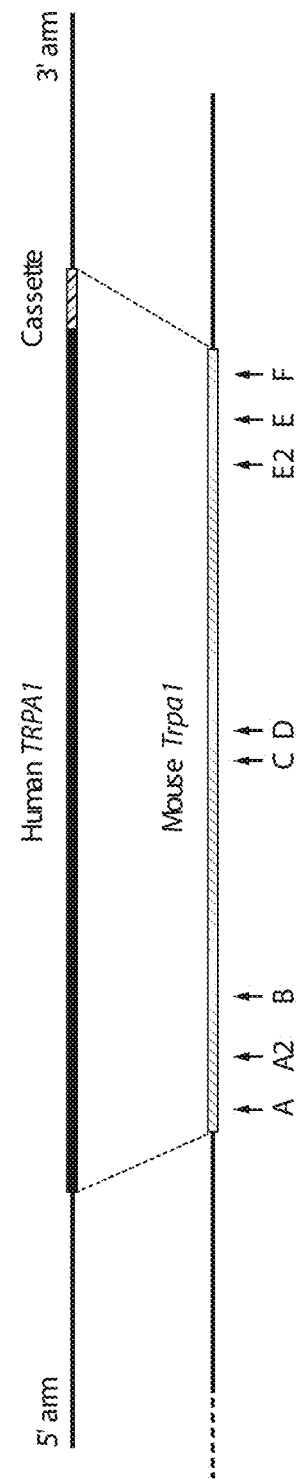
FIG. 9 shows a schematic for simultaneous deletion of the mouse Trpa1 gene and replacement with a corresponding human TRPA1 version using an LTVEC and either one or two 5' region (A, A2, B), middle region (C, D), and 3' region (E2, E, F) gRNAs. The LTVEC is shown in the top portion of the figure, and the mouse Trpa1 gene locus is shown in the bottom portion of the figure. The positions of the Cas9 cleavage sites guided by the eight guide RNAs are indicated by the arrows below the mouse gene sequence.

In another set of experiments, the LTVEC was designed to create a 45.3 kb deletion of the mouse Trpa1 (transient receptor potential cation channel, subfamily A, member 1) gene and a simultaneous replacement with a 54.5 kb fragment of the homologous human TRPA1 gene (FIG. 9). The LTVEC comprised the 54.5 kb fragment of the human TRPA1 gene flanked by homology arms containing 41.0 kb and 58.0 kb of genomic DNA derived from parts of the mouse Trpa1 locus that flank the 45.3 kb sequence of the mouse Trpa1 gene intended for deletion. In separate experiments, the Trpa1 humanizing LTVEC was combined with a plasmid encoding Cas9 and a second plasmid encoding one of eight gRNAs (A, A2, B, C, D, E2, E, and F; see Table 1) designed to create double-strand breaks within the region of the mouse Trpa1 gene that was targeted for deletion. The gRNAs were designed to avoid recognition of any sequence in the inserted portion of the human TRPA1 gene. In other experiments, we combined the LTVEC and the Cas9-encoding plasmid with plasmids encoding two different gRNAs that target different sites within the Trpa1 gene that was targeted for deletion.

The results of the CRISPR/Cas9-assisted humanization of the Trpa1 gene are shown in Table 6 and are similar to the results obtained for CRISPR/Cas9-assisted humanization of the Lrp5 and C5 (Hc) genes. The targeting efficiency with LTVEC alone was 0.3%, and addition of Cas9 and gRNAs increased the targeting efficiency for six of the eight gRNAs tested. Combining the B and F gRNAs increased the total Trpa1 targeting efficiency to 3.4% by increasing the frequency of the heterozygous, hemizygous, and homozygous targeting events. We also found ES cell clones with large CRISPR-induced deletions on both alleles (observed at a frequency of 0.3%).

TABLE 6

Screening Results for CRISPR/Cas9-Assisted Humanization of the Trpa1 Gene Using Individual gRNAs and Combined gRNAs.

| gRNA | Distance of gRNA Site from 5'/3' Ends of Targeted Deletion (bp) | Targeting Efficiency by Allele Type | | | | |
|---|---|---|---|---|---|---|
| | | Het. Targ. (% Eff.) | Hemi. Targ. (% Eff.) | Homo. Targ. (% Eff.) | Total Targ. (% Eff.) | Homo. Del. (% Eff.) |
| A | 100 (5') | 1.0 | | | 1.0 | |
| A2 | 500 (5') | 2.1 | | | 2.1 | |
| B | 1000 (5') | 1.4 | | | 1.4 | |
| C | 25600 (5')/19740 (3') | 1.0 | | | 1.0 | |
| D | 26970 (5')/18370 (3') | 2.1 | | | 2.1 | |
| E2 | 1000 (3') | 0.0 | | | 0.0 | |
| E | 500 (3') | 0.0 | | | 0.0 | |
| F | 100 (3') | 0.7 | | | 0.7 | |
| B + F | B: 1000 (5') F: 100 (3') | 2.8 | 0.3 | 0.3 | 3.4 | 0.3 |
| None | N/A | 0.3 | | | 0.3 | |

As these examples illustrate, use of dual guide RNAs at widely separated sites improved the enhancement of heterozygous humanization compared with single gRNAs. In addition, use of dual guide RNAs promoted biallelic events compared to single gRNAs. In contrast to targeting with one gRNA, targeting with two gRNAs results in the creation of homozygously targeted cells (Hum/Hum) in which both alleles had a targeted humanization, homozygously deleted cells (A/A) in which neither allele was targeted with the humanizing LTVEC but both had large deletions, and hemizygously targeted cells (Hum/A) in which one allele had a targeted humanization and the other had a large dual gRNA/Cas9-induced deletion. First, we found correctly targeted clones that had precise and identical very large humanizations at both target alleles (e.g., cells that were homozygous for the targeted gene modification). Although homozygously targeted clones were also observed when we used one gRNA to achieve Lrp5 humanization, they occurred at a much lower frequency than when we employed two gRNAs (see Table 2). Likewise, we did not observe homozygous targeting when using one gRNA to achieve C5 (Hc) humanization or Trpa1 humanization, but we did observe homozygous targeting when using two gRNAs with the targeting vector (see Tables 4 and 6). Similarly, we found correctly targeted clones that were hemizygous for the gene modification (i.e., they had a precisely targeted humanization on one allele and a very large, sometimes gene ablating, deletion on the other allele) for Lrp5 targeting, C5 (Hc) targeting, Ror I targeting, and Trpa1 targeting. Such modifications did not occur at all when using one gRNA to achieve Lrp5, C5 (Hc), Ror1, or Trpa1 humanization (see Tables 2, 4, 5, and 6, respectively).

Second, we found clones that had identical very large deletions (>45 kb) induced by Cas9 cleavage events guided by both gRNAs on both targeted alleles (i.e., the cells were homozygous for a large, sometimes gene-ablating, deletion at the target locus). These types of mutations do not require the targeting vector directed against the same gene. For example, as shown in Table 4, we have obtained ES cells with homozygous CRISPR-induced deletions by combining Cas9 and two gRNAs with a targeting vector directed against a different gene unrelated to the one targeted by the gRNAs. Thus, a Cas9 nuclease guided by two gRNAs can induce a large deletion in cells without addition of a targeting vector. In such cases, transient or stable drug selection provided by a vector that expresses a drug resistance gene can facilitate the isolation of rare homozygous deletion clones by enrichment for ES cells that have taken up DNA.

Example 2. Analysis of Large Deletions Induced by Combined gRNAs

Allele Structures for Large Deletions Induced by Combined gRNAs

Additional sequence analysis was performed on clones comprising large deletions induced by Cas9 cleavage events guided by two gRNAs (see Table 7). These large deletions appeared to be independent of the LTVEC-directed homologous recombination events at the same locus in that we obtained large deletions at the Lrp5 locus at approximately the same frequency when we combined the gRNAs with either an Lrp5 LTVEC or one targeting the Ch25h gene nearly 30 Mb away (data not shown). To characterize the large deletions, we performed deletion-spanning PCRs on 37 clones, 15 hemizygous and 22 with biallelic large deletions, from four humanizations, and sequenced individual clones of the PCR products. The sequences confirmed the large deletions, which ranged from 38 kb to 109 kb. Two of the ES cell clones (Lrp5 clones AW-A8 and BP-D3) had perfectly repaired precise deletions (68.2 kb) between the predicted Cas9 cleavage sites, while one clone (Hc clone P-B12) had a single base pair insertion in addition to the 38.1 kb deletion. Twenty-seven of the ES cell clones had deletions that extended beyond the Cas9 cleavage sites, consistent with imprecise repair by non-homologous end joining (NHEJ). The remaining seven ES cell clones had mutations that combined apparent NHEJ-induced deletions and insertions (e.g., Lrp5 clone BP-F6 and Hc clone O-E4), four of which had insertions of greater than 200 bp that we could map to their source genomic loci (data not shown). The 210 bp insertion in Lrp5 clone BO-E9 was in an inverted orientation with respect to an identical sequence lying approximately 2,600 bp outside of the gRNA F target site in the centromeric direction (chromosome 19+, 3589138-3589347). This sequence was present in the long 3' homology arm of the Lrp5 LTVEC. Lrp5 clones BP-F6 and BP-G7 were derived from an experiment in which we combined Lrp5 gRNAs A and F with Cas9 and an LTVEC that targeted the Ch25h gene 30 Mb away from Lrp5 in the telomeric direction. Clone BP-F6 had a 266 bp insertion that appeared to be derived from one end of the Ch25h LTVEC in that it was composed of a 103 bp fragment identical to part of the vector backbone linked to a 163 bp fragment that was identical to a sequence near Ch25h and also present in the long arm of the LTVEC (chromosome 19+, 34478136-34478298); this fragment was inserted at the deletion in an inverted orientation with respect to the endogenous chromosomal sequence. Hc clone O-E4 had a 254 bp insertion that was inverted with respect to an identical sequence found within the deleted sequence approximately 3.1 kb away from the gRNA A recognition site. The 1,304 bp insertion in Hc clone S-D5 was composed of two fragments: a 1,238 bp piece that was in the same orientation as an identical sequence found within the deleted sequence approximately 1.4 kb away from the predicted gRNA E2-directed Cas9 cleavage site and a second 66 bp piece that was a duplication in an inverted orientation of an identical sequence 25 bp outside of the gRNA E2 cut site.

as a template for homologous recombination repair of Cas9 cleavages on the homologous chromosome. We took advantage of the 129S6SvEvTac (129) and C57BL/6NTac (B6) F1 hybrid composition of the VGF1 ES cell line (Poueymirou et al. (2007) Nat. Biotechnol. 25:91-99; Valenzuela et al. (2003) Nat. Biotechnol. 21:652-659) to assay for gene conversion as loss of heterozygosity (Lefebvre et al. (2001) Nat. Genet. 27:257-258) for structural (SV) and single nucleotide (SNV) variants between the strains around the Lrp5 locus on chromosome 19 (see FIG. 5 for the five SV assays and ten SNV assays used below) and the Hc locus on chromosome 2 (not shown). To confirm that any loss of

TABLE 7

Allele Structures for Large Deletions Induced by Combined gRNAs.

| Gene | ES Cell Clone | Genotype[1] | gRNAs | Positions Within Targeted Deletion (bp) | Size of Deletion (kb) | Additional Sequence Deleted (bp) | Insertion (bp) | PCR Clones |
|---|---|---|---|---|---|---|---|---|
| Lrp5 | AW-A8 | Δ/Δ | A + F | 5'-50/50-3' | 68.2 | — | — | 40 |
| | BO-E9 | Δ/Δ | | | | 12 | 210 | 17 |
| | BP-D3 | Δ/Δ | | | | — | — | 11 |
| | BP-F6 | Δ/Δ | | | | 30 | 266 | 6 |
| | BP-G7 | Δ/Δ | | | | 77 | | 9 |
| | BA-A7 | Δ/Δ | A + E2 | 5'-50/1,000-3' | 67.3 | 7 | | 19 |
| | BA-C7 | Δ/Δ | | | | 84 | | 32 |
| Hc | N-A11 | Δ/Δ | A + C | 5'-100/38,200-3' | 38.1 | 14 | | 12 |
| | N-D4 | Δ/Δ | | | | 10 | | 15 |
| | N-D11 | Hum/Δ | | | | 20 | | 10 |
| | | | | | | 10 | | 1 |
| | N-E1 | Hum/Δ | | | | 10 | | 13 |
| | N-E9 | Hum/Δ | | | | 20 | | 16 |
| | O-C5 | Hum/Δ | | | | 31 | | 21 |
| | O-D2 | Hum/Δ | | | | 5 | | 12 |
| | O-E4 | Hum/Δ | | | | 19 | 254 | 18 |
| | O-E5 | Hum/Δ | | | | 35 | 2 | 16 |
| | O-E6 | Hum/Δ | | | | 6 | | 17 |
| | O-F11 | Hum/Δ | | | | 12 | 7 | 18 |
| | O-F12 | Hum/Δ | | | | 41 | | 6 |
| | | | | | | 35 | | 1 |
| | P-B12 | Δ/Δ | | | | | 1 | 7 |
| | P-C12 | Δ/Δ | | | | 20 | | 15 |
| | P-D1 | Δ/Δ | | | | 33 | | 10 |
| | P-G8 | Δ/Δ | | | | 5 | | 2 |
| | Q-F5 | Hum/Δ | A + E2 | 5'-100/100-3' | 75.6 | 3 | 3 | 15 |
| | Q-F10 | Δ/Δ | | | | 46 | | 13 |
| | R-A5 | Δ/Δ | | | | 18 | | 14 |
| | R-A7 | Δ/Δ | | | | 37 | | 15 |
| | R-A9 | Hum/Δ | | | | 261 | | 8 |
| | R-C8 | Hum/Δ | | | | 180 | | 11 |
| | R-D12 | Hum/Δ | | | | 182 | | 10 |
| | R-F11 | Hum/Δ | | | | 19 | | 11 |
| | S-A11 | Δ/Δ | | | | 122 | | 11 |
| | | | | | | 46 | | 1 |
| | S-D5 | Δ/Δ | | | | 216 | 1304 | 8 |
| Ror1 | Y-B5 | Δ/Δ | A + F | 5'-200/200-3' | 109 | 18 | | 6 |
| | Y-C7 | Δ/Δ | | | | 23 | | 7 |
| | Y-E1 | Δ/Δ | | | | 12 | | 3 |
| Trpa1 | AD-C7 | Δ/Δ | B + F | 5'-1,000/100-3' | 44.6 | 30 | | 8 |

[1]Hum/+, targeted humanization of one of the two native alleles resulting in a heterozygous genotype; Hum/Δ, a biallelic modification in which one allele has a targeted humanization and the other has a large Cas9-gRNA-induced deletion resulting in a hemizygous genotype; Hum/Hum, a biallelic modification in which both alleles have a targeted humanization resulting in a homozygous genotype; Δ/Δ a biallelic modification in which both alleles have a large Cas9-gRNA-induced deletion.

Evidence for Gene Conversion at Homozygous Alleles

Twenty-one of the 22 ES cell clones with biallelic large deletions had only a single, unique sequence (Table 7), indicating that they were homozygous alleles. For Hc clone S-A11, we found the same sequence in 11 of 12 PCR clones. The single clone with a different sequence might suggest two different deletion alleles, but we also found the same result for two of the Hc hemizygous clones, N-D11 and O-F12. The distinct homozygous deletion alleles in multiple clones suggested they might have arisen by a gene conversion mechanism in which a deletion on one chromosome served heterozygosity was not the result of whole chromosome loss, we performed chromosome copy number (CCN) assays at sites that were identical between the 129 and B6 strains. For Lrp5 humanized or deleted alleles we assayed multiple SVs and SNVs positioned from 1.2 Mb away from Lrp5 in the telomeric direction to the end of the long arm of chromosome 19 (FIG. 5). Because of Lrp5's location close to the centromere, we found no SVs and only one SNV on the centromeric side of the gene. For Hc, we were able to assay for multiple SVs and SNVs on either side of the gene on chromosome 2 (not shown). The results for six of the Lrp5 clones are shown in FIGS. 10A-E and 11A-C.

FIG. 10A-E shows results for five SV assays, whose positions ranged from 13.7 Mb away from Lrp5 to 56.7 Mb away near the telomeric end of the long arm. The five SV assays produced two different sized products for the 129 (larger) and B6 (smaller) alleles in the 129, B6, and VGF1 controls. The approximate positions of the SV assays on the chromosome 19 map are shown in FIG. 5 (see assay SV 13.7, assay SV 20.0, assay SV 36.9, assay SV 48.3, and assay SV 56.7). The assay number represents the number of Mb telomeric to Lrp5. Primers for these assays are shown in Table 1, and the results are shown in FIG. 10A-E. Two of the clones, BC-H9 ($Lrp^{Hum/Hum}$, gRNA B2) and BR-B4 ($Lrp5^{Hum/Hum}$, gRNA D), displayed a loss of heterozygosity that retained all of the B6 SV alleles, while a third clone, BO-A8 ($Lrp5^{Hum/Hum}$, gRNAs A+F), retained all of the 129 alleles. The other three clones, BO-F10 ($Lrp5^{Hum/Hum}$, gRNAs A+F), BO-G11 ($Lrp5^{Hum/Hum}$, gRNAs A+F), and BP-G7 ($Lrp5^{\Delta/\Delta}$, gRNAs A+F), remained heterozygous.

Figure 11A:
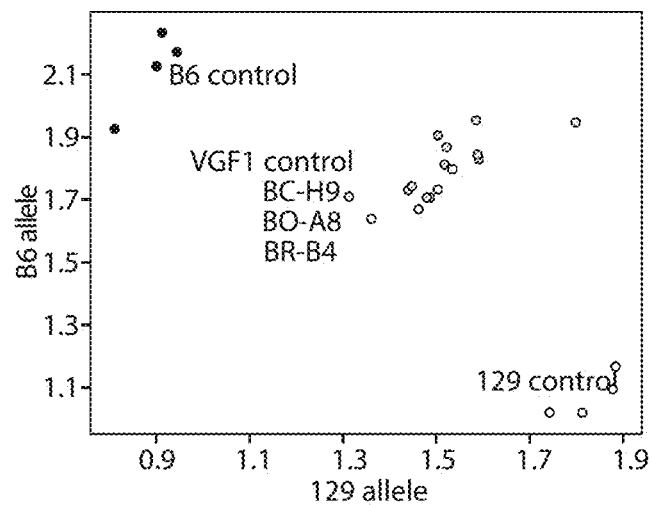
FIGS. 11A-C show allelic discrimination plots for the 0.32 Mb centromeric of Lrp5 (FIG. 11A), 1.2 Mb telomeric of Lrp5 (FIG. 11B), and 57.2 Mb telomeric of Lrp5 (FIG. 11C). The values on each axis represent relative fluorescence intensity. The plots depict four replicates for each sample, which are shown as solid dots (B6 allele), open dots (129 allele), and dots with diagonal lines (both B6/129 alleles).
Figure 11B:
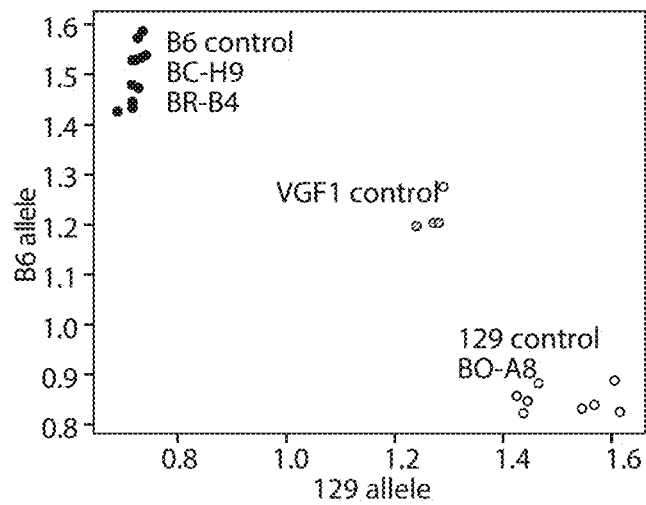
Figure 11C:
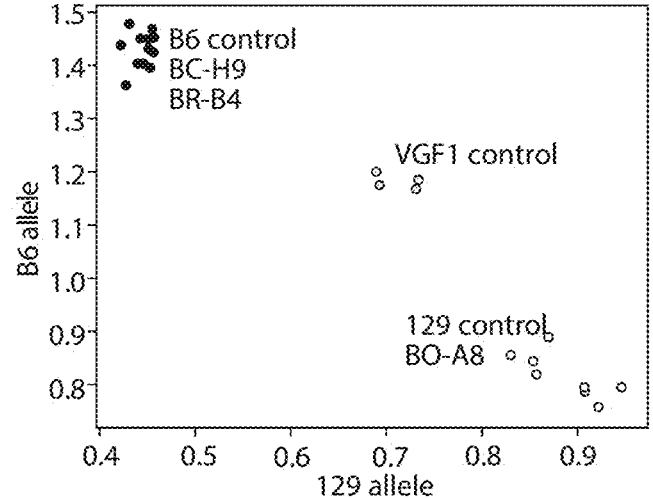

In addition, single nucleotide variants (SNVs) between the 129 and B6 alleles were assayed by TaqMan® allelic discrimination assays. The approximate positions of the SNV assays on the chromosome 19 map in FIG. 5 are shown by arrowheads with assay numbers underneath, and their distances (in Mb) from the Lrp5 locus are given below. The distances (in Mb) from the Lrp5 locus are as follows: 0.32 centromeric of Lrp5 (C2), 1.2 telomeric of Lrp5 (T3), 11.1 telomeric of Lrp5 (T6), 13.2 telomeric of Lrp5 (T7), 17.5 telomeric of Lrp5 (T8), 25.8 telomeric of Lrp5 (T9), 33.0 telomeric of Lrp5 (T10), 38.3 telomeric of Lrp5 (T11), 49.6 telomeric of Lrp5 (T13), and 57.2 telomeric of Lrp5 (T14). The 129-specific and B6-specific probes and the primer pairs are shown in Table 1. The results for three clones (BC-H9, BO-A8, and BR-B4) that showed telomeric loss-of-heterozygosity (LOH) by SV assays are shown in FIG. 11A-C. The SNV assays (FIG. 11A-C and data not shown) confirmed the gene conversion events over the long arm of chromosome 19 on the telomeric side of Lrp5 (SNV 1.2 and SNV 57.2; see FIG. 11B and FIG. 11C, respectively), but the SNV 0.32 assay (see FIG. 11A) showed that all clones remained heterozygous for an allele 320 kb away from Lrp5 on the centromeric side. Of the 24 $Lrp5^{Hum/Hum}$ or $Lrp5^{\Delta/\Delta}$ clones assayed, we found six that had evidence of loss of heterozygosity over the entire long arm of chromosome 19 on the telomeric side of Lrp5. Five of the clones (four $Lrp5^{Hum/Hum}$ and one $Lrp5^{\Delta/\Delta}$) converted from heterozygous to homozygous B6, while a sixth clone ($Lrp5^{Hum/Hum}$) converted to homozygous 129. CCN assays demonstrated retention of two copies of chromosome 19. Similar loss of heterozygosity assays for 21 Hc homozygous clones revealed that two, R-E2 ($Hc^{Hum/Hum}$, gRNAs A+F) and R-E8 ($Hc^{\Delta/\Delta}$, gRNAs A+F), showed loss of heterozygosity to homozygous 129 for all SVs and SNVs on the telomeric side of the Hc gene while retaining heterozygosity for all alleles on the centromeric side. CCN assays indicated no loss of chromosome 2.

Our results demonstrate for the first time that CRISPR/Cas9 can enhance homology-directed repair for large single-step humanizations of over 100 kb, which expands the possibilities for large-scale genome engineering. The most remarkable and unexpected benefit of combining LTVECs and gRNA/Cas9 was their ability to promote homozygous targeted humanizations. Although biallelic mutations and homozygous targeting events have been reported in other CRISPR/Cas9 experiments, most of these gene modifications and insertions have been orders of magnitude smaller than our humanized alleles. Prior to the use of CRISPR/Cas9, we had never found homozygous targeting by an LTVEC, nor had we seen simultaneous targeting of more than one gene when we combined multiple LTVECs targeting separate genes. Given this experience, the gRNA/Cas9-induced homozygous targeting suggested that rather than two LTVECs separately targeting both alleles, an initial targeting event on one allele might serve as a template for the homologous conversion of the other allele promoted by one or more Cas9 cuts. The revelation that the dual gRNA/Cas9-induced large biallelic deletions were also homozygous (Table 7) provided further support for a gene conversion mechanism.

Loss of heterozygosity assays (FIG. 5) demonstrated that large-scale gene conversion of multiple alleles covering a large fragment of the chromosome on the telomeric side of the target gene was responsible for some of the homozygous humanizations and large deletions. This type of long-range directional gene conversion is consistent with mitotic recombination between the replicated chromatids of homologous chromosomes in the G2 phase of the cell cycle (Lefebvre et al. (2001) Nat. Genet. 27:257-258) (FIG. 12). Although it explained only a minority of the homozygous events, this mechanism could provide a means by which gRNA/Cas9 cleavage can be used to promote large-scale conversion from heterozygous to homozygous for multiple alleles over a large portion of a chromosome. Most of the homozygous events, however, appear to have been the result of local gene conversion whose mechanism deserves further investigation.

Further evidence for long-range directional gene conversion was provided by analysis of three clones obtained after electroporating F1H4 hybrid ES cells (which are comprised of 50% 129SvS6 strain and 50% C57BL/6N strain) with plasmids encoding Lrp5 gRNAs A and F, a plasmid encoding Cas9, and an LTVEC that targeted the Ch25h gene 30 Mb away from Lrp5 in the telomeric direction. Three clones initially scored as wild type following primary screening using TaqMan® assays inside the predicted deletion between the 2 gRNAs (500 bp away at the 5' end and 2 kb at the 3' end), but subsequent TaqMan® allelic discrimination assays assaying single nucleotide variants (SNVs) between the 129 and B6 alleles surprisingly revealed loss of heterozygosity. The SNV assays used were one centromeric assay (SNV 0.32) and two telomeric assays (SNV 1.2 and SNV 57.2) (see FIG. 5). As shown in Table 8, the centromeric SNV assay (0.32 Mb) confirmed retention of heterozygosity in all three clones. However, both telomeric SNV assays showed that BP-E7 and BP-H4 were homozygous for the 129 allele, and both telomeric SNV assays showed that BP-E6 was homozygous for the B6 allele. All three clones showed retention of two copies of chromosome 19, and all three clones were transgenic for LTVEC targeting (i.e., the Ch25h locus was targeted). These results open the possibility to forced homozygosity using targeted CRISPR/Cas9 cleavage.

TABLE 8

Screening Results for SNV Allelic Discrimination Assays.

| Clone | SNV 0.32 | SNV 1.2 | SNV 57.2 |
|---|---|---|---|
| BP-E7 | 129/B6 | 129/129 | 129/129 |
| BP-H4 | 129/B6 | 129/129 | 129/129 |
| BP-E6 | 129/B6 | B6/B6 | B6/B6 |

Several possible mechanisms can explain the results observed in the CRISPR/Cas9-assisted LTVEC humanization experiments in mouse F1H4 hybrid ES cells (which are comprised of 50% 129SvS6 strain and 50% C57BL/6N strain) (see FIG. 16A-F). Such mechanisms could occur through reciprocal chromatid exchange by mitotic cross over (see FIG. 16A-C), or by chromatid copying by break-induced replication (see FIG. 16D-E). In either case, a heterozygous modification could occur in which either the 129 chromosome or the B6 chromosome is targeted by the LTVEC before genome replication (see FIGS. 16A and 16D). Alternatively, a single 129 chromatid or a single B6 chromatid could be targeted by the LTVEC after genome replication, followed by inter-chromatid gene conversion (see FIGS. 16B and 16E). Alternatively, there can be a lack of LTVEC targeting at the target genomic locus, but Cas9 cleavage can occur on either the 129 or B6 chromosome (see FIGS. 16C and 16F). This latter possibility can explain the results seen with the BP-E7, BP-H4, and BP-E6 clones. The potential outcomes are shown in FIGS. 16A-F. For FIG. 16F, it is also possible to observe loss of heterozygosity (LOH) retaining the B6 alleles if the Cas9 cleaves a 129 chromatid. In the experiments described above, loss of heterozygosity events have been observed resulting in both alleles being targeted (Hum/Hum) or both alleles being wild type alleles (+/+).

Example 3. Effect of LTVEC Homology Arm Sizes on Targeting Efficiency

To determine the effect of homology arm size on targeting efficiency, two LTVECs designed to create a 76 kb deletion of the mouse gene for complement component 5 (C5 or Hc (hemolytic complement)) and a simultaneous replacement with a 97 kb fragment of the homologous human C5 gene were compared (FIG. 13). The target locus comprised exon 2 to the stop codon of the C5 (Hc) gene. The first LTVEC comprised the 97 kb fragment of the human C5 gene flanked by homology arms containing 35 kb and 31 kb of genomic DNA derived from parts of the mouse C5 (Hc) locus that flank the 76 kb sequence of the mouse C5 (Hc) gene intended for deletion (see targeting vector labeled LTVEC in FIG. 13). The second LTVEC comprised the 97 kb fragment of the human C5 gene flanked by homology arms containing 5 kb each of genomic DNA derived from parts of the mouse C5 (Hc) locus that flank the 76 kb sequence of the mouse C5 (Hc) gene intended for deletion (see targeting vector labeled sTVEC in FIG. 13).

In separate experiments, the C5 (Hc) humanizing LTVECs were combined with a plasmid encoding Cas9 and a second plasmid encoding one or two of six gRNAs (A, B, C, D, E, and E2; see Table 1) designed to create double-strand breaks within the region of the mouse C5 (Hc) gene that was targeted for deletion. The gRNAs were designed to avoid recognition of any sequence in the inserted portion of the human C5 gene.

The results of the CRISPR/Cas9-assisted humanization of the C5 (Hc) gene are shown in Table 9. The targeting efficiency of the first LTVEC alone (homology arms of 35 kb and 31 kb) was higher than the targeting efficiency of the second LTVEC alone (homology arms of 5 kb and 5 kb). However, the total targeting efficiencies of each LTVEC when combined with gRNAs A and E2 were nearly identical (see Table 9), indicating that homology arm sizes of 5 kb (i.e., sum total of 10 kb) are sufficient for facilitating the increase in targeting efficiency observed when targeting the C5 (Hc) locus using CRISPR/Cas9 in combination with LTVEC targeting.

TABLE 9

Screening Results for CRISPR/Cas9-Assisted Humanization of the C5 (Hc) Gene Using LTVECs with Different Homology Arm Sizes.

| gRNA | LTVEC | Targeting Efficiencies (%) by LOA Screening | | | |
|---|---|---|---|---|---|
| | | Heterozygous | Hemizygous | Homozygous | Total |
| A + E2 | 1 | 12.8 | 6.4 | 3.8 | 23.0 |
| None | 1 | 8.3 | 0 | 0 | 8.3 |
| A + E2 | 2 | 7.2 | 13.1 | 4.3 | 24.6 |
| None | 2 | 5.4 | 0 | 0 | 5.4 |

Figure 14:
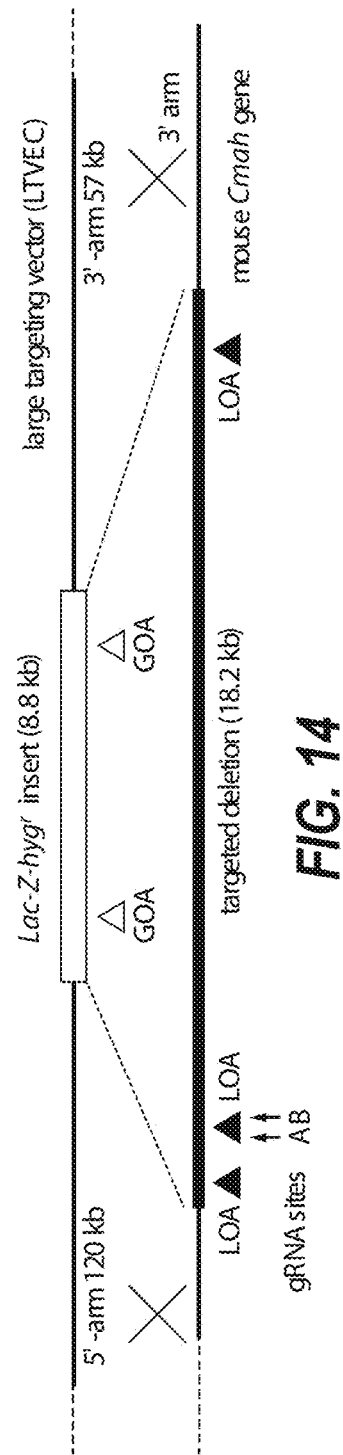
FIG. 14 shows a schematic for simultaneous deletion of the first five exons of the mouse Cmah gene and replacement with a lacZ reporter and a hygromycin resistance selection cassette using an LTVEC and two 5' region (A, B) gRNAs. The LTVEC is shown in the top portion of the figure, and the mouse Cmah gene locus is shown in the bottom portion of the figure. The positions of the Cas9 cleavage sites guided by the two guide RNAs are indicated by the vertical arrows below the mouse gene sequence, and the positions of the GOA assays that quantify the insert copy number and the LOA assays that quantify the mouse sequence targeted for deletion are indicated by the triangles.

Example 4. Effect of Shorter Distances Between CRISPR RNA Recognition Sequences on Targeting Efficiency To determine the effect of shorter distances between CRISPR RNA recognition sequences and cleavage sites on targeting efficiency, an LTVEC designed to create an 18.2 kb deletion of the mouse gene for cytidine monophosphate-N-acetylneuraminic acid hydroxylase (Cmah) and a simultaneous replacement with an insert comprising a lacZ reporter and a hygromycin resistance selection cassette. The LTVEC was used with two gRNAs targeting closely spaced sequences (FIG. 14). The target locus comprised the first five exons of the Cmah gene. The LTVEC comprised the 8.8 kb lacZ-hyg$^r$ insert flanked by homology arms containing 120 kb and 57 kb of genomic DNA derived from parts of the mouse Cmah locus that flank the 18.2 kb sequence of the mouse Cmah gene intended for deletion. The LTVEC was combined with plasmids encoding Cas9 and two gRNAs (A and B) designed to create double-strand breaks near the 5' end of the region of the mouse Cmah gene that was targeted for deletion. The two gRNAs targeted closely spaced sequences near the ATG at the 5' end of the sequence intended for deletion, with the targeted cleavage sites being 27 bp apart (see FIG. 15). Cleavage with Cas9 guided by the two gRNAs produces a blunt-ended excised sequence of 27 bp. LTVEC alone was used as a control.

Drug-resistant ES cell clones were screened for targeted humanizations by modification-of-allele assays (Valenzuela et al. (2003) *Nat. Biotechnol.* 21:652-659; Frendewey et al. (2010) *Methods Enzymol.* 476:295-307) for sequences within the deletion and for sequences within the drug selection cassette and the human gene insert. Clones were scored as correctly targeted if they had lost one of the two endogenous mouse gene sequences and gained one copy of the lacZ-hyg$^r$ insert. In addition, real-time PCR assays recognizing sequences in the homology arms of the LTVEC, referred to as retention assays, were used to verify correct targeting of the LTVEC into the mouse genome. Determining the copy number of these retention assays provided further clarification to help distinguish correctly targeted ES clones, which retained a copy number of two, from clones in which a large Cas9-induced deletion of the target mouse locus coincides with random integration of the LTVEC elsewhere in the genome, in which case retention assays had a copy number of three (or more). The ability of paired gRNAs to create large Cas9-mediated deletions at the target mouse locus meant that standard LOA and GOA assays as previously described could be augmented by retention assays to provide further clarification and to verify correct targeting. Therefore, retention assays were designed and used in conjunction with LOA and GOA assays.

The results of the Cmah targeting experiment are summarized in Table 10. In the control targeting experiment with LTVEC alone, 5.4% (3/56) of the screened clones had a heterozygous (Het) deletion-replacement mutation; 95% of the clones remained wild type (WT) at the Cmah locus. In the CRISPR targeting experiment, we observed five different mutant allele types in addition to a few WT clones. We observed three types of LTVEC-targeted alleles: (1) Het; (2) Hom (homozygous deletion-replacement); and (3) Hemi (deletion-replacement on one allele and a gRNA/Cas9-induced mutation on the other allele). These three types make up 43.5% (106/244) of all the clones screened. Compared with LTVEC alone, we observed an 8-fold enhancement of Cmah gene targeting in which at least one allele was targeted. We also observed two types of alleles carrying only gRNA/Cas9-indel mutations: (1) Het, in which we detected an indel on one of the two WT alleles; and (2) biallelic indel mutations, which could be either homozygous (Hom) or hemizygous (Hemi). Only 3.7% of the clones screened remained WT with no detectable mutation at the Cmah locus. Overall, more than 94% of the clones had Cas9-induced mutations when the combination of gRNAs A and B was used.

lipoprotein receptor-related protein 5) gene encoding the ectodomain and optionally a simultaneous replacement with a 4-nucleotide insertion through use of a single-stranded DNA donor sequence (124 nucleotides in length) with a 4-nucleotide insert flanked by two 60-nucleotide homology arms. The 4-nucleotide insert created a restriction enzyme site upon insertion into the target locus. In separate experiments, Cas9 protein in the form of protein was delivered by cytoplasmic injection (CI), or Cas9 in the form of mRNA was delivered by pronuclear injection (PNI) or electroporation (EP). The Cas9 was combined with two gRNAs (A+F) designed to create double-strand breaks within the region of the mouse Lrp5 gene that was targeted for deletion, and optionally with a homologous recombination donor. The gRNAs were injected in RNA form. The frequency of resulting monoallelic and biallelic mutations was then assessed.

The results are summarized in Table 11, including NHEJ-mediated deletion between the target sites for the two guide RNAs or deletion assisted by homology-directed repair with the ssDNA donor. Biallelic mutations were observed when the paired guide RNAs and Cas9 were introduced together with the ssDNA donor via cytoplasmic injection. In each

TABLE 10

Screening Results for Cmah Targeting.

| | Control Targeting (LTVEC alone) | | | CRISPR Targeting: LTVEC + Cas9 + gRNAs A + B | | | |
|---|---|---|---|---|---|---|---|
| Mutation | Allele Type | Genotype | % of Clones Screened | Mutation | Allele Type | Genotype | % of Clones Screened |
| Deletion-Replacement | Het | lacZ/+ | 5.4 | Deletion-Replacement | Het | lacZ/+ | 2.5 |
| Deletion-Replacement | Hom | lacZ/lacZ | 0 | Deletion-Replacement | Hom | lacZ/lacZ | 15 |
| Deletion-Replacement/Indel | Hemi | lacZ/indel | 0 | Deletion-Replacement/Indel | Hemi | lacZ/indel | 26 |
| Indel | Het | indel/+ | 0 | Indel | Het | indel/+ | 11 |
| Indel | Hom or Hemi | indel/indel | 0 | Indel | Hom or Hemi | indel/indel | 42 |
| None | WT | +/+ | 95 | None | WT | +/+ | 3.7 |

Example 5. Large Collapse Using Paired gRNAs in One-Cell Stage Embryos

To achieve a large targeted deletion in one-cell stage embryos, an experiment was designed to create a 68 kb deletion of the portion of the mouse Lrp5 (low-density observed biallelic mutation, one chromosome was modified via NHEJ-mediated deletion and one chromosome was modified via HDR-assisted deletion. These results indicate that cytoplasmic mRNA piezo injections result in consistent homology directed repair with the potential for homozygous recombination with a donor.

TABLE 11

Comparison of Cas9 Delivery Methods.

| | | | | | Monoallelic Mutation | | Biallelic Mutation | |
|---|---|---|---|---|---|---|---|---|
| Target | HR Donor | Delivery | Cas9 | Concentration (mg) Cas9/sgRNA/Donor | NHEJ Collapse | HDR Collapse | NHEJ Collapse | HDR Collapse |
| Lrp5 - 68 kb Collapse (A + F sgRNA) | – | PNI | Protein | 50/60/0 | 7% | N/A | 0% | N/A |
| | | CI | mRNA | 100/100/0 | 15% | N/A | N/A | N/A |
| | | EP | mRNA | 250/150/0 | 3% | N/A | 0% | N/A |
| Lrp5 - 68 kb Collapse (A + F sgRNA) | + | PNI | N/A | N/A | N/A | N/A | N/A | N/A |
| | | CI | mRNA | 100/50/100 | 16.6% | 19.4% | 5.5% | 5.5% |
| | | EP | mRNA | 250/200/250 | 1.4% | 2.1% | 0% | 0% |

Figure 17A:
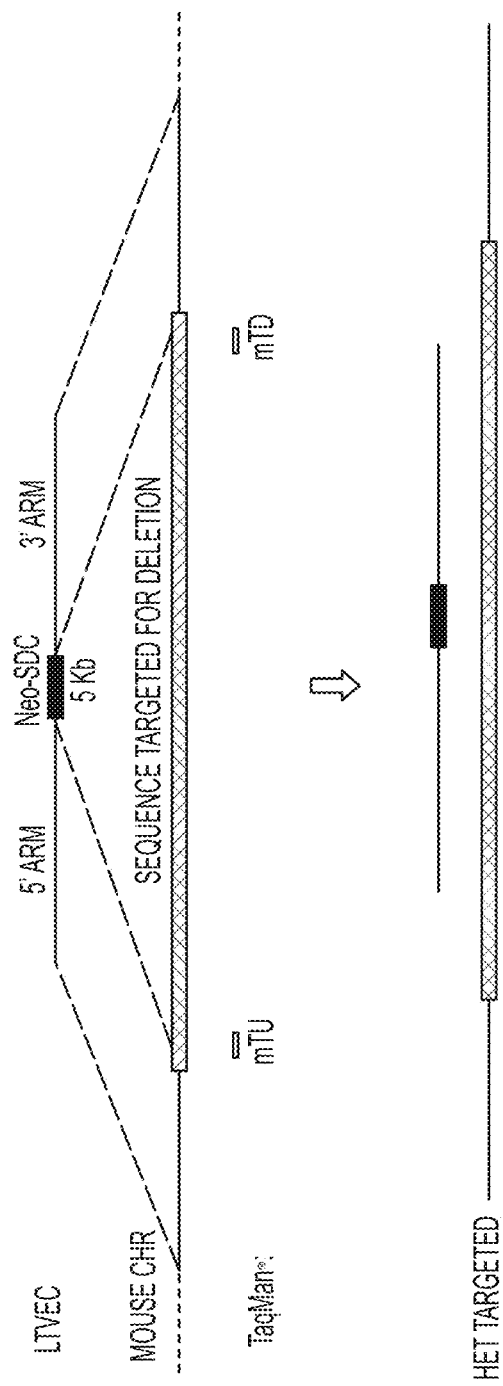
FIG. 17A-C show screening strategies for targeted modifications.

Example 6. Retention Assays for Distinguishing Between Targeted Insertions and Transgenic Insertions and Between Targeted Deletions and Deletions Extending Beyond Targeted Region Standard modification-of-allele (MOA) screening strategies (see, e.g., FIG. 17A) determine TaqMan® copy number by comparing an average of four biological replicate Ct values for each sample to the Ct median of all samples. For loss-of-allele, TaqMan® probes are used against the upstream (mTU) and downstream (mTD) regions of the region of the target genomic locus that is being targeted for deletion. For gain-of-allele, TaqMan® probes are used against the neomycin resistance cassette. However, such probes could be designed against any region of the nucleic acid insert. For a diploid, heterozygous targeted clone, the TaqMan® copy number for each of the mTU, mTD, and Neo probes should be one. For diploid, homozygous targeted clones, the TaqMan® copy number for each of mTU and mTD should be zero, and the TaqMan® copy number for Neo should be two. Likewise, for diploid, untargeted clones, the TaqMan® copy number for each of mTU and mTD should be two, and the TaqMan® copy number for Neo should be zero. For diploid, heterozygous collapsed clones, the TaqMan® copy number for mTU and mTD should be one, and the copy number for Neo should be zero. For diploid, homozygous collapsed clones, the TaqMan® copy number for each of mTU, mTD, and Neo should be zero.

Because paired gRNAs can create large Cas-mediated deletions at a target genomic locus, however, it can be useful augment standard LOA and GOA assays to verify correct targeting by LTVECs. For example, LOA and GOA assays alone may not distinguish correctly targeted cell clones from clones in which a large Cas-induced deletion of the target genomic locus coincides with random integration of a LTVEC elsewhere in the genome. Because the selection pressure in the targeted cell is based on the selection cassette, random transgenic integration of the LTVEC elsewhere in the genome will generally include the selection cassette and adjacent regions of the LTVEC but will exclude more distal regions of the LTVEC. For example, if LOA and GOA assays are used to assess targeted integration of the LTVEC, and the GOA assay utilizes probes against the selection cassette, a heterozygous deletion at the target genomic locus combined with a random transgenic integration of the LTVEC will give the same readout as a heterozygous targeted integration of the LTVEC at the target genomic locus. To verify correct targeting by the LTVEC, retention assays can be used, alone or in conjunction with LOA and/or GOA assays.

Figure 17B:
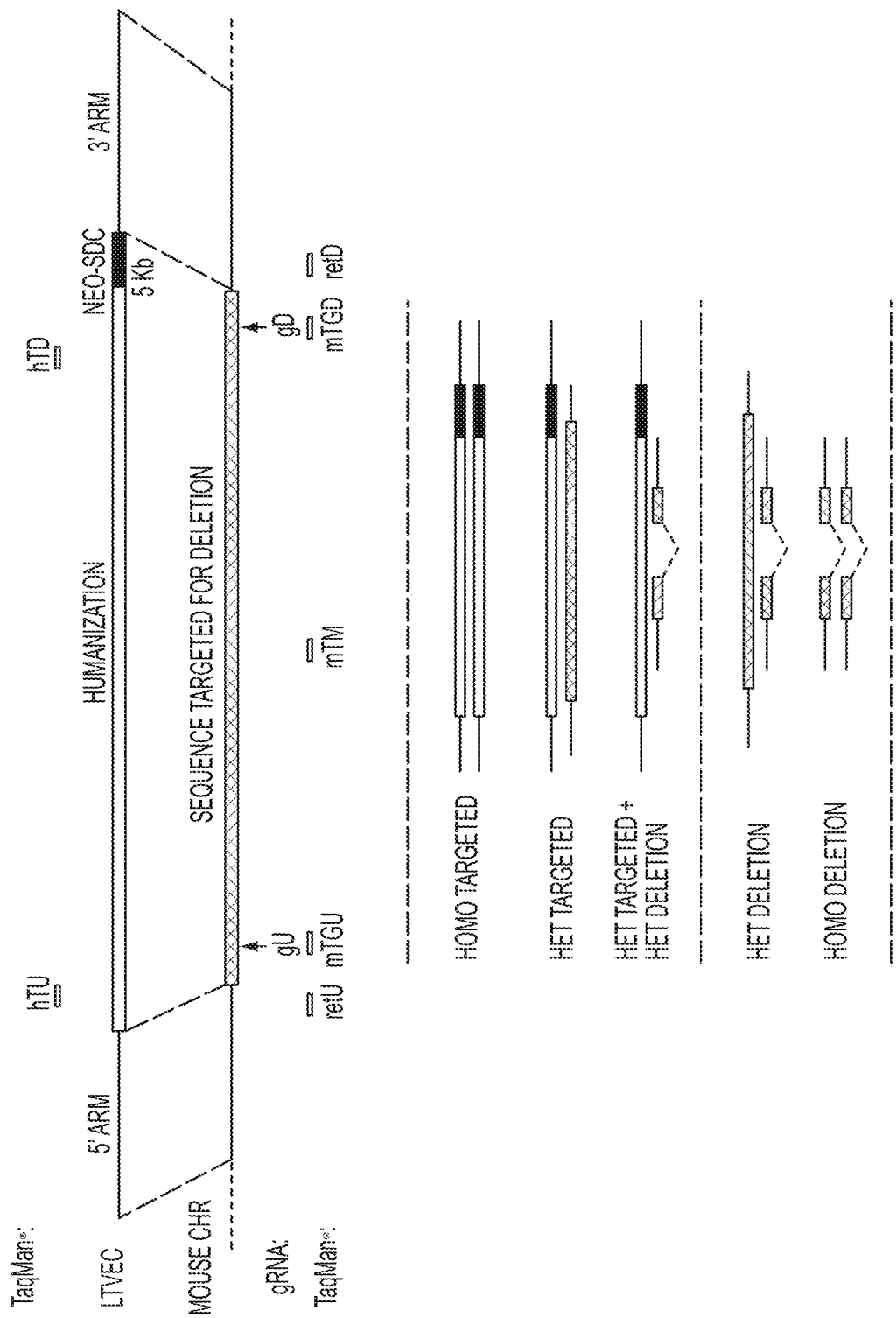

When TaqMan® retention assays, upstream and downstream probes corresponding to the 5' target sequence for the 5' homology arm (retU probe) and the 3' target sequence for the 3' homology arm (retD probe) are used (see FIG. 17B, which shows use of TaqMan® retention assays in combination with GOA and LOA assays to screen for CRISPR/Cas9-assisted humanization using neomycin selection). FIG. 17B also shows how different probes within the nucleic acid insert can be used for GOA assays (see upstream hTU probe and downstream hTD probe). GOA, LOA, and retention assay outcomes for different types of targeted modifications and transgenic insertions are shown in Table 12.

TABLE 12

Predicted Copy Number Readouts of GOA, LOA, and Retention Assays for Different Modification Types.

| Modification Type | retU | mTGU | mTM | mTGD | retD | Neo |
|---|---|---|---|---|---|---|
| Homo targeted | 2 | 0 | 0 | 0 | 2 | 2 |
| Het targeted | 2 | 1 | 1 | 1 | 2 | 1 |
| Het targeted + Het collapse | 2 | 0 | 0 | 0 | 2 | 1 |
| Het Collapse | 2 | 1 | 1 | 1 | 2 | 0 |
| Het collapse with transgenic insertion | 2 | 1 | 1 | 1 | 3* | 1* |
| Homo collapse | 2 | 0 | 0 | 0 | 2 | 0 |
| Homo collapse with transgenic insertion | 2 | 0 | 0 | 0 | 3* | 1* |

Figure 17C:
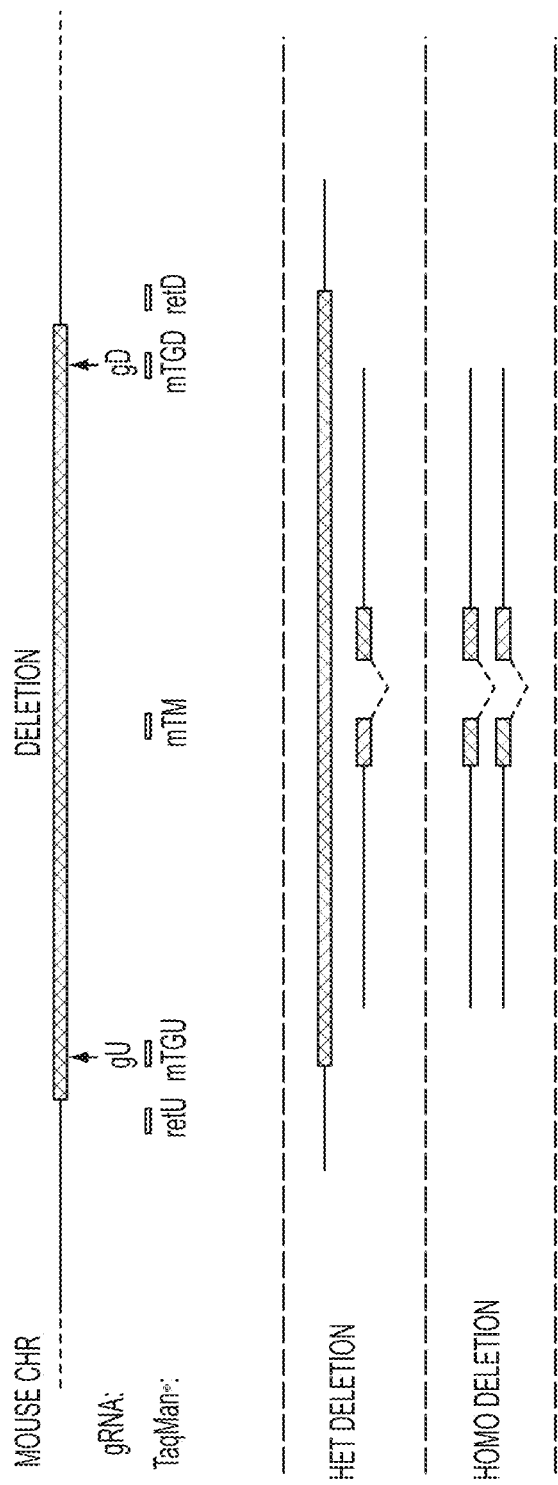

TaqMan retention assays can also be used in combination with LOA assays to screen for CRISPR/Cas9-assisted deletions using paired gRNAs (see FIG. 17C). In such assays, the copy numbers for retU and retD should remain two in all cases. Copy numbers less than two indicate large Cas9-mediated deletions extending beyond the region being targeted for deletion. LOA and retention assay outcomes for different types of collapse-related modifications are shown in Table 13.

TABLE 13

Predicted Copy Number Readouts of LOA and Retention Assays for Different Collapse Modifications.

| Modification Type | retU | mTGU | mTM | mTGD | retD |
|---|---|---|---|---|---|
| Homo collapse | 2 | 0 | 0 | 0 | 2 |
| Het collapse | 2 | 1 | 1 | 1 | 2 |
| Het collapse with additional downstream deletion | 2 | 1 | 1 | 1 | 1* |

Example 7. CRISPR/Cas9-Mediated Targeting Using Four Guide RNAs

To effect a precise, single-step deletion of an approximately 900 kb region of a modified mouse immunoglobulin heavy chain locus and simultaneous replacement with a Pgk-Neo insert (phosphoglycerate kinase I promoter operably linked to neomycin phosphotransferase gene) flanked by loxP sites, we introduced by electroporation into mouse ES cells the following nucleic acid molecules: (1) an LTVEC (2) a plasmid encoding a Cas9 endonuclease; and (3) one or more plasmids encoding four CRISPR single guide RNAs (gRNAs). In each experiment, the LTVEC was linearized. The locus targeted for modification was an approximately 900 kb region of a mouse immunoglobulin heavy chain locus with variable region gene segments ($V_H$, $D_H$, $J_H$) replaced with human counterparts (see FIG. 18). The LTVEC comprised the Pgk-Neo insert having a length of approximately 2 kb flanked by a 19 kb 5' homology arm and a 13 kb 3' homology arm designed to direct a homologous recombination event that deletes the approximately 900 kb region of the target locus and insert the drug selection cassette that directs the expression of neomycin phosphotransferase to impart resistance to G418.

Figure 18:
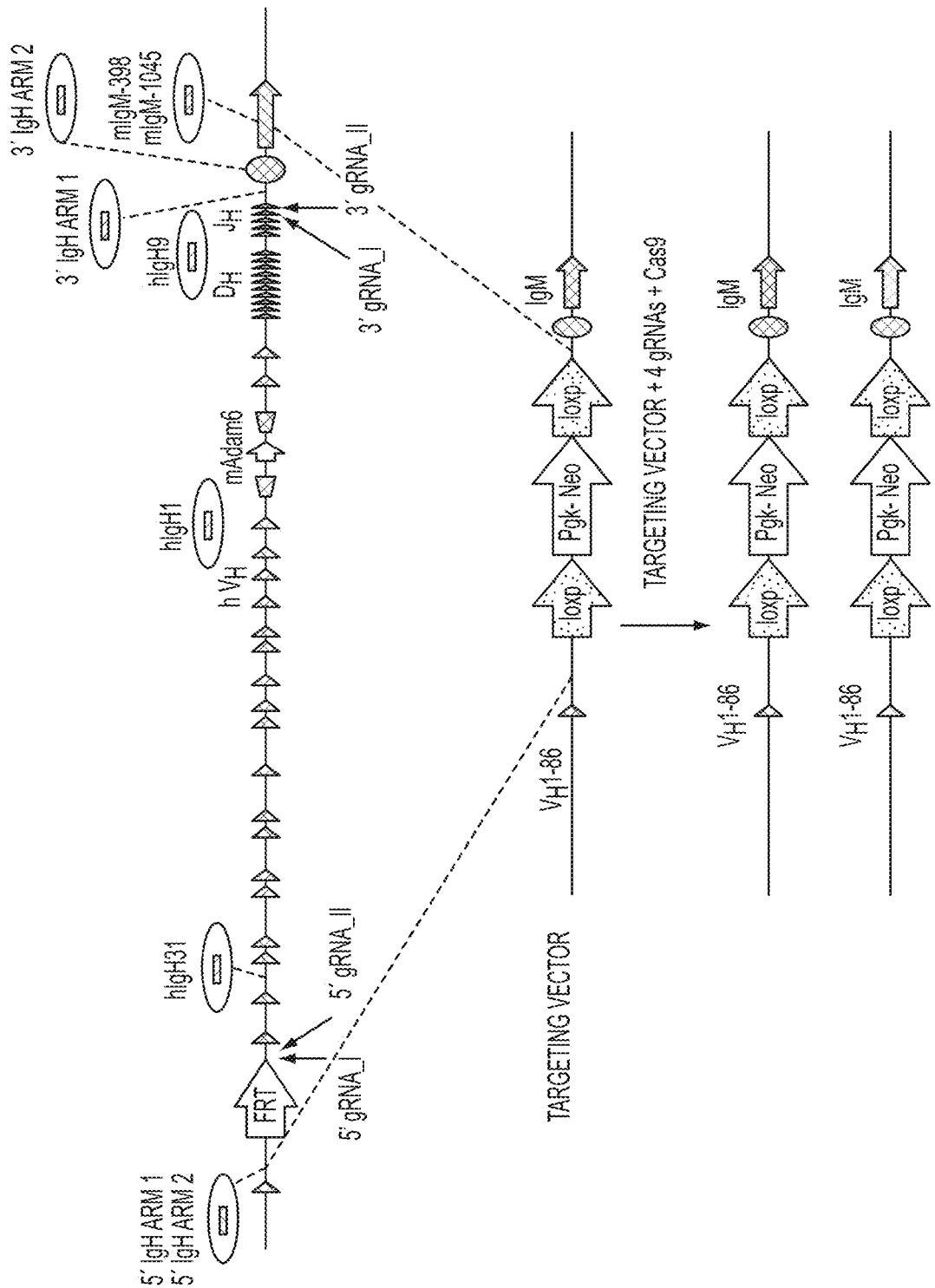
FIG. 18 shows schematics (not to scale) of an approximately 900 kb region of a mouse immunoglobulin heavy chain locus with variable region gene segments replaced with human counterparts (triangles) and a targeting vector with a Pgk-Neo insert (phosphoglycerate kinase I promoter operably linked to neomycin phosphotransferase gene) flanked by loxP sites. Two gRNAs are used to cleave the mouse immunoglobulin heavy chain locus at the 5' end and two gRNAs are used to cleave the locus at the 3' end, and the targeting vector deletes and replaces the mouse immunoglobulin heavy chain locus with the Pgk-Neo insert. The positions of the Cas9 cleavage sites guided by the four guide RNAs are indicated by the vertical arrows below the target locus. The encircled horizontal lines represent TaqMan® probes for modification of allele (MOA) assays (hIgH31, hIgH1, mIgHA1, mIgHA7, and hIgH9) and retention assays (5' IgH Arm 1, 5' IgH Arm 2, mIgM-398, and mIgM-1045).

Of the four gRNAs that were used, two directed Cas9 cleavage near the 5' end of the target locus (5' gRNA_I and 5' gRNA_II in FIG. 18), and two directed Cas9 cleavage near the 3' end of the target locus (3' gRNA_I and 3' gRNA_II in FIG. 18). The 5' gRNA_I and 5' gRNA_II target sequences were approximately 150 bp apart from each other, and the 3' gRNA_I and 3' gRNA_II target sequences overlapped, with the 3' gRNA_II target site shifted 1 bp relative to the 3' gRNA_I target site.

ES cells that took up the LTVEC and incorporated it into their genomes were able to grow and form colonies on a tissue culture dish in a growth medium containing the antibiotic drug. We picked drug resistant colonies and screened them by the modification-of-allele method (Valenzuela et al. (2003) *Nat. Biotech.* 21:652-660; Frendewey et al. (2010) *Methods Enzymol.* 476:295-307; incorporated herein by reference in their entireties) to identify clones that had the correctly targeted humanized allele (see Table 14 below). In addition, real-time PCR assays recognizing sequences in the homology arms of the LTVEC, referred to as retention assays, were used to verify correct targeting of the LTVEC into the mouse genome (see Table 14 below).

TABLE 14

Probes Used to Confirm Targeting with LTVEC and 4 gRNAs.

| Probe | Assay | SEQ ID NO | Distance To | Kb |
|---|---|---|---|---|
| 5' IgH Arm 1 | Retention | 148 | 5' gRNAs | 1.5 |
| 5' IgH Arm 2 | Retention | 173 | 5' gRNAs | 0.315 |
| hIgH31 | LOA | 136 | 5' gRNAs | 154 |
| hIgH1 | LOA | 142 | 5' gRNAs | 747 |
| hIgH1 | LOA | 142 | 3' gRNAs | 116 |
| hIgH9 | LOA | 139 | 3' gRNAs | 3.2 |
| 3' IgH Arm 1 | Retention | 176 | 3' gRNAs | 0.484 |
| 3' IgH Arm 2 | Retention | 157 | 3' gRNAs | 1.2 |
| mIgM-398 | Retention | 151 | 3' gRNAs | 6.4 |
| mIgM-1045 | Retention | 154 | 3' gRNAs | 7 |

In the resulting targeted ES cells, the approximately 900 kb region was deleted and replaced with the Pgk-Neo insert in both alleles (see FIG. 18). This large deletion and replacement was achieved with an unexpectedly high efficiency (approximately 1.2% efficiency for biallelic deletion).

We claim:

1. A method for modifying a genome within a mammalian cell in vitro that is heterozygous for a first allele, comprising:
   (I) contacting the genome with:
   (a) a Cas protein;
   (b) a first guide RNA, wherein the first guide RNA comprises a first tracrRNA and a first CRISPR RNA that hybridizes to a first non-allele-specific CRISPR RNA recognition sequence, wherein the cell comprises a chromosome pair of first and second homologous chromosomes comprising a genomic locus, wherein the first allele is at the genomic locus on the first homologous chromosome, and the CRISPR RNA recognition sequence is centromeric to the genomic locus on the second homologous chromosome; and
   (c) a second guide RNA, wherein the second guide RNA comprises a second tracrRNA and a second CRISPR RNA that hybridizes to a second non-allele-specific CRISPR RNA recognition sequence centromeric to the genomic locus on the second homologous chromosome,
   wherein the first allele is at least 100 kb from the first CRISPR RNA recognition sequence,
   wherein the Cas protein and the first guide RNA do not naturally occur together,
   wherein the Cas protein is a Cas9 protein and has nuclease activity on both strands of double-stranded DNA, and
   wherein the Cas protein cleaves the first CRISPR RNA recognition sequence on the second homologous chromosome to generate a double-strand break and the cell is modified to become homozygous for the first allele; and
   (II) identifying a modified cell that is homozygous for the first allele.

2. The method of claim 1, wherein step (I) comprises introducing into the cell: (a) the Cas protein or a nucleic acid encoding the Cas protein; and (b) the first guide RNA or a DNA encoding the first guide RNA.

3. The method of claim 2, wherein step (I) comprises introducing into the cell the nucleic acid encoding the Cas protein and introducing into the cell the first guide RNA, wherein the nucleic acid encoding the Cas protein is an RNA.

4. The method of claim 2, wherein step (I) comprises introducing into the cell the nucleic acid encoding the Cas protein and the DNA encoding the first guide RNA, wherein the nucleic acid encoding the Cas protein is a DNA.

5. The method of claim 2, wherein the Cas protein and the first guide RNA are introduced into the cell as a first protein-RNA complex.

6. The method of claim 4, wherein the first CRISPR RNA and the first tracrRNA are separate RNA molecules, and wherein:
   (1) the DNA encoding the Cas protein is operably linked to a first promoter in a first expression construct;
   (2) the DNA encoding the first CRISPR RNA is operably linked to a second promoter in a second expression construct; and
   (3) the DNA encoding the first tracrRNA is operably linked to a third promoter in a third expression construct;
   wherein the first, second, and third promoters are active in the cell.

7. The method of claim 6, wherein the first, second, and third expression constructs are components of a single nucleic acid molecule.

8. The method of claim 4, wherein:
   (1) the DNA encoding the Cas protein is operably linked to a first promoter in a first expression construct; and/or
   (2) the DNA encoding the first guide RNA is operably linked to a second promoter in a second expression construct,
   wherein the first and second promoters are active in the cell.

9. The method of claim 8, wherein the first and second expression constructs are components of a single nucleic acid molecule.

10. The method of claim 1, wherein the double-strand break is repaired in the cell, and wherein repair of the double-strand break results in loss of heterozygosity that occurs telomeric of the double-strand break.

11. The method of claim 1, wherein step (I) further comprises introducing into the cell the second guide RNA or a DNA encoding the second guide RNA.

12. The method of claim 1, wherein the Cas protein cleaves the first CRISPR RNA recognition sequence and the second CRISPR RNA recognition sequence.

13. The method of claim 1, wherein the first CRISPR RNA recognition sequence is from 100 bp to 1 kb, 1 kb to 10 kb, 10 kb to 100 kb, 100 kb to 1 Mb, 1 Mb to 10 Mb, 10 Mb to 20 Mb, 20 Mb to 30 Mb, 30 Mb to 40 Mb, 40 Mb to 50 Mb, 50 Mb to 60 Mb, 60 Mb to 70 Mb, 70 Mb to 80 Mb, 80 Mb to 90 Mb, or 90 Mb to 100 Mb from the centromere.

14. The method of claim 1, wherein the first allele is from 100 kb to 1 Mb, 1 Mb to 10 Mb, 10 Mb to 20 Mb, 20 Mb to 30 Mb, 30 Mb to 40 Mb, 40 Mb to 50 Mb, 50 Mb to 60 Mb, 60 Mb to 70 Mb 70 Mb to 80 Mb, 80 Mb to 90 Mb, or 90 Mb to 100 Mb from the first CRISPR RNA recognition sequence.

15. The method of claim 1, wherein the first allele is at least 1 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb from the first CRISPR RNA recognition sequence.

16. The method of claim 1, wherein a region of the second homologous chromosome is modified to become homozygous for the first allele by loss of heterozygosity, wherein the region of the second homologous chromosome being replaced by loss of heterozygosity is from 100 bp to 1 kb, 1 kb to 10 kb, 10 to 100 kb, 100 kb to 1 Mb, 1 Mb to 10 Mb, 10 Mb to 20 Mb, 20 Mb to 30 Mb, 30 Mb to 40 Mb, 40 Mb to 50 Mb, 50 Mb to 60 Mb, 60 Mb to 70 Mb, 70 Mb to 80 Mb, 80 Mb to 90 Mb, or 90 Mb to 100 Mb.

17. The method of claim 1, wherein a region of the second homologous chromosome is modified to become homozygous for the first allele by loss of heterozygosity, wherein the region of the second homologous chromosome being replaced by loss of heterozygosity is at least 100 bp, at least 1 kb, at least 10 kb, at least 100 kb, at least 1 Mb, at least 10 Mb, at least 20 Mb, at least 30 Mb, at least 40 Mb, at least 50 Mb, at least 60 Mb, at least 70 Mb, at least 80 Mb, at least 90 Mb, or at least 100 Mb.

18. The method of claim 1, wherein:
(1) the first allele comprises a mutation; or
(2) the first allele is a wild type allele, and the genomic locus on the second homologous chromosome comprises a mutation.

19. The method of claim 18, wherein the first allele comprises the mutation, wherein the mutation is a targeted modification.

20. The method of claim 1, wherein the cell is a human cell, a non-human cell, a rodent cell, a mouse cell, a rat cell, a pluripotent cell, a non-pluripotent cell, a non-human pluripotent cell, a human pluripotent cell, a rodent pluripotent cell, a mouse pluripotent cell, a rat pluripotent cell, a mouse embryonic stem (ES) cell, a rat ES cell, a non-human mammalian ES cell, a human adult stem cell, a developmentally restricted human progenitor cell, a human induced pluripotent stem (iPS) cell, a non-human mammalian one-cell stage embryo, or a mouse one-cell stage embryo.

21. The method of claim 20, wherein the cell is the human iPS cell.

22. The method of claim 20, wherein the cell is the mouse ES cell or the rat ES cell.

23. The method of claim 22, wherein the cell is the mouse ES cell.

24. The method of claim 1, wherein the first CRISPR RNA and the first tracrRNA in the first guide RNA are fused together.

25. The method of claim 1, wherein the first CRISPR RNA and the first tracrRNA are separate RNA molecules.

26. The method of claim 1, wherein the cell has been modified to decrease non-homologous end joining (NHEJ) and/or to increase gene conversion or homology-directed repair (HDR).

27. The method of claim 26, wherein the cell has been modified to decrease the expression or activity of one or more of the following: DNA-PK, PARP1, and ligase IV.

28. The method of claim 27, wherein the decrease in expression or activity is inducible, reversible, temporally specific, and/or spatially specific.

29. The method of claim 1, wherein the identifying in step (II) comprises a modification-of-allele assay.

30. The method of claim 1, wherein the identifying in step (II) comprises screening for loss of heterozygosity.

31. The method of claim 30, wherein the screening comprises performing a structural variant polymorphism PCR assay and/or a single nucleotide variant allelic discrimination assay telomeric of the first CRISPR RNA recognition sequence.

32. The method of claim 31, wherein the screening comprises performing multiple structural variant polymorphism PCR assays and/or multiple single nucleotide variant allelic discrimination assays at different positions telomeric of the first CRISPR RNA recognition sequence.

33. The method of claim 1, wherein the cell is heterozygous for one or more additional alleles, wherein the chromosome pair of first and second homologous chromosomes comprises one or more additional genomic loci, wherein the one or more additional alleles are at the one or more additional genomic loci on the first homologous chromosome, wherein the first CRISPR RNA recognition sequence is centromeric to the one or more genomic loci on the second homologous chromosome, the cell is modified to become homozygous for the one or more additional alleles, and step (II) comprises identifying a modified cell that is homozygous for the one or more additional alleles.

* * * * *

UNITED STATES PATENT AND TRADEMARK OFFICE
CERTIFICATE OF CORRECTION

PATENT NO. : 11,697,828 B2  
APPLICATION NO. : 16/572124  
DATED : July 11, 2023  
INVENTOR(S) : David Frendewey et al.

Page 1 of 1

It is certified that error appears in the above-identified patent and that said Letters Patent is hereby corrected as shown below:

On the Title Page

Item (73) Assignee:  
Delete "Regeneran" and replace it with --Regeneron--

Signed and Sealed this  
Twelfth Day of September, 2023

*Katherine Kelly Vidal*

Katherine Kelly Vidal  
*Director of the United States Patent and Trademark Office*